United States Patent
Zhao et al.

(10) Patent No.: US 11,884,661 B2
(45) Date of Patent: *Jan. 30, 2024

(54) 3-SUBSTITUTED PROPIONIC ACIDS AS αV INTEGRIN INHIBITORS

(71) Applicant: BRISTOL-MYERS SQUIBB COMPANY, Princeton, NJ (US)

(72) Inventors: Guohua Zhao, Princeton, NJ (US); Pratik Devasthale, Plainsboro, NJ (US); Xiang-Yang Ye, Princeton, NJ (US); Kumaravel Selvakumar, Bangalore (IN); Suresh Dhanusu, Hosur (IN); Palanikumar Balasubramanian, Hosur (IN); Leatte R. Guernon, Pipersville, PA (US); Rita Civiello, Killingworth, CT (US); Xiaojun Han, Cheshire, CT (US); Michael Frederick Parker, Higganum, CT (US); Swanee E. Jacutin-Porte, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 260 days.

This patent is subject to a terminal disclaimer.

(21) Appl. No.: 17/184,179

(22) Filed: Feb. 24, 2021

(65) Prior Publication Data

US 2021/0188847 A1 Jun. 24, 2021

Related U.S. Application Data

(63) Continuation of application No. 16/347,844, filed as application No. PCT/US2017/060376 on Nov. 7, 2017, now Pat. No. 10,968,219.

(60) Provisional application No. 62/418,848, filed on Nov. 8, 2016.

(51) Int. Cl.

| C07D 471/04 | (2006.01) |
| C07D 491/04 | (2006.01) |
| C07D 519/00 | (2006.01) |
| A61P 11/00 | (2006.01) |
| A61P 19/10 | (2006.01) |
| A61P 35/00 | (2006.01) |
| A61P 37/06 | (2006.01) |

(52) U.S. Cl.
CPC ............ *C07D 471/04* (2013.01); *A61P 11/00* (2018.01); *A61P 19/10* (2018.01); *A61P 35/00* (2018.01); *A61P 37/06* (2018.01); *C07D 491/04* (2013.01); *C07D 519/00* (2013.01)

(58) Field of Classification Search
CPC .. C07D 471/04; C07D 491/04; C07D 519/00; A61P 11/00; A61P 19/10; A61P 35/00; A61P 37/06

See application file for complete search history.

(56) References Cited

U.S. PATENT DOCUMENTS

| 5,273,989 | A | 12/1993 | Schwab et al. |
| 5,760,029 | A | 6/1998 | Jadhav et al. |
| 6,090,944 | A | 7/2000 | Hutchinson |
| 6,114,328 | A | 9/2000 | Wityak et al. |
| 8,927,534 | B2 | 1/2015 | Zischinsky et al. |
| 10,968,219 | B2* | 4/2021 | Zhao .................. C07D 491/04 |
| 2008/0045521 | A1* | 2/2008 | Arnould .................. A61P 43/00 546/264 |
| 2008/0255183 | A1 | 10/2008 | Arnould et al. |
| 2016/0264566 | A1 | 9/2016 | DeGrado et al. |

FOREIGN PATENT DOCUMENTS

| WO | 9930709 A1 | 6/1999 |
| WO | 19930709 A1 | 6/1999 |
| WO | 199926945 A1 | 6/1999 |
| WO | 2002060438 A1 | 8/2002 |
| WO | 04058254 A1 | 7/2004 |
| WO | 2004058761 A1 | 7/2004 |
| WO | 2006108040 A1 | 10/2006 |
| WO | 07088041 A1 | 8/2007 |
| WO | 2007141473 A1 | 12/2007 |
| WO | 2011098603 A1 | 8/2011 |
| WO | 2014154725 A1 | 10/2014 |
| WO | 2015091426 A1 | 6/2015 |
| WO | 2016046225 A1 | 3/2016 |
| WO | 2016046226 A1 | 3/2016 |
| WO | 2016046230 A1 | 3/2016 |
| WO | 2016046241 A1 | 3/2016 |
| WO | 2016134223 A2 | 8/2016 |

OTHER PUBLICATIONS

Kapp et al., "Integrin Modulators: a patent review", Expert Opinion on Therapeutic Patents, vol. 23(10), pp. 1273-1295 (2013).

(Continued)

*Primary Examiner* — Erich A Leeser
(74) *Attorney, Agent, or Firm* — Gary Greenblatt

(57) ABSTRACT

The present invention provides compounds of Formula (I):

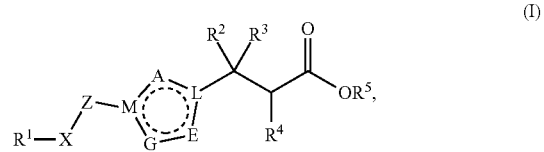

or stereoisomers, tautomers, or pharmaceutically acceptable salts or solvates thereof, wherein all the variables are as defined herein. These compounds are antagonists to α$_V$-containing integrins. This invention also relates to pharmaceutical compositions comprising these compounds and methods of treating a disease, disorder, or condition associated with dysregulation of α$_V$-containing integrins, such as pathological fibrosis, transplant rejection, cancer, osteoporosis, and inflammatory disorders, by using the compounds and pharmaceutical compositions.

11 Claims, No Drawings

(56) References Cited

OTHER PUBLICATIONS

Piras, M. et al., "High-Affinity "Click" RGD Peptidomimetics as Radiolabeled Probes for Imaging αvβ3 Integrin", ChemMedChem, 2017, vol. 12, pp. 1142-1151.

Raboisson, P. et al., "Identification of novel short chain 4-substituted indoles as potent αvβ3 antagonist using structure-based drug design", European Journal of Medicinal Chemistry, vol. 42, pp. 334-343 (2007).

Kumano-Kuramochi, et al., "Identification of 4-hydroxy-2-nonenal-histidine adducts that serve as ligands for human lectin-like oxidized LDL receptor-1", Biochem. J. (2012) 442, 171-180.

* cited by examiner

3-SUBSTITUTED PROPIONIC ACIDS AS αV INTEGRIN INHIBITORS

CROSS REFERENCE TO RELATED APPLICATION

This application is a continuation application of U.S. application Ser. No. 16/347,844, filed May 7, 2019, which is a national phase application under 35 U.S.C. § 371 of International Patent Application No. PCT/US2017/060376, filed Nov. 7, 2017, which claims priority to U.S. Provisional Application Ser. No. 62/418,848 filed Nov. 8, 2016, which are expressly incorporated fully herein by reference.

FIELD OF THE INVENTION

The present invention relates to substituted 3-azolopropionic acids as αV integrin antagonists, pharmaceutical compositions comprising such compounds and to their use in therapy, especially in the treatment or prophylaxis of diseases, disorders, and conditions for which an αV integrin antagonist is indicated in a human.

BACKGROUND OF THE INVENTION

Integrins belong to a large family of α/β heterodimeric transmembrane proteins that are involved in cell adhesion to a wide variety of extracellular matrix proteins, cell-cell interactions, cell migration, proliferation, survival, and in maintenance of tissue integrity (Barczyk et al. *Cell and Tissue Research* 2010, 339, 269; Srichai, M. B.; Zent, R. in *Cell-Extracellular Matrix Interactions in Cancer,* 2010). In mammals, there are 24 α/β integrin heterodimers known from various combinations of 18 alpha and 8 beta subunits. Transforming Growth Factor-β (TGF-β) has a central role in driving a number of pathological processes underlying fibrosis, cell growth, and autoimmune diseases. Alpha V (αV) Integrins, that include αVβ1, αVβ3, αVβ5, αVβ6, and αVβ8, are involved in a critical pathway that leads to the conversion of latent TGF-β to its active form (Henderson, N. C.; Sheppard, D. *Biochim, Biophys. Acta* 2013, 1832, 891). Thus, antagonism of such αV integrin-mediated activation of latent TGF-β provides a viable therapeutic approach to intervene in TGF-β-driven pathological states (Sheppard, D. *Eur. Resp. Rev.* 2008, 17, 157; Goodman, S. L.; Picard, M. *Trends Pharmacol. Sciences* 2012, 33(7), 405; Hinz, B. *Nature Medicine* 2013, 19(12), 1567; Pozzi, A.; Zent, R. *J. Am. Soc. Nephrol.* 2013, 24(7), 1034). All five αV integrins belong to a small subset (8 out of 24) of integrins that recognize the Arginine-Glycine-Aspartic acid (RGD) motif present in their native ligands such as fibronectin, vitronectin, and Latency-Associated Peptide (LAP).

The expression of αV integrin subtypes varies significantly. For example, αVβ6 is expressed on epithelial cells at very low levels in healthy tissue but is significantly upregulated during inflammation and wound healing. αVβ3 and αVβ5 are expressed on osteoclasts, endothelial, smooth muscle, and solid tumor cells, as well as on pericytes and podocytes, while αVβ1 is expressed on activated fibroblasts and mesangial cells.

Fibrotic conditions that represent major unmet medical needs are Idiopathic Pulmonary Fibrosis (IPF), liver and kidney fibrosis, Non-Alcoholic Fatty Liver Disease (NAFLD), Non-Alcoholic Steato-Hepatitis (NASH), as well as systemic sclerosis. Two drugs, pirfenidone an nintedanib, that act by non-integrin-mediated mechanisms, have recently been approved for treatment of IPF. The present invention relates to compounds that inhibit or antagonize the action of one or more of the αV integrins in the treatment of pathological conditions, such as fibrosis and cancer, mediated by these integrins.

A number of selective or nonselective small molecule, peptidic, and antibody-based antagonists of αV integrins have been reported in the literature (Kapp, T. G. et al. *Expert Opin. Ther. Patents* 2013, 23(10), 1273; O'Day, S. et al. *Brit. J. Cancer* 2011, 105(3), 346; Pickarski, M. et al. *Oncol. Rep.* 2015, 33, 2737; Wirth, M. et al. *Eur. Urol.* 2014, 897; Henderson, N. C. et al. *Nature Medicine* 2012, 19(12), 1617; Horan, G. S. et al. *Am. J. Resp. Crit. Care Med.* 2008, 177, 56; Puthawala, K. et al. *Am. J. Resp. Crit. Care Med.* 2008, 177, 82; Reed, N. I. et al. *Sci. Transl. Med.* 2015, 7(288), 288ra79; Anderson, N. A. et al. WO 2014/154725 A1, WO 2016/046225 A1, WO 2016/046226 A1, WO 2016/046230 A1, WO 2016/046241 A1).

SUMMARY OF THE INVENTION

In one aspect, the present invention provides compounds of Formula (I), (IIa), (IIb), (IIc), (IId), (IIe), (IIf), (IIIa), (IIIb), (IVa) and (IVb) as well as the subgenera and species thereof, including stereoisomers, tautomers, pharmaceutically acceptable salts, and solvates thereof, which are useful as αV integrin antagonists.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with dysregulation of $α_v$-containing integrins in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used for the manufacture of a medicament for the treatment of a disease, disorder, or condition associated with dysregulation of $α_v$-containing integrins in a patient.

Other features and advantages of the invention will be apparent from the following detailed description and claims.

DETAILED DESCRIPTION OF THE INVENTION

The present application provides compounds, including all stereoisomers, solvates, prodrugs and pharmaceutically acceptable salt and solvate forms thereof, according to Formula I. The present application also provides pharmaceutical compositions containing at least one compound according to Formula I, or a stereoisomer, a tautomer, or a pharmaceutically acceptable salt or a solvate thereof, and optionally at least one additional therapeutic agent. Additionally, the present application provides methods for treating a patient suffering from an αV Integrin-modulated disease or disorder such as for example, Idiopathic Pulmonary Fibrosis (IPF), liver and kidney fibrosis, Non-Alcoholic Fatty Liver Disease (NAFLD), Non-Alcoholic Steato-Hepatitis (NASH), cardiac fibrosis, and systemic sclerosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

I. Compounds of the Invention

In one embodiment, the present invention provides, inter alia, a compound of Formula (I):

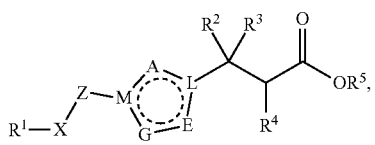

(I)

or a stereoisomer, a tautomer, or a pharmaceutically acceptable salt or a solvate thereof, wherein:
  A, E, and G are independently N, O, S, $NR^{6a}$, $CHR^{6b}$ or $CR^{6b}$;
  M and L are independently N or C; with the proviso that M and L are not both N;
  as indicated by the dotted circle, the ring formed by A, E, G, M, and L can be fully saturated, partically saturated, or unsaturated; and the ring formed by A, E, G, M, and L can be either aromatic or non-aromatic;
  $R^1$ is an Arginine mimetic moiety selected from the group consisting of

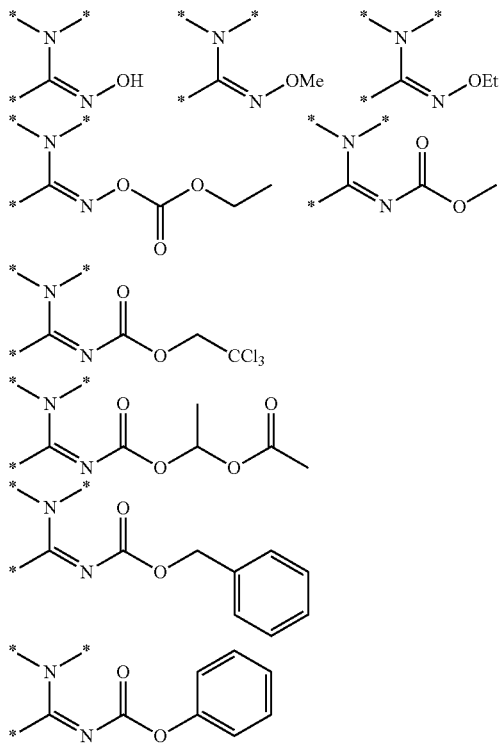

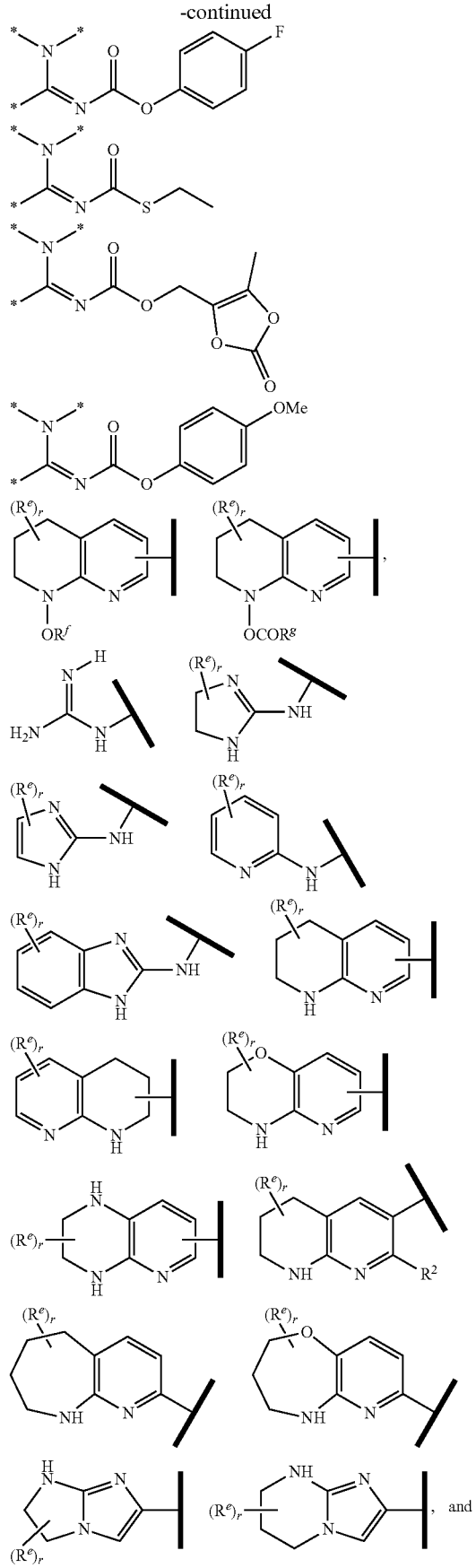

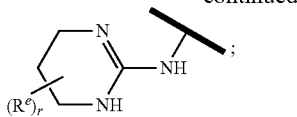

one of the asterisks in each of the arginine mimetics moiety is an attachment point to X, and the other two asterisks are hydrogen;

$R^f$=H, Me, Et, COOEt;

$R^g$=CH$_3$, CH$_2$CH$_3$, CH$_2$CCl$_3$, phenyl, 4-fluorophenyl, 4-methoxyphenyl, benzyl,

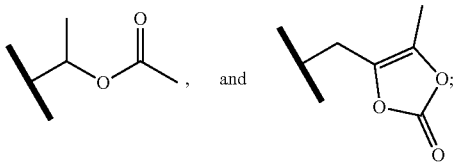

$R^e$ is OH, $C_{1-4}$ alkyl, halo, haloalkyl, $C_{1-4}$ cycloalkyl, amino, amido, carbamate, or sulfonamide;

r is an integer of 0, 1, 2, or 3;

X is a $C_{1-6}$ alkylene substituted with 0, 1, or 2 $R^{7b}$;

Z is a covalent bond, O, S, NH, —O—($C_{1-3}$ alkylene)-, —S—($C_{1-3}$ alkylene)-, or —NH—($C_{1-3}$ alkylene)-, wherein the $C_{1-3}$ alkylene is each independently substituted with 0, 1, or 2 $R^{7a}$;

$R^2$ is hydrogen or $C_{1-6}$ alkyl; or alternatively, $R^2$ and $R^3$, together with the atoms to which they are attached, form a carbocyclyl or a heterocyclyl, wherein the carbocyclyl and heterocyclyl are each independently substituted with 0, 1, 2, or 3 $R^{12}$;

$R^3$ is hydrogen, $C_{1-6}$ alkyl, 3- to 10-membered carbocyclyl, carbocyclylalkyl, 6- to 10-membered aryl, arylalkyl, 3- to 14-membered heterocyclyl, heterocyclylalkyl, 5- to 14-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^8$;

$R^4$ is hydrogen, $C_{1-10}$ alkyl, 3- to 10-membered carbocyclyl, carbocyclylalkyl, 3- to 10-membered heterocyclyl, heterocyclylalkyl, 6- to 10-membered aryl, arylalkyl, 5- to 14-membered heteroaryl, heteroarylalkyl, NR$^a$R$^b$, OR$^a$, S(O)$_n$R$^{10}$, C(O)NR$^a$R$^b$, NHC(O)OR$^a$, NHC(O)NR$^a$R$^b$, NHC(O)R$^{10}$, OC(O)NR$^a$R$^b$, OC(O)R$^{10}$, NHS(O)$_n$NR$^a$R$^b$, or NHS(O)$_n$R$^{10}$; wherein the alkyl, carbocyclyl, heterocyclyl, aryl, and heteroaryl, by themselves or as part of another group, are each independently substituted with 0, 1, 2, or 3 $R^9$;

n is an integer of 1 or 2;

$R^5$ is H, $R^{5a}$, or a structural moiety selected from

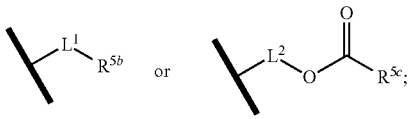

$L^1$ and $L^2$ are each independently $C_{1-4}$ alkylene;

$R^{5a}$ and $R^{5b}$ are each independently $C_{1-6}$ alkyl, phenyl, or 5- to 7-membered heterocyclyl; wherein the alkyl, phenyl, and heterocyclyl are each independently substituted with 0 to 3 $R^{5d}$;

$R^{5c}$ is $C_{1-5}$ alkyl or 5- to 7-membered carbocyclyl; wherein the alkyl and carbocyclyl are each independently substituted with 0 to 3 $R^{5d}$;

$R^{5d}$, at each occurrence, is independently halo, OH, alkoxy, oxo, or alkyl; or alternatively, two adjacent $R^{5d}$, together with the atoms to which they are attached, form a carbocyclyl moiety;

$R^{6a}$ is each independently hydrogen, $C_{1-6}$ alkyl, haloalkyl, alkoxy, amino, haloalkoxy, hydroxyalkyl, aminoalkyl, or $C_{3-5}$ cycloalkyl, wherein the cycloalkyl is substituted with 0, 1, 2, or 3 halo, cyano, nitro, amino, or OH;

$R^{6b}$ is each independently hydrogen, halo, cyano, nitro, amino, OH, $C_{1-6}$ alkyl, haloalkyl, alkoxy, haloalkoxy, hydroxyalkyl, aminoalkyl, or $C_{3-5}$ cycloalkyl, wherein the cycloalkyl is substituted with 0, 1, 2, or 3 halo, cyano, nitro, amino, or OH;

$R^{7a}$ and $R^{7b}$ are each independently halo, cyano, hydroxyl, amino, $C_{1-6}$ alkyl, haloalkyl, hydroxyalkyl, aminoalkyl, alkoxy, haloalkoxy, amido, carbamate, or sulfonamide;

$R^8$ is each independently halo, cyano, oxo, nitro, OH, NR$^a$R$^b$, $C_{1-6}$ alkyl, alkoxy, alkylamino, haloalkyl, haloalkoxy, haloaminoalkyl, hydroxyalkyl, aminoalkyl, alkylsulfonyl, sulfonamide, 3 to 6 membered carbocyclyl, 3 to 6 membered heterocyclyl, 6- to 10-membered aryl, or 5- to 10-membered heteroaryl; or alternatively, two $R^8$ at adjacent positions, together with the atoms to which they are attached, form a carbocyclyl or heterocyclyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^9$ at each occurrence is independently halo, cyano, nitro, OH, NR$^a$R$^b$, $C_{1-6}$ alkyl, alkoxy, alkylamino, haloalkyl, haloalkoxy, haloaminoalkyl, hydroxyalkyl, aminoalkyl, alkylsulfonyl, sulfonamide, 3 to 6 membered carbocyclyl, 3 to 6 membered heterocyclyl, 6- to 10-membered aryl, or 5- to 10-membered heteroaryl; or alternatively, two $R^9$ at adjacent positions, together with the atoms to which they are attached, form a carbocyclyl or heterocyclyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide $R^{10}$ is $C_{1-6}$ alkyl, 3- to 10-membered carbocyclyl, 3- to 10-membered heterocyclyl, 6- to 10-membered aryl, or 5- to 10-membered heteroaryl; wherein the alkyl, carbocyclyl, heterocyclyl are each independently substituted with 0, 1, 2, or 3 $R^{11}$;

R¹¹ is halo, cyano, nitro, OH, amino, $C_{1-6}$ alkyl, alkoxy, 3- to 10-membered carbocyclyl, 3- to 10-membered heterocyclyl, 6- to 10-membered aryl, or 5- to 10-membered heteroaryl; wherein the aryl, alkyl, cycloalkyl, heteroaryl, and cycloheteroalkyl are each independently substituted with 0, 1, 2, or 3 R¹³;

$R^a$ and $R^b$, at each occurrence, are independently hydrogen, $C_{1-10}$ alkyl, 3- to 10-membered carbocyclyl, or 3- to 10-membered heterocyclyl; wherein the alkyl, carbocyclyl, heterocyclyl are each independently substituted with 0, 1, 2, or 3 R¹⁴; and R¹², R¹³ and R¹⁴, at each occurrence, are independently halo, cyano, nitro, OH, amino, $C_{1-6}$ alkyl, alkoxy, aminoalkyl, haloalkyl, haloalkoxy, haloaminoalkyl, 3 to 6 membered carbocyclyl, or 3 to 6 membered heterocyclyl, 6- to 10-membered aryl, or 5- to 10-membered heteroaryl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide.

In one embodiment of Formula (I), Z is a covalent bond.

In one embodiment of Formula (I), A, L, E, G, and L form a ring moiety selected from pyrazole, pyrrole, thiazole, furan, thiophene, imidazole, oxazole, isoxazole, isothiazole, triazole, oxadiazole, thiadiazole, pyrrolidine, tetrahydrofuran, imidazolidine, pyrazolidine, oxazolidine, isoxazolidine, thiazolidine, isothiazolidine, and dioxolane; wherein the ring moiety is substituted with 0, 1, or 2 $R^{6a}$ or $R^{6b}$.

In one embodiment of Formula (I), A, L, E, G, and L form a ring moiety selected from the following structural formula:

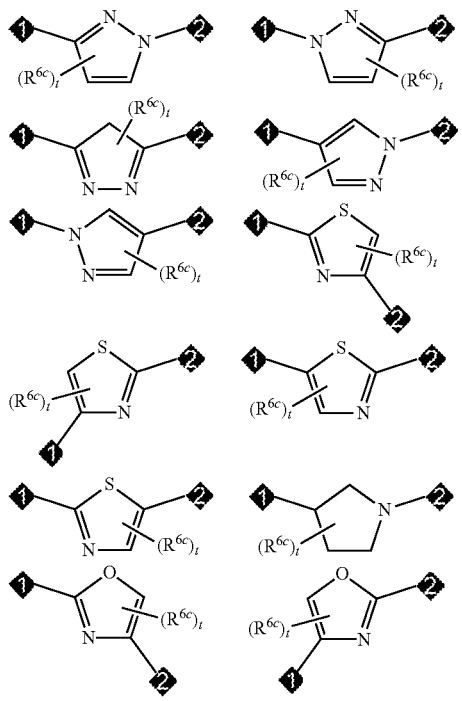

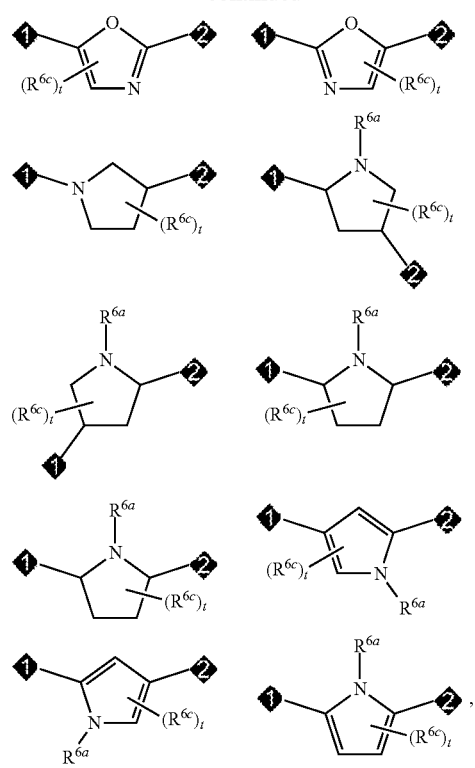

❶ Attachment point for X;
❷ Attachment point for a carbon atom;

wherein $R^{6a}$ is the same as defined in claim 1, (e.g., $R^{6a}$ is hydrogen); $R^{6c}$ is halo, cyano, nitro, amino, OH, $C_{1-6}$ alkyl, haloalkyl, alkoxy, haloalkoxy, hydroxyalkyl, aminoalkyl, or $C_{3-5}$ cycloalkyl, wherein the cycloalkyl is substituted with 0, 1, 2, or 3 halo, cyano, nitro, amino, or OH; and t is an integer of 0, 1, or 2.

In one embodiment of Formula (I), R³ is selected from the group consisting of hydrogen,

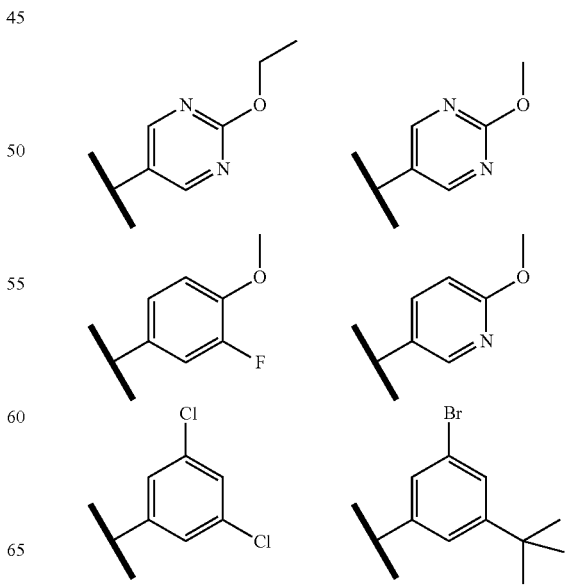

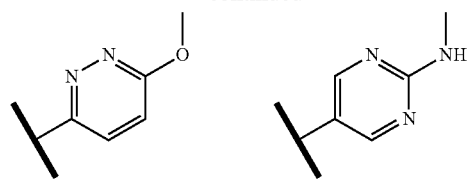
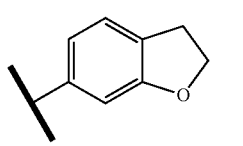 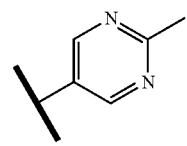
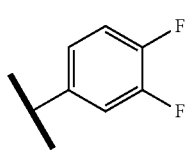 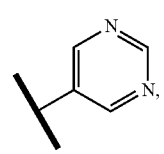
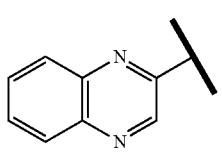 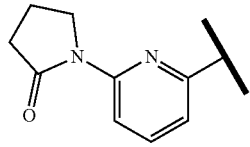
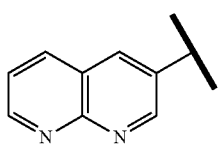 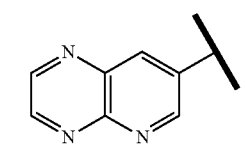
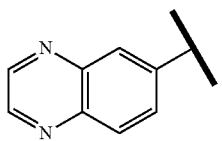 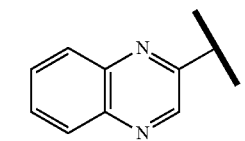
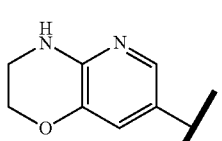 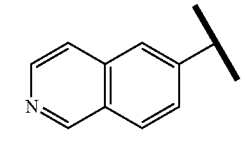
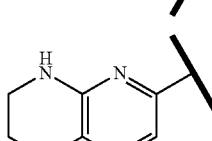 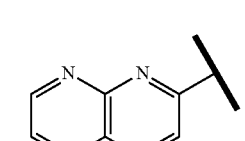
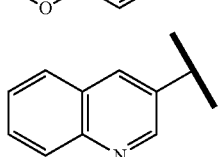 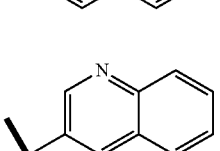
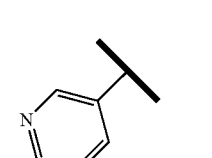 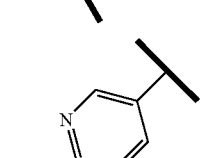
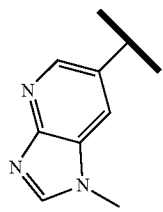 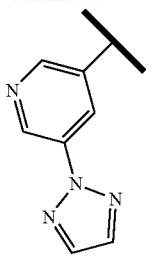 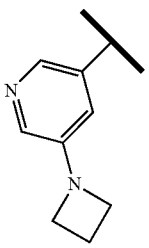
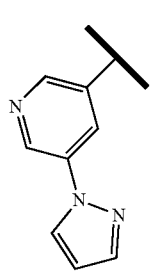 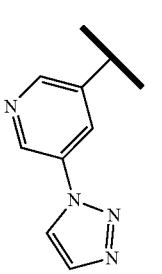 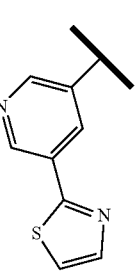
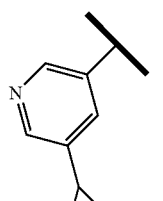 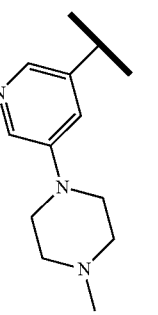 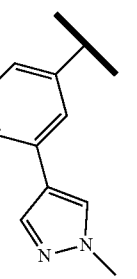
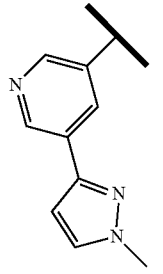 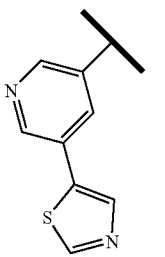 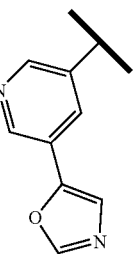
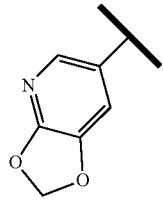 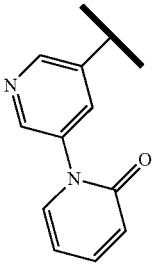 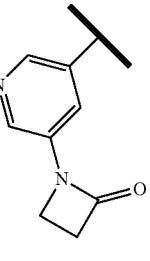
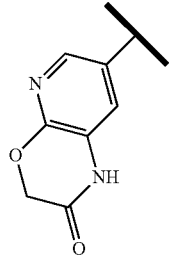 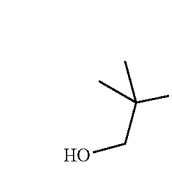

-continued

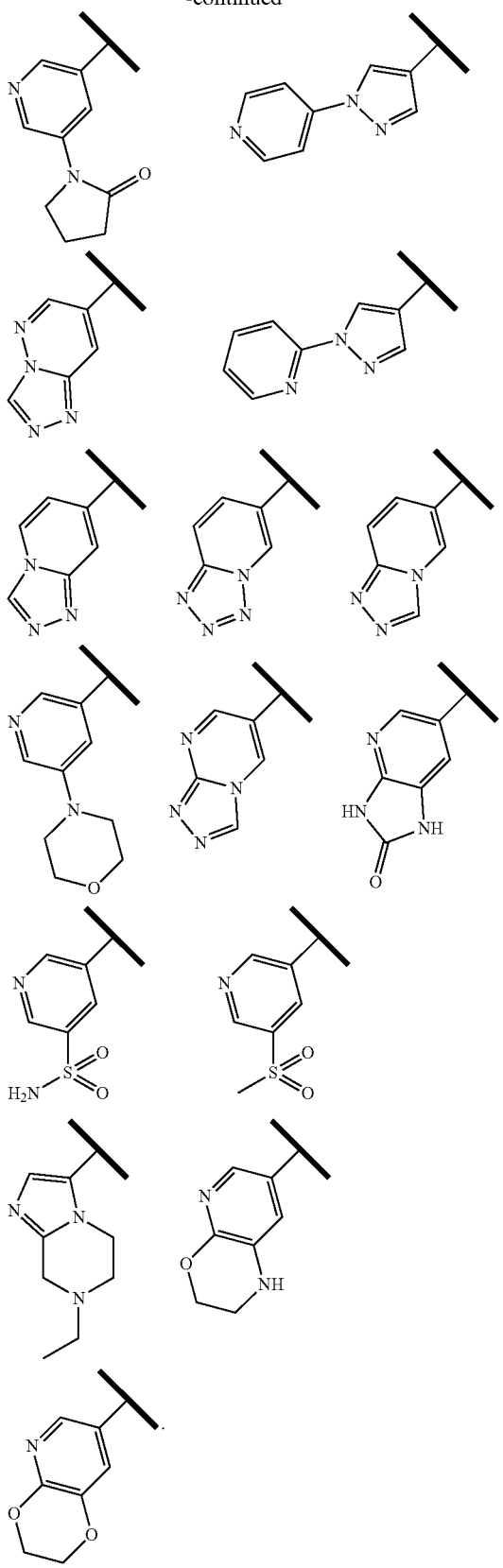

In one embodiment of Formula (I), $R^4$ is selected from hydrogen and the following structural moiety

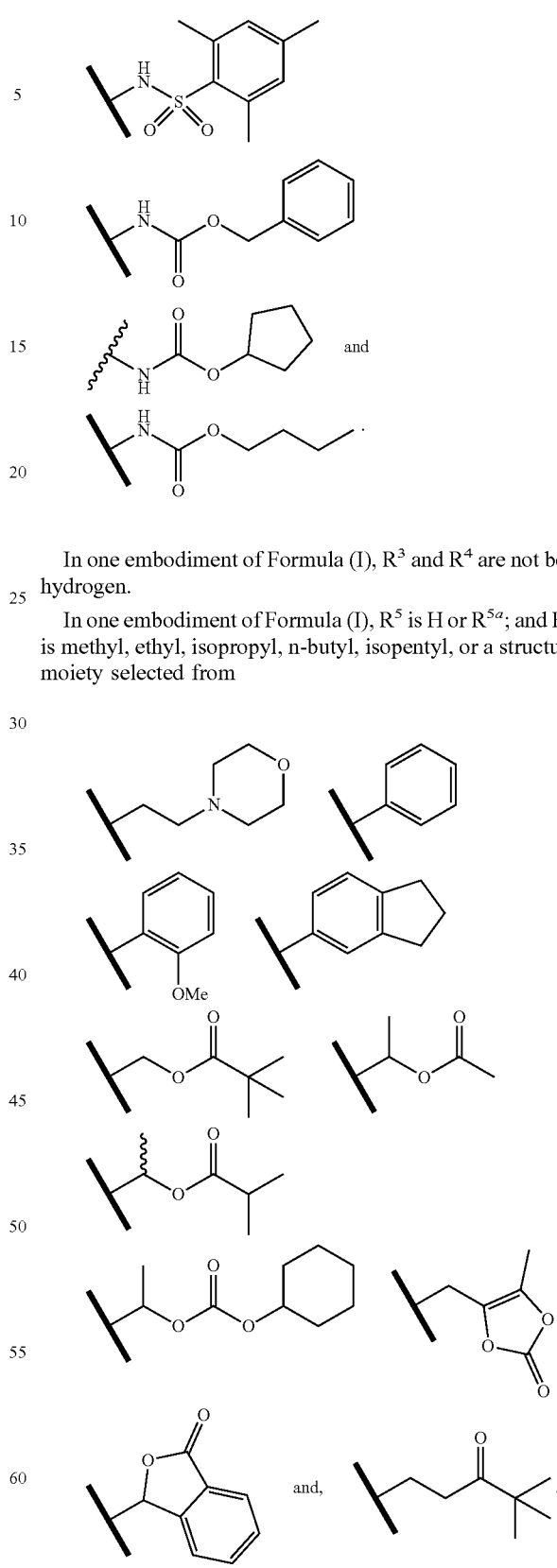

In one embodiment of Formula (I), $R^3$ and $R^4$ are not both hydrogen.

In one embodiment of Formula (I), $R^5$ is H or $R^{5a}$; and $R^{5a}$ is methyl, ethyl, isopropyl, n-butyl, isopentyl, or a structural moiety selected from In one embodiment of Formula (I), the compound is represented by structural Formula (IIa), (IIb), (IIc), or (IId):

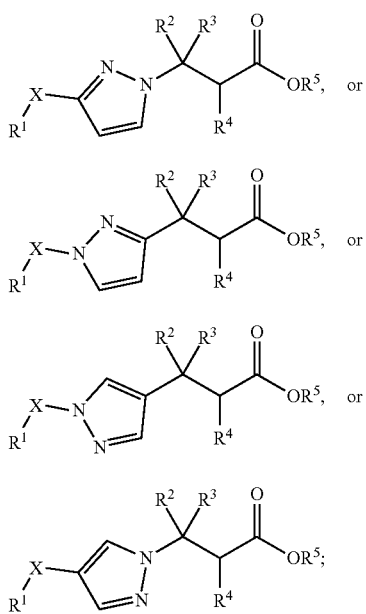
wherein X, $R^1$, $R^2$, $R^3$, and $R^4$ are the same as defined in Formula (I); and
$R^5$ is H, methyl, ethyl, isopropyl, n-butyl, isopentyl, or a structural moiety selected from
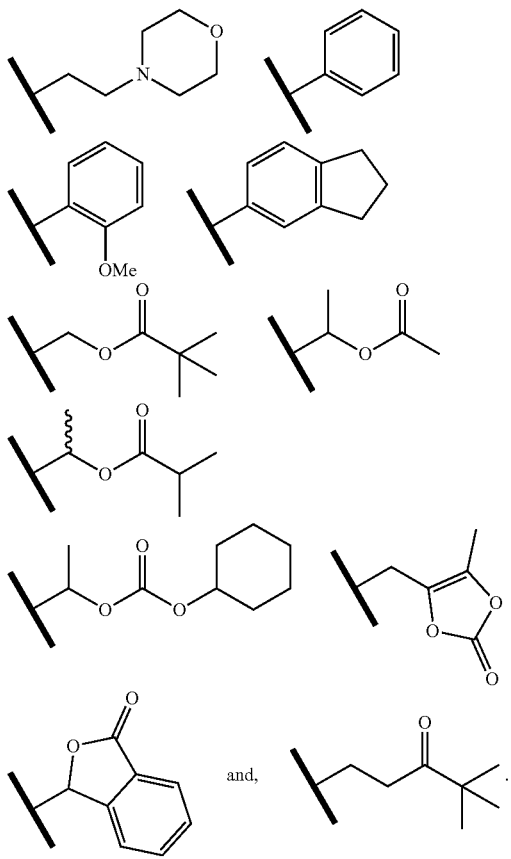
In one embodiment of Formula (IIa), (IIb), (IIc), or (IId), $R^1$ is selected from a structural formula selected from the group consisting of
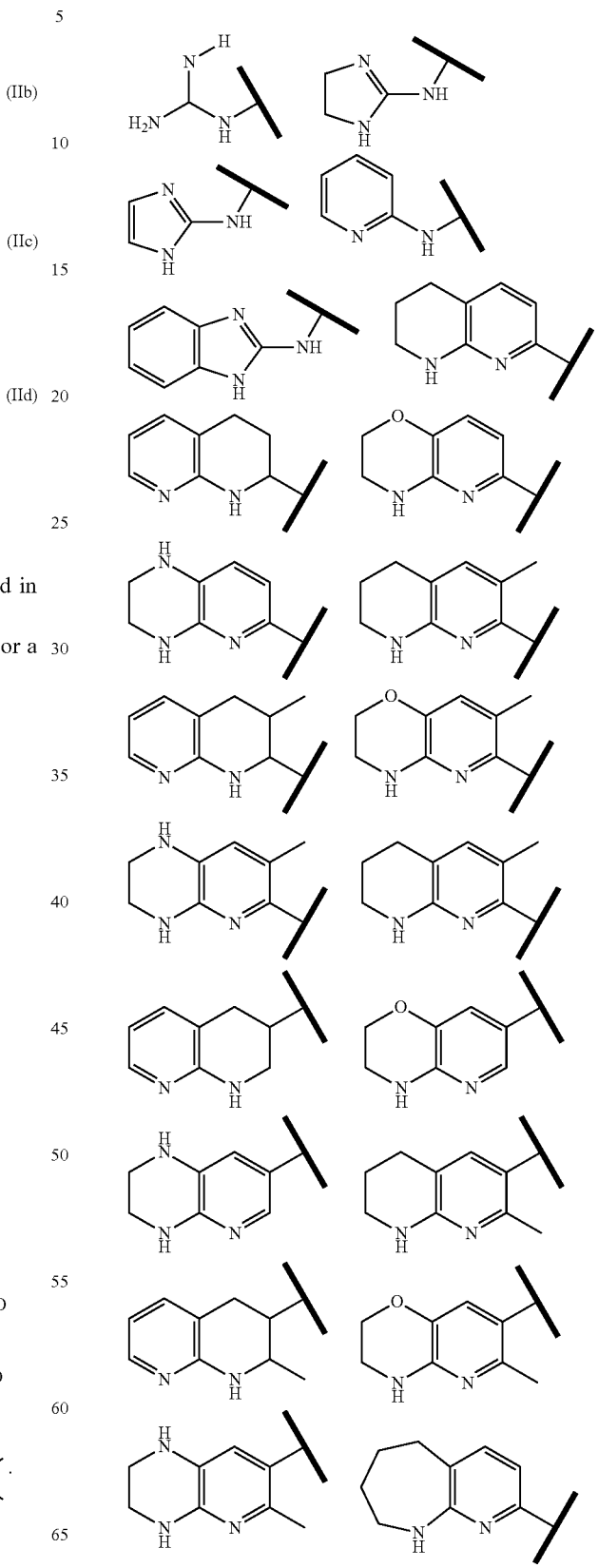

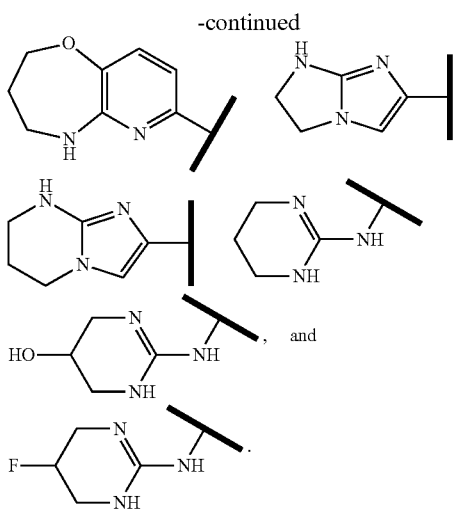

In one embodiment of Formula (IIa), (IIb), (IIe), or (IId), X is $C_{2-5}$ alkylene.

In one embodiment of Formula (IIa), (IIb), (IIe), or (IId), $R^2$ is hydrogen.

In one embodiment of Formula (IIa), (IIb), (IIe), or (IId), $R^3$ is $C_{1-6}$ alkyl, 3- to 6-membered carbocyclyl, carbocyclylalkyl, 6- to 10-membered aryl, arylalkyl, 3- to 10-membered heterocyclyl, heterocyclylalkyl, 5- to 10-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^8$; and $R^4$ is hydrogen.

In one embodiment of Formula (IIa), (IIb), (IIe), or (IId), $R^3$ is hydrogen; and $R^4$ is $C_{1-10}$ alkyl, 3- to 10-membered carbocyclyl, carbocyclylalkyl, 3- to 10-membered heterocyclyl, heterocyclylalkyl, 6- to 10-membered aryl, arylalkyl, 5- to 10-membered heteroaryl, heteroarylalkyl, $NR^aR^b$, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$; wherein the alkyl, carbocyclyl, heterocyclyl, aryl, and heteroaryl, by themselves or as part of another group, are each independently substituted with 0, 1, 2, or 3 $R^9$.

In one embodiment of Formula (IIa), (IIb), (IIe), or (IId), $R^5$ is hydrogen.

In one embodiment of Formula (I), the compound is represented by structural Formula (IIe) or (IIf):

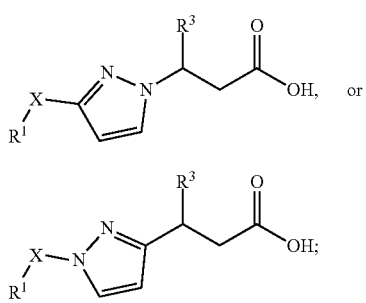

wherein
X is $C_3$ or $C_4$ alkylene;
$R^3$ is 3- to 6-membered carbocyclyl, 6- to 12-membered aryl, 3- to 12-membered heterocyclyl, 5- to 12-membered heteroaryl, wherein the carbocyclyl, heterocyclyl, aryl, and heteroaryl, are each independently substituted with 0, 1, 2, or 3 $R^8$;

$R^8$ is each independently halo, cyano, OH, amino, $C_{1-6}$ alkyl, alkoxy, aminoalkyl, haloalkyl, haloalkoxy, haloaminoalkyl, 5- or 6-membered heterocyclyl, or 5- or 6-membered heteroaryl; wherein the heterocyclyl and heteroaryl are each independently substituted with 0, 1, or 2 halo, cyano, OH, amino, $C_{1-6}$ alkyl, alkoxy, aminoalkyl, haloalkyl, haloalkoxy, haloaminoalkyl; and $R^1$ is selected from a structural formula selected from the group consisting of

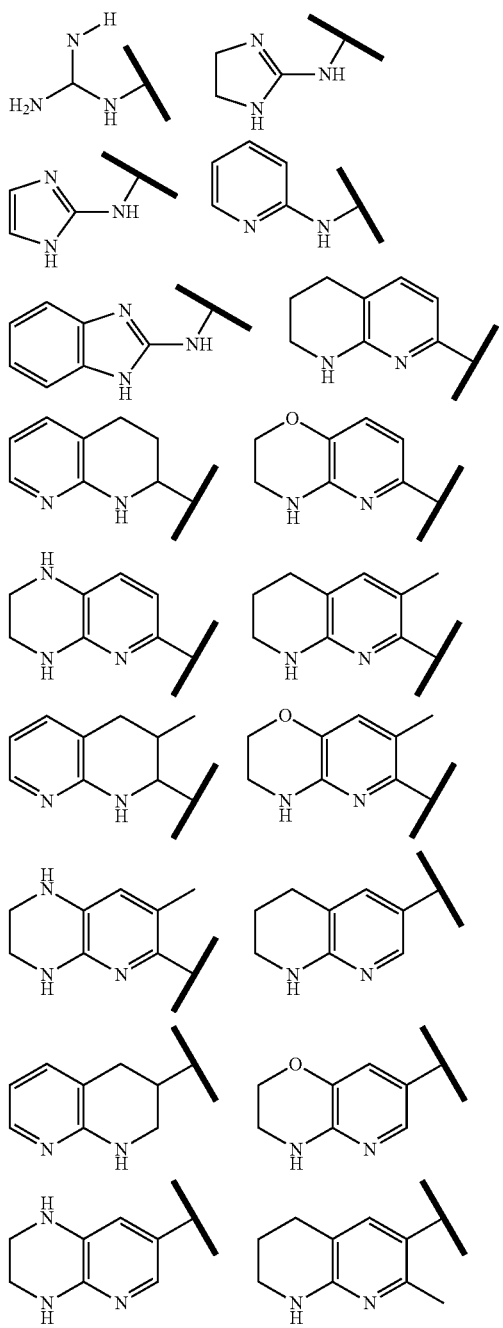

-continued

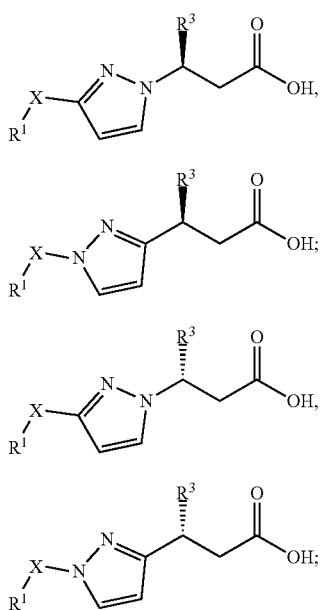

In one embodiment of Formula (IIe) or (IIf), the compound is represented by the following structural formulae:

(IIe1)

(IIf1)

(IIe2)

(IIf2)

In one embodiment of Formula (IIe) or (IIf), X is —CH$_2$CH$_2$CH$_2$— or —CH$_2$CH$_2$CH$_2$CH$_2$—;

In one embodiment of Formula (IIe) or (IIf), R$^3$ is phenyl, 5- to 6-membered monocyclic heterocyclyl, 10- to 12-membered bicyclic heterocyclyl, 5- or 6-membered monocyclic heteroaryl, or 10- to 12-membered bicyclic heteroaryl; wherein the heterocyclyl, phenyl, and heteroaryl, are each independently substituted with 0, 1, 2, or 3 R$^8$. In another embodiment, R$^3$ is phenyl, pyridinyl, pyrimidinyl, dihydrobenzofuranyl, dihydrodioxinopyridinyl, or quinolinyl, each of which is optionally substituted with 0, 1, 2, or 3 R$^8$.

In one embodiment of Formula (IIe) or (IIf), R is

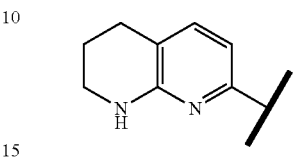

In one embodiment of Formula (I), the compound is represented by structural Formula (IIIa) or (IIIb):

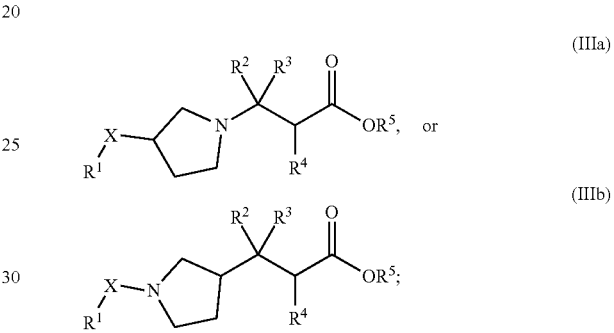

wherein X, R$^1$, R$^2$, R$^3$, and R$^4$ are the same as defined in Formula (I) above; and R$^5$ is H, methyl, ethyl, isopropyl, n-butyl, isopentyl, or a structural moiety selected from

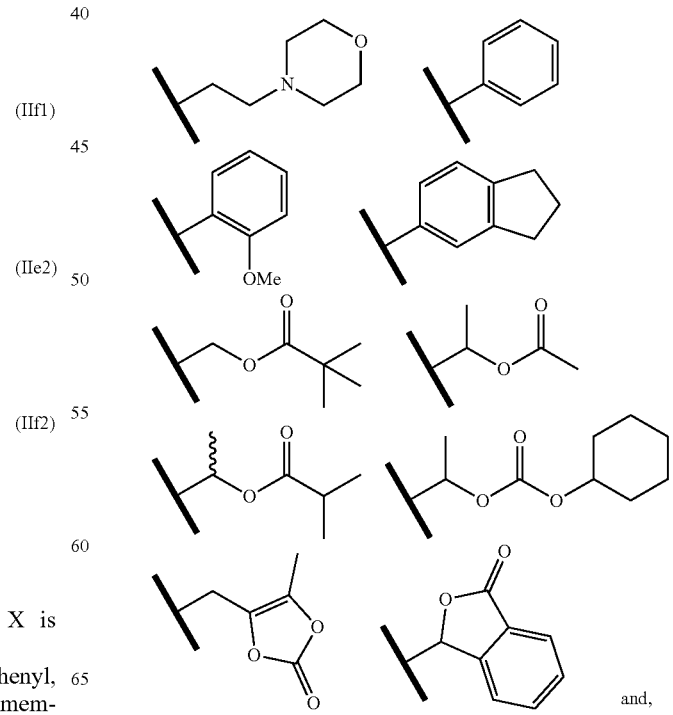

and,

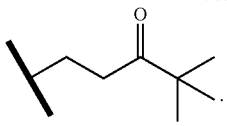

In one embodiment of Formula (IIIa), the compound is represented by structural Formula (IIIa-1) or (IIIa-2):

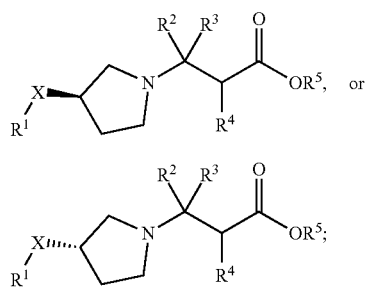

wherein X, $R^1$, $R^2$, $R^3$, $R^4$, and $R^5$ are the same as defined in Formula (IIIa) above.

In one embodiment of Formula (IIIb), the compound is represented by structural Formula (IIIb-1) or (IIIb-2):

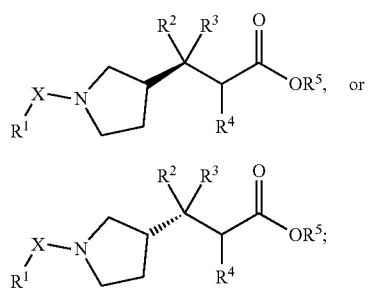

wherein X, $R^1$, $R^2$, $R^3$, $R^4$, and $R^5$ are the same as defined in Formula (IIIb) above.

In one embodiment of Formula (IIIa) or (IIIb), $R^1$ is selected from a structural formula selected from the group consisting of

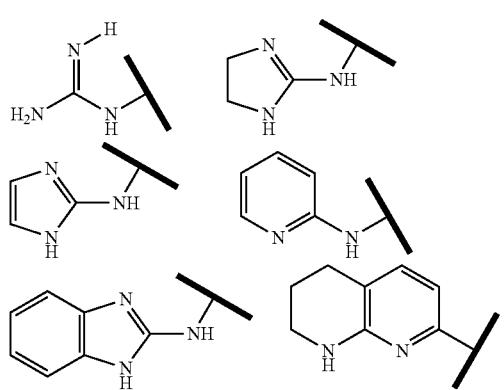

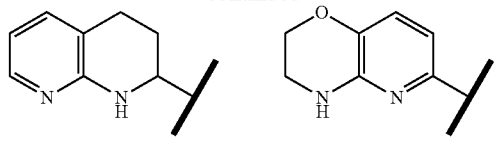
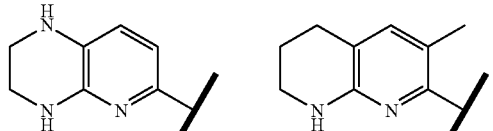
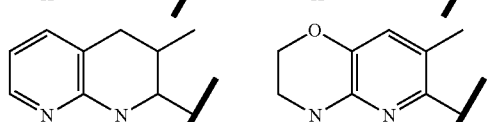
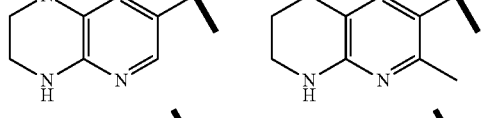
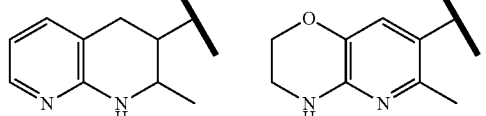
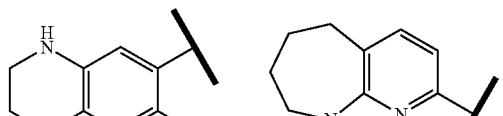

In one embodiment of Formula (IIIa) or (IIIb), X is $C_{2-5}$ alkylene.

In one embodiment of Formula (IIIa) or (IIIb), $R^2$ is hydrogen.

In one embodiment of Formula (IIIa) or (IIIb), $R^3$ is $C_{1-6}$ alkyl, 3- to 6-membered carbocyclyl, carbocyclylalkyl, 6- to 10-membered aryl, arylalkyl, 3- to 10-membered heterocyclyl, heterocyclylalkyl, 5- to 10-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^8$; and $R^4$ is hydrogen.

In one embodiment of Formula (IIIa) or (IIIb), $R^3$ is hydrogen; and $R^4$ is $C_{1-10}$ alkyl, 3- to 10-membered carbocyclyl, carbocyclylalkyl, 3- to 10-membered heterocyclyl, heterocyclylalkyl, 6- to 10-membered aryl, arylalkyl, 5- to 10-membered heteroaryl, heteroarylalkyl, $NR^aR^b$, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$; wherein the alkyl, carbocyclyl, heterocyclyl, aryl, and heteroaryl, by themselves or as part of another group, are each independently substituted with 0, 1, 2, or 3 $R^9$.

In one embodiment of Formula (IIIa) or (IIIb), $R^5$ is hydrogen.

In one embodiment of Formula (I), the compound is represented by structural Formula (IVa) or (IVb):

(IVa)

(IVb)

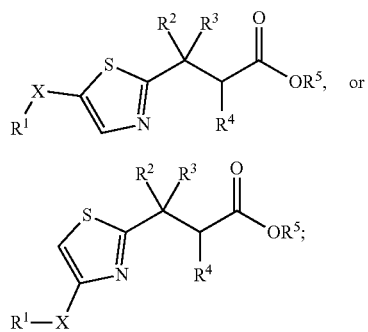

wherein X, $R^1$, $R^2$, $R^3$, and $R^4$ are the same as defined in Formula (I) above; and $R^5$ is H, methyl, ethyl, isopropyl, n-butyl, isopentyl, or a structural moiety selected from

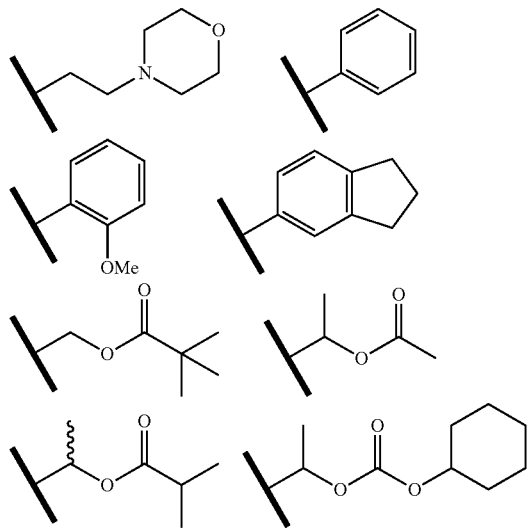

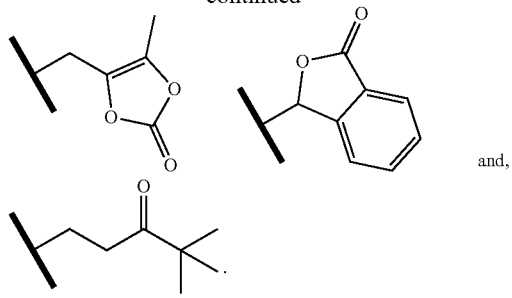

-continued

In one embodiment of Formula (IVa) or (IVb), $R^1$ is selected from a structural formula selected from the group consisting of

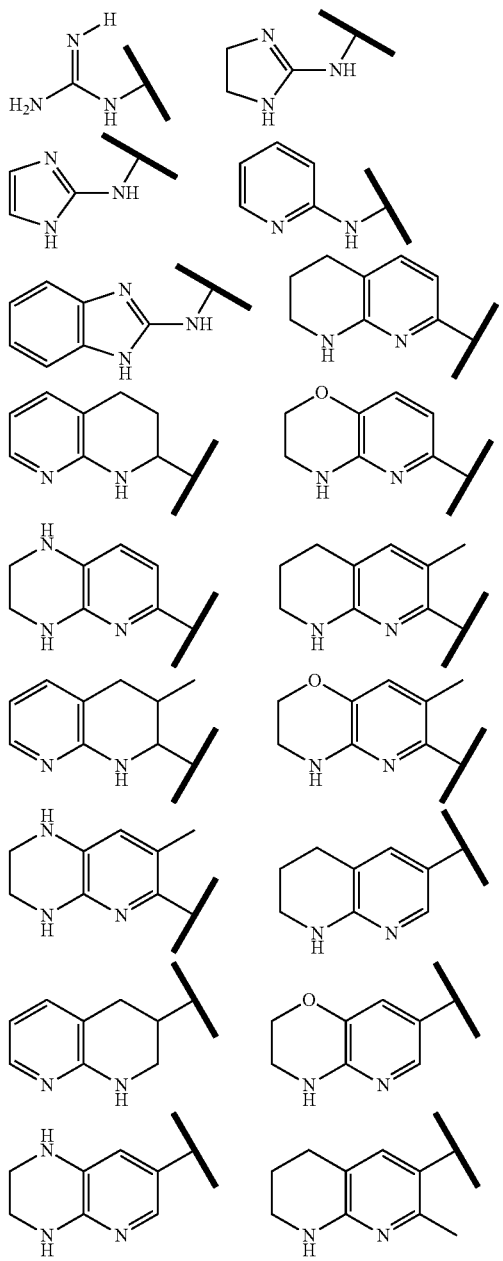

and,

-continued

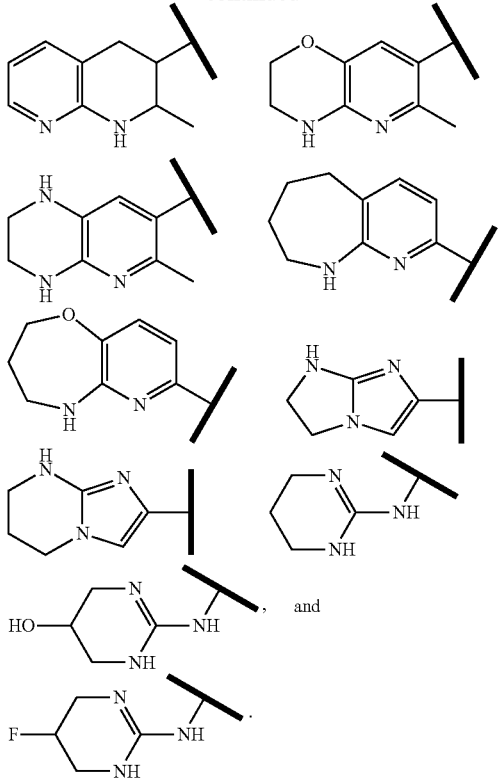

In one embodiment of Formula (IVa) or (IVb), X is $C_{2-5}$ alkylene.

In one embodiment of Formula (IVa) or (IVb), $R^2$ is hydrogen.

In one embodiment of Formula (IVa) or (IVb), $R^3$ is $C_{1-6}$ alkyl, 3- to 6-membered carbocyclyl, carbocyclylalkyl, 6- to 10-membered aryl, arylalkyl, 3- to 10-membered heterocyclyl, heterocyclylalkyl, 5- to 10-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^8$; and $R^4$ is hydrogen.

In one embodiment of Formula (IVa) or (IVb), $R^3$ is hydrogen; and $R^4$ is $C_{1-10}$ alkyl, 3- to 10-membered carbocyclyl, carbocyclylalkyl, 3- to 10-membered heterocyclyl, heterocyclylalkyl, 6- to 10-membered aryl, arylalkyl, 5- to 10-membered heteroaryl, heteroarylalkyl, $NR^aR^b$, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$; wherein the alkyl, carbocyclyl, heterocyclyl, aryl, and heteroaryl, by themselves or as part of another group, are each independently substituted with 0, 1, 2, or 3 $R^9$.

In one embodiment of Formula (IVa) or (IVb), $R^5$ is hydrogen.

In one embodiment of Formula (I), the compound is represented by structural Formula (Va) or (Vb):

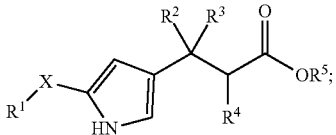
(Va)

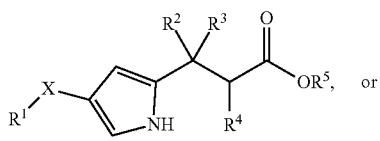
(Vb)

wherein X, $R^1$, $R^2$, $R^3$, and $R^4$ are the same as defined in Formula (I) above; and $R^5$ is H, methyl, ethyl, isopropyl, n-butyl, isopentyl, or a structural moiety selected from

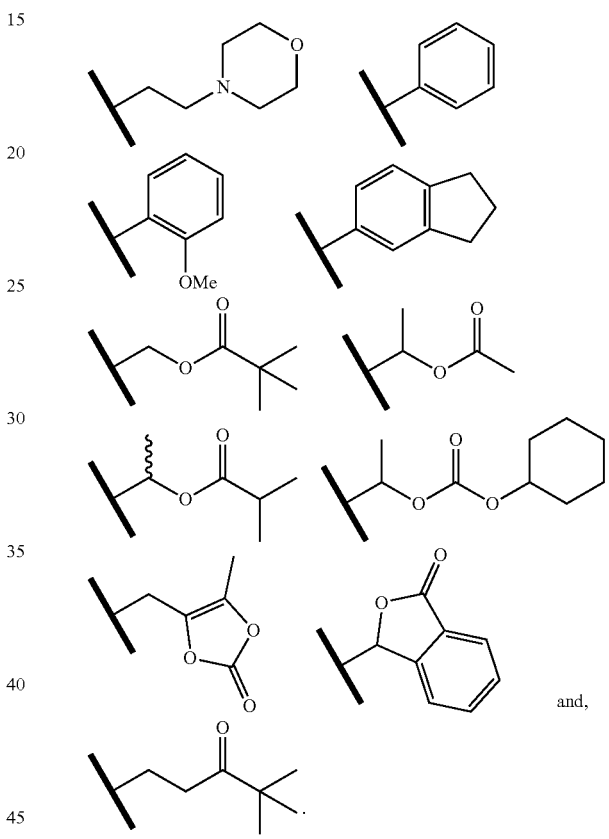

and,

In one embodiment of Formula (Va) or (Vb), $R^1$ is selected from a structural formula selected from the group consisting of

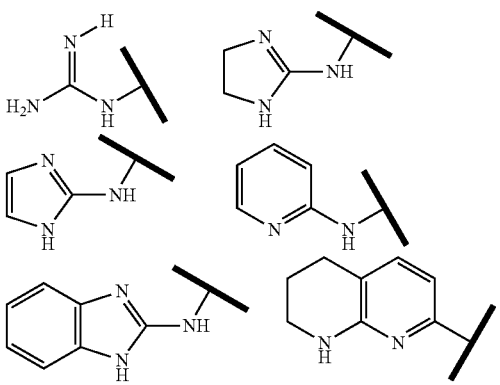

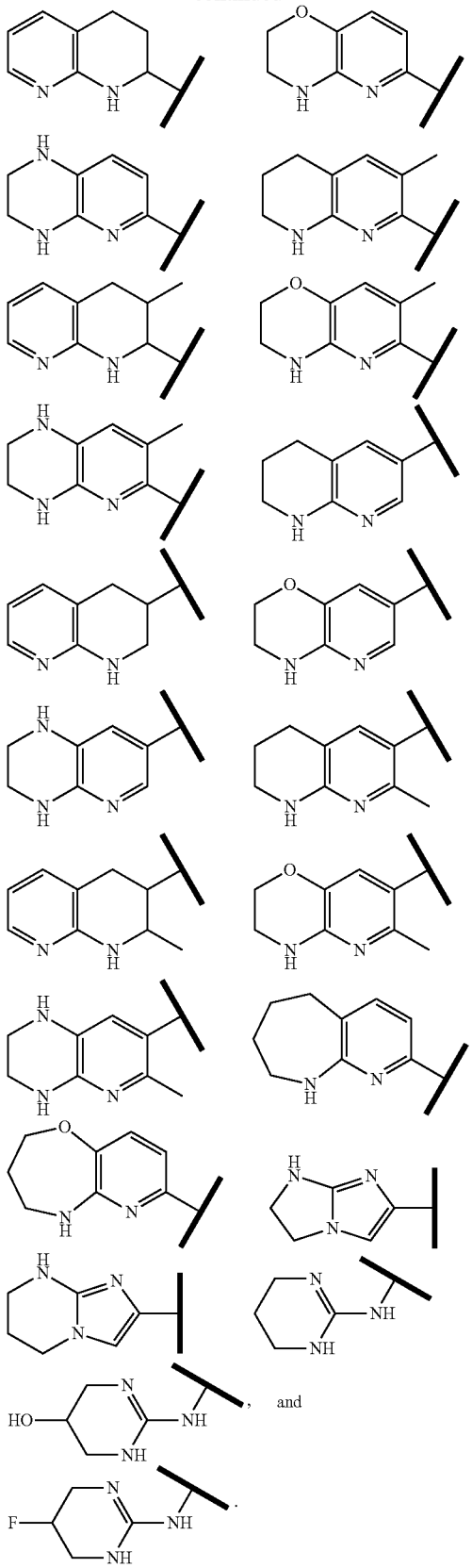

In one embodiment of Formula (Va) or (Vb), X is $C_{2-5}$ alkylene.

In one embodiment of Formula (Va) or (Vb), $R^2$ is hydrogen.

In one embodiment of Formula (Va) or (Vb), $R^3$ is $C_{1-6}$ alkyl, 3- to 6-membered carbocyclyl, carbocyclylalkyl, 6- to 10-membered aryl, arylalkyl, 3- to 10-membered heterocyclyl, heterocyclylalkyl, 5- to 10-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^8$; and $R^4$ is hydrogen.

In one embodiment of Formula (Va) or (Vb), $R^3$ is hydrogen; and $R^4$ is $C_{1-10}$ alkyl, 3- to 10-membered carbocyclyl, carbocyclylalkyl, 3- to 10-membered heterocyclyl, heterocyclylalkyl, 6- to 10-membered aryl, arylalkyl, 5- to 10-membered heteroaryl, heteroarylalkyl, $NR^aR^b$, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$; wherein the alkyl, carbocyclyl, heterocyclyl, aryl, and heteroaryl, by themselves or as part of another group, are each independently substituted with 0, 1, 2, or 3 $R^9$.

In one embodiment of Formula (Va) or (Vb), $R^5$ is hydrogen.

In one embodiment, the present invention provides, inter alia, compounds selected from any one of the Examples as described in the specification, or a stereoisomer, a tautomer, or a pharmaceutically acceptable salt or solvate thereof.

II. Pharmaceutical Compositions, Therapeutic Utilities, and Combinations

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of $\alpha_V$ integrins in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an integrin receptor antagonizing effect in a patient comprising administering a therapeutically effective amount of a compound of the present invention, or a stereoisomer, a tautomer, or a pharmaceutically acceptable salt or solvate thereof, to the patient. In one embodiment, the integrin receptor antagonizing effect is an antagonizing effect to any of $\alpha_V\beta6$, $\alpha_V\beta1$, $\alpha_V\beta3$, $\alpha_V\beta5$, and $\alpha_V\beta8$; or a combination of one or more of $\alpha_V\beta6$, $\alpha_V\beta1$, $\alpha_V\beta3$, $\alpha_V\beta5$, and $\alpha_V\beta8$. For example, the integrin receptor antagonizing effect can be an $\alpha_V\beta6$, $\alpha_V\beta1$, $\alpha_V\beta3$, $\alpha_V\beta5$, and $\alpha_V\beta8$ antagonizing effect.

In some embodiments, the disease, disorder, or condition is associated with fibrosis, including pulmonary, liver, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of $\alpha_V$ integrins that can be prevented, modulated, or treated according to the present invention include, but are not limited to, transplant injection, fibrotic disorders (e.g., idiopathic pulmonary fibrosis (IPF), interstitial lung disease, liver fibrosis, kidney fibrosis, skin fibrosis, systemic sclerosis), inflammatory disorders (e.g., acute hepatitis, chronic hepatitis, non-alcoholic steatohepatitis (NASH), psoriasis, irritable bowel syndrome (IBS), inflammatory bowel disease (IBD)), osteoporosis, as well as cell-proliferative disorders (e.g., cancer, myeloma, fibroma, hepatocarcinoma, leukemia, Kaposi's sarcoma, solid tumors).

The fibrotic disorders, inflammatory disorders, as well as cell-proliferative disorders that are suitable to be prevented or treated by the compounds of the present invention include, but are not limited to, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, non-alcoholic fatty liver disease (NAFLD), alcoholic or non-alcoholic steatohepatitis (NASH), acute hepatitis, chronic hepatitis, liver cirrhosis, primary sclerosing cholangitis, drug-induced hepatitis, biliary cirrhosis, portal hypertension, regenerative failure, liver hypofunction, hepatic blood flow disorder, nephropathy, pneumonia, psoriasis, irritable bowel syndrome (IBS), inflammatory bowel disease (IBD), abnormal pancreatic secretion, benign prostatic hyperplasia, neuropathic bladder disease, spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocarcinoma, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-$\alpha_V\beta6$ monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol.

3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, Sar$^9$, Met($O_2$)$^{11}$—Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as Idiopathic Pulmonary Fibrosis (IPF), liver and kidney fibrosis, Non-Alcoholic Fatty Liver Disease (NALFD), Non-Alcoholic Steato-Hepatitis (NASH), cardiac fibrosis, and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997), ACC inhibitors (for example, CP-640186 and NDI-010976), FGF21 agonist (for example, LY2405319), caspase inhibitors (for example, emricasan), NOX4 inhibitors (for example, GKT137831), MGAT2 inhibitor, and bile acid/fatty acid conjugates (for example aramchol). The $\alpha_V$ inhibitors of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day.

Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., FXR agonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the $\alpha_V$ integrins. Such compounds may be provided in a commercial kit, for example, for use in pharmaceutical research involving $\alpha_V$ integrins activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

III. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention, Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. As used herein, "a compound of the invention" or "compounds of the invention" means one or more compounds encompassed by any one of Formula (I), (IIa), (IIb), (IIe), (IId), (IIe), (IIf), (IIIa), (IIIb), (IVa) and (IVb), or a stereoisomer, a tautomer, or a pharmaceutically acceptable salt or solvate thereof.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or $sp^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$. "Benzyl" can also be represented by formula "Bn".

The term "lower alkoxy", "alkoxy" or "alkyloxy", "aryloxy" or "aralkoxy" refers to any of the above alkyl, aralkyl or aryl groups linked to an oxygen atom. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "lower alkylthio", "alkylthio", "thioalkoxy", "arylthio", or "aralkylthio" represents an alkyl, aryl, or aralkyl group as defined above with the indicated number of carbon atoms attached through a sulphur bridge; for example methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_1$, $C_2$, $C_3$, $C_4$, $C_5$, and $C_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by —$S(O)_2R'$, while sulfonamide may be represented by —$S(O)_2NR^cR^d$. R' is $C_1$ to $C_6$ alkyl; and $R^c$ and $R^d$ are the same as defined below for "amino".

The term "amino" is defined as —$NR^cR^d$, wherein $R^c$ and $R^d$ are independently hydrogen or $C_{1-6}$ alkyl; or alternatively, $R^c$ and $R^d$, taken together with the atoms to which they are attached, form a 3- to 8-membered carbocyclic or heterocyclic ring which is optionally substituted with one or more group selected from halo, cyano, hydroxyl, amino, oxo, $C_{1-6}$ alkyl, alkoxy, and alkylamino. Examples of alkylamino group include, without limitation, —$NH_2$, methylamino, ethylamino, propylamino, isopropylamino and the like.

The term "alkylamino" refers to an alkyl group on which one of the hydrogen atoms is replaced by an amino group. For example, alkylamino may be represented by $N(R^cR^d)$-alkylene-. "$C_1$ to $C_6$" or "$C_{1-6}$" alkylamino" (or alkylamino), is intended to include $C_1$, $C_2$, $C_3$, $C_4$, $C_5$, and $C_6$ alkylamino groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "$C_1$ to $C_6$ haloalkyl" or "$C_{1-6}$ haloalkyl" (or haloalkyl), is intended to include $C_1$, $C_2$, $C_3$, $C_4$, $C_5$, and $C_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or Cl, preferably F, such as polyfluoroalkyl, for example, $CF_3CH_2$, $CF_3$ or $CF_3CF_2CH_2$.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or Cl, preferably F, such as polyfluoroalkoxy, for example, $CF_3CH_2O$, $CF_3O$ or $CF_3CF_2CH_2O$.

"Hydroxylalkyl" is intended to include both branched and straight-chain saturated aliphatic hydrocarbon groups having the specified number of carbon atoms, substituted with 1 or more hydroxyl (OH). "$C_1$ to $C_6$ hydroxylalkyl" (or hydroxylalkyl), is intended to include $C_1$, $C_2$, $C_3$, $C_4$, $C_5$, and $C_6$ hydroxylalkyl groups.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems.

"$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic" is intended to mean any stable 3-, 4-, 5-, 6-, 7-, or 8-membered monocyclic or 5-, 6-, 7-, 8-, 9-, 10-, 11-, 12-, or 13-membered polycyclic (including bicyclic or tricyclic) hydrocarbon ring, any of which may be saturated or partially unsaturated. That is, the term "carbocycle", "carbocyclyl", or "carbocyclic" includes, without limitation, cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, indanyl, adamantyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, indanyl, and tetrahydronaphthyl. A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

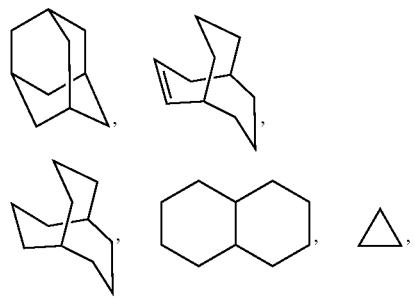

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated or partially unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from the group consisting of N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of hetercyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of heteroaryl include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings, for example,

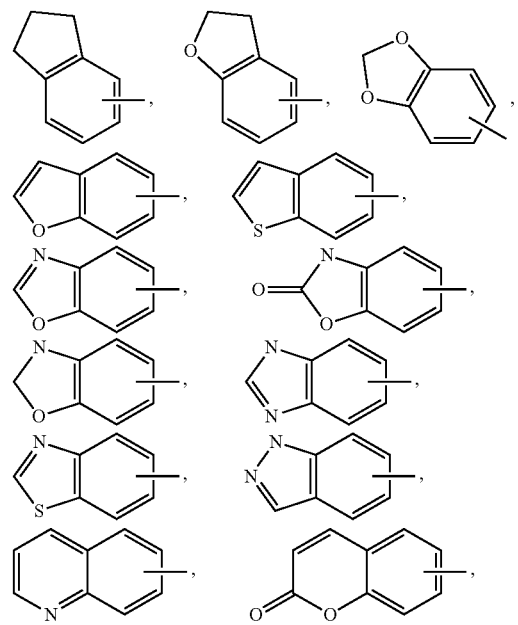

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

In accordance with a convention used in the art, a bond pointing to a bold line, such as ⋎ as used in structural formulas herein, depicts the bond that is the point of attachment of the moiety or substituent to the core or backbone structure.

In accordance with a convention used in the art, a wavy bond in a structural formula, such as

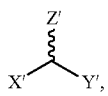

is used to depict a stereogenic center of the carbon atom to which X', Y', and Z' are attached and is intended to represent both enantiomers in a single figure. That is, a structural formula with such as wavy bond denotes each of the enantiomers individually, such as

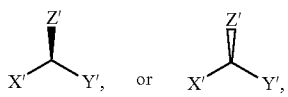

as well as a racemic mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

When a dotted ring is used within a ring structure, this indicates that the ring structure may be saturated, partially saturated or unsaturated.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule For example, one skilled in the art would readily understand that a 1,2,3-triazole exists in two tautomeric forms as defined above:

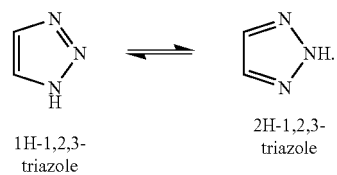 [SMILES: c1c[nH]nn1 ; c1cn[nH]n1]

1H-1,2,3-triazole    2H-1,2,3-triazole

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention.

Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, PA (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines.

In addition, the compounds of the present invention may have prodrug forms. Any compound that will be converted in vivo to provide the bioactive agent is a prodrug within the scope and spirit of the invention. The term "prodrug" as used herein encompasses both the prodrugs based on the carboxylic acid residue, i.e., "prodrug esters", and the prodrugs based on the arginine mimetics moiety, i.e., "prodrugs of arginine mimetics". Such prodrugs are preferably administered orally since hydrolysis in many instances occurs principally under the influence of the digestive enzymes. Parenteral administration may be used where the ester per se is active, or in those instances where hydrolysis occurs in the blood.

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Examples of such prodrug esters include:

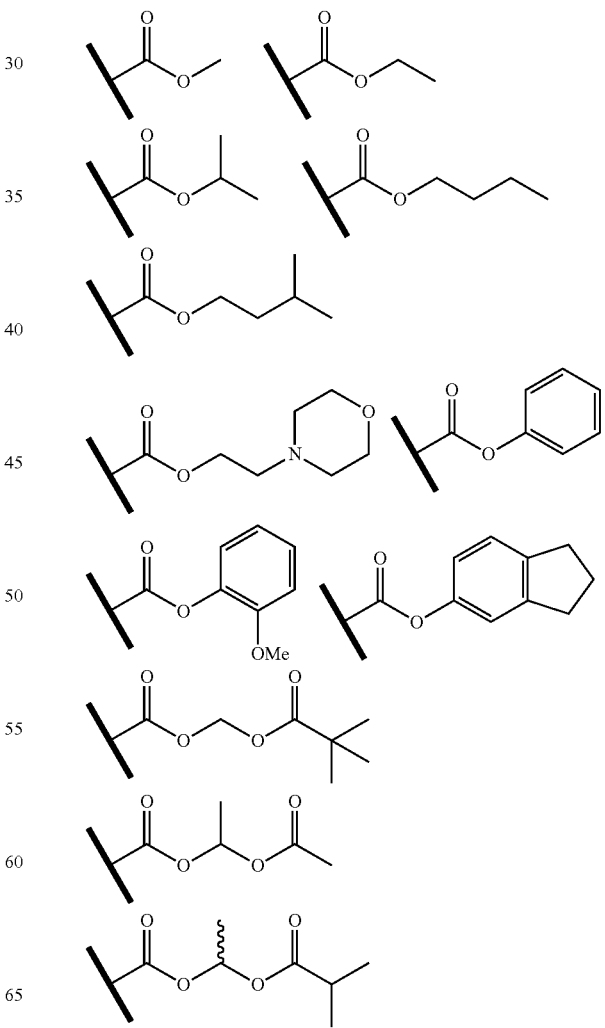

The compounds of the present invention contain an arginine mimetics moiety which can form physiologically hydrolyzable esters that serve as prodrugs, i.e., "prodrugs of arginine mimetics", by being hydrolyzed in the body to yield the compounds of the present invention per se. Representative examples of prodrugs of arginine mimetics include:

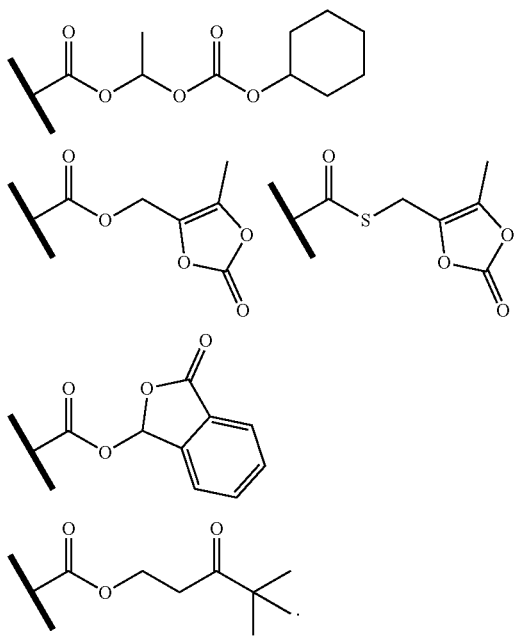

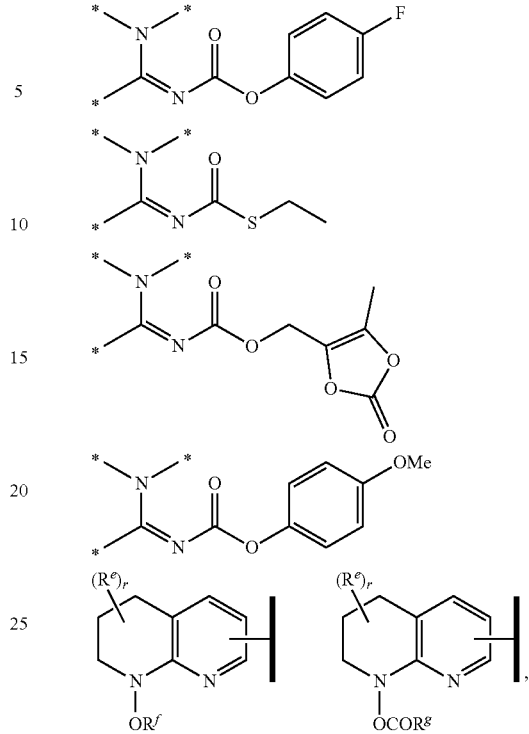

wherein, one of the asterisks in each of the arginine mimetics moiety is an attachment point to the parent molecule and the other two asterisks are hydrogen; $R^f$=H, Me, Et, COOEt; $R^g$=CH$_3$, CH$_2$CH$_3$, CH$_2$CCl$_3$, phenyl, 4-fluorophenyl, 4-methoxyphenyl, benzyl,

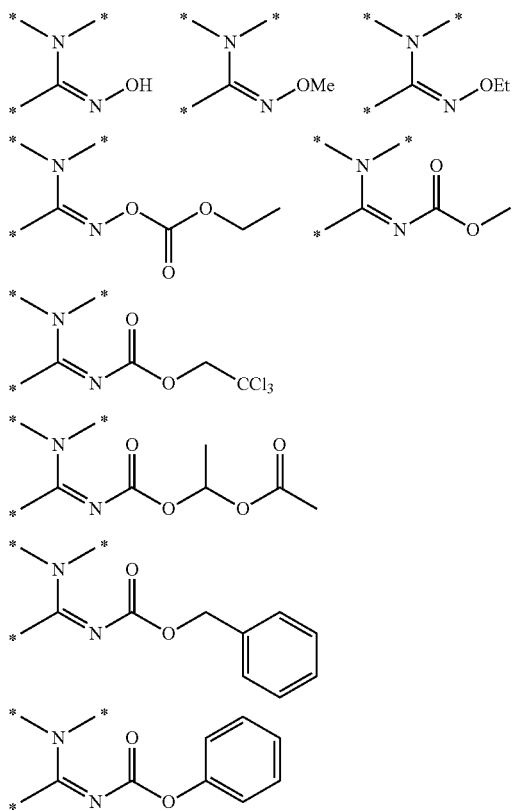

$R^e$ is OH, $C_{1-4}$ alkyl, halo, haloalkyl, or $C_{1-4}$ cycloalkyl; and r is an integer of 0, 1, 2, or 3.

Furthermore, various forms of prodrugs are well known in the art. For examples of such prodrug derivatives, see:

Bundgaard, H., ed., *Design of Prodrugs*, Elsevier (1985), and Widder, K. et al., eds., *Methods in Enzymology*, 112:309-396, Academic Press (1985);

Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

Bundgaard, H., *Adv. Drug Deliv. Rev.*, 8:1-38 (1992);

Bundgaard, H. et al., *J. Pharm. Sci.*, 77:285 (1988); and

Kakeya, N. et al., *Chem. Pharm. Bull.*, 32:692 (1984).

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, CA (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
$Boc_2O$ di-tert-butyl dicarbonate
ACN acetonitrile
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz carbobenzyloxy
DCM or $CH_2Cl_2$ dichloromethane
$CH_3CN$ or ACN acetonitrile
CDCE deutero-chloroform
$CHCl_3$ chloroform
mCPBA or m-CPBA meta-chloroperbenzoic acid
$Cs_2CO_3$ cesium carbonate
$Cu(OAC)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DEA diethylamine
DMP or Dess-Martin 1,1,1-tris(acetyloxy)-1,1-dihydro-1,2-beniziodoxol-3-(1H)-one Periodinane
DIC or DIPCDI diisopropylcarbodiimide
DIEA, DIPEA or diisopropylethylamine Hunig's Base
DMAP 4-dimethylaminopyridine
DME 1,2-dimethoxy ethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium (I) trifluoromethane sulfonate
$Et_3N$ or TEA triethylamine
EtOAc ethyl acetate
$Et_2O$ diethyl ether
EtOH ethanol
GMF glass microfiber filter
Grubbs II (1,3-bis(2,4,6-trimethylphenyl)-2-imidazohdi-nylidene)dichloro (phenylmethylene)(triycyclohex-ylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexanes
HOBt or HOBT 1-hydroxybenzotriazole H₂O₂ hydrogen peroxide
IBX 2-iodoxybenzoic acid
H₂SO₄ sulfuric acid
Jones reagent CrO₃ in aqueous H₂SO₄, 2 M
K₂CO₃ potassium carbonate
K₂HPO₄ potassium phosphate dibasic
KOAc potassium acetate
K₃PO₄ potassium phosphate
LAH lithium aluminum hydride
LG leaving group
LiOH lithium hydroxide
MeOH methanol
MgSO₄ magnesium sulfate
MsCl methanesulfonyl chloride
MsOH or MSA methylsulfonic acid
NaCl sodium chloride
NaH sodium hydride
NaHCO₃ sodium bicarbonate
Na₂CO₃ sodium carbonate
NaOH sodium hydroxide
Na₂SO₃ sodium sulfite
Na₂SO₄ sodium sulfate
NBS N-bromosuccinimide
NCS N-chlorosuccinimide
NH₃ ammonia
NH₄Cl ammonium chloride
NH₄OH ammonium hydroxide
NH₄COOH ammonium formate
NMM N-methylmorpholine
OTf triflate or trifluoromethanesulfonate
Pd₂(dba)₃ tris(dibenzylideneacetone)dipalladium(0)
Pd(OAc)₂ palladium(II) acetate
Pd/C palladium on carbon
Pd(dppf)Cl₂ [1,1'-bis(diphenylphosphino)-ferrocene]dichloropalladium(II)
Ph₃PCl₂ triphenylphosphine dichloride
PG protecting group
POCl₃ phosphorus oxychloride
PPTS pyridinium p-toluenesulfonate
i-PrOH or IPA isopropanol
PS Polystyrene
PtO₂ platinum oxide
rt room temperature
SEM-Cl 2-(trimethysilyl)ethoxymethyl chloride
SiO₂ silica oxide
SnCl₂ tin(II) chloride
TBAI tetra-n-butylammonium iodide
TFA trifluoroacetic acid
THF tetrahydrofuran
TMSCHN₂ trimethylsilyldiazomethane
T3P propane phosphonic acid anhydride
TRIS tris (hydroxymethyl) aminomethane
pTsOH p-toluenesulfonic acid
TsCl p-tolunesulfonyl chloride IV. Methods of Preparation The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds described in this invention. A particularly useful compendium of synthetic methods which may be applicable to the preparation of compounds of the present invention may be found in Larock, R. C., *Comprehensive Organic Transformations*, 2$^{nd}$ edition VCH, New York (1999).

The compounds of the present invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used. A particularly useful compendium of synthetic methods which may be applicable to the preparation of compounds of the present invention may be found in Larock, R. C., *Comprehensive Organic Transformations*, 2$^{nd}$ edition VCH, New York (1999).

Generic Schemes

Compounds of the present invention, represented by Formula (T), can be prepared according to the general routes shown in Schemes 1 to 7. Compounds where L=N and M=C can be obtained as shown in Scheme 1 starting from bromide 1. An aza-Michael addition of 1 to unsaturated ester 2 can yield ester 3. Compound 3 can then be coupled with an appropriate alkene such as 4 using standard Heck coupling conditions (Felpin, F.-X.; Nassar-Hardy, L.; Le Callonnec, F.; Fouquet, E. *Tetrahedron* 2011, <57, 2815-2831) to provide ester 5. Reduction of the naphthyridine and the alkene followed by ester deprotection can yield compounds of Formula (T). It will be apparent to those skilled in the art that single stereoisomers can obtained via chiral HPLC or SFC preparative purifications of suitable intermediates from this sequence (such as 3 or 5) or the final acids of Formula (I').

Scheme 1: General Scheme for preparation of Formula (I') where L = N, M = C

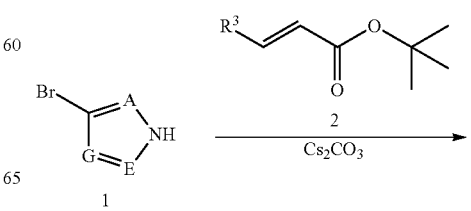

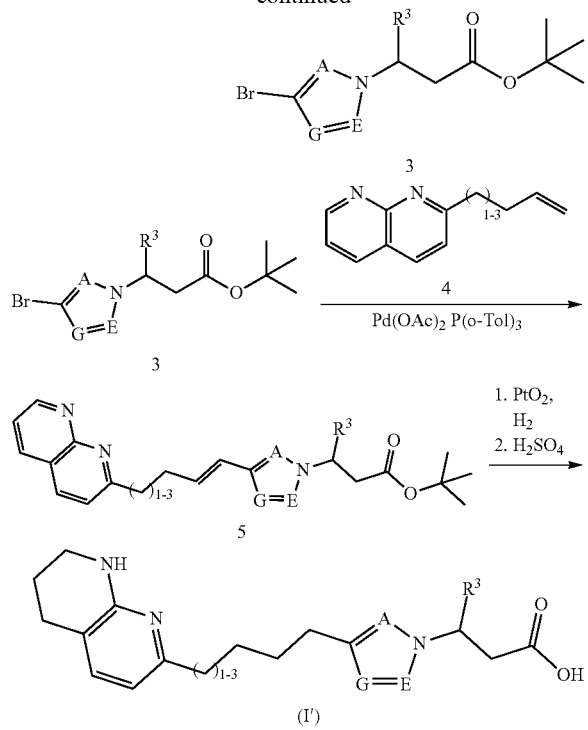

Scheme 2 describes synthesis of compounds of Formula (I') where M=C, L=N, and X=(CH$_2$)$_3$. Thus, as shown in Method A, bromide 3 can be coupled with a suitable alkene, exemplified by 4-hydroxy-1-butene in Scheme 2, via a Heck coupling protocol in the presence of palladium acetate and a phosphine ligand. Subsequent oxidation of the alcohol and reduction of the double bond can yield ketone 6. Ketone 6 can be alternatively obtained via a Sonogashira coupling of bromide 3 with a suitable alkyne, exemplified by 4-hydroxy-1-butyne in Scheme 2, followed by reduction of the triple bond and oxidation of the alcohol to the ketone. Condensation of 6 with 2-amino-3-formylpyridine under Friedländer conditions (Jose Marco-Contelles; Elena Perez-Mayoral; Abdelouahid Samadi; Mana do Carmo Carreiras; Elena Soriano (2009). "Recent Advances in the Friedlander Reaction". *Chemical Reviews*. 109 (6): 2652-71) can yield the corresponding naphthyridine, which upon partial reduction and deprotection of the ester can provide compounds of Formula (I'). An alternative method of obtaining compounds of Formula (I') is shown in Scheme 2, Method B, where, in contrast to Method A, the Sonogashira coupling and naphthyridine ring formation precede the aza-Michael reaction. Thus, N-Boc protected bromide 7 can be transformed into 8 using the protocol described for Method A. Subsequently, Friedländer naphthyridine ring formation as described earlier, followed by partial reduction of the naphthyridine ring and removal of the Boc group can yield 9. Aza-Michael under basic conditions and ester hydrolysis can afford compounds of Formula (I').

Scheme 2. General method for the preparation of Formula (I') where X = (CH$_2$)$_3$, L = N, M = C Method A

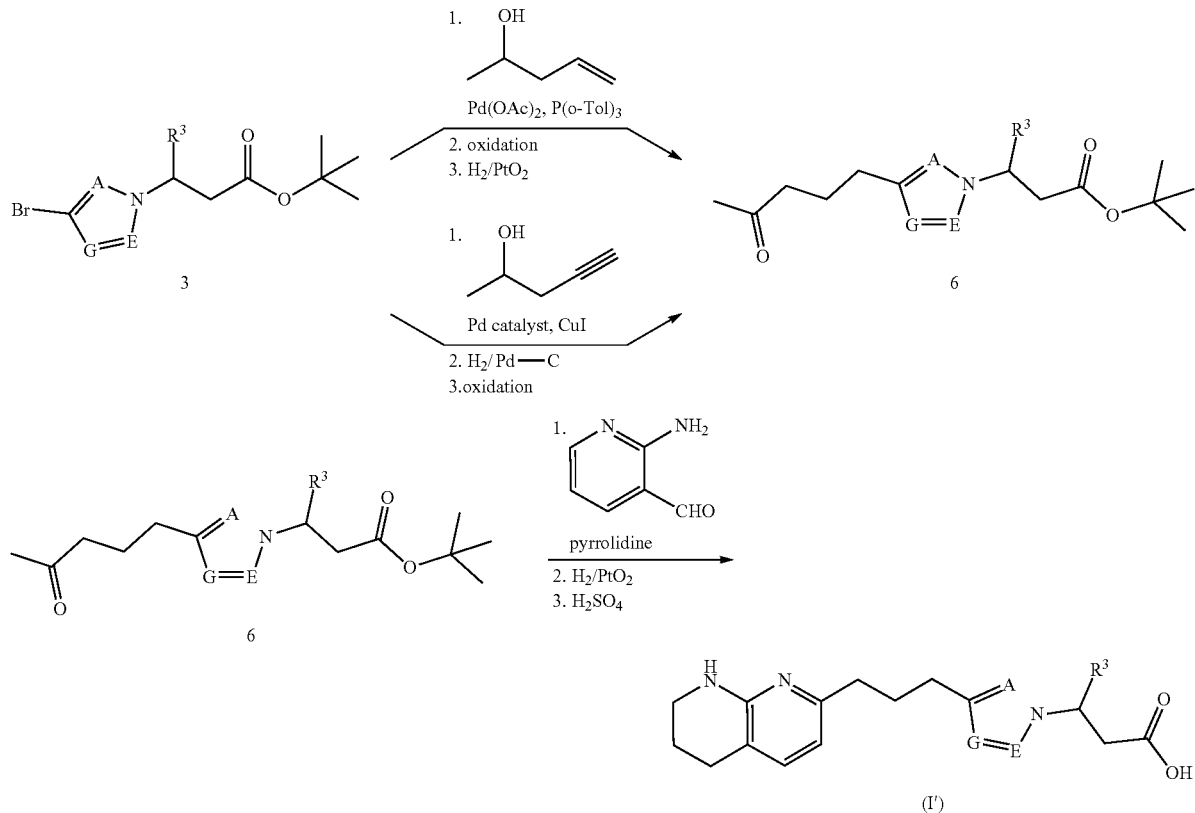

-continued

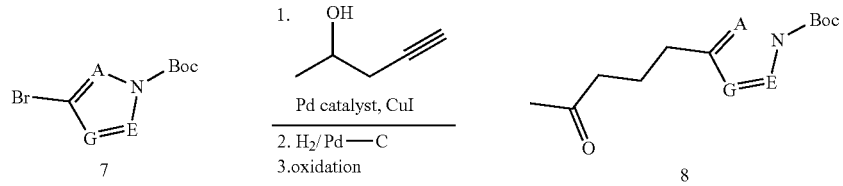

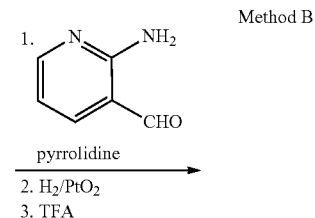

Method B

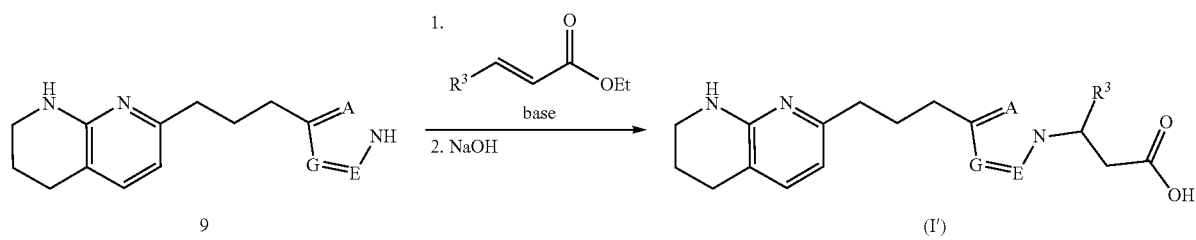

Compounds of Formula (I') where M=N, L=C, and R⁴≠H can be synthesized as shown in Scheme 3, exemplified with a compound where $R^4$=NHCbz. Condensation of aldehyde 10 with a suitable $R^4$-substituted Horner-Emmons reagent (11) followed by alkene reduction and reprotection of the amine can yield intermediate 12. N-alkylation of 12 with chloride 13 followed by cleavage of the ketal can afford ketone 14. Subsequent naphthyridine ring formation via Friedländer condensation followed by partial reduction can afford 15. A 3-step sequence that removes the Boc group, re-functionalizes the primary amine by reacting with CbzCl, and hydrolyzes the resulting ester can yield compounds of Formula (I'). Compounds of Formula (I') where X=(CH₂)₂ can be obtained via a Mitsunobu coupling with alcohol 16, followed by deprotection of the Boc groups, acylation of the free amine with CBzCl, and final ester hydrolysis. Using either of the methods shown in Scheme 3, compounds of Formula (I') where X=(CH₂)₃₋₆ can also be accessed.

Scheme 3: General Scheme for preparation of Formula (I') where L = C, M = N

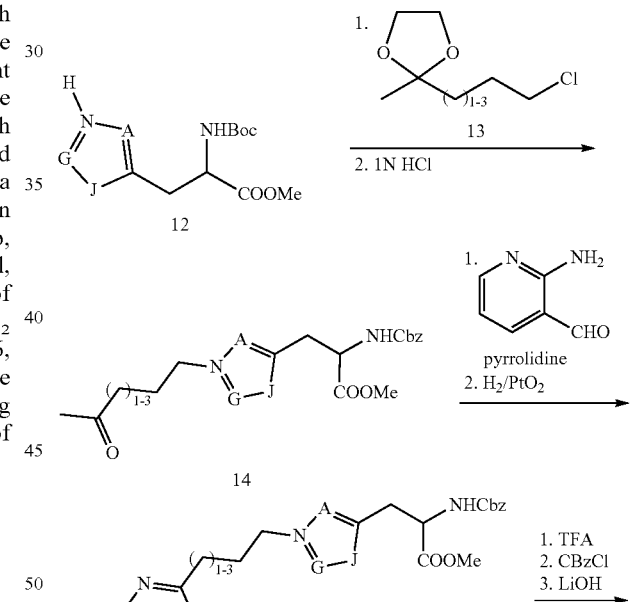

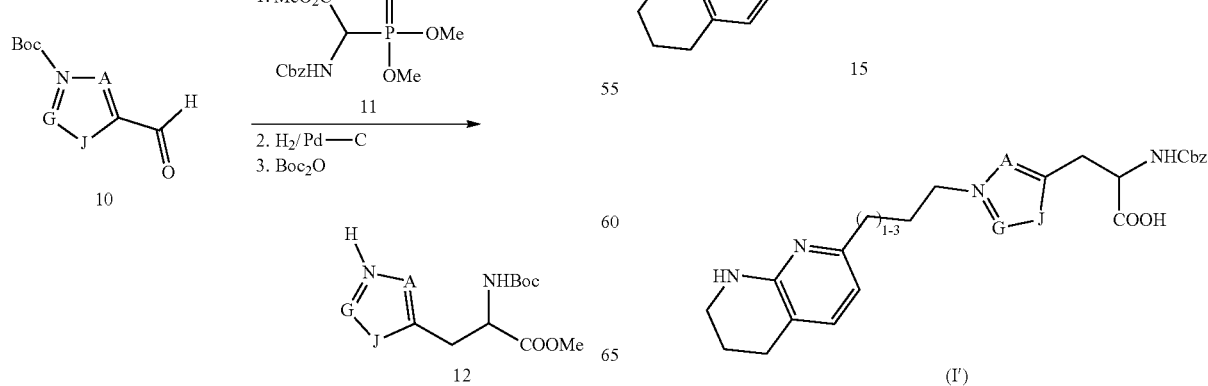

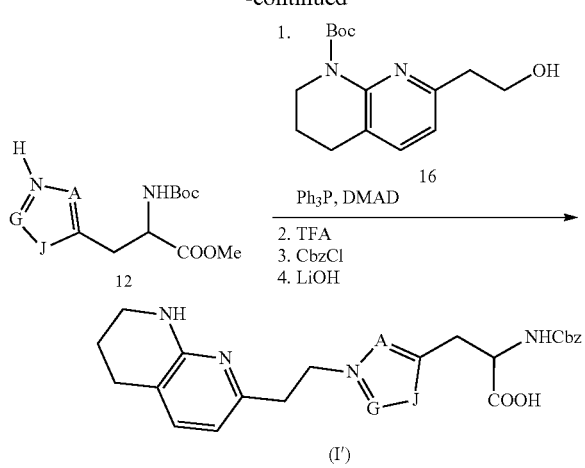

Compounds of Formula (I') where M=N, L=C, and R³≠H can be obtained by starting from aldehyde 10. Condensation of 10 with a suitable phosphorous reagent can yield the corresponding unsaturated ester which can be protected (for example, with a tosyl group) to obtain 17. A Hayashi reaction (Hayashi, T. *Synlett* 2001, 879-887) with a suitable boronic acid in the presence of a rhodium catalyst adds the R³ group in a conjugate manner to yield 18 after removal of the protecting group. Further functionalization as described before to allow installation of a desired arginine mimic incorporating linkers of various lengths can afford compounds of Formula (I').

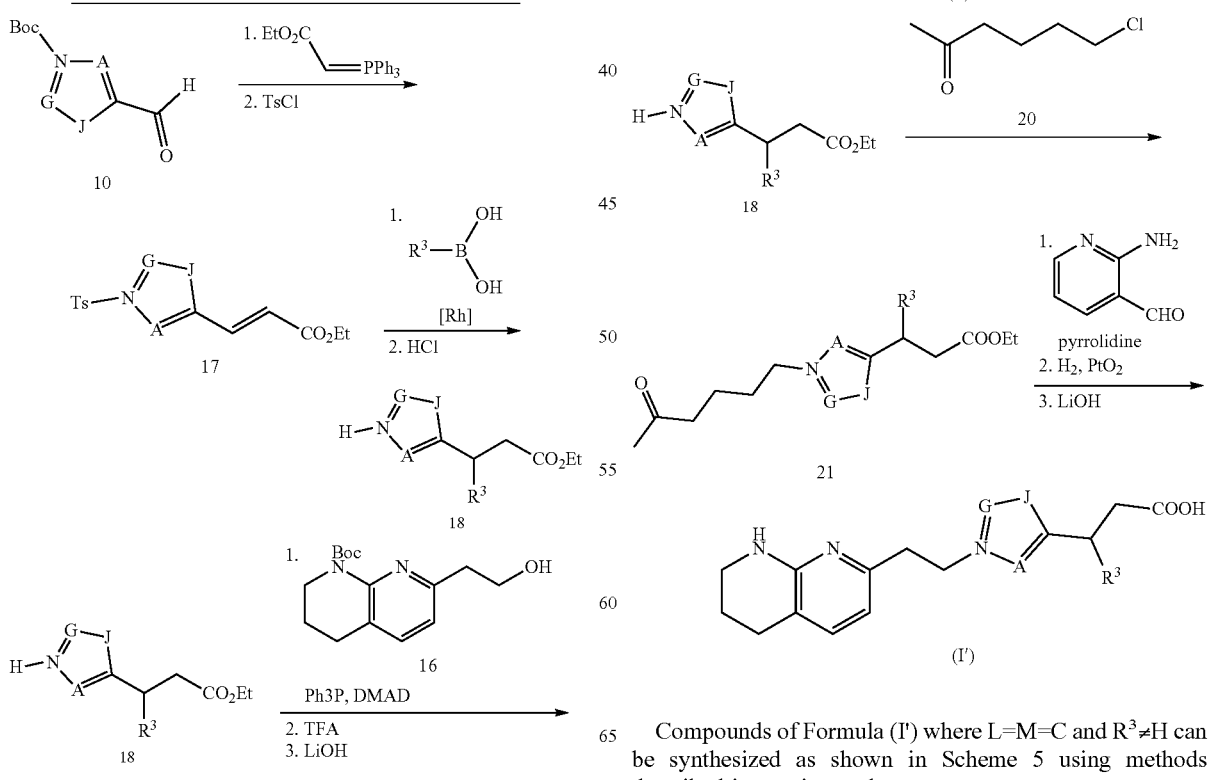

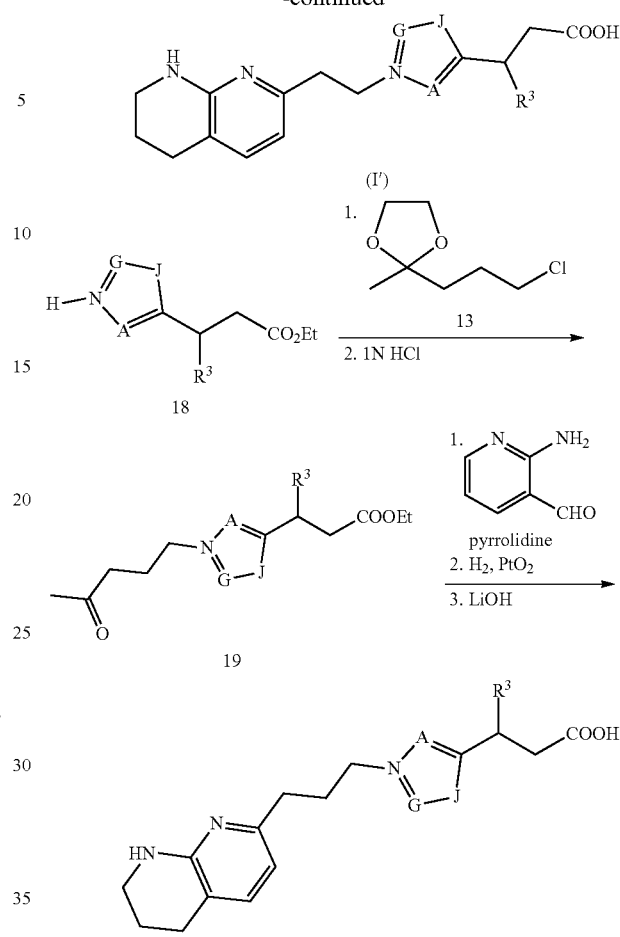

Compounds of Formula (I') where L=M=C and R³≠H can be synthesized as shown in Scheme 5 using methods described in previous schemes.

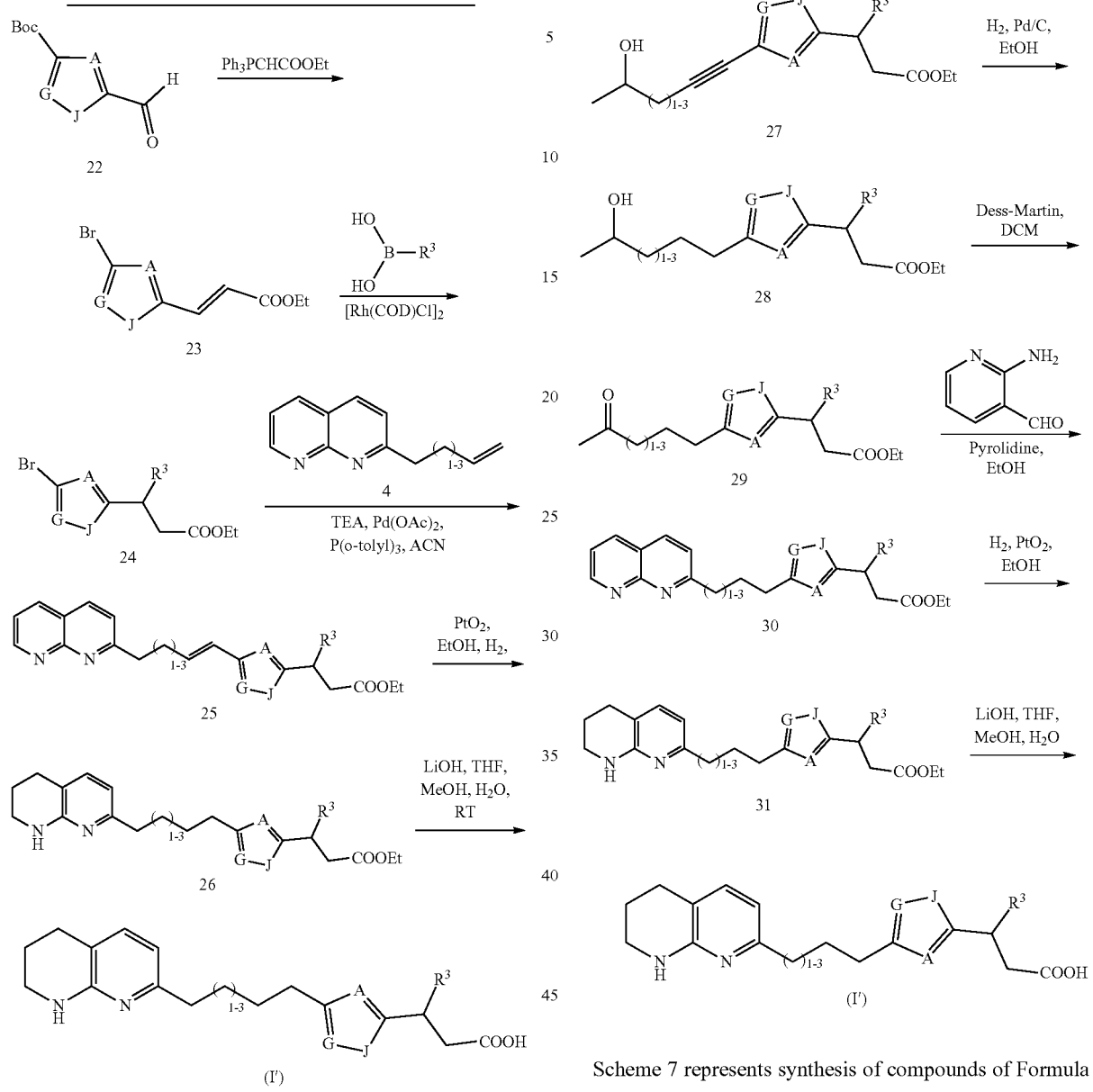

Scheme 6 describes synthesis of compounds of Formula (I') where L=M=C and $R^3 \neq H$ which can be prepared using methods similar to those described in Scheme 2.

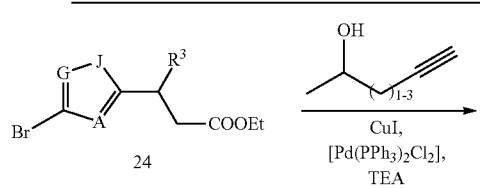

Scheme 7 represents synthesis of compounds of Formula (I') where the L=N and, A, G, E, M are $CHR^{6b}$. Deprotonation and alkylation of γ-butyrolactone (32) followed by reductive ring opening can yield a diol which can be converted to the bis-mesylate 34. Other leaving groups such as tosylate, chloride, or bromide can also be utilized in place of the mesylate to facilitate the subsequent pyrrolidine ring formation with 2-aminoester 35. Aminoesters such as 35 can be prepared using methods known in the literature (for example, Hutchinson, J. H. et al. *J. Med Chem.* 2003, 46, 4790; Henderson, N. C. et al. *Nature Medicine* 2013, 19, 1617). Wacker oxidation of the resulting alkene (36) followed by further transformations similar to the ones described earlier can yield compounds of formula (I').

Scheme 7: General Scheme for preparation of Formula (I') where L = N; A, G, E, and M = CHR$^{6b}$

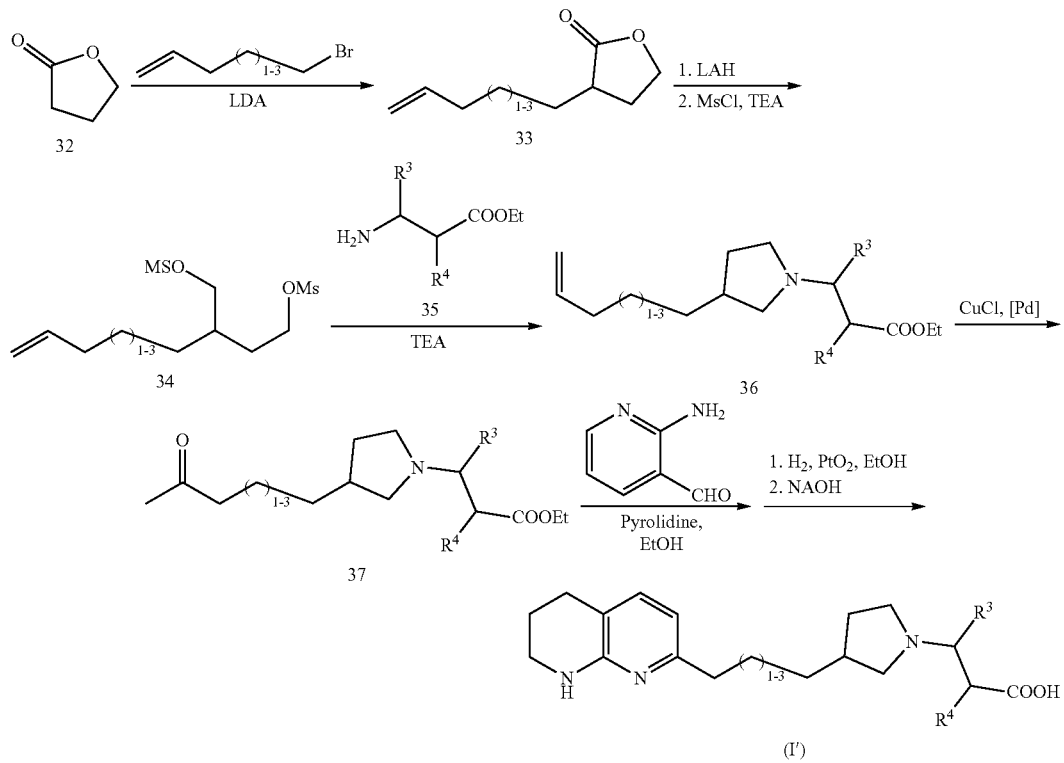

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

HPLC/MS and Preparatory/Analytical HPLC Methods Employed in Characterization or Purification of Examples NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$H NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

The term HPLC refers to a Shimadzu high performance liquid chromatography instrument with one of following methods:

HPLC-1: Sunfire C18 column (4.6×150 mm) 3.5 µm, gradient from 10 to 100% B:A for 12 min, then 3 min hold at 100% B.

Mobile phase A: 0.05% TFA in water:CH$_3$CN (95:5)

Mobile phase B: 0.05% TFA in CH$_3$CN:water (95:5)

TFA Buffer pH=2.5; Flow rate: 1 mF/min; Wavelength: 254 nm, 220 nm.

HPLC-2: XBridge Phenyl (4.6×150 mm) 3.5 µm, gradient from 10 to 100% B:A for 12 min, then 3 min hold at 100% B.

Mobile phase A: 0.05% TFA in water:CH$_3$CN (95:5)

Mobile phase B: 0.05% TFA in CH$_3$CN:water (95:5)

TFA Buffer pH=2.5; Flow rate: 1 mF/min; Wavelength: 254 nm, 220 nm.

HPLC-3: Chiralpak AD-H, 4.6×250 mm, 5 µm.

Mobile Phase: 30% EtOH-heptane (1:1)/70% CO$_2$

Flow rate=40 mF/min, 100 bar, 35° C.; Wavelength: 220 nm

HPLC-4: Waters Acquity UPFC BEH C18, 2.1×50 mm, 1.7-µm particles;

Mobile Phase A: 5:95 CH$_3$CN:water with 10 mM NH$_4$OAc;

Mobile Phase B: 95:5 CH$_3$CN:water with 10 mM NH$_4$OAc;

Temperature: 50° C.; Gradient: 0-100% B over 3 min, then a 0.75-min hold at 100% B; Flow: 1.11 mF/min; Detection: UV at 220 nm.

HPLC-5: Waters Acquity UPFC BEH C18, 2.1×50 mm, 1.7-µm particles;

Mobile Phase A: 5:95 CH$_3$CN:water with 0.1% TFA;

Mobile Phase B: 95:5 CH$_3$CN:water with 0.1% TFA;

Temperature: 50° C.; Gradient: 0-100% B over 3 min, then a 0.75-min hold at 100% B;

Flow: 1.11 mL/min; Detection: UV at 220 nm.

Example 1

(±)-3-(6-Methoxypyridin-3-yl)-3-(3-(4-(5,6,7,8-tetrahydro-1,8-naphthyridin-2-yl)butyl)-1H-pyrazol-1-yl)propanoic acid

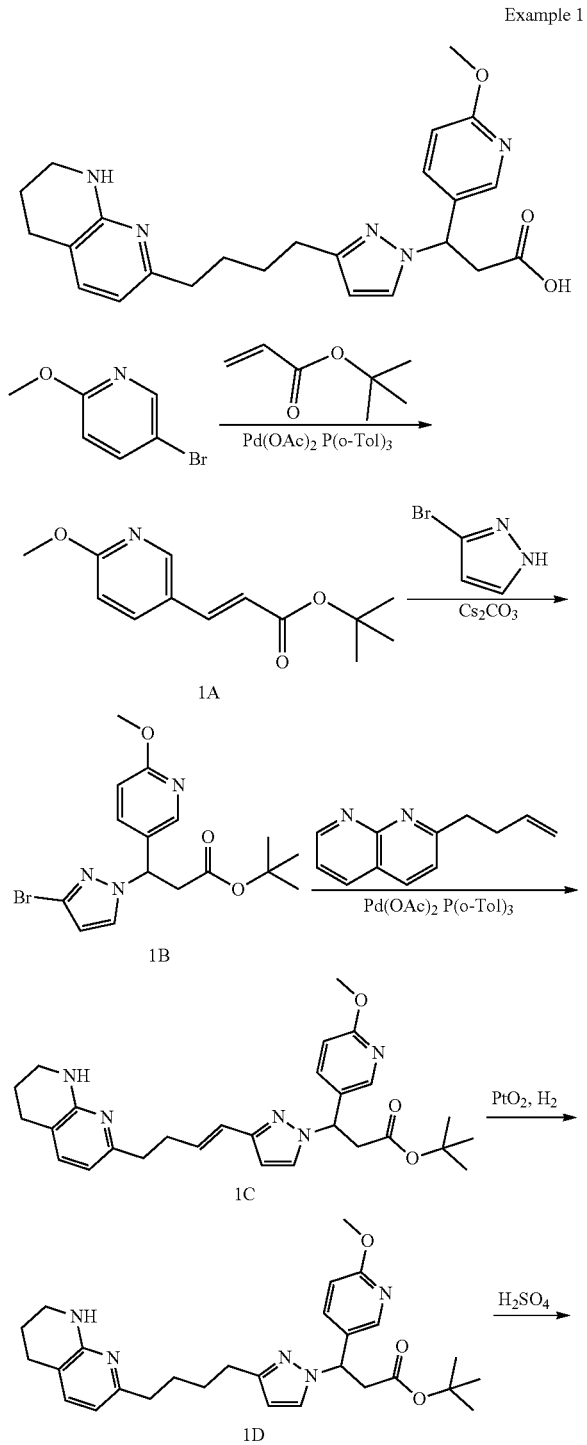

Example 1

Example 1A

A solution of 5-bromo-2-methoxypyridine (2.5 g, 13.30 mmol), tert-butyl acrylate (6.75 mL, 46.5 mmol), triethylamine (5.00 mL, 35.9 mmol), palladium(II) acetate (0.336 g, 1.498 mmol) and tri-o-tolylphosphine (0.673 g, 2.211 mmol) in MeCN (3.09 mL) was degassed with Ar for 10 min. Then the reaction mixture was heated at 90° C. for 18 h. The solvent was removed in vacuo, toluene was added (10 mL) and the mixture was concentrated. Ether was added and the mixture was filtered through a pad of silica gel eluting with ether. The solvent was removed and the residue was purified by flash chromatography (0 to 60% ethyl acetate/hexanes) to yield Example 1A (1.125 g, 4.78 mmol, 36% yield) as a light yellow solid. LCMS (ES): m/z 236.2 [M+H]$^+$. $^1$H NMR (400 MHz, CDCl$_3$) δ 7.49 (d, J=15.8 Hz, 1H), 7.31-7.18 (m, 3H), 6.95 (t, J=8.5 Hz, 1H), 6.24 (d, J=16.1 Hz, 1H), 3.93 (s, 3H), 1.54 (s, 9H).

Example 1B

To a solution of 3-bromo-1H-pyrazole (94 mg, 0.638 mmol) and cesium carbonate (208 mg, 0.638 mmol) in acetonitrile (4 mL) under Ar was added Example 1A (150 mg, 0.638 mmol) and the mixture was heated in microwave reactor at 80° C. for 60 min. After cooling down to the room temperature, the mixture was partitioned between EtOAc (20 mL) and H$_2$O (20 mL). The combined organic phase was dried (anhydrous MgSO$_4$) and the solvent removed in vacuo. The crude product was purified by flash chromatography (0 to 20% ethyl acetate/hexanes) to yield Example 1B (126.5 mg, 0.331 mmol, 52% yield) as a white solid. $^1$H NMR (500 MHz, CDCl$_3$) δ 8.21-8.10 (m, 1H), 7.64 (dd, J=8.7, 2.6 Hz, 1H), 7.32 (d, J=2.2 Hz, 1H), 6.75 (d, J=8.5 Hz, 1H), 6.26 (d, J=2.5 Hz, 1H), 5.65 (dd, J=8.8, 6.3 Hz, 1H), 3.95 (s, 3H), 3.54-3.42 (m, 1H), 3.03 (s, 1H), 1.38 (s, 9H)

Example 1C

A solution of Example 1B (25 mg, 0.065 mmol), 2-(but-3-en-1-yl)-1,8-naphthyridine (12.05 mg, 0.065 mmol), triethylamine (0.025 mL, 0.177 mmol), palladium(II) acetate (1.655 mg, 7.37 μmol) and tri-o-tolylphosphine (3.31 mg, 10.88 μmol) in ACN (0.6 mL) was degassed with Ar for 10 min. Then the reaction mixture was heated at 90° C. for 12 h. The reaction mixture was concentrated and the crude product was purified by flash chromatography (0 to 100% ethyl acetate/hexanes) to give Example 1C (22.7 mg, 0.047 mmol, 72% yield) as a yellow solid. LCMS (ES): m/z 486.1 [M+H]$^+$.

Example 1D

A solution of Example 1C (20 mg, 0.041 mmol) and PtO$_2$ (1.871 mg, 8.24 μmol) in EtOH (0.4 mL) was stirred under H$_2$ (balloon, 1 atm) for 16 h. After filtration on a pad of CELITE®, it was concentrated to afford Example 1D (20.2 mg, 0.041 mmol, 100% yield) as an off-white solid which was used in the next step without further purification. LCMS (ES): m/z 492.1 [M+H]$^+$.

Example 1

To a solution of Example 1D (20 mg, 0.041 mmol) was added sulfuric acid (3M aq.) (0.098 mL, 0.297 mmol). The mixture was stirred at 40° C. for 3 h. The reaction mixture was cooled to room temperature and adjusted to pH 6 using 50% aq. NaOH. The reaction mixture was extracted with CHCl₃ (3×) and the combined organic layers were washed with brine, dried over anhydrous Na₂SO₄, filtered and concentrated. The mixture was purified by preparative LC/MS (Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min) to give Example 1 (11.4 mg, 0.026 mmol, 64% yield). LC/MS (m/z)=436.0 (M+H)⁺. ¹H NMR (500 MHz, DMSO-d₆) δ 8.11 (s, 1H), 7.76-7.56 (m, 2H), 7.05 (d, J=7.2 Hz, 1H), 6.74 (d, J=8.6 Hz, 1H), 6.24 (d, J=7.2 Hz, 1H), 5.99 (s, 1H), 5.76-5.66 (m, 1H), 3.80 (s, 2H), 3.60-3.50 (m, 1H), 3.39-3.28 (m, 1H), 3.26-3.20 (m, 2H), 3.11-3.02 (m, 1H), 2.63-2.57 (m, 2H), 2.50-2.47 (m, 4H), 2.42 (br. s., 1H), 1.91 (s, 1H), 1.80-1.69 (m, 2H), 1.53 (br. s., 4H). Human αVβ6 IC50 (nM)=6.0; Human αVβ3 IC50 (nM)=2.4; Human αVβ5 IC50 (nM)=1.5; and Human αVβ8 IC50 (nM)=262.

Example 2

(±)-3-(6-Methoxypyridin-3-yl)-3-(3-(3-(5,6,7,8-tetrahydro-1,8-naphthyridin-2-yl)propyl)-1H-pyrazol-1-yl)propanoic acid

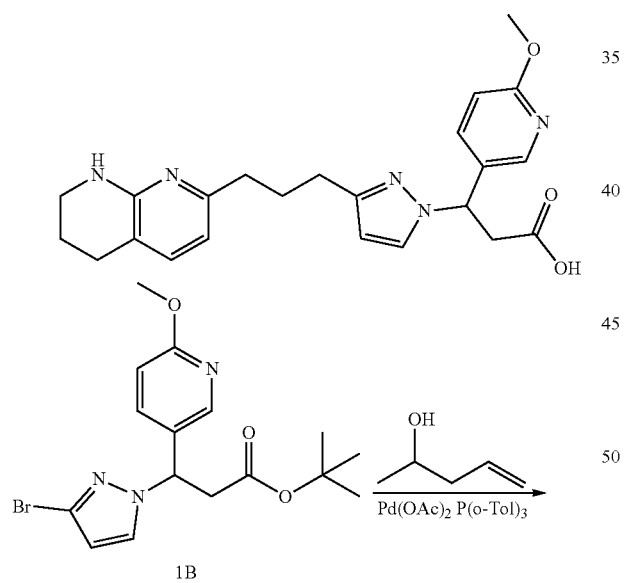

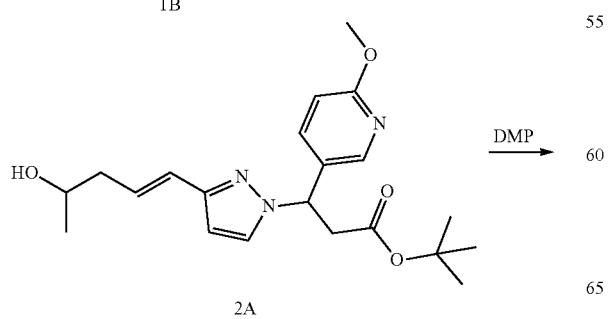

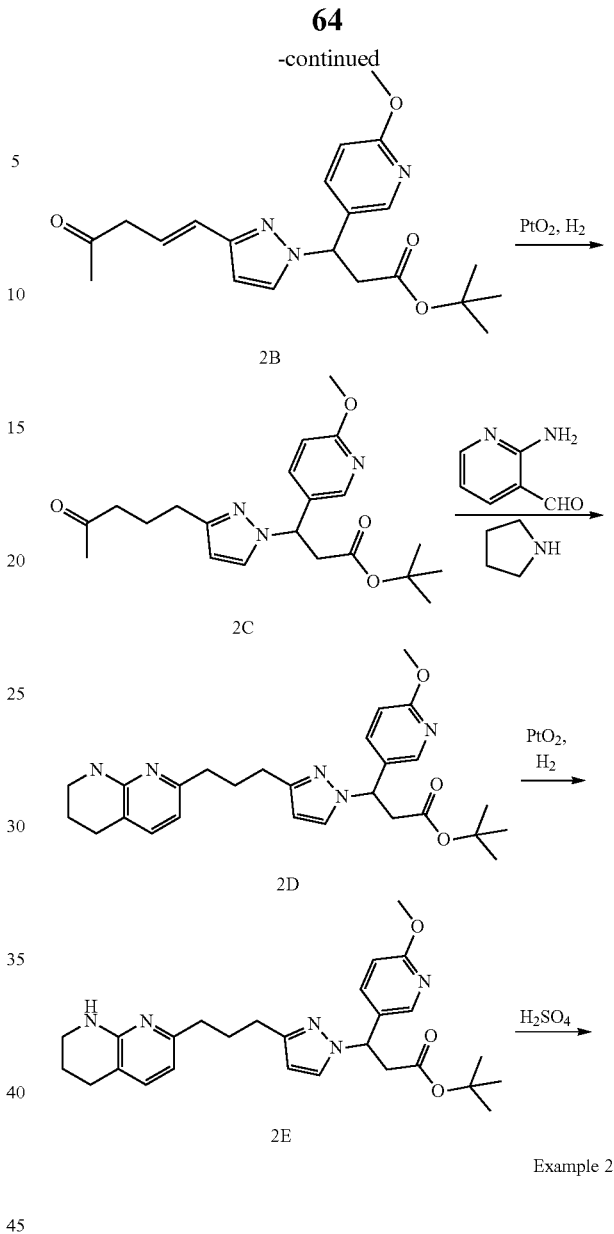

Example 2A

A solution of 1B (50 mg, 0.131 mmol), pent-4-en-2-ol (0.047 mL, 0.458 mmol), triethylamine (0.049 mL, 0.353 mmol), palladium(II) acetate (3.31 mg, 0.015 mmol) and tri-o-tolylphosphine (6.62 mg, 0.022 mmol) in ACN (1.3 mL) was degassed with Ar for 10 min. Then the mixture was heated at 90° C. for 16 h. The crude mixture was concentrated and purified by flash chromatography (0 to 50% ethyl acetate/hexanes) to give Example 2A (29.1 mg, 0.075 mmol, 58% yield) as a yellow solid. LCMS (ES): m/z 388.3 [M+H]⁺.

Example 2B

To a solution of Example 2A (29 mg, 0.075 mmol) in CH₂Cl₂ (0.7 mL) at room temperature was added Dess-Martin periodinane (38.1 mg, 0.090 mmol). The mixture was diluted with Et₂O and filtered through a pad of CELITE® and concentrated. The crude product was purified by flash chromatography (0 to 30% ethyl acetate/hexanes) to yield Example 2B (20 mg, 0.052 mmol, 69% yield) as a white solid. LCMS (ES): m/z 386.1 [M+H]$^+$.

Example 2C

A solution of Example 2B (20 mg, 0.052 mmol) and PtO$_2$ (2.357 mg, 10.38 μmol) in EtOH (0.4 mL) was stirred under H$_2$ (1 atm) for 16 h. After filtration on a pad of CELITE®, the mixture was concentrated which was used in the next step without further purification. LCMS (ES): m/z 388.1 [M+H]$^+$.

Example 2D

A solution of Example 2C (20 mg, 0.052 mmol) in CH$_2$Cl$_2$ (0.1 mL) and MeOH (0.300 mL) was added pyrrolidine (1.2 eq, 9.4 μL) followed by addition of 2-aminonicotinaldehyde (6.30 mg, 0.052 mmol). The mixture was then stirred at room temperature for 16 h. The reaction mixture was concentrated to give Example 2D (24.4 mg, 0.052 mmol, 100% yield) as a dark brown oil. The compound was used for the next step without further purification. LCMS (ES): m/z 444.2 [M+H]$^+$.

Example 2E

A solution of Example 2D (24 mg, 0.051 mmol) and PtO$_2$ (2.302 mg, 10.14 μmol) in EtOH (0.4 mL) was stirred under H$_2$ (1 atm) (0.102 mg, 0.051 mmol) for 16 h. After filtration on a pad of CELITE® and concentration, Example 2E was isolated as an off-white solid which was used in the next step without further purification. LCMS (ES): m/z 478.1 [M+H]$^+$.

Example 2

To a solution of Example 2E (24.2 mg, 0.051 mmol) in ethyl acetate (0.2 mL) was added sulfuric acid (3 M aq., 0.122 mL, 0.370 mmol). The aqueous layer was separated and stirred at 40° C. for 3 h. The reaction mixture was cooled to room temperature and adjusted to pH 6 using 50% aq. NaOH. The reaction mixture was extracted with CHCl$_3$ (3×) and the combined organic layers were washed with brine, dried over anhydrous Na$_2$SO$_4$, filtered, and concentrated. The mixture was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min to yield Example 2 (4.9 mg, 0.012 mmol, 23% yield). LCMS (ES): m/z 422.0 [M+H]$^+$. $^1$H NMR (500 MHz) δ 8.50 (s, 1H), 7.59 (d, J=2.2 Hz, 1H), 7.45 (d, J=8.9 Hz, 1H), 7.29 (d, J=7.7 Hz, 1H), 6.92 (d, J=8.9 Hz, 1H), 6.57 (d, J=7.7 Hz, 1H), 6.26 (d, J=2.2 Hz, 1H), 5.74 (dd, J=8.7, 5.7 Hz, 1H), 3.91 (s, 3H), 3.42 (dtd, J=11.3, 5.5, 3.2 Hz, 1H), 3.40 (dd, J=14.9, 5.7 Hz, 1H), 3.35 (dtd, J=11.3, 5.5, 4.4 Hz, 1H), 3.29 (dd, J=14.9, 8.7 Hz, 1H), 2.82 (t, J=7.5 Hz, 2H), 2.66 (t, J=7.5 Hz, 2H), 2.53 (td, J=7.0, −16.4 Hz, 1H), 2.45 (td, J=7.0, −16.4 Hz, 1H), 1.96 (quin, J=7.5 Hz, 2H), 1.94 (dtt, J=13.4, 7.0, 5.5 Hz, 1H), 1.94-1.89 (m, 1H), 1.87 (dtt, J=13.4, 7.0, 5.5 Hz, 1H). Human αVβ6 IC50 (nM)=6.8; Human αVβ3 IC50 (nM)=2.7; Human αVβ5 IC50 (nM) =0.34; and Human αVβ8 IC50 (nM)=420.

Example 3 and Example 4

3-(6-Methoxypyridin-3-yl)-3-(3-(3-(5,6,7,8-tetrahydro-1,8-naphthyridin-2-yl)propyl)-1H-pyrazol-1-yl)propanoic acid (Example 3, Enantiomer 1)

3-(6-Methoxypyridin-3-yl)-3-(3-(3-(5,6,7,8-tetrahydro-1,8-naphthyridin-2-yl)propyl)-1H-pyrazol-1-yl)propanoic acid (Example 4, Enantiomer 2)

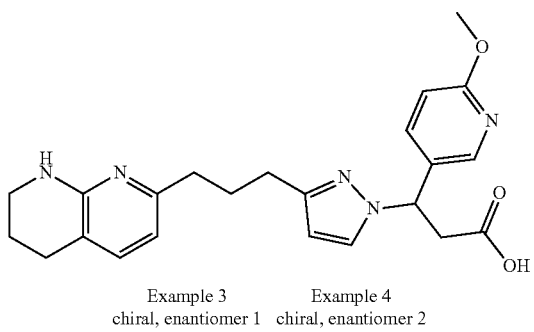

Example 3  Example 4
chiral, enantiomer 1  chiral, enantiomer 2

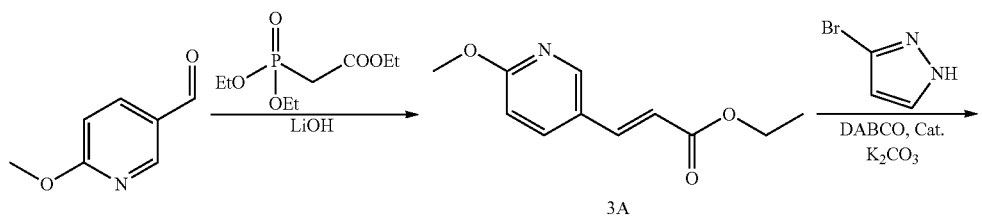

3A

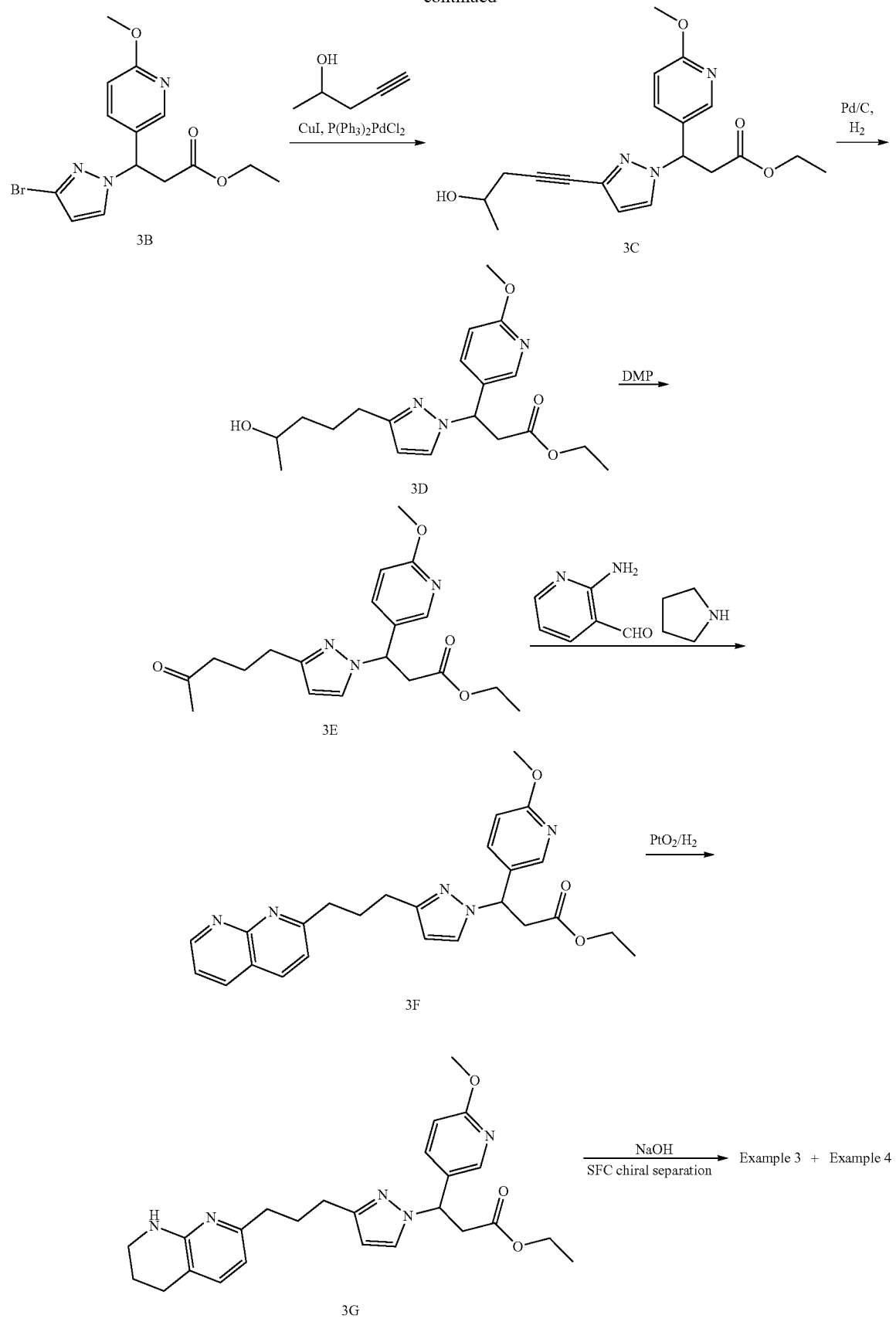

Example 3A

To the suspension of 6-methoxynicotinaldehyde (24 g, 175 mmol) in THF (420 mL) was added 60 g molecular sieves (4 Å) followed by ethyl 2-(diethoxyphosphoryl)acetate (42.0 mL, 210 mmol), and LiOH (5.03 g, 210 mmol). The reaction was stirred at room temperature overnight. The reaction was filtered over CELITE® and concentrated. The residue was dissolved in EtOAc and washed with sat. NaHCO$_3$ (2×) followed by brine (2×). The organic layer was dried (anhydrous Na$_2$SO$_4$) and concentrated. Purification by flash chromatography gave Example 3A (31 g, 85%). $^1$H NMR (400 MHz, CDCl$_3$) δ 8.30 (d, J=2.4 Hz, 1H), 7.79 (dd, J=8.8, 2.4 Hz, 1H), 7.65 (d, J=16.1 Hz, 1H), 6.79 (d, J=8.6 Hz, 1H), 6.36 (d, J=16.1 Hz, 1H), 4.29 (q, J=7.1 Hz, 2H), 3.99 (s, 3H), 1.36 (t, J=7.0 Hz, 3H)

Example 3B

A mixture of 3-bromo-1H-pyrazole (22.62 g, 154 mmol), DABCO (15.70 g, 140 mmol), Example 3A (29 g, 140 mmol), potassium carbonate (0.193 g, 1.399 mmol) and acetonitrile (280 mL) was stirred at 75° C. overnight. The reaction was quenched with brine and extracted with EtOAc. The organic layer was dried (Na$_2$SO$_4$) and concentrated. Purification by flash chromatography gave Example 3B (25 g, 50%). $^1$H NMR (400 MHz, CDCl₃) δ 8.15 (d, J=2.4 Hz, 1H), 7.63 (dd, J=8.7, 2.6 Hz, 1H), 7.33 (d, J=2.3 Hz, 1H), 6.74 (d, J=8.6 Hz, 1H), 6.25 (d, J=2.3 Hz, 1H), 5.70 (dd, J=8.5, 6.4 Hz, 1H), 4.28-4.03 (m, 2H), 3.93 (s, 3H), 3.57 (dd, J=16.4, 8.6 Hz, 1H), 3.08 (dd, J=16.5, 6.4 Hz, 1H), 1.20 (t, J=7.2 Hz, 3H)

Example 3C

A mixture of Example 3B (6.0 g, 16.94 mmol), pent-4-yn-2-ol (2.396 mL, 25.4 mmol), triethylamine (9.44 mL, 67.8 mmol), bis(triphenylphosphine)palladium(II) chloride (0.713 g, 1.016 mmol) and copper(I) iodide (0.129 g, 0.678 mmol) in DMF (33.9 mL) was stirred at 80° C. for 2 h. The reaction was diluted with EtOAc, washed with brine 3 times, dried over anhydrous Na$_2$SO$_4$, the solids were filtered, and the filtrate was concentrated. Purification by flash chromatography gave Example 3C (4 g, 68%). LCMS (ES): m/z 358.3 [M+H]$^+$.

Example 3D

A solution of Example 3C (22 g, 61.6 mmol) and Pd—C (9.17 g, 8.62 mmol) in EtOH (308 mL) was stirred under a H$_2$ (balloon, 1 atm) overnight. After filtration on a pad of CELITE® and concentration, Example 3D (20 g, 55.3 mmol, 90% yield) was isolated as a brown oil which was used in the next step without further purification. LCMS (ES): m/z 362.2 [M+H]$^+$.

Example 3E

To a solution of Example 3D in CH$_2$Cl$_2$ (277 mL) at room temperature was added Dess-Martin periodinane (32.9 g, 77 mmol). After 1 hour, the mixture was diluted with Et$_2$O, filtered, and the filtrate was concentrated. Purification by flash chromatography gave Example 3E (15.7 g, 79%). LCMS (ES): m/z 360.1 [M+H]$^+$.

Example 3F

A solution of Example 3E (15.7 g, 43.7 mmol) in CH$_2$Cl$_2$ (21.84 mL) and EtOH (65.5 mL) was added pyrrolidine (7.95 mL, 96 mmol) followed by addition of 2-aminonicotinaldehyde (5.87 g, 48.0 mmol). The mixture was then stirred at room temperature for 20 h. The mixture was concentrated at 45° C. to give Example 3F.

The crude material was used as such in the next step. LCMS (ES): m/z 446.1 [M+H]$^+$.

Example 3G

A solution of Example 3F (19.47 g, 43.7 mmol) and PtO$_2$ (1.489 g, 6.56 mmol) in EtOH (146 mL) was stirred under H$_2$ for 16 h. After filtration through a CELITE® pad and concentration, Example 3G (19.60 g, 43.60 mmol, 100% yield) was obtained as a dark oil, which was used in the next step without further purification. LCMS (ES): m/z 450.1 [M+H]$^+$.

Example 3 and Example 4

A mixture of Example 3G (580 mg, 1.290 mmol) and 1M sodium hydroxide solution (3871 μL, 3.87 mmol) in MeOH (8601 μL) was stirred at room temperature for 1 h. Methanol was removed under reduced pressure. The residue was diluted with water and pH was adjusted to 5-6 using 1N HCl dropwise. The product was extracted with chloroform three times, dried over Na$_2$SO$_4$ and concentrated. The crude material was separated by SFC (Chiralpak AD-H (3×25 cm, 5 μm), 100 bar, 45° C., 160 mL/min, CO$_2$/MeOH:ACN [1:1 (v/v)] w 0.1% NH$_4$OH (60/40)) to give Example 3 (210 mg, 38%) and Example 4 (190 mg, 34%). Example 3: LCMS (ES): m/z 422.0 [M+H]$^+$. $^1$H NMR (400 MHz, DMSO-d$_6$) δ 8.18-8.08 (m, 1H), 7.79-7.63 (m, 2H), 7.02 (d, J=7.2 Hz, 1H), 6.77 (d, J=8.6 Hz, 1H), 6.36-6.19 (m, 2H), 6.03 (d, J=2.2 Hz, 1H), 5.72 (dd, J=8.8, 6.4 Hz, 1H), 3.82 (s, 3H), 3.53-3.04 (m, 7H), 2.64-2.57 (m, 2H), 2.48-2.39 (m, 3H), 1.96-1.70 (m, 2H). Human αVβ6 IC50 (nM)=3.2; Human αVβ1 IC50 (nM)=65; Human αVβ3 IC50 (nM)=3.2; Human αVβ5 IC50 (nM)=11; and Human αVβ8 IC50 (nM)=1,120. Example 4: LCMS (ES): m/z 422.0 [M+H]$^+$. $^1$H NMR (400 MHz, DMSO-d$_6$) δ 8.13 (d, J=2.3 Hz, 1H), 8.23-7.96 (m, 1H), 7.78-7.59 (m, 2H), 7.02 (d, J=7.2 Hz, 1H), 6.77 (d, J=8.6 Hz, 1H), 6.32-6.20 (m, 2H), 6.03 (d, J=2.2 Hz, 1H), 5.72 (dd, J=8.7, 6.4 Hz, 1H), 3.81 (s, 3H), 3.51-2.99 (m, 7H), 2.63-2.56 (m, 2H), 2.44 (dd, J=14.9, 7.5 Hz, 3H), 1.91-1.64 (m, 2H). Human αVβ6 IC50 (nM)=210.

Example 5

(±)-2-(((Benzyloxy)carbonyl)amino)-3-(1-(2-(5,6,7,8-tetrahydro-1,8-naphthyridin-2-yl)ethyl)-1H-pyrazol-4-yl)propanoic acid

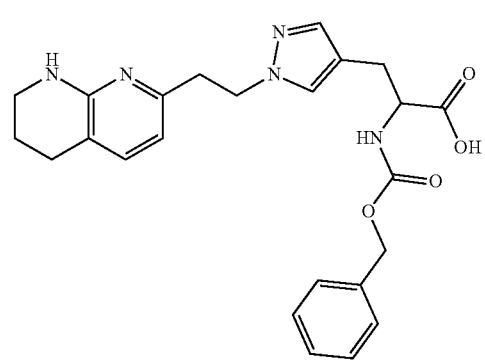

Example 5

-continued

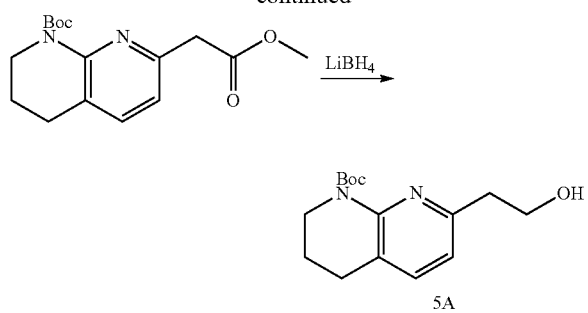
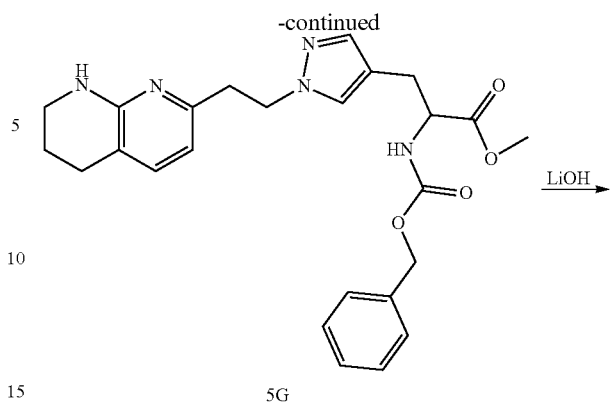

Example 5

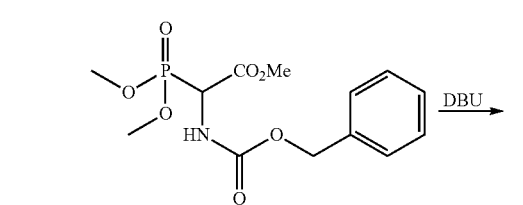

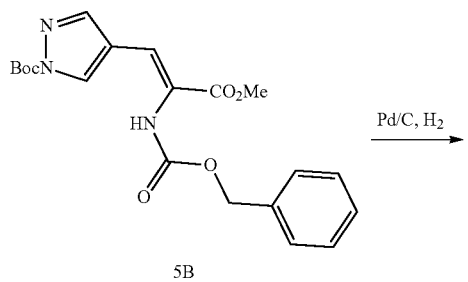

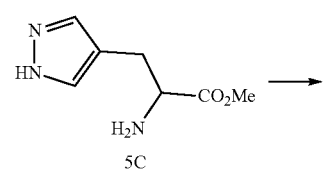

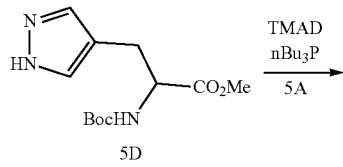

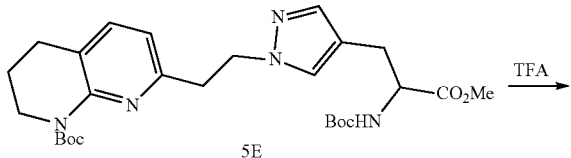

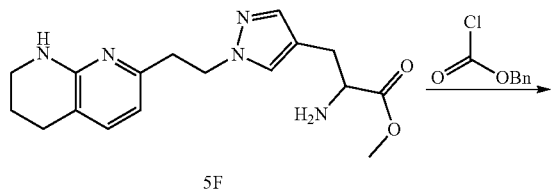

Example 5A

To a solution of tert-butyl 7-(2-methoxy-2-oxoethyl)-3,4-dihydro-1,8-naphthyridine-1(2H)-carboxylate (1 g, 3.26 mmol) in THF (20 mL) was added a 2M solution of lithium borohydride (2.122 mL, 4.24 mmol) in THF. The reaction mixture was stirred at room temperature overnight. Water was added slowly to the reaction mixture and the resulting mixture stirred for 10 min at room temperature. The mixture was diluted with EtOAc then extracted 3 times with EtOAc. The combined organic layers were dried over $Na_2SO_4$, filtered and concentrated. Purification by flash chromatography gave Example 5A (782 mg, 86%). LCMS (ES): m/z 279.1 $[M+H]^+$.

Example 5B

To a solution of methyl 2-(((benzyloxy)carbonyl)amino)-2-(dimethoxyphosphoryl)acetate (101 mg, 0.306 mmol) in DCM (1 mL) was added DBU (0.042 mL, 0.280 mmol). The reaction mixture was stirred for 10 minutes under Ar at room temperature. A solution of tert-butyl 4-formyl-1H-pyrazole-1-carboxylate (50 mg, 0.255 mmol) in DCM (0.5 mL) was added to the reaction mixture. The reaction mixture was stirred at room temperature under Ar for 1 h. The mixture was concentrated and purified by flash chromatography to give Example 5B (76 mg, 74%). LCMS (ES): m/z 402.2 $[M+H]^+$.

Example 5C

To a solution of Example 5B (90 mg, 0.299 mmol) in MeOH (7 mL) was added HOAc (0.1 mL) and 10% Pd/C (40 mg, 0.038 mmol). The mixture was stirred under $H_2$ (1 atm) overnight. The mixture was filtered and concentrated. The crude mixture was used for the next step without purification. LCMS (ES): m/z 170.1 $[M+H]^+$.

Example 5D

To a solution of Example 5C (50 mg, 0.296 mmol) in THF (3 mL) and $H_2O$ (1.5 mL) was added sodium bicarbonate (74.5 mg, 0.887 mmol) and $Boc_2O$ (0.106 mL, 0.458 mmol). The reaction mixture was stirred at room temperature for 1 h. The mixture was extracted with EtOAc (30 mL). The organic layers were combined and concentrated. The mixture was purified by preparative HPLC (Phenomenex Luna Axia 5μ C18 30×100 mm; 10 min gradient from 85% A:

15% B to 0% A: 100% B (A=90% H₂O/10% ACN+0.1% TFA); (B=90% ACN/10% H₂O+0.1% TFA); detection at 220 nm) to give Example 5D (35 mg, 44%). LCMS (ES): m/z 270.1 [M+H]⁺.

Example 5E

To a mixture of Example 5D and Example 5A (20.67 mg, 0.074 mmol) in toluene (619 μL) was added tris(butyl) phosphine (37.1 μL, 0.149 mmol) and 1,1'-azobis(N,N-dimethylformamide) (25.6 mg, 0.149 mmol). The mixture was stirred at room temperature under Ar overnight. The reaction mixture was concentrated and the crude was purified by prep HPLC (Phenomenex Luna Axia 5μ C18 30×100 mm; 10 min gradient from 85% A: 15% B to 0% A: 100% B (A=90% H₂O/10% ACN+0.1% TFA); (B=90% ACN/10% H₂O+0.1% TFA); detection at 220 nm) to give Example 5E (4 mg, 10%). LCMS (ES): m/z 530.4 [M+H]⁺.

Example 5F

To a solution of Example 5E (4 mg, 7.55 μmol) in TFA (0.2 mL) and DCM (1 mL) was stirred at room temperature for 4 h. The solvent was removed and the residue was used in the next reaction without further purification. LCMS (ES): m/z 430.3 [M+H]⁺.

Example 5G

To a solution of Example 5F (2.48 mg, 7.53 μmol), sodium bicarbonate (5 mg, 0.060 mmol) in THF (1.5 mL) and H₂O (0.5 mL) was added benzyl carbonochloridate (5 mg, 0.029 mmol). The reaction mixture was stirred at room temperature for 1 h. The solvent was evaporated. The aqueous residue was extracted with EtOAc (2×5 mL). The organic layers were combined and concentrated to give crude Example 5F which was used for the next step without further purification. LCMS (ES): m/z 463.3 [M+H]⁺.

Example 5

A solution of Example 5G (3.5 mg, 7.55 μmol), LiOH (3 mg, 0.125 mmol) in THF (1 mL) and H₂O (0.5 mL) was stirred at room temperature overnight. The reaction mixture was purified by preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 3-minute hold at 100% B; Flow: 20 mL/min. to give Example 5 (3.3 mg, 96%). LCMS (ES): m/z 450.3 [M+H]⁺. ¹H NMR (500 MHz, CD₃OD) δ 7.45-7.20 (m, 9H), 6.35 (br d, J=13 Hz, 1H), 5.21-5.00 (m, 2H), 4.66-4.49 (m, 2H), 4.34 (td, J=6.4, 1.4 Hz, 2H), 4.20 (t, J=5.4 Hz, 1H), 3.43-3.37 (m, 2H), 3.02 (t, J=6.3 Hz, 2H), 2.93 (br dd, J=8.0, 5.9 Hz, 2H), 2.71 (br t, J=6.0 Hz, 2H), 1.87 (quin, J=5.6 Hz, 2H). Human αVβ6 IC50 (nM)=5,000.

Example 6

(±)-2-(((Benzyloxy)carbonyl)amino)-3-(1-(3-(5,6,7,8-tetrahydro-1,8-naphthyridin-2-yl)propyl)-1N-pyrazol-4-yl)propanoic acid

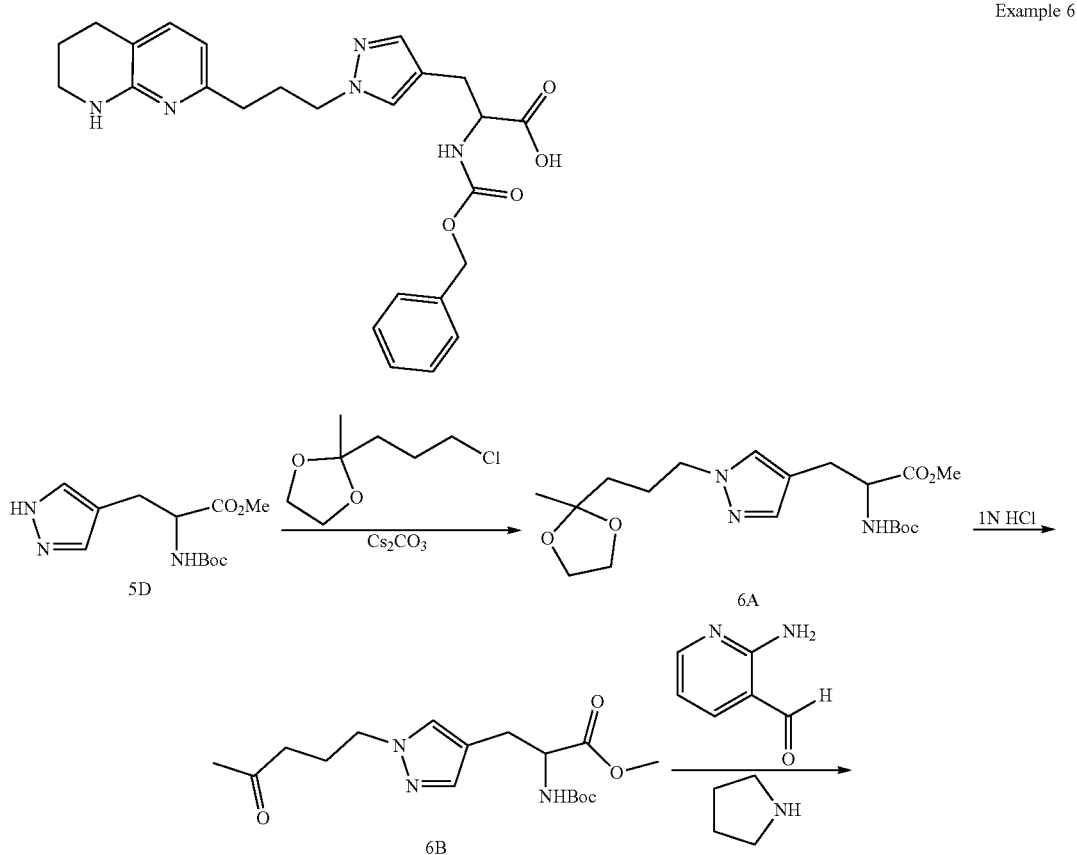

Example 6

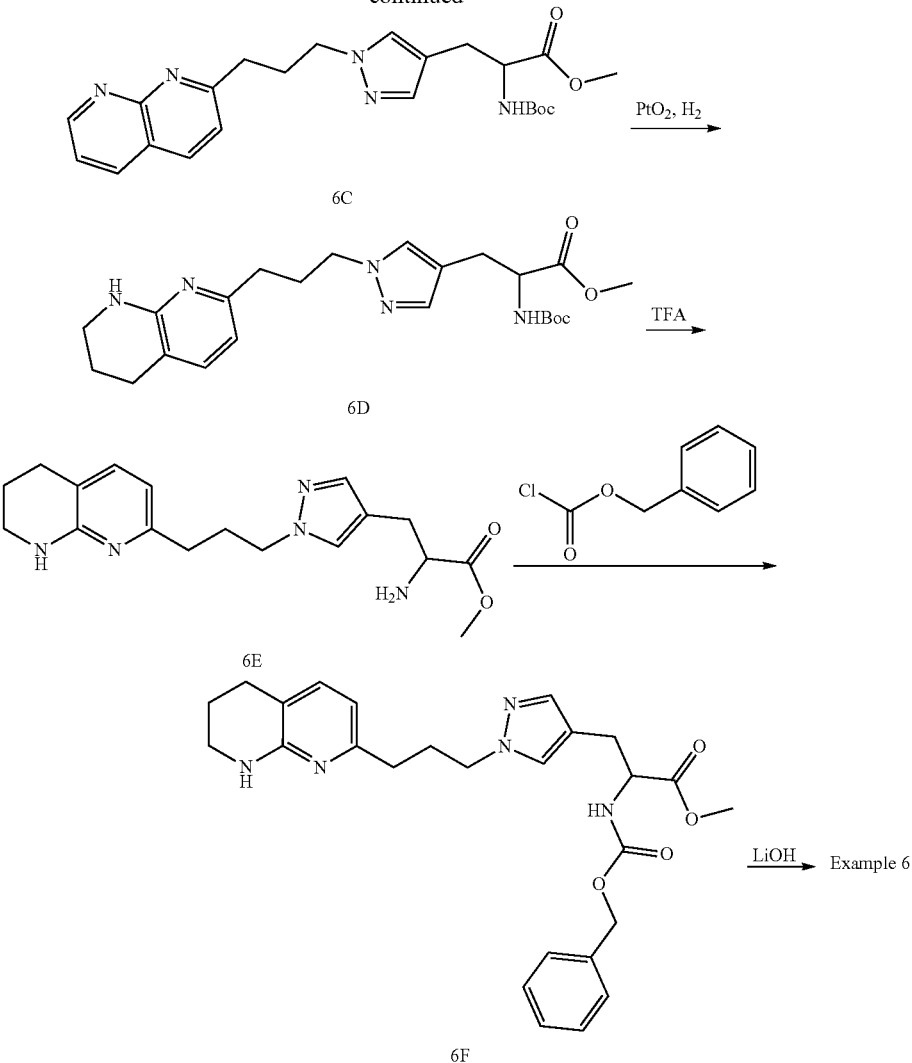

Example 6A

To a solution of Example 5D (26 mg, 0.065 mmol, 59% yield) in acetonitrile (1 mL) was added 2-(3-chloropropyl)-2-methyl-1,3-dioxolane (40 mg, 0.243 mmol) and $Cs_2CO_3$ (100 mg, 0.307 mmol). The reaction mixture was heated at 110° C. for 1 h. The mixture was filtered, the filtrate was concentrated, and the crude product was further purified by prep HPLC (Phenomenex Luna Axia 5μ C18 30×100 mm; 10 min gradient from 85% A: 15% B to 0% A: 100% B (A=90% $H_2O$/10% ACN+0.1% TFA); (B=90% ACN/10% $H_2O$+0.1% TFA); detection at 220 nm) to give Example 6A (26 mg, 59%). LCMS (ES): m/z 398.3 $[M+H]^+$.

Example 6B

To a solution of Example 6A (10 mg, 0.028 mmol, 94% yield) in THF (0.5 mL) was added 1N HCl (0.5 mL, 0.500 mmol). The reaction mixture was stirred at room temperature for 1 h. The solvent was evaporated and water (1 mL) was added. The mixture was extracted with EtOAc (3×5 mL). The organic layers were combined and concentrated to give crude Example 6B which was used for the next step without further purification. LCMS (ES): m/z 354.2 $[M+H]^+$.

Example 6C

To a solution of Example 6B (22 mg, 0.062 mmol) in EtOH (1 mL) was added 2-aminonicotinaldehyde (11.40 mg, 0.093 mmol) and pyrrolidine (10.30 μl, 0.125 mmol). The mixture was stirred at room temperature for 2 h and heated at reflux for 1 h. The solvent was evaporated and the crude product was purified by prep HPLC (Phenomenex Luna Axia 5μ C18 30×100 mm; 10 min gradient from 85% A: 15% B to 0% A: 100% B (A=90% $H_2O$/10% ACN+0.1% TFA); (B=90% ACN/10% $H_2O$+0.1% TFA); detection at 220 nm) to give Example 6C (3.5 mg, 13%). LCMS (ES): m/z 440.1 $[M+H]^+$.

Example 6D

To a solution of Example 6C (3.5 mg, 7.96 μmol) in ethanol (2 mL) was added $PtO_2$ (0.362 mg, 1.593 μmol). The mixture was stirred under a $H_2$ atmosphere (balloon, 1 atm)

overnight. The mixture was filtered through a CELITE® pad and the filtrate concentrated to give Example 6D as a viscous oil. LCMS (ES): m/z 444.3 [M+H]⁺.

Example 6E

To a solution of Example 6D (3.5 mg, 7.89 μmol) in CH$_2$Cl$_2$ (1 mL) was added TFA (0.4 mL). The mixture was stirred at room temperature for 2 h. The mixture was concentrated and the crude material was used for the next step without purification. LCMS (ES): m/z 344.1 [M+H]⁺.

Example 6F

To a solution of Example 6E (2.7 mg, 7.86 μmol), sodium bicarbonate (5 mg, 0.060 mmol) in THF (1.5 mL) and H$_2$O (0.5 mL) was added benzyl carbonochloridate (5 mg, 0.029 mmol). The reaction mixture was stirred at room temperature for 1 h. The solvent was evaporated. The aqueous residue was extracted with EtOAc (2×5 mL). The organic layers were collected and concentrated to give Example 6F, which was used for the next step without further purification. LCMS (ES): m/z 478.3 [M+H]⁺.

Example 6

To a solution of Example 6F (3.75 mg, 7.85 μmol) in THF (1 mL) and water (0.5 mL) was added lithium hydroxide (3 mg, 0.125 mmol) and MeOH (0.1 mL). The reaction mixture was stirred at room temperature for 40 min. The solvent was removed under reduced pressure and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 3-40% B over 25 minutes, then a 5-minute hold at 100% B; Flow: 20 mL/min. to give Example 6 (1.2 mg, 30%). LCMS (ES): m/z 464.1 [M+H]⁺. $^1$H NMR (500 MHz, CD$_3$OD) δ 7.62-7.15 (m, 8H), 6.55 (d, J=7.3 Hz, 1H), 5.39-4.97 (m, 3H), 4.19 (br t, J=5.1 Hz, 1H), 4.13-3.93 (m, 2H), 3.46 (t, J=5.6 Hz, 2H), 2.96 (br d, J=5.2 Hz, 2H), 2.78 (t, J=6.2 Hz, 2H), 2.54-2.39 (m, 1H), 2.31-2.10 (m, 3H), 2.01-1.87 (m, 2H). Human αVβ6 IC50 (nM)=80.

Example 7

(±)-3-(6-Methoxypyridin-3-yl)-3-(1-(3-(5,6,7,8-tetrahydro-1,8-naphthyridin-2-yl)propyl)-1H-pyrazol-4-yl)propanoic acid (Racemate)

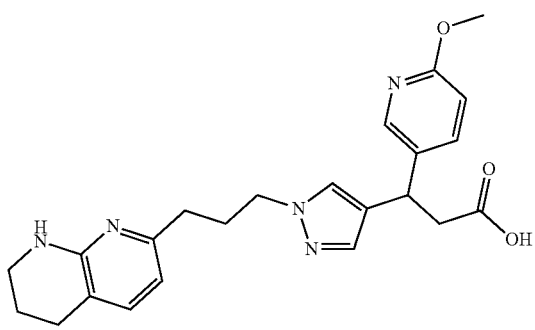

Example 7

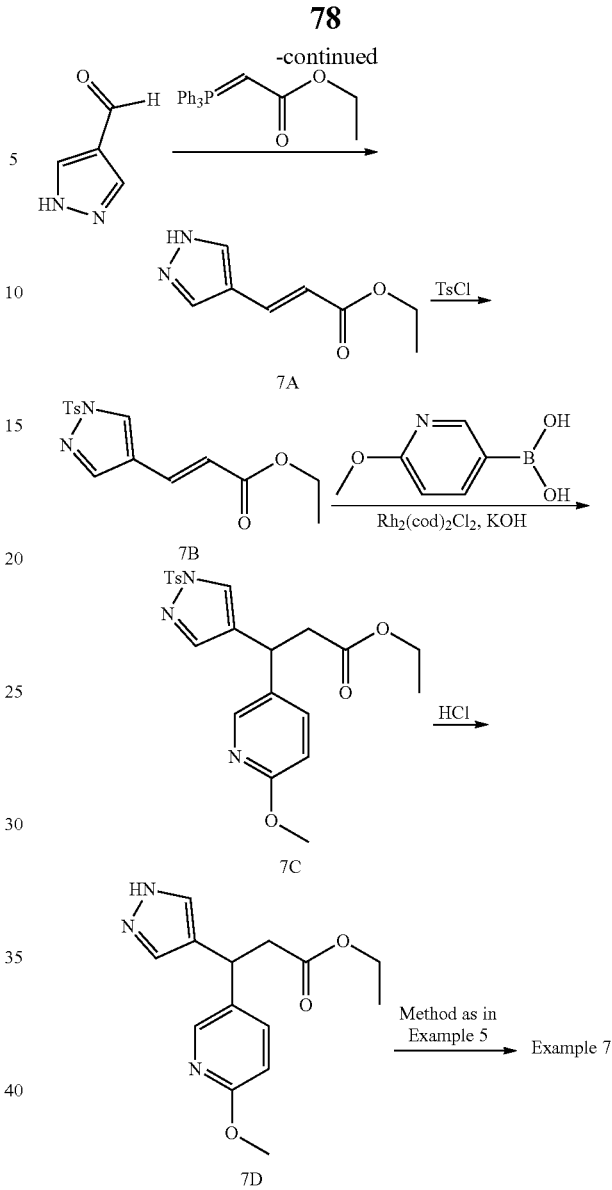

Example 7A

To a solution of 1H-pyrazole-4-carbaldehyde (300 mg, 3.12 mmol) was added ethyl 2-(triphenylphosphoranylidene)acetate (1360 mg, 3.90 mmol) in toluene (10 mL). The mixture was heated at 90° C. for 2 h. The solvent was removed in vacuo. The crude material was purified by flash chromatography to afford Example 7A (450 mg, 2.71 mmol, 87% yield) as a white solid. LCMS (ES): m/z 167.1 [M+H]⁺.

Example 7B

To a mixture of Example 7A in CH$_2$Cl$_2$ (35 mL) was added 4-methylbenzene-1-sulfonyl chloride (952 mg, 4.99 mmol) and TEA (2.088 mL, 14.98 mmol). The reaction mixture was stirred at room temperature for 3 h. The solvent was evaporated and the mixture was diluted with 30 mL water and extracted with EtOAc (50×3 mL). The organic layers were combined, concentrated and purified by flash chromatography to give Example 7B (1.15 g, 72%). LCMS (ES): m/z 321.2 [M+H]⁺. $^1$H NMR (400 MHz, CDCl$_3$) δ

8.24 (s, 1H), 7.93 (d, J=8.4 Hz, 2H), 7.89 (s, 1H), 7.51 (d, J=16.1 Hz, 1H), 7.38 (d, J=8.1 Hz, 2H), 6.27 (d, J=16.0 Hz, 1H), 4.26 (q, J=7.1 Hz, 2H), 2.46 (s, 3H), 1.33 (t, J=7.1 Hz, 3H).

Example 7C

To a degassed solution of (6-methoxypyridin-3-yl)boronic acid (477 mg, 3.12 mmol) and Example 7B (500 mg, 1.56 mmol) in dioxane (7804 μL) and THF (7804 μL) was added 1N potassium hydroxide (3121 μl, 3.12 mmol) and chloro(1,5-cyclooctadiene)rhodium(I) dimer (92 mg, 0.187 mmol). The mixture was heated at 80° C. 2 h. The mixture was diluted with 10 mL water and extracted with EtOAc (25×3 mL). The organic portions were combined, concentrated, and purified by flash chromatography to give Example 7C (206 mg, 30%). LCMS (ES): m/z 430.0 [M+H]+.

Example 7D

To a solution of Example 7C (206 mg, 0.480 mmol) was added 4M HCl in dioxane (1 mL) and ethanol (0.3 mL). The reaction mixture was stirred for 0.5 h. The mixture was concentrated and purified by prep HPLC (Phenomenex Luna Axia 5μ C18 30×100 mm; 10 min gradient from 85% A: 15% B to 0% A: 100% B (A=90% H₂O/10% ACN+0.1% TFA); (B=90% ACN/10% H₂O+0.1% TFA); detection at 220 nm) to give Example 7D (578 mg, 87%). LCMS (ES): m/z 276.1 [M+H]+.

Example 7 was prepared from Example 7D according to the method described in Example 6. LCMS (ES): m/z 422.1 [M+H]+. ¹H NMR (500 MHz, CD₃OD) δ 8.04 (d, J=1.9 Hz, 1H), 7.63 (dd, J=8.5, 2.1 Hz, 1H), 7.50 (s, 1H), 7.41-7.20 (m, 2H), 6.75 (d, J=8.6 Hz, 1H), 6.45 (br d, J=7.2 Hz, 1H), 4.38 (br t, J=8.0 Hz, 1H), 4.11 (td, J=13.7, 7.1 Hz, 2H), 3.87 (s, 3H), 3.51-3.38 (m, 2H), 2.89-2.68 (m, 3H), 2.53-2.45 (m, 1H), 2.42-2.30 (m, 1H), 2.28-2.04 (m, 2H), 1.98-1.79 (m, 3H), 1.40-1.21 (m, 1H). Human αVβ6 IC50 (nM)=323.

Example 8

(A)-3-(6-Methoxypyridin-3-yl)-3-(1-(3-(5,6,7,8-tetrahydro-1,8-naphthyridin-2-yl)propyl)-1H-pyrazol-4-yl)propanoic acid

Example 9

(R)-3-(6-Methoxypyridin-3-yl)-3-(1-(3-(5,6,7,8-tetrahydro-1,8-naphthyridin-2-yl)propyl)-1H-pyrazol-4-yl)propanoic acid

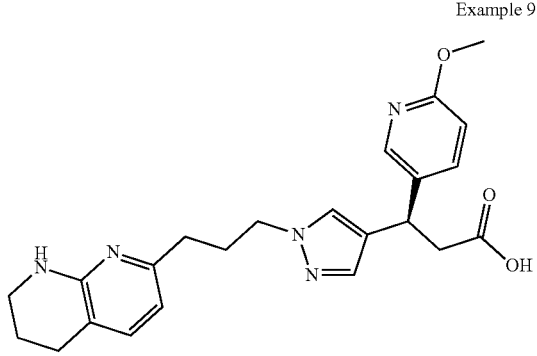

BMT-305248

Example 9

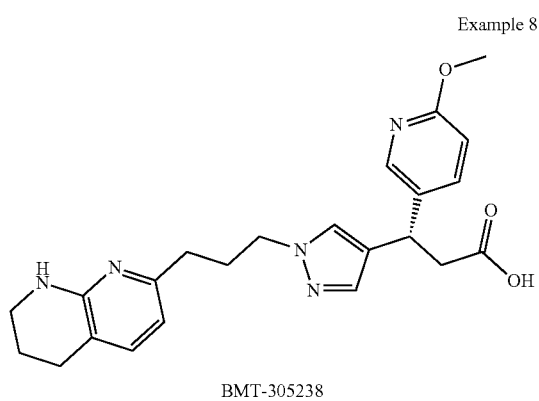

BMT-305238

Example 8

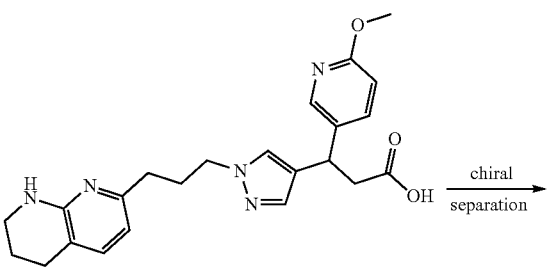

Example 7

Example 8 + Example 9

Example 8 and Example 9

Example 7 (110 mg, 0.26 mmol) was separated by SFC [Berger MGII SFC Prep, Column: Chiralpak AD-H, 21×250 mm, 5 micron Mobile Phase: 20% B=10 mM ammonium acetate in (50:50) Acetonitrile/MeOH-80% CO₂, 150 bar, flow conditions: 45 mL/min, 120 bar, 40° C. Detector Wavelength: 265 nm; Injection details: 0.5 mL of 22.2 mg/mL in MeOH/ACN] to give Example 8 (38 mg, 28%) and Example 9 (41 mg, 30%). Example 8: ¹H NMR (400 MHz, CD₃OD) δ 8.07 (d, J=2.0 Hz, 1H), 7.65 (br d, J=8.4 Hz, 1H), 7.53 (s, 1H), 7.43-7.26 (m, 2H), 6.77 (d, J=8.6 Hz, 1H), 6.48 (d, J=7.5 Hz, 1H), 4.40 (t, J=7.9 Hz, 1H), 4.22-4.02 (m, 2H), 3.89 (s, 3H), 3.56-3.41 (m, 2H), 2.91-2.71 (m, 3H), 2.59-2.33 (m, 2H), 2.28-2.08 (m, 2H), 2.06-1.85 (m, 3H). Human αVβ6 IC50 (nM)=64.

Example 9

¹H NMR (400 MHz, CD₃OD) δ 8.07 (d, J=2.0 Hz, 1H), 7.65 (br d, J=8.4 Hz, 1H), 7.53 (s, 1H), 7.43-7.26 (m, 2H), 6.77 (d, J=8.6 Hz, 1H), 6.48 (d, J=7.5 Hz, 1H), 4.40 (t, J=IP Hz, 1H), 4.22-4.02 (m, 2H), 3.89 (s, 3H), 3.56-3.41 (m, 2H), 2.91-2.71 (m, 3H), 2.59-2.33 (m, 2H), 2.28-2.08 (m, 2H), 2.06-1.85 (m, 3H). Human αVβ6 IC50 (nM)=213.

Example 10
(±)-3-(3-Fluoro-4-methoxyphenyl)-3-(4-(3-(5,6,7,8-tetrahydro-1,8-naphthyridin-2-yl)propyl)-1H-pyrrol-2-yl)propanoic acid
Example 10
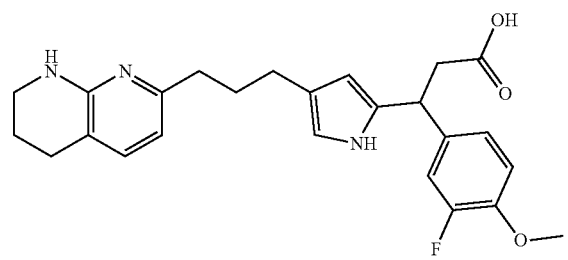
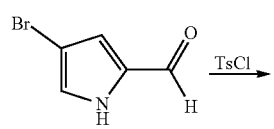
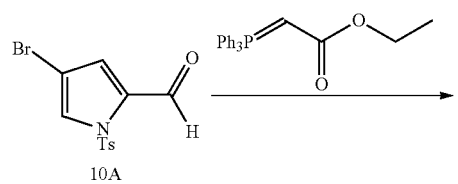
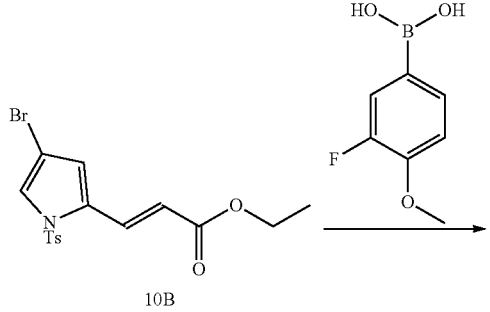
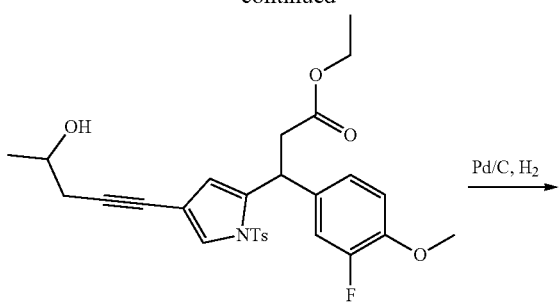
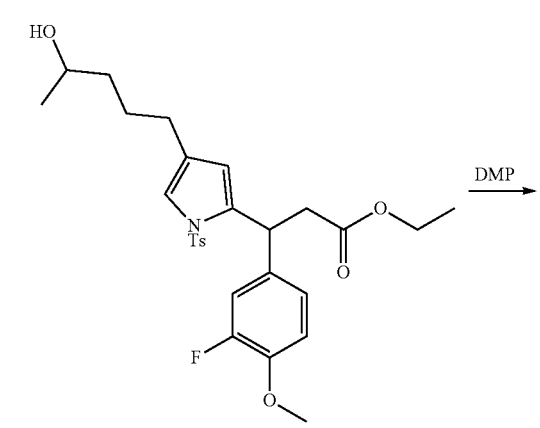
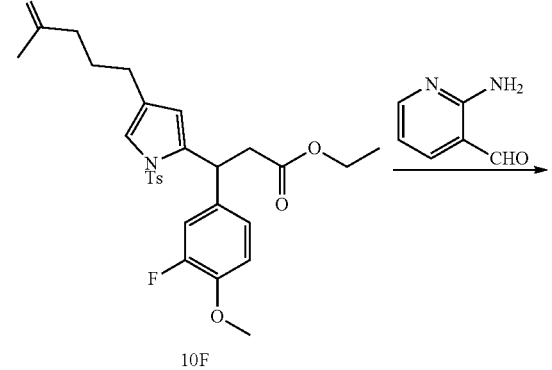
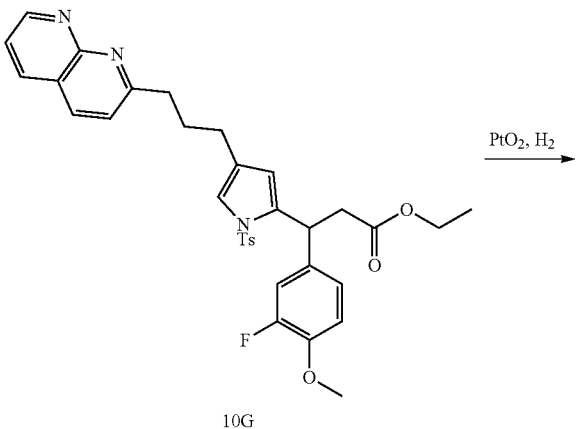

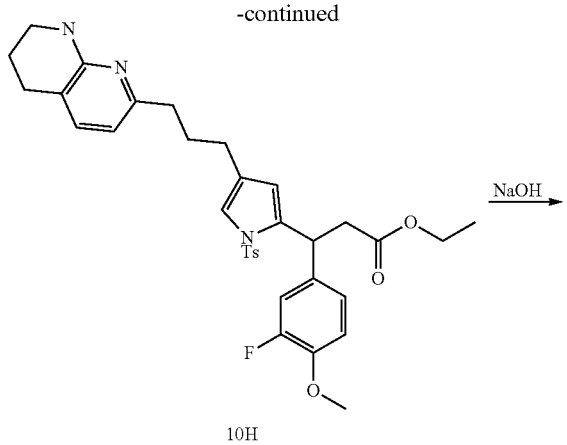

10H

Example 10

Example 10A

To a stirred suspension of NaH (60% in mineral oil) (0.138 g, 3.45 mmol) in THF (19.16 mL) at 23° C. was added 4-bromo-1H-pyrrole-2-carbaldehyde (0.500 g, 2.87 mmol) and the reaction mixture stirred at 23° C. under $N_2$ for 1 h. TsCl (0.603 g, 3.16 mmol) was added and the reaction mixture stirred at 23° C. under $N_2$ for 23 h. The reaction mixture was quenched with sat. $NH_4Cl$ and extracted with EtOAc. The organic layer was washed with water, brine, dried over anhydrous $Na_2SO_4$, filtered and concentrated. The crude product was purified by chromatography (0 to 25% hexanes/EtOAc) to yield Example 10A (0.774 g, 2.358 mmol, 82% yield) as a white solid. $^1$H NMR (500 MHz, $CDCl_3$) δ 9.96 (s, 1H), 7.84-7.78 (m, 2H), 7.58 (d, J=1.7 Hz, 1H), 7.36 (d, J=8.0 Hz, 2H), 7.11 (d, J=1.9 Hz, 1H), 2.45 (s, 3H). LCMS (ES): m/z 330.1 [M+H]$^+$.

Example 10B

A solution of Example 10A (0.544 g, 1.658 mmol) and ethyl 2-(triphenylphosphoranylidene)acetate (0.722 g, 2.072 mmol) in toluene (5.31 mL) were heated at 90° C. for 2 h. The reaction mixture was cooled to room temperature and the solvent was removed in vacuo. The crude product was purified by chromatography (0 to 30% hexanes/EtOAc) to yield Example 10B (0.347 g, 0.871 mmol, 53% yield). LCMS (ES): m/z 398.3 [M+H]$^+$. $^1$H NMR (500 MHz, DMSO) δ 7.89 (d, J=16.0 Hz, 1H), 7.85 (d, J=1.4 Hz, 1H), 7.80 (d, J=8.3 Hz, 2H), 7.50 (d, J=8.3 Hz, 2H), 7.26 (d, J=1.4 Hz, 1H), 6.46 (d, J=16.0 Hz, 1H), 4.18 (q, J=7.1 Hz, 2H), 2.39 (s, 3H), 1.25 (t, J=7.2 Hz, 3H).

Example 10C

To a degassed solution of (3-fluoro-4-methoxyphenyl) boronic acid (0.296 g, 1.743 mmol) and Example 10B (0.347 g, 0.871 mmol) in dioxane (8.71 mL) was added KOH (1M aq.) (1.743 mL, 1.743 mmol) and chloro(1,5-cyclooctadiene)rhodium(1) dimer (0.052 g, 0.105 mmol). The mixture was degassed for 10 min and heated at 100° C. for 1 h. The reaction mixture was cooled to room temperature, diluted with water and extracted with EtOAc (3×). The combined organic layers were dried over anhydrous $Na_2SO_4$, filtered and concentrated. The crude was purified by flash chromatography (0 to 25% hexanes/EtOAc) to yield Example 10C (0.264 g, 0.503 mmol, 58% yield) as a clear oil. LCMS (ES): m/z 524.3 [M+H]$^+$.

Example 10D

A mixture of Example 10C (0.264 g, 0.503 mmol), pent-4-yn-2-ol (0.071 mL, 0.755 mmol), triethylamine (0.281 mL, 2.014 mmol), bis(triphenylphosphine)palladium (II) chloride (0.021 g, 0.030 mmol) and copper(I) iodide (3.84 mg, 0.020 mmol) in DMF (2.52 mL) was stirred at 80° C. for 18 h. The reaction mixture was cooled to room temperature, diluted with EtOAc and washed with 10% aq. LiCl. The organic layer was washed with brine, dried over anhydrous $Na_2SO_4$, filtered and concentrated. The crude product was purified by flash chromatography (0 to 50% hexanes/ethyl acetate) to yield Example 10D (0.122 g, 0.231 mmol, 46% yield) as a yellow oil. LCMS (ES): m/z 528.5 [M+H]$^+$.

Example 10E

A mixture of Example 10D (0.120 g, 0.227 mmol) and Pd/C (0.073 g, 0.068 mmol) in EtOH (1.995 mL) was stirred under a $H_2$ atmosphere (balloon, 1 atm, 0.458 mg, 0.227 mmol) for 2.5 h. After filtration through a pad of CELITE® and concentration, Example 10E (0.110 g, 0.207 mmol, 91% yield) was isolated as a clear oil which was used in the next step without further purification. LCMS (ES): m/z 532.2 [M+H]$^+$.

Example 10F

To a solution of Example 10E (0.110 g, 0.207 mmol) in $CH_2Cl_2$ (1.035 mL) at room temperature was added Dess-Martin periodinane (0.105 g, 0.248 mmol) and the reaction mixture stirred at room temperature for 2 h. The mixture was diluted with $Et_2O$, filtered through CELITE® and the filtrate was concentrated. The crude product was purified by flash chromatography (0 to 35% hexanes/ethyl acetate) to yield Example 10F (0.0613 g, 0.116 mmol, 56% yield) as a light yellow oil. LCMS (ES): m/z 530.5 [M+H]$^+$. $^1$H NMR (500 MHz, $CD_3OD$) δ 7.36 (d, J=8.3 Hz, 2H), 7.15 (d, J=8.3 Hz, 2H), 7.12 (s, 1H), 6.89-6.80 (m, 1H), 6.79-6.72 (m, 1H), 6.56 (dd, J=12.5, 2.1 Hz, 1H), 6.21 (d, J=1.1 Hz, 1H), 4.98 (t, J=8.1 Hz, 1H), 4.01 (q, J=7.2 Hz, 2H), 3.82 (s, 3H), 2.89-2.69 (m, 2H), 2.45 (dt, J=18.1, 7.3 Hz, 4H), 2.35 (s, 3H), 2.11 (s, 3H), 1.85-1.75 (m, 2H), 1.10 (t, J=7.2 Hz, 3H).

Example 10G

To a solution of Example 10F (60 mg, 0.113 mmol) in $CH_2Cl_2$ (0.100 mL) and EtOH (0.300 mL) was added pyrrolidine (0.011 mL, 0.136 mmol) followed by 2-aminonicotinaldehyde (13.84 mg, 0.113 mmol). The mixture was then stirred at room temperature overnight. The crude product was purified by flash chromatography (0 to 50% DCM/EtOAc) to give Example 10G (58 mg, 83%). LCMS (ES): m/z 616.6 [M+H]$^+$. $^1$H NMR (500 MHz, $CDCl_3$) δ 9.12 (dd, J=4.1, 1.9 Hz, 1H), 8.19 (dd, J=8.0, 1.9 Hz, 1H), 8.13 (d, J=8.3 Hz, 1H), 7.48 (dd, J=8.1, 4.3 Hz, 1H), 7.39 (d, J=8.3 Hz, 3H), 7.16-7.04 (m, 3H), 6.80-6.76 (m, 2H), 6.62 (dd, J=12.4, 1.9 Hz, 1H), 6.09 (s, 1H), 4.98 (t, J=8.0 Hz, 1H), 4.08-3.99 (m, 2H), 3.84 (s, 3H), 3.10 (t, J=7.7 Hz, 2H), 2.83 (d, J=7.4 Hz, 1H), 2.76-2.67 (m, 1H), 2.56 (t, J=7.6 Hz, 2H), 2.36 (s, 3H), 2.25-2.14 (m, 2H), 1.14 (t, J=7.2 Hz, 3H).

Example 10H

A solution of Example 10G (57.9 mg, 0.094 mmol) and $PtO_2$ (4.27 mg, 0.019 mmol) in EtOH (1.710 mL) was stirred under an H₂ (balloon, 1 atm) for 20 h. The solvent was removed in vacuo. This material was purified by Prep. HPLC (XBridge Prep C18 5u OBD 19×100 mm, 10 min gradient, 15 min run, 15% to 100% Solvent B=90% MeOH-10% H₂O-0.1% TFA, Solvent A=10% MeOH-90% H₂O-0.1% TFA to yield Example 10H (49.6 mg, 0.068 mmol, 72% yield). LCMS (ES): m/z 620.6 [M+H]⁺. ¹H NMR (500 MHz, CD₃OD) δ 7.54 (d, J=7.4 Hz, 1H), 7.38-7.30 (m, 2H), 7.19-7.08 (m, 3H), 6.82 (d, J=8.5 Hz, 1H), 6.78-6.73 (m, 1H), 6.57 (d, J=7.4 Hz, 1H), 6.52 (dd, J=12.5, 2.1 Hz, 1H), 6.22 (d, J=1.4 Hz, 1H), 4.96 (t, J=8.0 Hz, 1H), 4.01 (q, J=7.1 Hz, 2H), 3.81 (s, 3H), 3.53-3.46 (m, 2H), 2.84-2.75 (m, 4H), 2.71 (t, J=7.7 Hz, 2H), 2.54 (t, J=7.3 Hz, 2H), 2.34 (s, 3H), 2.01-1.92 (m, 4H), 1.10 (t, J=1.2 Hz, 3H).

Example 10

To a solution of Example 10H (49.6 mg, 0.068 mmol) in EtOH (0.500 mL) was added NaOH (0.169 mL, 0.338 mmol) and the reaction mixture stirred at room temperature overnight. The solvent was removed in vacuo and purification by via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 3-40% B over 25 minutes, then a 5-minute hold at 100% B; Flow: 20 mL/min. to give Example 10 (14 mg, 44%). LCMS (ES): m/z 438.2 [M+H]⁺. ¹H NMR (500 MHz, CD₃OD) δ 7.43 (d, J=7.4 Hz, 1H), 7.02-6.83 (m, 4H), 6.51 (d, J=7.3 Hz, 1H), 5.86 (s, 1H), 4.36 (dd, J=9.3, 6.6 Hz, 1H), 3.81 (s, 3H), 3.45 (t, J=5.5 Hz, 2H), 2.86-2.80 (m, 1H), 2.76 (t, J=6.1 Hz, 2H), 2.73-2.68 (m, 1H), 2.58 (t, J=7.7 Hz, 2H), 2.53-2.40 (m, 2H), 1.95-1.86 (m, 4H). Human αVβ6 IC50 (nM)=136.

Example 11

(±)-3-(6-Methoxypyridin-3-yl)-3-(1-(4-(5,6,7,8-tetrahydro-1,8-naphthyridin-2-yl)butyl)-1H-pyrazol-4-yl)propanoic acid

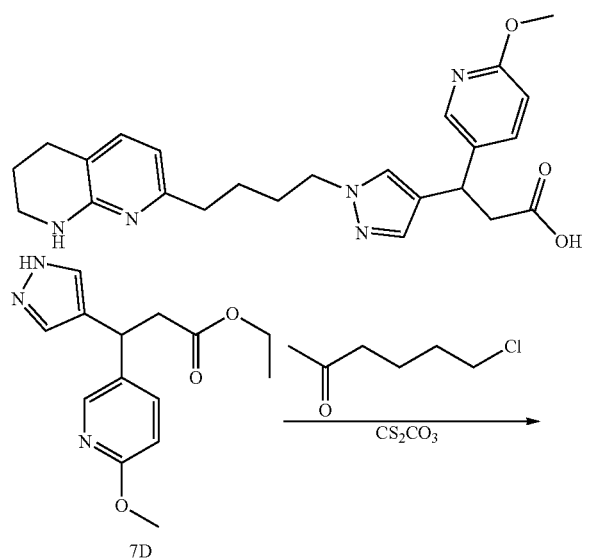

Example 11

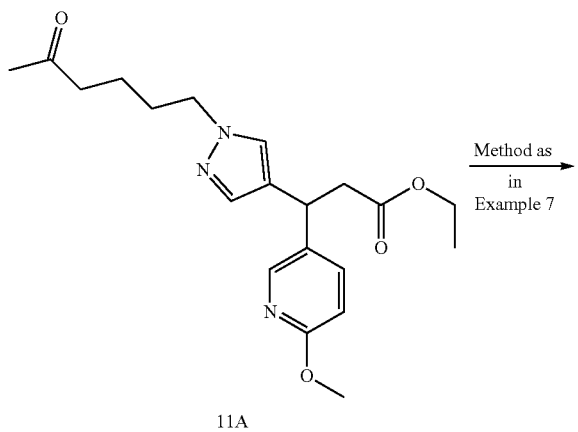

11A

Example 11A

To a solution of Example 7D (70 mg, 0.139 mmol) in acetonitrile (3 mL) was added 6-chlorohexan-2-one (70 mg, 0.520 mmol) and Cs₂CO₃ (200 mg, 0.614 mmol). The mixture was stirred at room temperature overnight. The solid was filtered and the filtrate concentrated. Purification by flash chromatography gave Example 11A (58 mg, 61%). LCMS (ES): m/z 374.4 [M+H]⁺.

Example 11 was prepared from Example 11A according to the method described in Example 10. LCMS (ES): m/z 436.2 [M+H]⁺. ¹H NMR (500 MHz, CD₃OD) δ 8.04 (s, 1H), 7.75 (s, 1H), 7.67-7.59 (m, 1H), 7.40 (br d, J=7.2 Hz, 1H), 7.30 (s, 1H), 6.75 (d, J=8.6 Hz, 1H), 6.43 (br d, J=7.2 Hz, 1H), 4.37 (br dd, J=10.4, 6.2 Hz, 1H), 4.26-4.04 (m, 2H), 3.87 (s, 3H), 3.44 (br t, J=5.3 Hz, 2H), 2.89-2.68 (m, 4H), 2.57-2.40 (m, 2H), 1.95-1.77 (m, 4H), 1.49-1.14 (m, 2H). Human αVβ6 IC50 (nM)=100.

Example 12

(S)-3-(6-Hydroxypyridin-3-yl)-3-(3-(3-(5,6,7,8-tetrahydro-1,8-naphthyridin-2-yl)propyl)-1H-pyrazol-1-yl)propanoic acid Example 12

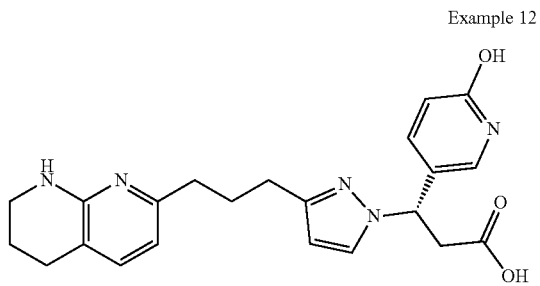

87

-continued

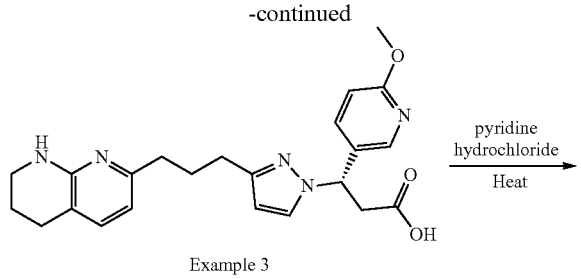

Example 3 pyridine
hydrochloride
—————→
Heat

Example 12

Example 12

A mixture of Example 3 (10 mg, 0.024 mmol) and pyridine hydrochloride (34.3 mg, 0.297 mmol) was heated at 125° C. for 7.5 min. The reaction mixture was cooled to room temperature. This material was purified by Prep. HPLC (Phenomenex Luna AXIA 5u C18 21.2×100 mm, 10 min gradient, 12 min run, 0% to 100% Solvent B=90% ACN-10% H$_2$O-0.1% TFA, Solvent A=10% ACN-90% H$_2$O-0.1% TFA) to give Example 12 (2.8 mg, 29%). $^1$H NMR (400 MHz, CD$_3$OD) δ 7.62-7.53 (m, 2H), 7.42-7.34 (m, 2H), 6.51-6.42 (m, 2H), 6.10 (d, J=2.4 Hz, 1H), 5.62 (dd, J=9.0, 6.4 Hz, 1H), 3.48-3.40 (m, 2H), 3.10 (dd, J=14.7, 9.0 Hz, 1H), 2.94 (dd, J=14.6, 6.3 Hz, 1H), 2.76 (t, J=6.2 Hz, 2H), 2.64-2.55 (m, 4H), 2.04-1.95 (m, 2H), 1.89 (br. s., 2H). LCMS (ES): m/z 408.4 [M+H]$^+$. Human αVβ6 IC50 (nM) =31.

Example 13 (Enantiomer 1) and Example 14 (Enantiomer 2)

3-(6-Methoxypyridin-3-yl)-3-(4-(4-(5,6,7,8-tetra-hydro-1,8-naphthyridin-2-yl)butyl)thiazol-2-yl)pro-panoic acid (Chiral)

Example 13 and Example 14

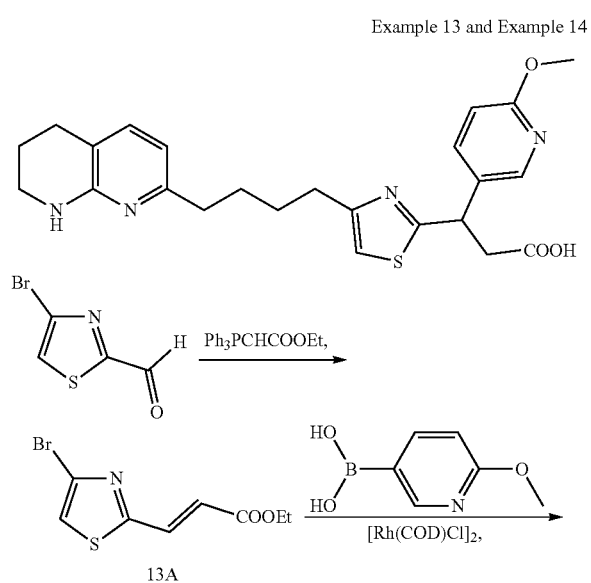

88

-continued

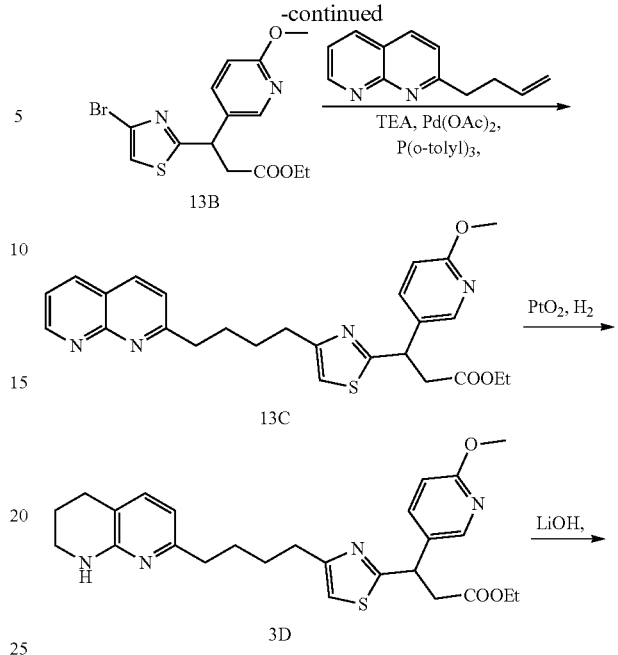

Example 13A

To a stirred solution of 4-bromothiazole-2-carbaldehyde (2 g, 10.41 mmol) in toluene (30 mL) under nitrogen atmosphere was added (carbethoxymethylene)triph-enylphosphorane (4.35 g, 12.5 mmol) and the resulting reaction mixture was stirred at 100° C. for 16 h. The reaction mixture was concentrated and the crude product was purified by combiflash chromatography (24 g Redisep® SiO$_2$ column, eluting with 23% EtOAc in n-hexanes) to afford 13A (2 g, 73%) as a white solid. $^1$H NMR (400 MHz, CDCl$_3$) δ 7.67 (d, J=16.00 Hz, 1H), 7.29 (s, 1H), 6.75 (d, J=15.6 Hz, 1H), 4.28 (q, J=7.20 Hz, 2H), 1.33 (t, J=7.20 Hz, 3H). LCMS (ES): m/z 264.2 [M+H]$^+$.

Example 13B

A stirred solution of Example 13A in 1,4-dioxane (10 mL) and water (1 mL) was purged with argon for 5 min. Chloro(1,5-cyclooctadiene)rhodium(I) dimer (47 mg, 0.095 mmol) and TEA (0.53 mL, 3.81 mmol) were added and the resulting reaction mixture was stirred at 85° C. for 16 h. The reaction mixture was slowly poured into water (50 mL) and extracted with EtOAc (2×20 mL). The combined organic layer was washed with brine (50 mL), dried (Na$_2$SO$_4$), filtered and concentrated. The crude product was purified by combiflash chromatography (12 g Redisep® SiO$_2$ column, eluting with 22% EtOAc in n-hexanes) to afford 13B (230 mg, 33%) as a pale brown oil. $^1$H NMR (400 MHz, CDCl$_3$) δ 8.13 (d, J=2.40 Hz, 1H), 7.55 (dd, J=2.80, 8.60 Hz, 1H), 7.10 (s, 1H), 6.71 (d, J=8.40 Hz, 1H), 4.75 (t, J=7.60 Hz, 1H), 4.07 (q, J=6.40 Hz, 2H), 3.91 (s, 3H), 3.42 (dd, J=7.20, 16.00 Hz, 1H), 2.96 (dd, J=7.20, 16.80 Hz, 1H), 1.17 (t, J=7.20 Hz, 3H). LCMS (ES): m/z 371.0 [M+H]$^+$.

Example 13C

To a stirred solution of Example 13B (300 mg, 0.81 mmol) and 2-(but-3-en-1-yl)-1,8-naphthyridine (149 mg, 0.81 mmol) in acetonitrile (4 mL) under argon atmosphere was added tri-o-tolylphosphine (36.9 mg, 0.121 mmol), palladium(II) acetate (18.14 mg, 0.081 mmol) and TEA (0.282 mL, 2.0 mmol) and the resulting reaction mixture was stirred at 80° C. for 16 h. The reaction mixture was cooled to room temperature, filtered, concentrated and the crude product was purified by combiflash chromatography (24 g Redisep® SiO$_2$ column, eluting with 4% MeOH in CHCl$_3$) to afford 13C (320 mg, 83%) as a brown oil. LCMS (ES): m/z 475.0 [M+H]$^+$.

Example 13D

To a solution of Example 3C (200 mg, 0.421 mmol) in ethanol (8 mL) was added platinum(IV) oxide (2 mg, 8.81 µmol) under nitrogen atmosphere. The reaction mixture was purged with hydrogen and stirred under hydrogen bladder pressure at room temperature for 16 h. The reaction mixture was filtered and the filtrate was concentrated to afford 13D (180 mg, 63%) as a pale yellow oil (crude). LCMS (ES): m/z 481.4 [M+H]$^+$.

Example 13 and Example 14: To a stirred solution of Example 13D (150 mg, 0.312 mmol), in THF (3 mL) and methanol (3 mL) mixture was added a solution of LiOH·H$_2$O (15 mg, 0.31 mmol) in water (3 mL) and the resulting reaction mixture was stirred at room temperature for 4 h. Then citric acid (120 mg, 0.624 mmol) was added and the mixture was stirred further at room temperature for 1 h. The reaction mixture was filtered, concentrated and the crude racemic product was purified by preparative HPLC (Column: INTERSIL ODS C18 (250×19) mm 5 micron; M. Phase A: 10 mM NH$_4$OAc in water; M. Phase B: Acetonitrile, flow rate: 17.0 mL/min; time (min)/% B: 0/20, 8/40, 14/60; Detection: UV at 254 nm) followed by chiral preparative HPLC (Column: Lux-cellulose C4 (250×21.2) mm 5 micron column; flow rate: 19.0 mL/min; Mobile Phase B: 0.1% DEA in MeOH; time (min)/% B: 0/100, 20/100, temperature: 35° C.; Detection: UV at 254 nm) to afford Example 13 (35 mg, 27%) as a white solid (first-eluting isomer). LCMS (ES): m/z 453.2 [M+H]$^+$. $^1$H NMR (400 MHz, CD$_3$OD) δ 8.14 (d, J=1.20 Hz, 1H), 7.72 (dd, J=8.60 & 2.40 Hz, 1H), 7.42 (d, J=5.20 Hz, 1H), 6.99 (s, 1H), 6.78 (d, J=7.20 Hz, 1H), 6.46 (d, J=7.60 Hz, 1H), 4.81-4.81 (m, 1H), 3.90 (s, 3H), 3.48-3.47 (m, 2H), 3.30-3.40 (m, 1H), 2.77-2.86 (m, 5H), 2.56-2.65 (m, 2H), 1.91-1.95 (m, 3H), 1.71-1.74 (m, 1H), 1.46-1.49 (m, 2H). Human αVβ6 IC50 (nM)=77. Example 14 (32 mg, 24%) was isolated as the second-eluting isomer as a white solid. LCMS (ES): m/z 453.2 [M+H]$^+$. $^1$H NMR (400 MHz, CD$_3$OD) δ 8.14 (d, J=1.20 Hz, 1H), 7.72 (dd, J=8.60 & 2.40 Hz, 1H), 7.42 (d, J=5.20 Hz, 1H), 6.99 (s, 1H), 6.78 (d, J=7.20 Hz, 1H), 6.46 (d, J=7.60 Hz, 1H), 4.81-4.81 (m, 1H), 3.90 (s, 3H), 3.48-3.47 (m, 2H), 3.30-3.40 (m, 1H), 2.77-2.86 (m, 5H), 2.56-2.65 (m, 2H), 1.91-1.95 (m, 3H), 1.71-1.74 (m, 1H), 1.46-1.49 (m, 2H). Human αVβ6 IC50 (nM)=2.1; Human αVβ1 IC50 (nM)=241; Human αVβ3 IC50 (nM)=1.9; Human αVβ5 IC50 (nM)=11; and Human αVβ8 IC50 (nM)=510.

Example 15 (Enantiomer 1) and Example 16 (Enantiomer 2)

3-(6-Methoxypyridin-3-yl)-3-(4-(3-(5,6,7,8-tetrahydro-1,8-naphthyridin-2-yl)propyl)thiazol-2-yl) propanoic acid

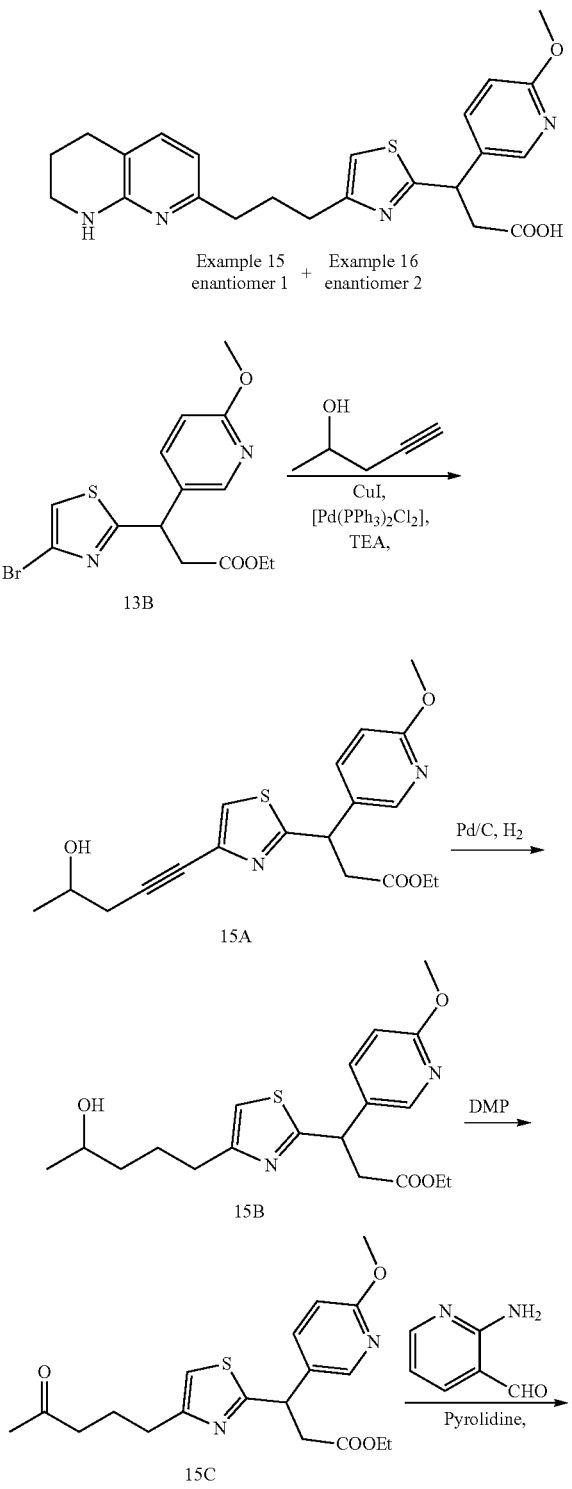

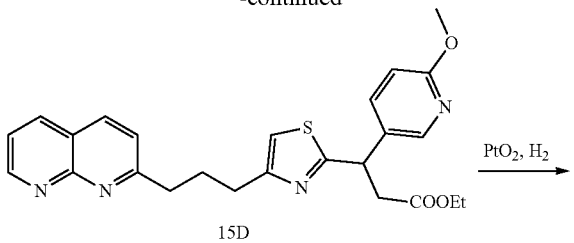

15D

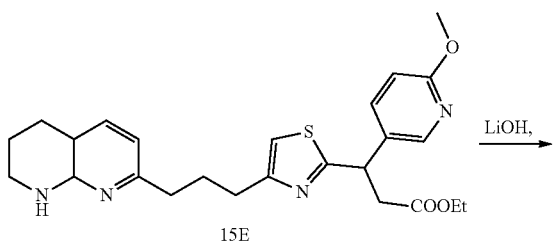

15E

Example 15 enantiomer 1 + Example 16 enantiomer 2

Example 15A

To a stirred solution of Example 13B (400 mg, 1.08 mmol), pent-4-yn-2-ol (109 mg, 1.29 mmol) in TEA (8 mL) under nitrogen atmosphere was added copper(I) iodide (10.26 mg, 0.05 mmol) followed by bis(triphenylphosphine) palladium (II) dichloride (38 mg, 0.05 mmol) and the resulting reaction mixture was degassed with argon gas for 2 min and then stirred at 80° C. for 16 h. The reaction mixture was filtered, concentrated and the crude product was purified by combiflash chromatography (24 g Redisep® SiO$_2$ column, eluting with 54% EtOAc in pet ether) to afford 15A (190 mg, 47%) as a pale yellow oil. $^1$H NMR (400 MHz, CDCl$_3$) δ 8.14 (d, J=2.40 Hz, 1H), 7.56 (dd, J=8.80 & 2.40 Hz, 1H), 7.27 (s, 1H), 6.71 (d, J=8.40 Hz, 1H), 4.73 (t, J=7.20 Hz, 1H), 4.08 (q, J=7.20 Hz, 2H), 3.90-4.00 (m, 1H), 3.92 (s, 3H), 3.44 (dd, J=16.00 & 6.80 Hz, 1H), 2.96 (dd, J=12.40 & 8.00 Hz, 1H), 2.50-2.60 (m, 2H), 1.28 (d, J=12.00 Hz, 3H), 1.19 (t, J=7.20 Hz, 3H). LCMS (ES): m/z 375.0 [M+H]$^+$.

Example 15B

To a degassed solution of Example 15A (200 mg, 0.534 mmol) in EtOH (5 mL) was added 10% palladium on carbon (2 mg, 0.019 mmol) and the resulting reaction mixture was stirred under hydrogen bladder pressure at room temperature for 16 h. The reaction mixture was filtered through CELITE® pad and the filtrate concentrated to afford 15B (170 mg, 84%) as a pale yellow oil. LCMS (ES): m/z 379.4 [M+H]$^+$.

Example 15C

To a solution of Example 15B (300 mg, 0.79 mmol) in dichloromethane (15 mL) was added DMP (672 mg, 1.59 mmol) at 0° C. and the resulting mixture was stirred at room temperature for 60 min. The reaction mass was diluted with dichloromethane (20 mL), washed with 20% sodium bicarbonate solution (20 mL), brine solution (10 mL), dried (Na$_2$SO$_4$), filtered and the filtrate concentrated. The crude product was purified by combiflash chromatography (24 g Redisep® SiO$_2$ column, eluting with 62% EtOAc in pet ether) to afford 15C (150 mg, 50%) as a pale yellow oil. $^1$H NMR (400 MHz, CDCE) δ 8.16 (d, J=2.40 Hz, 1H), 7.58 (dd, J=8.80 & 2.40 Hz, 1H), 6.75 (s, 1H), 6.70 (d, J=8.40 Hz, 1H), 4.76 (t, J=7.60 Hz, 1H), 4.11 (q, J=7.20 Hz, 2H), 3.94 (s, 3H), 3.40 (dd, J=16.40 & 6.80 Hz, 1H), 2.95 (dd, J=16.0 & 8.40 Hz, 1H), 2.70-2.80 (m, 2H), 2.45-2.55 (m, 2H), 2.15 (s, 3H), 1.90-2.00 (m, 2H), 1.12 (t, J=7.20 Hz, 3H). LCMS (ES): m/z 377.0 [M+H]$^+$.

Example 15D

To a solution of Example 15C (130 mg, 0.35 mmol) and 2-aminonicotinaldehyde (51 mg, 0.41 mmol) in ethanol (5 mL) under nitrogen was added pyrrolidine (0.029 mL, 0.35 mmol) and the resulting mixture was stirred at 70° C. for 4 h. The reaction mixture was concentrated and the crude product was purified by combiflash chromatography (24 g Redisep® SiO$_2$ column, eluting with 100% EtOAc to afford 15D (150 mg, 82%) as a pale yellow oil. $^1$H NMR (400 MHz, CDCl$_3$) δ 9.08 (d, J=2.40 Hz, 1H), 8.15 (d, J=1.60 Hz, 1H), 8.14 (d, J=2.0 Hz, 1H), 8.09 (d, J=8.4 Hz, 1H), 7.57 (dd, J=8.80 & 2.40 Hz, 1H), 7.45 (dd, J=8.80 & 2.80 Hz, 1H), 7.38 (d, J=8.40 Hz, 1H), 6.79 (s, 1H), 6.70 (d, J=8.40 Hz, 1H), 4.76 (t, J=7.60 Hz, 1H), 4.06 (q, J=7.20 Hz, 2H), 3.92 (s, 3H), 3.40 (dd, J=16.40 & 6.80 Hz, 1H), 3.10 (dd, J=16.0 & 7.60 Hz, 2H), 2.99 (dd, J=16.0 & 8.40 Hz, 1H), 2.86 (t, J=7.20 Hz, 2H), 2.33 (m, 2H), 1.15 (t, J=7.20 Hz, 3H). LCMS (ES): m/z 463.2 [M+H]$^+$.

Example 15E

To a stirred solution of Example 15D (180 mg, 0.39 mmol) in ethanol (8 mL) was added platinum(IV) oxide (2 mg, 8.81 μmol) under nitrogen atmosphere and the reaction mixture was purged with hydrogen and stirred under hydrogen bladder pressure at room temperature for 16 h. The reaction mixture was filtered and the filtrate concentrated to afford 15E (170 mg, 94%) as a pale yellow oil. $^1$H NMR (400 MHz, CD$_3$OD) δ 8.13 (d, J=3.20 Hz, 1H), 7.68 (dd, J=11.20 & 3.20 Hz, 1H), 7.35 (d, J=10.0 Hz, 1H), 7.05 (s, 1H), 6.77 (d, J=11.0 Hz, 1H), 6.49 (d, J=8.40 Hz, 1H), 4.80-4.90 (m, 1H), 4.06 (q, J=7.20 Hz, 2H), 3.90 (s, 3H), 3.40-3.50 (m, 3H), 3.10 (dd, J=16.0 & 7.60 Hz, 1H), 2.70-2.80 (m, 4H), 2.65 (t, J=10.0 Hz, 2H), 2.06 (t, J=10.0 Hz, 2H), 1.90-2.00 (m, 2H), 1.15 (t, J=7.20 Hz, 3H). LCMS (ES): m/z 467.2 [M+H]$^+$.

Example 15 and Example 16

To a stirred solution of Example 15E (150 mg, 0.32 mmol) in THF (3 mL) and methanol (3 mL) was added a solution of LiOH·H$_2$O (15 mg, 0.64 mmol) in water (3 mL) and the resulting reaction mixture was stirred at room temperature for 4 h. Then citric acid (124 mg, 0.64 mmol) was added and the mixture stirred further at room temperature for 1 h. The reaction mixture was filtered, concentrated and the crude racemic product was purified by preparative HPLC (Column: SYMMETRY C18 (250×19) mm 5 micron; M. Phase A: 10 mM NH$_4$OAC in water (Ph=4.5); M. Phase B: Acetonitrile, flow rate: 18.0 mL/min; time (min)/% B: 0/20, 5/40, 14/60; Detection: UV at 254 nm) and then separated into individual enantiomers by chiral SFC (Chiralpak AD-H (250×21) mm, 5u;% CO$_2$: 60%; % Co solvent: 40%(0.2% DEA in methanol); Total Flow: 70 g/min; back pressure: 100 bar; temperature: 25° C.; detection: UV at 238 nm) to afford Example 15 (30 mg, 21%) as a white solid (first-eluting isomer). $^1$H NMR (400 MHz, CD$_3$OD) δ 8.14

(d, J=1.20 Hz, 1H), 7.69 (dd, J=2.80, 8.60 Hz, 1H), 7.47 (d, J=7.20 Hz, 1H), 7.04 (s, 1H), 6.80 (d, J=8.80 Hz, 1H), 6.56 (d, J=7.60 Hz, 1H), 4.75-4.80 (m, 1H), 3.91 (s, 3H), 3.42-3.50 (m, 2H), 3.15-3.16 (m, 1H), 2.76-2.87 (m, 5H), 2.55-2.61 (m, 2H), 1.95-2.14 (m, 2H), 1.92-1.93 (m, 2H). LCMS (ES): m/z 439.2 [M+H]$^+$. Human αVβ6 IC50 (nM)=0.7; Human αVβ1 IC50 (nM)=55; Human αVβ3 IC50 (nM)=1.4; and Human αVβ8 IC50 (nM)=330. Example 16 (31 mg, 22%, white solid) was isolated as a second-eluting isomer. $^1$H NMR (400 MHz, CD$_3$OD) δ 8.14 (d, J=1.20 Hz, 1H), 7.69 (dd, J=2.80, 8.60 Hz, 1H), 7.47 (d, J=7.20 Hz, 1H), 7.04 (s, 1H), 6.80 (d, J=8.80 Hz, 1H), 6.56 (d, J=7.60 Hz, 1H), 4.75-4.80 (m, 1H), 3.91 (s, 3H), 3.42-3.50 (m, 2H), 3.15-3.16 (m, 1H), 2.76-2.87 (m, 5H), 2.55-2.61 (m, 2H), 1.95-2.14 (m, 2H), 1.92-1.93 (m, 2H). LCMS (ES): m/z 439.2 [M+H]$^+$. Human αVβ6 IC50 (nM)=36.

Example 17 (Enantiomer 1) and Example 18 (Enantiomer 2)

3-(6-Methoxypyridin-3-yl)-3-(5-(4-(5,6,7,8-tetra-hydro-1,8-naphthyridin-2-yl)butyl)thiazol-2-yl)propanoic acid

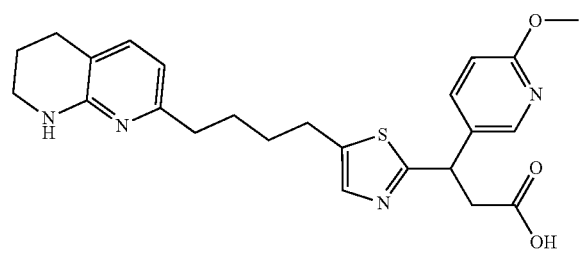

Example 17
Enantiomer 1

Example 18
Enantiomer 2

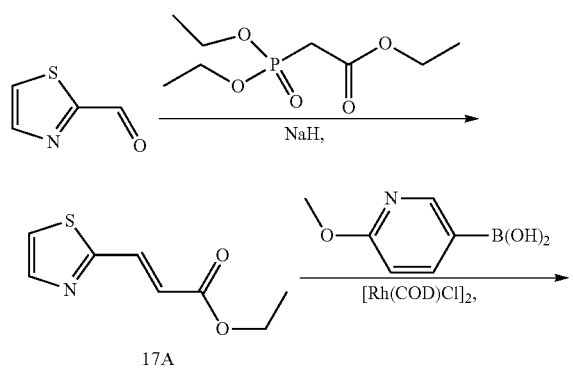

17A

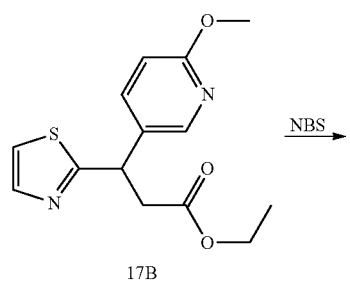

17B

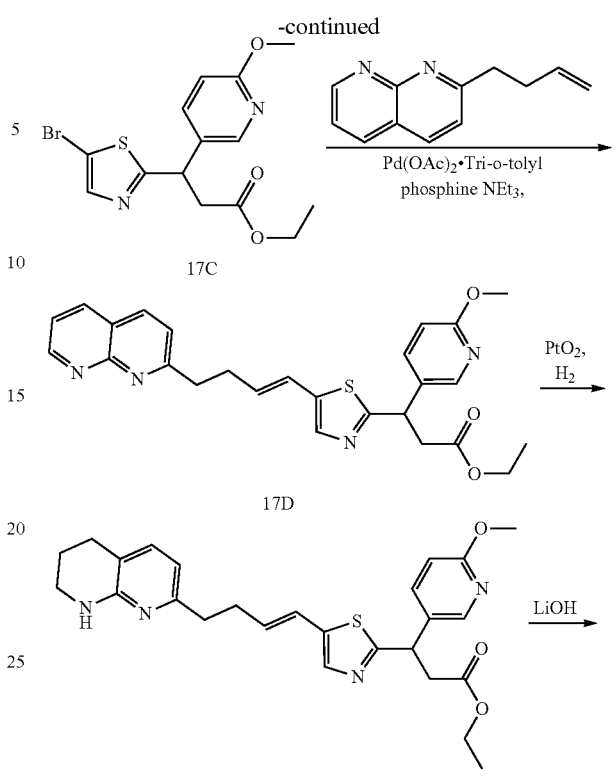

Example 17A

To a solution of triethyl phosphonoacetate (12.88 g, 57.5 mmol) in THF (100 mL) at 0° C. was added NaH (2.12 g, 53 mmol) portion-wise and the resulting reaction mixture was stirred at the same temperature for 1 h. Thiazole-2-carbaldehyde (5 g, 44 mmol) in THF (100 mF) was added and the resulting reaction mixture was stirred at room temperature for 16 h. The reaction mixture was quenched with ice-cold water (100 mF) and extracted with EtOAc (2×200 mF). The combined organic layer was washed with water, brine, dried (Na$_2$SO$_4$), filtered and the filtrate concentrated to afford 17A (6 g, 74%) as a colorless oil. $^1$H NMR (300 MHz, CDCl$_3$) δ 7.20 (d, J=3.30 Hz, 1H), 7.80 (d, J=15.0 Hz, 1H), 7.42 (d, J=3.30 Hz, 1H), 6.71 (d, J=15.0 Hz, 1H), 4.28 (q, J=7.20 Hz, 2H), 1.34 (t, J=7.20 Hz, 3H).

Example 17B

To a stirred solution of Example 17A (2 g, 10.92 mmol) in dioxane (45 mF) and water (15 mF) was added (6-methoxypyridin-3-yl)boronic acid (2.50 g, 16.37 mmol) and the resulting reaction mixture was purged with argon for 10 min. TEA (1.37 mF, 9.82 mmol) and chloro(1,5-cyclooctadiene)rhodium(I) dimer (0.27 g, 0.55 mmol) was added and the resulting reaction mixture was heated to 80° C. and stirred for 16 h. The reaction mixture was cooled to room temperature, diluted with water (50 mL) and extracted with EtOAc (2×50 mL). The combined organic layer was dried (Na$_2$SO$_4$), filtered and the filtrate concentrated. The crude product was purified by combiflash chromatography (40 g Redisep® SiO$_2$ column, eluting with 25% EtOAc in/r-hexanes) to afford 17B (1 g, 31%) as a pale brown solid. $^1$H NMR (400 MHz, CDCl$_3$) δ 8.14 (d, J=2.8 Hz, 1H), 7.70 (d, J=3.2 Hz, 1H), 7.55 (dd, J=8.4 & 2.40 Hz, 1H), 7.21 (s, 1H), 6.69 (s, 1H), 4.82 (t, J=7.60 Hz, 1H), 4.08 (q, J=7.20 Hz, 2H), 3.92 (s, 3H), 3.42 (dd, J=16.0 & 7.20 Hz, 1H), 2.99 (dd, J=16.0 & 7.20 Hz, 1H), 1.17 (t, J=7.20 Hz, 3H). LCMS (ES): m/z 293.2 [M+H]$^+$.

Example 17C

To a stirred solution of Example 17B (700 mg, 2.39 mmol) in DMF (10 mL) was added NBS (639 mg, 3.59 mmol) portion-wise at room temperature and the resulting reaction mixture was stirred at room temperature for 40 h. The reaction mixture was diluted with ice-cold water (10 mL) and extracted with EtOAc (2×25 mL). The combined organic layer was washed with water, brine, dried (Na$_2$SO$_4$), filtered and the filtrate concentrated. The crude product was purified by combiflash chromatography (12 g Redisep® SiO$_2$ column, eluting with 10% EtOAc in n-hexanes) to afford 17C (300 mg, 34%) as a brown oil. $^1$H NMR (300 MHz, CDCl$_3$) δ 8.11 (s, 1H), 7.45-7.60 (m, 2H), 6.71 (d, J=8.70 Hz, 1H), 4.71 (t, J=7.60 Hz, 1H), 4.09 (q, J=7.20 Hz, 2H), 3.92 (s, 3H), 3.38 (dd, J=16.0 & 7.2 Hz, 1H), 2.92 (dd, J=16.0 & 7.2 Hz, 1H), 1.18 (t, J=7.20 Hz, 3H). LCMS (ES): m/z 373.0 [M+H]$^+$.

Example 17D

To a stirred solution of Example 17C (100 mg, 0.27 mmol) in acetonitrile (5 mL) was added 2-(but-3-en-1-yl)-1,8-naphthyridine (74.4 mg, 0.4 mmol) and the reaction mixture was purged with nitrogen for 10 min. Triethylamine (82 mg, 0.808 mmol), tri-o-tolylphosphine (8.20 mg, 0.027 mmol), palladium acetate (6.1 mg, 0.027 mmol) were added and the reaction mixture was heated to 90° C. and stirred for 16 h. The reaction mixture was cooled to room temperature, filtered through CELITE®, and the filtrate was diluted with water (5 mL) and extracted with DCM (2×10 mL). The combined organic layer was dried (Na$_2$SO$_4$), filtered and the filtrate concentrated. The crude product was purified by combiflash chromatography (4 g Redisep® SiO$_2$ column, eluting with 3% methanol in chloroform to afford 17D (85 mg, 49%) as a pale brown oil. LCMS (ES): m/z 475.2 [M+H]$^+$.

Example 17E

Example 17D (85 mg, 0.13 mmol) in ethanol (5 mL) was purged with nitrogen for 5 min. Platinum(IV) oxide (10 mg, 0.044 mmol) was added and the resulting reaction mixture was stirred at room temperature under hydrogen balloon atmosphere for 16 h. The reaction mixture was filtered through a CELITE® pad and the filtrate concentrated to afford 17E (70 mg, 81%) as a pale brown oil. $^1$H NMR (400 MHz, CD$_3$OD) δ 8.11 (s, 1H), 7.67 (dd, J=8.80 & 2.40 Hz, 1H), 7.40 (s, 1H), 7.16 (d, J=7.20 Hz, 1H), 6.78 (d, J=8.40 Hz, 1H), 6.35 (d, J=7.20 Hz, 1H), 4.75-4.85 (m, 1H), 4.08 (q, J=7.20 Hz, 2H), 3.91 (s, 3H), 3.35-3.45 (m, 2H), 3.00-3.10 (m, 1H), 2.80-2.90 (m, 2H), 2.65-2.75 (m, 2H), 2.50-2.60 (m, 2H), 1.90-2.00 (m, 2H), 1.60-1.70 (m, 3H), 1.25-1.40 (m, 2H), 1.15 (t, J=7.20 Hz, 3H). LCMS (ES): m/z 481.0 [M+H]$^+$.

Example 17 and Example 18

To a stirred solution of Example 17E (70 mg, 0.146 mmol) in THF (2 mL) and MeOH (2 mL) was added a solution of LiOH·H$_2$O (12.22 mg, 0.29 mmol) in water (1 mL) and the resulting reaction mixture was stirred at room temperature for 40 h. After completion of the reaction, citric acid (22.39 mg, 0.117 mmol) was added and the reaction mixture was stirred further at room temperature for 10 min. The reaction mixture was concentrated and the crude product was purified by preparative reverse phase HPLC (Sunfire C18 (150×19) mm, 5 micron); Mobile Phase A: 10 mM CH$_3$COONH$_4$ in water; Mobile Phase B: Acetonitrile; flow rate: 17 mL/min; Time (min)/% B: 0/20, 24/70) and then separated into individual enantiomers by chiral SFC (Chiralpak AD-H (250×21) mm, 5u; 60% CO$_2$ and 40% DEA in methanol as co-solvent); Total Flow: 75 g/min; Back Pressure: 100 bar; Temperature: 25° C.; Detection: UV at 247 nM) to afford Example 17 (9 mg, 13%) as a white solid (first-eluting isomer). LCMS (ES): m/z 453.2 [M+H]$^+$. $^1$H NMR (400 MHz, CD$_3$OD) δ 8.01 (d, J=2.40 Hz, 1H), 7.60 (dd, J=2.40, 8.80 Hz, 1H), 7.27 (s, 1H), 7.24 (d, J=3.20 Hz, 1H), 6.65 (d, J=8.80 Hz, 1H), 6.34 (d, J=7.20 Hz, 1H), 4.66 (dd, J=6.80, 9.20 Hz, 1H), 3.77 (s, 3H), 3.29-3.36 (m, 2H), 3.01-3.15 (m, 1H), 2.71-2.84 (m, 3H), 2.65 (t, J=6.27 Hz, 2H), 2.41 (t, J=7.28 Hz, 2H) 1.71-1.88 (m, 2H), 1.43-1.67 (m, 4H). Human αVβ6 IC50 (nM)=16. Example 18 (8 mg, 12%, white solid) was isolated as the second-eluting isomer. $^1$H NMR (400 MHz, CD$_3$OD) δ 8.01 (d, J=2.40 Hz, 1H), 7.60 (dd, J=2.40, 8.80 Hz, 1H), 7.27 (s, 1H), 7.24 (d, J=3.20 Hz, 1H), 6.65 (d, J=8.80 Hz, 1H), 6.34 (d, J=7.20 Hz, 1H), 4.66 (dd, J=6.80, 9.20 Hz, 1H), 3.77 (s, 3H), 3.29-3.36 (m, 2H), 3.01-3.15 (m, 1H), 2.71-2.84 (m, 3H), 2.65 (t, J=621 Hz, 2H), 2.41 (t, J=7.28 Hz, 2H) 1.71-1.88 (m, 2H), 1.43-1.67 (m, 4H). LCMS (ES): m/z 453.2 [M+H]$^+$. Human αVβ6 IC50 (nM)=6.7.

Example 19 (Enantiomer 1) and Example 20 (Enantiomer 2)

3-(6-Methoxypyridin-3-yl)-3-(5-(3-(5,6,7,8-tetrahydro-1,8-naphthyridin-2-yl)propyl)thiazol-2-yl) propanoic acid

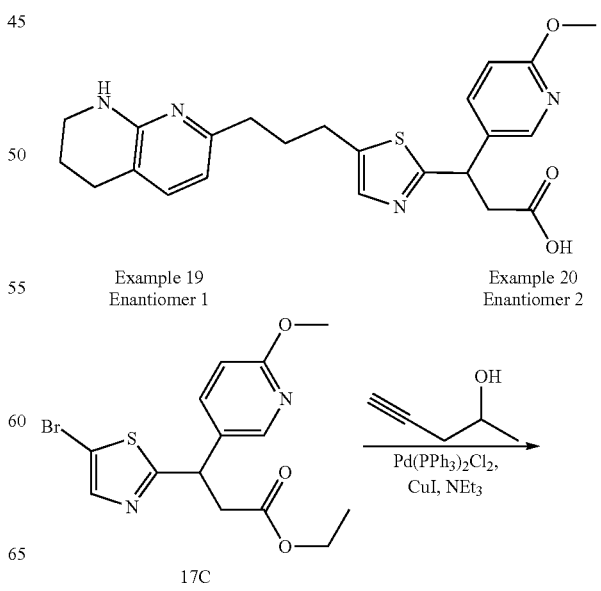

Example 19
Enantiomer 1

Example 20
Enantiomer 2

17C

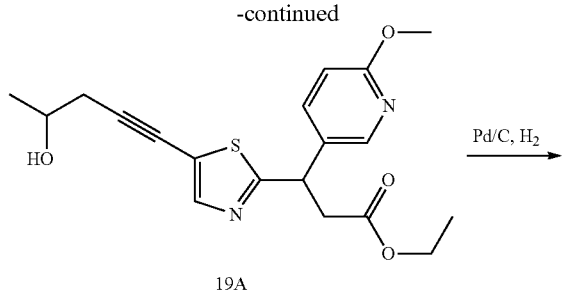

19A

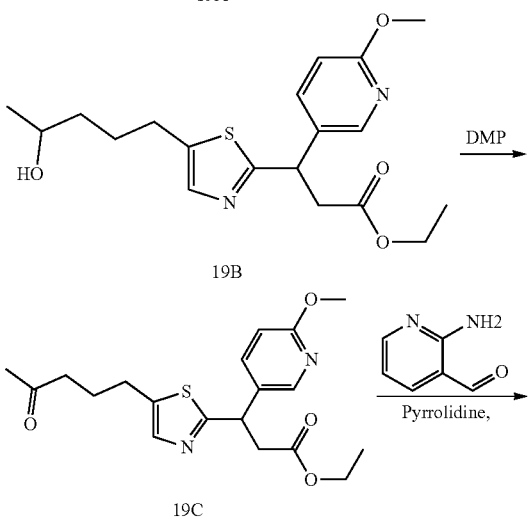

19B

19C

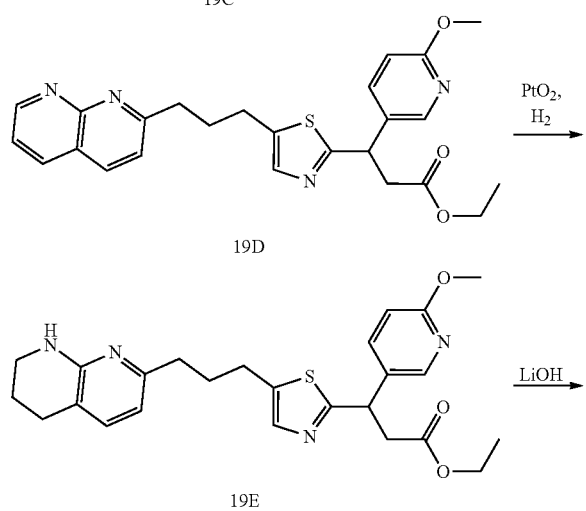

19D

19E

Example 19 + Example 20

Example 19A

To a stirred solution of Example 17C (300 mg, 0.808 mmol), pent-4-yn-2-ol (204 mg, 2.424 mmol) in TEA (10 mL) under nitrogen atmosphere was added copper(I) iodide (15 mg, 0.081 mmol) followed by PdCl$_2$(PPh$_3$)$_2$ (57 mg, 0.081 mmol) and the reaction mixture was degassed with argon for 2 min and then heated at 80° C. for 16 h. The reaction mixture was filtered, washed with EtOAc (5 mL), filtrate was concentrated. The crude product was purified by combiflash chromatography (24 g Redisep® SiO$_2$ column, eluting with 20% EtOAc in pet ether) to afford 19A (300 mg, 94%) as a brown oil. LCMS (ES): m/z 375.0 [M+H]$^+$.

Example 19B

To a degassed solution of Example 19A (280 mg, 0.748 mmol) in EtOH (2 mL) was added 10% palladium on carbon (28 mg, 0.026 mmol) and the resulting reaction mixture was stirred under hydrogen pressure at room temperature for 40 h. The reaction mixture was filtered through CELITE® pad and the filtrate concentrated to afford 19B (250 mg, 88%) as a pale yellow oil. LCMS (ES): m/z 379.0 [M+H]$^+$.

Example 19C

To a solution of Example 19B (250 mg, 0.661 mmol) in dichloromethane (2 mL) was added Dess Martin periodinane (560 mg, 1.321 mmol) at 0° C. and the resulting mixture was stirred at room temperature for 16 h. The reaction mass was diluted with dichloromethane (20 mL), washed with 20% sodium bicarbonate solution (20 mL), brine solution (10 mL), dried over sodium sulphate, filtered and the filtrate concentrated. The crude product was purified by combiflash chromatography (12 g Redisep® SiO$_2$ column, eluting with 45% EtOAc in pet ether) to afford 19C (170 mg, 68%) as a pale brown oil. $^1$H NMR (400 MHz, CD$_3$OD) δ 8.12 (d, J=2.80 Hz, 1H), 7.67 (dd, J=8.80 & 2.80 Hz, 1H), 7.41 (s, 1H), 6.78 (d, J=8.80 Hz, 1H), 4.80-4.90 (m, 1H), 4.10 (q, J=7.20 Hz, 2H), 3.91 (s, 3H), 3.35-3.45 (m, 1H), 3.00-3.10 (m, 1H), 2.80-2.90 (m, 2H), 2.50-2.60 (m, 2H), 2.12 (s, 3H), 1.80-1.90 (m, 2H), 1.18 (t, J=7.20 Hz, 3H). LCMS (ES): m/z 377.0 [M+H]$^+$.

Example 19D

To a solution of Example 19C (130 mg, 0.345 mmol), 2-aminonicotinaldehyde (46 mg, 0.380 mmol) in ethanol (5 mL) under nitrogen was added pyrrolidine (0.029 mL, 0.345 mmol) and the resulting reaction mixture was stirred at 80° C. for 16 h. The reaction mixture concentrated and the crude product was purified by combiflash chromatography (12 g Redisep® SiO$_2$ column, eluting with 3% MeOH in CHCl$_3$ to afford 19D (100 mg, 63%) as a brown oil. $^1$H NMR (400 MHz, CD$_3$OD) δ 9.05 (s, 1H), 8.42 (s, 1H), 8.33 (d, J=8.40 Hz, 1H), 8.12 (s, 1H), 7.60-7.70 (m, 2H), 7.65 (d, J=8.0 Hz, 1H), 7.54 (d, J=8.40 Hz, 1H), 6.78 (d, J=8.80 Hz, 1H), 4.75-4.80 (m, 1H), 4.10 (q, J=7.20 Hz, 2H), 3.91 (s, 3H), 2.95-3.20 (m, 4H), 2.20-2.30 (m, 2H), 1.30-1.45 (m, 2H), 1.15 (t, J=7.20 Hz, 3H). LCMS (ES): m/z 463.3 [M+H]$^+$.

Example 19E

To a stirred solution of Example 19D (100 mg, 0.216 mmol) in ethanol (25 mL) was added platinum(IV) oxide (10 mg, 0.044 mmol) under nitrogen atmosphere and the reaction mixture was purged with hydrogen and stirred under hydrogen bladder pressure at room temperature for 16 h. The reaction mixture was filtered and filtrate concentrated to afford 19E (80 mg, 79%) as a pale yellow oil. LCMS (ES): m/z 467.2 [M+H]$^+$.

Example 19 and Example 20

A solution of Example 19E (80 mg, 0.171 mmol) in THF (2 mL) and methanol (2 mL) was added to a solution of LiOH·H$_2$O (29 mg, 0.686 mmol) in water (1 mL) and the resulting reaction mixture was stirred at room temperature for 16 h. After the completion of the reaction, citric acid (99 mg, 0.514 mmol) was added and the mixture was stirred at room temperature for 10 min. The reaction mixture was filtered, concentrated and the crude product was purified by preparative HPLC (Inertsil ODS (250×20) mm, 5 micron); Mobile Phase A: 10 mM $CH_3COONH_4$ in water; Mobile Phase B: acetonitrile; flow rate: 17 mL/min; Time (min)/% B: 0/10, 12/55) and then separated into individual enantiomers by chiral preparative SFC (Chiralpak AD-H (250×21) mm, 5u; 60% $CO_2$ and 40% DEA in methanol as co-solvent); Total Flow: 75 g/min; Back Pressure: 100 bar; Temperature: 25° C.; Detection: UV at 247 nM) to afford Example 19 (23 mg, 20%, white solid) as the first-eluting isomer. $^1$H NMR (400 MHz, $CD_3OD$) δ 8.11 (d, J=2.51 Hz, 1H), 7.68 (dd, J=8.53, 2.51 Hz, 1H), 7.38 (s, 1H), 7.32 (d, J=7.03 Hz, 1H), 6.75 (d, J=8.53 Hz, 1H), 6.45 (d, J=7.53 Hz, 1H), 4.73-4.80 (m, 1H), 3.86 (s, 3H), 3.38-3.44 (m, 2H), 3.14-3.26 (m, 1H), 2.90-2.94 (m, 1H), 2.78-2.85 (m, 2H), 2.72 (t, J 5=6.27 Hz, 2H), 2.56-2.64 (m, 2H), 1.82-2.01 (m, 4H). LCMS (ES): m/z 439.2 [M+H]$^+$. Human αVβ6 IC50 (nM)=44. Example 20 (21 mg, 18%, white solid) was isolated as the second-eluting isomer. $^1$H NMR (400 MHz, $CD_3OD$) δ 8.11 (br. s., 1H), 7.68 (dd, J=8.53, 2.51 Hz, 1H), 7.38 (br. s., 1H), 7.32 (d, J=7.53 Hz, 1H), 6.75 (d, J=8.53 Hz, 1H), 6.45 (d, J=7.03 Hz, 1H), 4.73-4.80 (m, 1H), 3.88 (s, 3H), 3.37-3.43 (m, 2H), 3.20 (dd, J=14.81, 6.27 Hz, 1H), 2.79-2.98 (m, 3H), 2.73 (t, J=6.02 Hz, 2H), 2.61 (t, J=7.78 Hz, 2H), 1.78-2.06 (m, 4H). LCMS (ES): m/z 439.2 [M+H]$^+$. Human αVβ6 IC50 (nM)=18.

Example 21

(3S)-3-(6-Methoxypyridin-3-yl)-3-(3-(3-(5,6,7,8-tetrahydro-1,8-naphthyridin-2-yl)propyl)pyrrolidin-1-yl)propanoic acid (Diastereomeric)

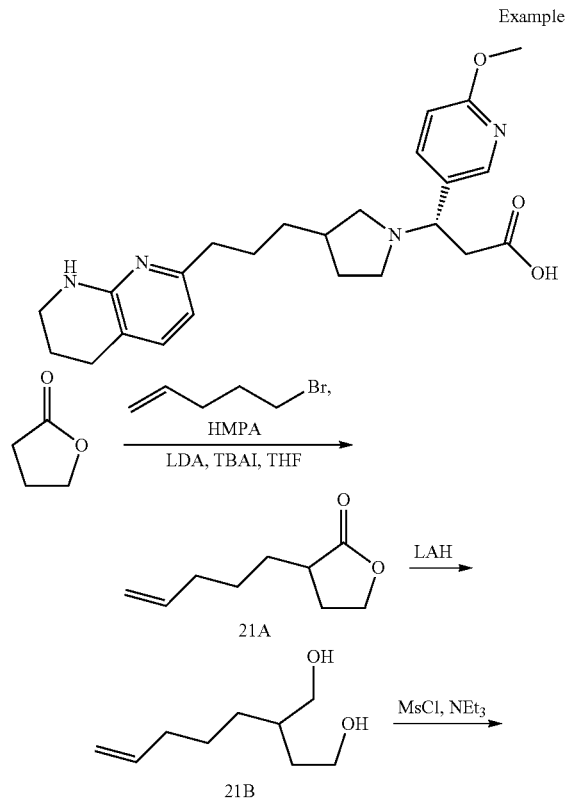

Example 21

Example 21

Example 21A

To a solution of diisopropylamine (0.994 mL, 6.98 mmol) in THF (9.44 mL) at 0° C. was added w-BuLi (1.6 M in hexanes, 4.16 mL, 6.66 mmol) dropwise. The reaction mixture was stirred at this temperature for 15 min. HMPA (5.63 mL, 32.3 mmol) was added dropwise and the reaction mixture was stirred at 0° C. for 15 min then cooled to −78° C. A solution of dihydrofuran-2(3H)-one (0.488 mL, 6.34 mmol) dissolved in THF (28.3 mL) was then added dropwise over a period of 30 min via syringe pump. The reaction mixture was stirred at −78° C. for 30 min. TBAI (0.358 g, 0.970 mmol) was then added in one portion followed by the dropwise addition of 5-bromopent-1-ene (0.826 mL, 6.98 mmol). The reaction mixture was stirred at −78° C. for 1 h then warmed to 0° C. and stirred for 3 h. The reaction mixture was quenched with sat. NH$_4$Cl and warmed to rt. The aqueous layer was extracted with EtOAc (3×) and the combined organic layers were washed with water, brine, dried over anhydrous Na$_2$SO$_4$ and concentrated in vacuo. The crude product was purified by flash chromatography (0 to 25% hexanes/EtOAc) to yield Example 21A (0.201 g, 1.30 mmol, 21% yield) as a light yellow oil. LCMS (ES): m/z 155 [M+H]$^+$. $^1$H NMR (500 MHz, CDCl$_3$) δ 5.81 (ddt, J=17.0, 10.3, 6.7 Hz, 1H), 5.10-4.90 (m, 2H), 4.35 (td, J=8.7, 3.0 Hz, 1H), 4.20 (td, J=9.4, 6.9 Hz, 1H), 2.62-2.49 (m, 1H), 2.45-2.35 (m, 1H), 2.18-2.06 (m, 2H), 2.00-1.83 (m, 2H), 1.56-1.38 (m, 3H).

Example 21B

LAH (1.0 M in THF) (5.84 mL, 5.84 mmol) was added dropwise to a solution of Example 21A (0.180 g, 1.17 mmol) in THF (3.5 mL) at 0° C. The reaction mixture was stirred at 0° C. for 30 min then refluxed for 1 h. The reaction mixture was then cooled to 0° C., diluted with diethyl ether and carefully quenched with water. The precipitate formed was filtered and the filtrate was sequentially washed with water and brine. The organic layer was separated, dried over anhydrous Na$_2$SO$_4$, concentrated in vacuo and air-dried under vacuum to yield Example 21B (0.183 g, 1.16 mmol, 99% yield) as a clear oil which was used as such for the next step. $^1$H NMR (500 MHz, CDCl$_3$) δ 5.81 (br dd, J=17.1, 10.2 Hz, 1H), 5.05-4.90 (m, 2H), 3.80 (ddd, J=10.7, 6.2, 4.5 Hz, 1H), 3.72-3.62 (m, 2H), 3.52 (dd, J=10.7, 6.9 Hz, 1H), 2.10-2.03 (m, 2H), 1.76-1.64 (m, 2H), 1.48-1.24 (m, 5H).

Example 21C

To a solution of Example 21B (180 mg, 1.14 mmol), DMAP (13.9 mg, 0.114 mmol) and triethylamine (0.476 mL, 3.41 mmol) in DCM (2.28 mL) was added MsCl (0.222 mL, 2.84 mmol) and the reaction mixture was stirred at 0° C. for 30 min and then at rt overnight. The reaction mixture was washed with water then 5% aq. NaHCO$_3$. The organic layer was dried over anhydrous Na$_2$SO$_4$, filtered and concentrated in vacuo. The crude product was purified by flash chromatography (0 to 60% hexanes/EtOAc) to yield Example 21C (293 mg, 0.932 mmol, 82% yield) as a light yellow oil. $^1$H NMR (500 MHz, CDCl$_3$) δ 5.79 (ddt, J=17.1, 10.3, 6.7 Hz, 1H), 5.08-4.95 (m, 2H), 4.38-4.28 (m, 2H), 4.25 (dd, J=9.9, 4.4 Hz, 1H), 4.19-4.13 (m, 1H), 3.04 (d, J=1.7 Hz, 6H), 2.11-2.05 (m, 2H), 1.99-1.94 (m, 1H), 1.94-1.81 (m, 2H), 1.51-1.37 (m, 4H).

Example 21D

A solution of Example 21C (268 mg, 0.852 mmol), (S)-Ethyl 3-amino-3-(6-methoxypyridin-3-yl)propanoate (287 mg, 1.28 mmol) and triethylamine (0.356 mL, 2.56 mmol) in 1,4-Dioxane (3.12 mL) was stirred at 75° C. for 16 h. Upon cooling to room temperature, the reaction mixture was diluted with water and extracted with EtOAc (3×). The combined organic layer was washed with brine, dried over anhydrous Na$_2$SO$_4$ and concentrated in vacuo. The crude product was purified by flash chromatography (0 to 100% hexanes/EtOAc) to yield Example 21D (76.5 mg, 0.221 mmol, 26% yield) as a light yellow oil. LCMS (ES): m/z 347 [M+H]$^+$.

Example 21E

A slurry of Example 21D (76.5 mg, 0.221 mmol) and PdCl$_2$ (39.2 mg, 0.221 mmol) and CuCl (65.6 mg, 0.662 mmol) in DMF (3.53 mL) and water (0.883 mL) was stirred under an O$_2$ atmosphere (balloon, 1 atm) at room temperature for 8 h. After filtration of the reaction mixture through a CELITE® pad and subsequent washing of the cake with EtOAc, the filtrate was washed with 10% LiCl, water and brine. The organic layer was dried over anhydrous Na$_2$SO$_4$, filtered and concentrated. The crude product was purified by flash chromatography (0 to 15% DCM/MeOH) to yield Example 21E (38.4 mg, 0.106 mmol, 48% yield) as a brown oil. LCMS (ES): m/z 363 [M+H]$^+$.

Example 21F

To a solution of Example 21E (38.4 mg, 0.106 mmol) in CH$_2$Cl$_2$ (0.167 mL) and EtOH (0.500 mL) was added pyrrolidine (0.011 mL, 0.127 mmol) followed by 2-aminonicotinaldehyde (12.9 mg, 0.106 mmol). The mixture was then stirred at room temperature overnight. The crude product was purified via preparative HPLC using the following conditions: Column: Phenomenex Luna AXIA 5u C18 21.2× 100 mm, Mobile Phase A: 10:90 methanol:water with 0.1% TFA; Mobile Phase B: 90:10 methanol:water with 0.1% TFA; Gradient: 5-100% B over 10 minutes, then a 5-minute hold at 100% B; Flow: 20 mL/min. to give Example 21F (30 mg, 0.067 mmol, 63% yield) as a yellow oil. LCMS (ES): m/z 449 [M+H]$^+$.

Example 21G

A slurry of Example 21F (30.0 mg, 0.067 mmol) and PtO$_2$ (3.04 mg, 0.013 mmol) in EtOH (1.22 mL) was stirred under a H$_2$ atmosphere (balloon, 1 atm) at room temperature for 5 h. After filtration of the reaction mixture through a CELITE® pad and subsequent washing of the cake with EtOH, the filtrate was concentrated in vacuo and air-dried under vacuum to yield Example 21G (26.6 mg, 0.059 mmol, 88% yield) as a brown oil which was used as such for the next step. LCMS (ES): m/z 453 [M+H]$^+$.

Example 21

To a solution of Example 21G (26.6 mg, 0.059 mmol) in EtOH (1.73 mL) was added 1M aq. NaOH (0.176 mL, 0.176 mmol) and the reaction mixture was stirred at room temperature overnight. The solvent was removed in vacuo and purified by preparative HPLC using the following conditions: Column: Luna AXIA C18, 30×100 mm, 5-µm particles; Mobile Phase A: 10:90 methanol:water with 10-mM ammonium acetate; Mobile Phase B: 90:10 methanol:water with 10-mM ammonium acetate; Gradient: 10-100% B over 10 minutes, then a 5-minute hold at 100% B; Flow: 40 mL/min. to give Example 21 (13.2 mg, 52%) as a tan solid. LCMS (ES): m/z 425 [M+H]$^+$. $^1$H NMR (500 MHz, CD$_3$OD) δ 8.26 (d, J=2.5 Hz, 1H), 7.91-7.82 (m, 1H), 7.24 (dd, J=7.2, 0.8 Hz, 1H), 6.88 (d, J=8.5 Hz, 1H), 6.41 (dd, J=7.3, 1.5 Hz, 1H), 4.52 (br t, J=6.2 Hz, 1H), 3.95 (s, 3H), 3.54-3.47 (m, 1H), 3.44-3.39 (m, 2H), 3.31-3.21 (m, 2H), 2.91 (s, 1H), 2.82 (br dd, J=14.9, 8.3 Hz, 2H), 2.74 (br t, J=6.2 Hz, 2H), 2.56 (t, J=7.2 Hz, 2H), 2.32 (br dd, J=14.9, 7.4 Hz, 1H), 2.22-2.11 (m, 1H), 1.91 (quin, J=5.9 Hz, 2H), 1.71-1.56 (m, 3H), 1.49-1.39 (m, 2H). Human αVβ6 IC50

(nM)=1.4; Human αVβ1 IC50 (nM)=6,500; Human αVβ3 IC50 (nM)=4.4; Human αVβ5 IC50 (nM)=10; and Human αVβ8 IC50 (nM)=180.

Example 22

(±)-3-(2-Methylpyrimidin-5-yl)-3-(3-(3-(5,6,7,8-tetrahydro-1,8-naphthyridin-2-yl)propyl)-1H-pyrazol-1-yl)propanoic acid

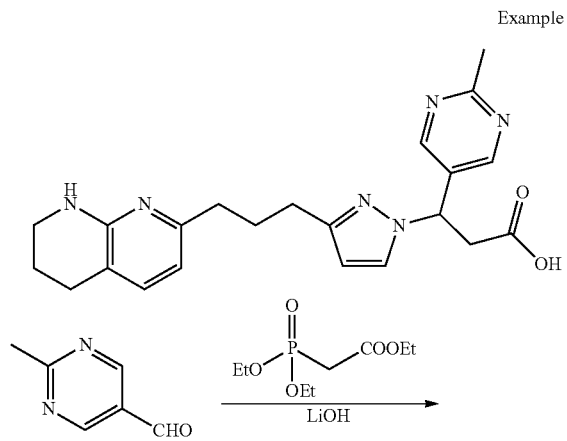

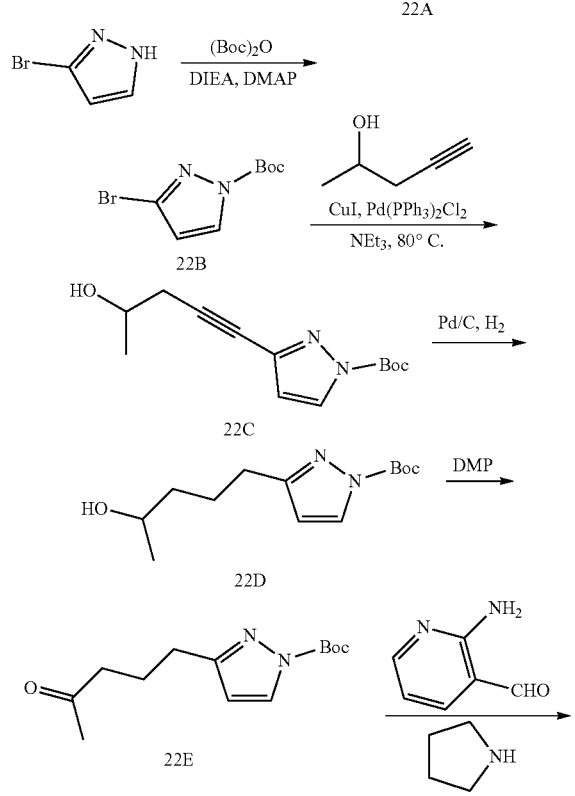

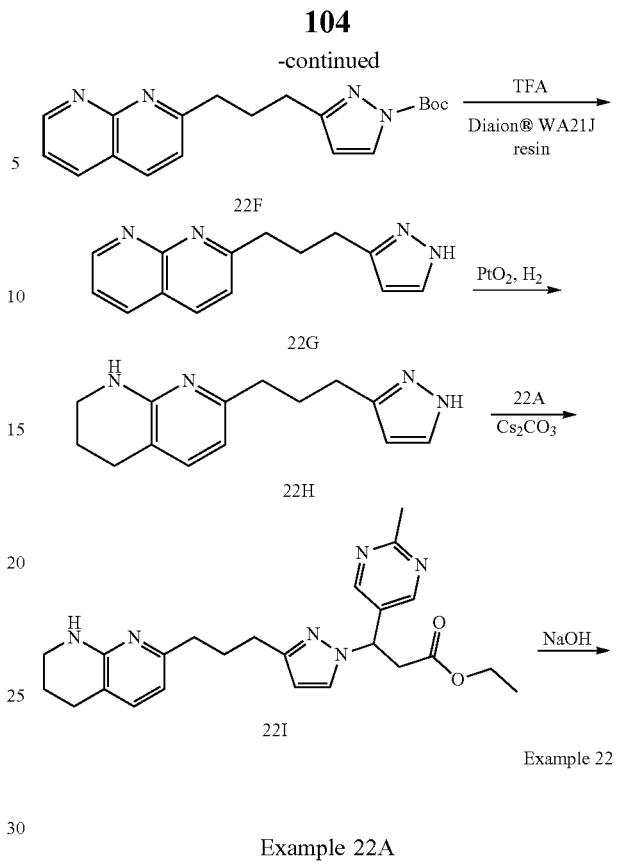

Example 22A

To a solution of 2-methylpyrimidine-5-carbaldehyde (1.0 g, 8.19 mmol) in THF (15 mL) was added 5 g of molecular sieves (4 Å) followed by ethyl 2-(diethoxyphosphoryl)acetate (1.967 mL, 9.83 mmol) and LiOH (0.235 g, 9.83 mmol). After stirring overnight at room temperature, the reaction was filtered over CELITE® and the volatiles were removed. The residue was dissolved in EtOAc and sequentially washed with 10% NaHCO₃ aq solution and brine. The organic layer was dried over anhydrous Na₂SO₄, filtered, and concentrated under reduced pressure. The crude product was purified by flash chromatography (0 to 50% EtOAc/Hexanes) to give Example 22A (0.841 g, 4.38 mmol, 53% yield) as a white solid. LCMS (ESI) m/z 193.1 (M+H)⁺. ¹H NMR (400 MHz, CDCl₃) δ 8.79 (s, 1H), 7.61 (d, J=16.3 Hz, 1H), 7.28 (s, 1H), 6.56 (d, J=16.3 Hz, 1H), 4.31 (d, J=7.2 Hz, 2H), 2.79 (s, 3H), 1.37 (t, J=7.2 Hz, 3H)

Example 22B

To a solution of 3-bromo-1H-pyrazole (5 g, 34.0 mmol) in CH₂Cl₂ (100 mL) was added DIEA (17.82 mL, 102 mmol) and di-tert-butyl dicarbonate (11.14 g, 51.0 mmol). A catalytic amount of DMAP (0.042 g, 0.340 mmol) was added, and the reaction was stirred at rt for 1 h. The reaction was then partitioned between CH₂Cl₂ and water. The organic layer was separated and washed with sat. NaCl. The organic layer was dried with anhydrous sodium sulfate, filtered, and concentrated. The crude product was purified by flash chromatography (0 to 10% hexanes/ethyl acetate) to yield Example 22B (7.73 g, 31.3 mmol, 92% yield) as a white solid. ¹H NMR (500 MHz, CDCl₃) δ 8.07 (s, 2H), 1.67 (s, 9H)

Example 22C

A mixture of Example 22B (7.0 g, 28.3 mmol), pent-4-yn-2-ol (4.01 mL, 42.5 mmol), triethylamine (15.79 mL, 113 mmol), bis(triphenylphosphine)palladium(II) chloride (1.193 g, 1.700 mmol) and copper(I) iodide (0.216 g, 1.133 mmol) in DMF (100 mL) was stirred at 80° C. for 2 h. The reaction was diluted with 300 mL of EtOAc, washed with 10% LiCl solution and brine, dried over anhydrous $Na_2SO_4$, and concentrated. The crude product was purified by flash chromatography (0 to 100% ethyl acetate/hexanes) to yield Example 22C (7.0 g, 28.0 mmol, 99% yield) as a tan solid. LCMS (ESI) m/z 251 (M+H)$^+$.

Example 22D

A mixture of Example 22C (6.60 g, 26.4 mmol) and Pd/C (8.42 g, 7.91 mmol) in MeOH (200 mL) was stirred under a $H_2$ atmosphere (balloon, 1 atm) for 16 h. After filtration on a pad of CELITE® and concentration, Example 22D (6.68 g, 26.3 mmol, 100% yield) was isolated as a light brown oil which was used in the next step without further purification. LCMS (ESI) m/z: 277.1 (M+Na)$^+$.

Example 22E

To a solution of Example 22D (6.60 g, 26.0 mmol) in $CH_2Cl_2$ (250 mL) at room temperature was added Dess-Martin periodinane (13.21 g, 31.1 mmol) and the reaction was stirred for 1 hour. The mixture was diluted with $Et_2O$, filtered through a CELITE® pad, and concentrated to give an off-white solid. The crude product was purified by flash chromatography (0 to 80% EtOAc/Hexanes) to yield Example 22E (4.61 g, 18.27 mmol, 70% yield) as a white solid. LCMS (ESI) m/z 253.1 (M+H)$^+$. $^1$H NMR (500 MHz, $CDCl_3$) δ 7.96 (d, J=2.8 Hz, 1H), 6.22 (d, J=2.8 Hz, 1H), 2.69 (t, J=7.6 Hz, 2H), 2.49 (t, J=7.3 Hz, 2H), 2.13 (s, 3H), 1.95 (quin, J=7.5 Hz, 2H), 1.63 (s, 9H).

Example 22F

A solution of Example 22E (4.49 g, 17.80 mmol) in $CH_2Cl_2$ (150 mL) was added pyrrolidine (3.24 mL, 39.20 mmol) followed by the addition of 2-aminonicotinaldehyde (2.173 g, 17.80 mmol). The mixture was then stirred at room temperature for 40 h and then concentrated. The crude product was purified by flash chromatography (0 to 10% MeOH/$CH_2Cl_2$) to yield Example 22F (4.26 g, 12.59 mmol, 71% yield). LCMS (ESI) m/z 339.1 (M+H)$^+$.

Example 22G

To a solution of Example 22F (2.31 g, 6.83 mmol) in $CH_2Cl_2$ (40 mL) was added TFA (10 mL, 130 mmol) at 0° C. under $N_2$ (1 atm) and the reaction mixture was allowed to warm up to rt and stirred at rt for 1 h under $N_2$ (1 atm). $CH_2Cl_2$ and TFA were removed under vacuum to give crude product as a brown oil. The crude product was purified by flash chromatography (0 to 10% MeOH/$CH_2Cl_2$) to give the TFA salt of Example 22G (2.03 g, 5.76 mmol, 84% yield) as a light brown oil. LCMS (ESI) m/z 240.1 (M+H)$^+$. $^1$H NMR (500 MHz, CDCE) δ 11.84 (br. s., 2H), 9.09 (dd, J=4.3, 1.5 Hz, 1H), 8.28 (dd, J=8.0, 1.7 Hz, 1H), 8.16 (d, J=8.3 Hz, 1H), 7.66 (d, J=1.9 Hz, 1H), 7.52 (dd, J=8.1, 4.5 Hz, 1H), 7.42 (d, J=8.3 Hz, 1H), 6.27-6.18 (m, 1H), 3.06 (t, J=13 Hz, 2H), 2.85 (s, 2H), 2.25 (d, J=7.4 Hz, 2H). To a solution of the TFA salt of Example 22G (2.0 g, 5.68 mmol) in MeOH (50 mL) was added Diaion WA21J Resin (10 g, 5.68 mmol) and the reaction was allowed to stir at rt under $N_2$ (1 atm) for 0.5 h. The resin was filtered, washed well with MeOH and the filtrate was concentrated to give Example 22G (1.168 g, 4.90 mmol, 86% yield) as a light brown oil which was used in the next step without further purification. LCMS (ESI) m/z: 239.1 (M+H)$^+$. $^1$H NMR (500 MHz, $CDCl_3$) δ 9.12 (dd, J=4.1, 1.9 Hz, 1H), 8.20 (dd, J=8.0, 1.9 Hz, 1H), 8.16-8.11 (m, 1H), 7.53 (d, J=1.4 Hz, 1H), 7.58-7.52 (m, 1H), 7.51-7.46 (m, 1H), 7.45-7.40 (m, 1H), 6.16 (s, 1H), 3.14 (t, J=7.4 Hz, 2H), 2.83 (t, J=7.3 Hz, 2H), 2.31 (t, J=7.3 Hz, 2H).

Example 22H

A slurry of Example 22G (900 mg, 3.78 mmol) and platinum(IV) oxide (172 mg, 0.755 mmol) in EtOH (8 mL) was stirred under a $H_2$ atmosphere (balloon, 1 atm) for 16 h. After filtration on a pad of CELITE® and concentration, Example 22H (911 mg, 3.76 mmol, 100% yield) was isolated as a light yellow oil which was used in the next step without further purification. LCMS (ESI) m/z: 243.1 (M+H)$^+$, Example 22I A mixture Example 22H (100 mg, 0.413 mmol) and cesium carbonate (403 mg, 1.238 mmol) in acetonitrile (2.0 mL) was stirred for 5 min. Example 22A (79 mg, 0.413 mmol) was added and the mixture was heated at 80° C. for 16 h. After cooling, the reaction was filtered and the filtrate was concentrated. The crude product was purified by flash chromatography (0 to 15% MeOH/$CH_2Cl_2$) to give Example 22I (90 mg, 0.207 mmol, 50% yield) as a light brown oil. LCMS (ESI) m/z 435.1 (M+H)$^+$.

Example 22

To a solution of Example 22I (63 mg, 0.145 mmol) in MeOH (1.5 mL) was added 1 M aq. NaOH (0.725 mL, 0.725 mmol) and the reaction mixture stirred at room temperature under Ar, 1 atm for 1 h. The mixture was purified by Prep. HPLC (Phenomenex Luna AXIA 5 u 21.2×100 mm, 10 min gradient, 17 min run, 0% to 70% Solvent A: 90% $H_2O$-10% ACN-0.1% TFA, Solvent B: 10% ACN-90% $H_2O$ 0.1% TFA) to give Example 22A (83 mg, 0.111 mmol, 3TFA, 76% yield) as a light brown oil. LCMS (ESI) m/z 407.0 (M+H)+. $^1$H NMR (500 MHz, DMSO-de) δ 8.61 (s, 2H), 7.83-7.70 (m, 1H), 7.19-7.01 (m, 1H), 6.36-6.22 (m, 1H), 6.13-6.01 (m, 1H), 5.85-5.69 (m, 1H), 3.24 (d, J=24.8 Hz, 2H), 2.63-2.57 (m, 4H), 2.49-2.44 (m, 2H), 2.43-2.37 (m, 2H), 1.95-1.87 (m, 2H), 1.86-1.76 (m, 2H), 1.73 (br. s., 2H), 1.05-0.93 (m, 1H). Human αVβ6 IC50 (nM)=64.

The following examples (in Table A) were prepared using methods analogous to the ones indicated in the table.

TABLE A

| Example | Structure & Name | Analytical Data | Method |
|---|---|---|---|
| 23 | 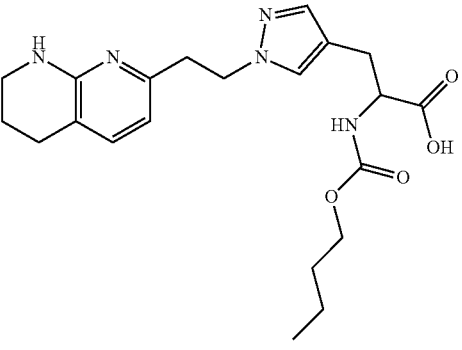 [SMILES: CCCCOC(=O)NC(Cc1cnn(CCc2ccc3c(n2)NCCC3)c1)C(=O)O]<br>(±)-2-((Butoxycarbonyl)amino)-3-(1-(2-(5,6,7,8-tetrahydro-1,8-naphthyridin-2-yl)ethyl)-1H-pyrazol-4-yl)propanoic acid | $^1$H NMR (500 MHz, CD$_3$OD) δ 7.43 (s, 1H), 7.37 (br d, J = 7.2 Hz, 1H), 7.28 (s, 1H), 6.40 (br d, J = 7.0 Hz, 1H), 4.34 (t, J = 6.4 Hz, 2H), 4.20 (br t, J = 5.6 Hz, 1H), 4.06 (br t, J = 6.6 Hz, 2H), 3.55-3.40 (m, 2H), 3.12-2.99 (m, 2H), 2.98-2.86 (m, 2H), 2.82-2.71 (m, 2H), 1.95-1.83 (m, 2H), 1.70-1.56 (m, 2H), 1.51-1.35 (m, 2H), 0.97 (t, J = 7.4 Hz, 3H) LC/MS (m/z) = 416.0 (M + H)$^+$. Human αVβ6 IC50 (nM) = 1,020. | Example 5 |
| 24 | 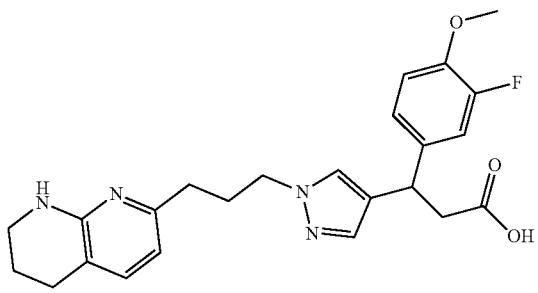 [SMILES: COc1ccc(C(CC(=O)O)c2cnn(CCCc3ccc4c(n3)NCCC4)c2)cc1F]<br>(±)-3-(3-Fluoro-4-methoxyphenyl)-3-(1-(3-(5,6,7,8-tetrahydro-1,8-naphthyridin-2-yl)propyl)-1H-pyrazol-4-yl)propanoic acid | $^1$H NMR (500 MHz, CD$_3$OD) δ 7.49 (s, 1H), 7.36 (d, J = 7.3 Hz, 1H), 7.27 (s, 1H), 7.07-6.94 (m, 3H), 6.47 (d, J = 7.3 Hz, 1H), 4.34 (t, J = 8.0 Hz, 1H), 4.20-4.00 (m, 2H), 3.83 (s, 3H), 3.49-3.39 (m, 2H), 2.79-2.71 (m, 4H), 2.57-2.43 (m, 1H), 2.39-2.29 (m, 1H), 2.24-2.07 (m, 2H), 1.95-1.84 (m, 2H) LC/MS (m/z) = 439.3 (M + H)$^+$. Human αVβ6 IC50 (nM) = 117. | Example 7 |
| 25 | 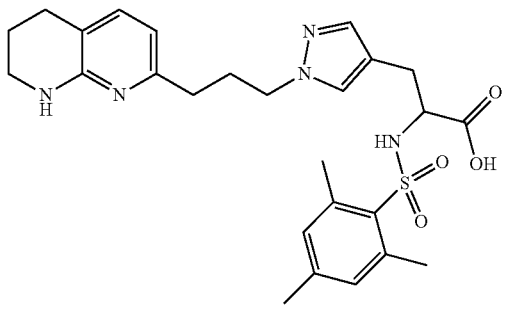 [SMILES: Cc1cc(C)c(S(=O)(=O)NC(Cc2cnn(CCCc3ccc4c(n3)NCCC4)c2)C(=O)O)c(C)c1]<br>(±)-3-(1-(3-(5,6,7,8-Tetrahydro-1,8-naphthyridin-2-yl)propyl)-1H-pyrazol-4-yl)-2-((2,4,6-trimethylphenyl)sulfonamido)propanoic acid | $^1$H NMR (500 MHz, CD$_3$OD) δ 7.52-7.39 (m, 1H), 7.31 (s, 1H), 7.26 (s, 1H), 7.01 (s, 2H), 6.57 (br s, 1H), 4.16-4.02 (m, 1H), 4.02-3.91 (m, 1H), 3.65 (t, J = 4.7 Hz, 1H), 3.43 (t, J = 5.6 Hz, 2H), 2.99-2.72 (m, 4H), 2.65-2.58 (m, 6H), 2.49 (br t, J = 6.6 Hz, 1H), 2.28 (s, 3H), 2.25-2.07 (m, 3H), 1.99-1.85 (m, 2H) LC/MS (m/z) = 511.9 (M + H)$^+$. Human αVβ6 IC50 (nM) = 395. | Example 6 |
| 26 | 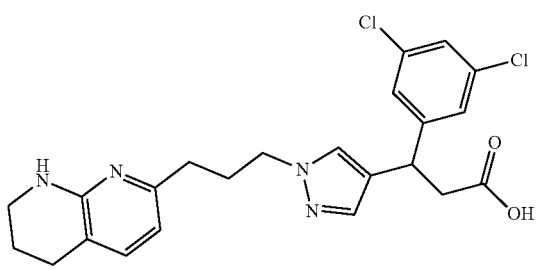 [SMILES: O=C(O)CC(c1cc(Cl)cc(Cl)c1)c1cnn(CCCc2ccc3c(n2)NCCC3)c1]<br>(±)-3-(3,5-Dichlorophenyl)-3-(1-(3-(5,6,7,8-tetrahydro-1,8-naphthyridin-2-yl)propyl)-1H-pyrazol-4-yl)propanoic acid | $^1$H NMR (500 MHz, CD$_3$OD) δ 7.59-7.52 (m, 1H), 7.38-7.22 (m, 5H), 6.54-6.42 (m, 1H), 4.40 (t, J = 8.0 Hz, 1H), 4.13 (dt, J = 11.0, 6.5 Hz, 2H), 3.48-3.37 (m, 2H), 2.81-2.68 (m, 4H), 2.54-2.34 (m, 2H), 2.16 (br d, J = 10.5 Hz, 2H), 1.96-1.84 (m, 2H) LC/MS (m/z) = 459.0 (M + H)$^+$. Human αVβ6 IC50 (nM) = 27. | Example 7 |

TABLE A-continued

| Example | Structure & Name | Analytical Data | Method |
|---|---|---|---|
| 27 | 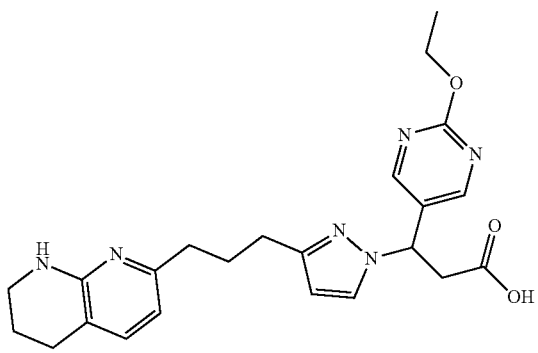 [SMILES: CCOc1ncc(C(CC(=O)O)n2ccc(CCCc3ccc4c(n3)NCCC4)n2)cn1]<br>(±)-3-(2-Ethoxypyrimidin-5-yl)-3-(3-(3-(5,6,7,8-tetrahydro-1,8-naphthyridin-2-yl)propyl)-1H-pyrazol-1-yl)propanoic acid | $^1$H NMR (500 MHz, CD$_3$OD) δ 8.55 (s, 2H), 8.46-8.42 (m, 1H), 7.76-7.72 (m, 1H), 7.61-7.55 (m, 1H), 6.65-6.57 (m, 1H), 6.18-6.15 (m, 1H), 5.89-5.84 (m, 1H), 4.43 (d, J = 6.9 Hz, 2H), 3.56-3.49 (m, 2H), 3.49-3.44 (m, 1H), 3.28 (dd, J = 16.6, 6.2 Hz, 1H), 2.86-2.80 (m, 2H), 2.75-2.67 (m, 3H), 2.11-2.01 (m, 2H), 2.00-1.94 (m, 2H), 1.40 (t, J = 7.0 Hz, 3H) LC/MS (m/z) = 437.0 (M + H)$^+$. Human αVβ6 IC50 (nM) = 9.4; Human αVβ1 IC50 (nM) = 144; Human αVβ3 IC50 (nM) = 2.3; Human αVβ5 IC50 (nM) = 0.76; and Human αVβ8 IC50 (nM) = 1,800. | Example 22 |
| 28 | 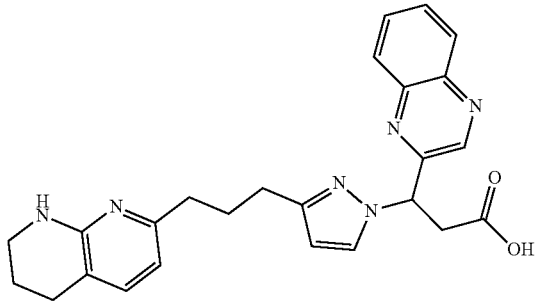 [SMILES: O=C(O)CC(c1cnc2ccccc2n1)n1ccc(CCCc2ccc3c(n2)NCCC3)n1]<br>(±)-3-(Quinoxalin-2-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-d$_6$) δ 8.70 (s, 1H), 7.99 (s, 2H), 7.79 (s, 2H), 7.72-7.67 (m, 1H), 7.55-7.48 (m, 1H), 6.48-6.40 (m, 1H), 5.99 (d, J = 1.7 Hz, 1H), 5.65 (s, 1H), 3.87-3.78 (m, 2H), 3.38 (br. s., 1H), 2.72 (br. s., 2H), 2.51 (br. s., 5H), 1.80 (d, J = 7.2 Hz, 4H). LC/MS (m/z) = 443.1 (M + H)$^+$. Human αVβ6 IC50 (nM) = 5,500. | Example 22 |
| 29 | 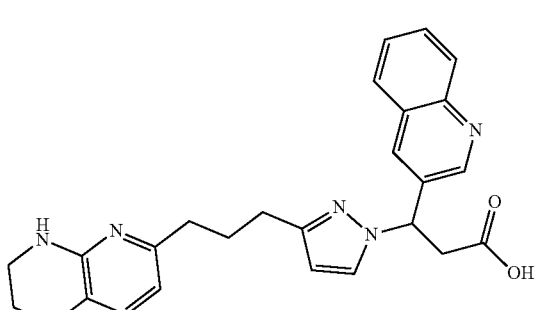<br>(±)-3-(Quinolin-3-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-d$_6$) δ 8.86 (s, 1H), 8.27 (s, 1H), 8.05-7.90 (m, 2H), 7.87-7.80 (m, 1H), 7.79-7.72 (m, 1H), 7.65-7.59 (m, 1H), 7.04-6.97 (m, 1H), 6.25-6.18 (m, 1H), 6.09-6.05 (m, 1H), 6.02-5.93 (m, 1H), 3.57 (br. s., 1H), 3.25-3.21 (m, 1H), 3.19-3.14 (m, 1H), 2.62-2.56 (m, 2H), 2.49-2.46 (m, 2H), 2.44-2.36 (m, 2H), 1.96-1.89 (m, 1H), 1.87-1.79 (m, 2H), 1.77-1.69 (m, 2H). LC/MS (m/z) = 442.2 (M + H)$^+$. Human αVβ6 IC50 (nM) = 11.20; Human αVβ1 IC50 (nM) = 286; Human αVβ3 IC50 (nM) = 1.7; Human αVβ5 IC50 (nM) = 6.5; and Human αVβ8 IC50 (nM) = 2,900. | Example 22 |

TABLE A-continued

| Example | Structure & Name | Analytical Data | Method |
|---|---|---|---|
| 30 | 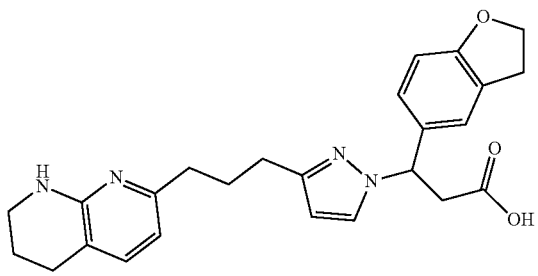 [SMILES: O=C(O)CC(c1ccc2c(c1)CCO2)n1ccc(CCCc2ccc3c(n2)NCCC3)n1]<br>(±)-3-(2,3-Dihydrobenzofuran-5-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 7.66 (br. s., 1H), 7.19 (br. s., 1H), 7.10-7.00 (m, 2H), 6.74-6.62 (m, 1H), 6.30-6.23 (m, 1H), 6.07-5.99 (m, 1H), 5.74-5.51 (m, 1H), 4.47 (t, J = 8.7 Hz, 2H), 3.23 (br. s., 2H), 3.15-3.06 (m, 2H), 2.60 (br. s., 2H), 2.51-2.40 (m, 6H), 1.89-1.79 (m, 2H), 1.78-1.65 (m, 2H). LC/MS (m/z) = 433.2 (M + H)$^+$. Human αVβ6 IC50 (nM) = 5.7; Human αVβ1 IC50 (nM) = 100; Human αVβ3 IC50 (nM) = 11; Human αVβ5 IC50 (nM) = 230; and Human αVβ8 IC50 (nM) = 2,010. | Example 22 |
| 31 | 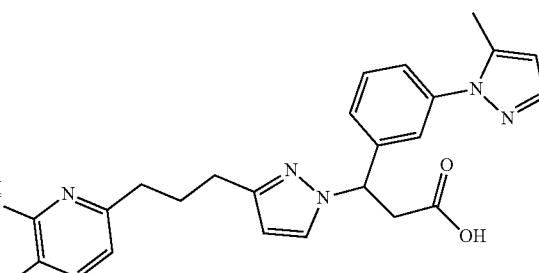<br>(±)-3-(3-(3,5-Dimethyl-1H-pyrazol-1-yl)phenyl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 7.77 (br s, 1H), 7.45-7.26 (m, 5H), 7.01 (d, J = 7.0 Hz, 1H), 6.22 (br d, J = 7.3 Hz, 2H), 6.05 (s, 2H), 5.81 (br s, 1H), 3.27-3.20 (m, 2H), 3.20-3.07 (m, 1H), 2.60 (br t, J = 6.1 Hz, 2H), 2.43 (br t, J = 7.5 Hz, 2H), 2.21 (s, 3H), 2.15 (s, 3H), 1.91 (br s, 2H), 1.88-1.80 (m, 2H), 1.80-1.69 (m, 2H), 1.00 (d, J = 6.1 Hz, 1H). LC/MS (m/z) = 485.0 (M + H)$^+$. Human αVβ6 IC50 (nM) = 5.2; Human αVβ1 IC50 (nM) = 63; Human αVβ3 IC50 (nM) = 7.5; and Human αVβ8 IC50 (nM) = 3,300. | Example 22 |
| 32 | 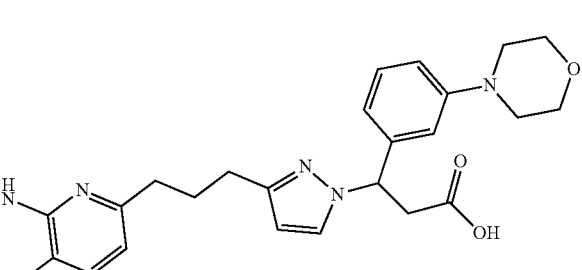<br>(±)-3-(3-Morpholinophenyl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 7.68 (s, 1H), 7.14 (t, J = 7.9 Hz, 1H), 7.10-6.97 (m, 1H), 6.83 (br s, 1H), 6.82-6.77 (m, 1H), 6.68 (br d, J = 7.4 Hz, 1H), 6.24 (d, J = 7.2 Hz, 1H), 6.02 (s, 1H), 5.71-5.60 (m, 1H), 3.69 (br s, 6H), 3.31-3.20 (m, 3H), 3.07-2.96 (m, 5H), 2.59 (br t, J = 5.9 Hz, 2H), 2.49-2.45 (m, 2H), 2.42 (br t, J = 7.5 Hz, 2H), 1.86-1.78 (m, 2H), 1.78-1.69 (m, 2H) LC/MS (m/z) = 476.2 (M + H)$^+$. Human αVβ6 IC50 (nM) = 4.3; Human αVβ1 IC50 (nM) = 43; Human αVβ3 IC50 (nM) = 5.5; and Human αVβ8 IC50 (nM) = 2,700. | Example 22 |

TABLE A-continued

| Example | Structure & Name | Analytical Data | Method |
|---|---|---|---|
| 33 | (±)-3-(Pyrido[2,3-b]pyrazin-7-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 9.16-9.00 (m, 3H), 8.29-8.17 (m, 1H), 7.58-7.49 (m, 1H), 7.03-6.91 (m, 1H), 6.25-6.10 (m, 3H), 3.64-3.51 (m, 1H), 3.38-3.11 (m, 3H), 2.99-2.90 (m, 1H), 2.77-2.68 (m, 1H), 1.98-1.67 (m, 4H), 1.33-1.14 (m, 3H), 1.00 (d, J = 6.1 Hz, 1H) LC/MS (m/z) = 444.4 (M + H)$^+$. Human αVβ6 IC50 (nM) = 2,800. | Example 22 |
| 34 | (±)-3-(2-Methoxypyrimidin-5-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 8.55 (s, 2H), 7.74 (s, 1H), 7.02 (br d, J = 7.2 Hz, 1H), 6.22 (br d, J = 7.2 Hz, 1H), 6.04 (s, 1H), 5.75 (br t, J = 7.4 Hz, 1H), 3.86 (s, 3H), 3.22 (br s, 3H), 3.17-3.07 (m, 1H), 2.65-2.56 (m, 2H), 2.48-2.43 (m, 2H), 2.44-2.34 (m, 2H), 1.85-1.76 (m, 2H), 1.73 (br d, J = 5.2 Hz, 2H). LC/MS (m/z) = 423.3 (M + H)$^+$. Human αVβ6 IC50 (nM) = 10. | Example 22 |
| 35 | (±)-3-(2,3-Dihydro-[1,4]dioxino[2,3-b]pyridin-7-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 7.70 (br d, J = 12.6 Hz, 2H), 7.23 (br s, 1H), 7.05 (br d, J = 7.0 Hz, 1H), 6.25 (br d, J = 7.2 Hz, 1H), 6.03 (s, 1H), 5.67 (br s, 1H), 4.34 (br s, 2H), 4.19 (br s, 2H), 3.31-3.19 (m, 1H), 3.16 (s, 1H), 2.59 (br s, 2H), 2.49-2.44 (m, 2H), 2.41 (br s, 2H), 1.95-1.85 (m, 2H), 1.85-1.76 (m, 2H), 1.73 (br s, 2H) LC/MS (m/z) = 450.4 (M + H)$^+$. Human αVβ6 IC50 (nM) = 17. | Example 22 |
| 36 | 3-(3-Fluoro-4-methoxyphenyl)-3-(4-(4-(5,6,7,8-tetrahydro-1,8-naphthyridin-2-yl)butyl)thiazol-2-yl)propanoic acid (Enantiomer 1) | $^1$H NMR (400 MHz, CD$_3$OD) δ 7.42 (d, J = 7.60 Hz, 1H), 7.05-7.13 (m, 3H), 6.95 (s, 1H), 6.46 (d, J = 7.60 Hz, 1H), 4.79-4.80 (m, 1H), 3.86 (s, 3H), 3.45 (t, J = 5.60 Hz, 2H), 3.23-3.26 (m, 1H), 2.73-2.85 (m, 5H), 2.54-2.64 (m, 2H), 1.91-2.01 (m, 3H), 1.73-1.82 (m, 1H), 1.47-1.49 (m, 2H). LC/MS (m/z) = 470.3 (M + H)$^+$. Human αVβ6 IC50 (nM) = 157. | Example 13 |

TABLE A-continued

| Example | Structure & Name | Analytical Data | Method |
|---|---|---|---|
| 37 | 3-(3-Fluoro-4-methoxyphenyl)-3-(4-(4-(5,6,7,8-tetrahydro-1,8-naphthyridin-2-yl)butyl)thiazol-2-yl)propanoic acid (Enantiomer 2) | $^1$H NMR (400 MHz, CD$_3$OD) δ 7.42 (d, J = 7.60 Hz, 1H), 7.05-7.13 (m, 3H), 6.95 (s, 1H), 6.46 (d, J = 7.60 Hz, 1H), 4.79-4.80 (m, 1H), 3.86 (s, 3H), 3.45 (t, J = 5.60 Hz, 2H), 3.23-3.26 (m, 1H), 2.73-2.85 (m, 5H), 2.54-2.64 (m, 2H), 1.91-2.01 (m, 3H), 1.73-1.82 (m, 1H), 1.47-1.49 (m, 2H). LC/MS (m/z) = 470.3 (M + H)$^+$. Human αVβ6 IC50 (nM) = 2.0; Human αVβ1 IC50 (nM) = 160; Human αVβ3 IC50 (nM) = 1.7; Human αVβ5 IC50 (nM) = 1.1; and Human αVβ8 IC50 (nM) = 870. | Example 13 |
| 38 | 3-(3-Fluoro-4-methoxyphenyl)-3-(4-(3-(5,6,7,8-tetrahydro-1,8-naphthyridin-2-yl)propyl)thiazol-2-yl)propanoic acid (Enantiomer 1) | $^1$H NMR (400 MHz, CD$_3$OD) δ 7.46 (d, J = 3.20 Hz, 1H), 7.03-7.13 (m, 4H), 6.56 (d, J = 7.20 Hz, 1H), 4.75-4.80 (m, 1H), 3.87 (s, 3H), 3.48-3.50 (m, 2H), 3.15-3.16 (m, 1H), 2.76-2.87 (m, 5H), 2.55-2.61 (m, 2H), 2.00-2.14 (m, 2H), 1.90-1.98 (m, 2H). LC/MS (m/z) = 456.2 (M + H)$^+$. Human αVβ6 IC50 (nM) = 2.1; Human αVβ1 IC50 (nM) = 66; Human αVβ3 IC50 (nM) = 2.3; and Human αVβ8 IC50 (nM) = 860. | Example 15 |
| 39 | 3-(3-Fluoro-4-methoxyphenyl)-3-(4-(3-(5,6,7,8-tetrahydro-1,8-naphthyridin-2-yl)propyl)thiazol-2-yl)propanoic acid (Enantiomer 2) | $^1$H NMR (400 MHz, CD$_3$OD) δ 7.46 (d, J = 3.20 Hz, 1H), 7.03-7.13 (m, 4H), 6.56 (d, J = 7.20 Hz, 1H), 4.75-4.80 (m, 1H), 3.87 (s, 3H), 3.48-3.50 (m, 2H), 3.15-3.16 (m, 1H), 2.76-2.87 (m, 5H), 2.55-2.61 (m, 2H), 2.00-2.14 (m, 2H), 1.90-1.98 (m, 2H). LC/MS (m/z) = 456.2 (M + H)$^+$. Human αVβ6 IC50 (nM) = 23. | Example 15 |
| 40 | (3-Fluoro-4-methoxyphenyl)-3-(5-(4-(5,6,7,8-tetrahydro-1,8-naphthyridin-2-yl)butyl)thiazol-2-yl)propanoic acid (Enantiomer 1) | $^1$H NMR (400 MHz, CD$_3$OD) δ 7.32-7.41 (m, 2 H), 7.12 (s, 1H), 7.10 (s, 1H), 7.00-7.07 (m, 1 H), 6.45 (d, J = 7.03 Hz, 1 H), 4.75 (dd, J = 9.54, 6.53 Hz, 1 H), 3.86 (s, 3 H), 3.42-3.48 (m, 2 H), 3.13-3.22 (m, 1 H), 2.82-2.95 (m, 3 H), 2.77 (t, J = 6.02 Hz, 2 H), 2.53 (t, J = 7.28 Hz, 2 H), 1.87-1.98 (m, 2 H), 1.56-1.78 (m, 4 H). LCMS (ES): m/z 470.2 [M + H]$^+$. Human αVβ6 IC50 (nM) = 17; Human αVβ3 IC50 (nM) = 28; Human αVβ5 IC50 (nM) = 10; and Human αVβ8 IC50 (nM) = 2,600. | Example 17 |

TABLE A-continued

| Example | Structure & Name | Analytical Data | Method |
|---|---|---|---|
| 41 | (3-Fluoro-4-methoxyphenyl)-3-(5-(4-(5,6,7,8-tetrahydro-1,8-naphthyridin-2-yl)butyl)thiazol-2-yl)propanoic acid (Enantiomer 2) | ¹H NMR (400 MHz, CD₃OD) δ 7.32-7.41 (m, 2 H), 7.12 (s, 1H), 7.10 (s, 1H), 7.00-7.07 (m, 1 H), 6.45 (d, J = 7.03 Hz, 1 H), 4.75 (dd, J = 9.54, 6.53 Hz, 1 H), 3.86 (s, 3 H), 3.42-3.48 (m, 2 H), 3.13-3.22 (m, 1 H), 2.82-2.95 (m, 3 H), 2.77 (t, J = 6.02 Hz, 2 H), 2.53 (t, J = 7.28 Hz, 2 H), 1.87-1.98 (m, 2 H), 1.56-1.78 (m, 4 H). LCMS (ES): m/z 470.2 [M + H]⁺. Human αVβ6 IC50 (nM) = 5.9. | Example 17 |
| 42 | 3-(3-Fluoro-4-methoxyphenyl)-3-(5-(3-(5,6,7,8-tetrahydro-1,8-naphthyridin-2-yl)propyl)thiazol-2-yl)propanoic acid (Enantiomer 1) | ¹H NMR (400 MHz, CD₃OD) δ 7.34-7.42 (m, 2H), 6.98-7.11 (m, 3H), 6.50 (d, J = 7.53 Hz, 1H), 4.65-4.78 (m, 1H), 3.86 (s, 3H), 3.41-3.46 (m, 2H), 3.17-3.26 (m, 1H), 2.90-2.98 (m, 1H), 2.86 (t, J = 7.28 Hz, 2H), 2.76 (t, J = 6.27 Hz, 2H), 2.60-2.66 (m, 2H), 1.86-2.02 (m, 4H). LCMS (ES): m/z 456.2 [M + H]⁺. Human αVβ6 IC50 (nM) = 28. | Example 19 |
| 43 | 3-(3-Fluoro-4-methoxyphenyl)-3-(5-(3-(5,6,7,8-tetrahydro-1,8-naphthyridin-2-yl)propyl)thiazol-2-yl)propanoic acid (Enantiomer 2) | ¹H NMR (400 MHz, CD₃OH) δ 7.34-7.42 (m, 2H), 6.98-7.11 (m, 3H), 6.50 (d, J = 7.53 Hz, 1H), 4.65-4.78 (m, 1H), 3.86 (s, 3H), 3.41-3.46 (m, 2H), 3.17-3.26 (m, 1H), 2.90-2.98 (m, 1H), 2.86 (t, J = 7.28 Hz, 2H), 2.60-2.66 (m, 2H), 1.86-2.02 (m, 4H), LCMS (ES): m/z 456.2 [M + H]⁺. Human αVβ6 IC50 (nM) = 18. | Example 19 |
| 44 | 3-(3-fluoro-4-methoxyphenyl)-3-(1-(4-(5,6,7,8-tetrahydro-1,8-naphthyridin-2-yl)butyl)-1H-pyrazol-4-yl)propanoic acid | ¹H NMR (500 MHz, CD₃OH) δ 7.73 (s, 1H), 7.40 (d, J = 7.3 Hz, 1H), 7.28 (s, 1H), 7.09-6.91 (m, 3H), 6.43 (d, J = 7.3 Hz, 1H), 4.33 (dd, J = 10.0, 6.7 Hz, 1H), 4.26-4.17 (m, 1H), 4.15-4.07 (m, 1H), 3.83 (s, 3H), 3.43 (t, J = 5,6 Hz, 2H), 2.80-2.70 (m, 4H), 2.57-2.40 (m, 2H), 1.94-1.79 (m, 4H), 1.49-1.34 (m,, 1H), 1.28-1.14 (m, 1H), LCMS (ES): m/z 453.4 [M + H]⁺. Human αVβ6 IC50 (nM) = 64. | Example 11 |

Example 45

(S)-3-(1-Methyl-6-oxo-1,6-dihydropyridin-3-yl)-3-(3-(3-(5,6,7,8-tetrahydro-1,8-naphthyridin-2-yl)propyl)-1H-pyrazol-1-yl)propanoic acid ditrifluoroacetic acid salt

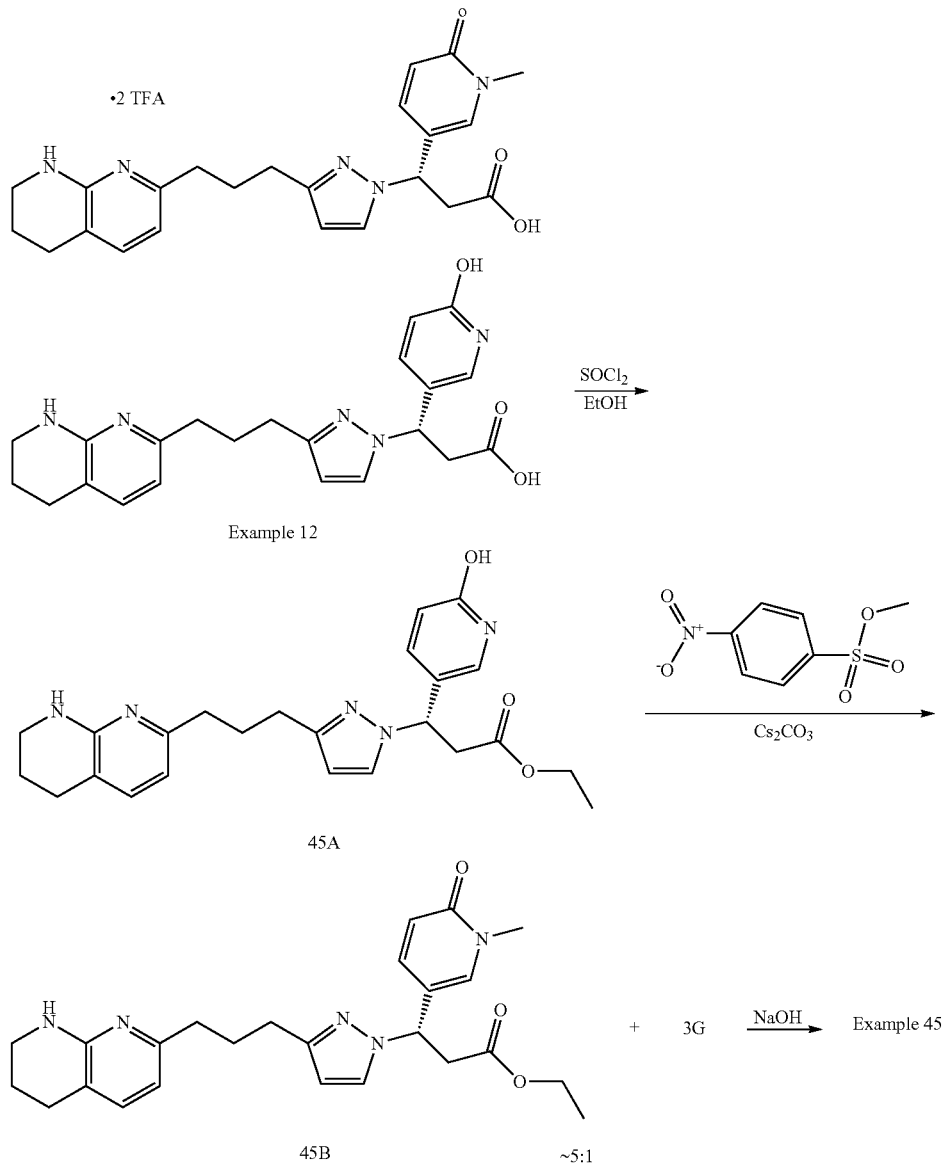

Example 45A

SOCl$_2$ (9.93 μL, 0.136 mmol) was added dropwise to a room temperature solution of Example 12 (37.6 mg, 0.059 mmol) in EtOH (0.592 mL). After stirring overnight, the solvent was removed in vacuo and the residue was dissolved in DCM and washed with sat. NaHCO$_3$ (2×). The organic phase was dried over anhydrous Na$_2$SO$_4$, filtered and concentrated in vacuo. The crude product was purified by flash chromatography (0 to 10% MeOH/DCM) to afford 45A (17.2 mg, 0.038 mmol, 64% yield) as a clear oil. LCMS (ES): m/z 436.5 [M+H]$^+$. $^1$H NMR (500 MHz, CD$_3$OD) δ 7.66-7.57 (m, 2H), 7.39 (d, J=2.2 Hz, 1H), 7.17 (d, J=7.4 Hz, 1H), 6.49 (d, J=9.6 Hz, 1H), 6.36 (d, J=7.2 Hz, 1H), 6.11 (d, J=2.2 Hz, 1H), 5.64 (dd, J=9.1, 6.3 Hz, 1H), 4.10-4.01 (m, 2H), 3.43-3.35 (m, 3H), 3.16 (dd, J=16.1, 6.2 Hz, 1H), 2.71 (t, J=6.2 Hz, 2H), 2.61 (t, J=7.6 Hz, 2H), 2.54 (t, J=7.6 Hz, 2H), 1.98-1.84 (m, 4H), 1.15 (t, J=7.0 Hz, 3H).

Example 45B

A mixture of Example 45A (10 mg, 0.023 mmol), methyl 4-nitrobenzenesulfonate (5.0 mg, 0.023 mmol) and Cs$_2$CO$_3$ (11.2 mg, 0.034 mmol) in DMF (0.221 mL) was stirred at room temperature. After 24 h, additional Cs$_2$CO$_3$ (2.8 mg) and methyl 4-nitrobenzene sulfonate (1.3 mg) were added and the reaction was stirred at room temperature for 7 h. The reaction mixture was diluted with DCM and filtered through a Celite® pad. The filtrate was concentrated in vacuo and the residue was purified by preparative HPLC (Column: Phenomenex Luna AXIA 5u C18 21.2×100 mm; Mobile Phase A: 10% MeOH-90% H₂O-0.1% TFA; Mobile Phase B: 90% MeOH-10% H₂O-0.1% TFA; Gradient: 0% to 100% B over 10 minutes, then a 5 minute hold at 100% B; Flow: 20 mL/min) to afford Example 45B, ditrifluoroacetic acid salt (10.1 mg, 0.013 mmol, 56% yield) as a clear oil. LCMS (ES): m/z 450.5 [M+H]⁺. ¹H NMR (500 MHz, CD₃OD) δ 7.72 (d, J=2.5 Hz, 1H), 7.65 (d, J=2.2 Hz, 1H), 7.59-7.49 (m, 2H), 6.59 (d, J=7.4 Hz, 1H), 6.49 (d, J=9.4 Hz, 1H), 6.13 (d, J=2.5 Hz, 1H), 5.64 (dd, J=9.4, 6.1 Hz, 1H), 4.07 (qd, J=7.1, 3.0 Hz, 2H), 3.54 (s, 3H), 3.49 (d, J=5.8 Hz, 2H), 3.41 (dd, J=16.2, 9.4 Hz, 1H), 3.16 (dd, J=16.2, 6.1 Hz, 1H), 2.81 (t, J=6.1 Hz, 2H), 2.68 (dt, J=15.8, 7.8 Hz, 4H), 2.07-1.89 (m, 4H), 1.15 (t, J=7.2 Hz, 3H) and Example 3G (3.2 mg, 4.72 μmol, 21% yield) as a clear od in ~5:1 ratio by analytical HPLC.

Example 45

To a solution of Example 45B (4.1 mg, 6.1 μmol) in EtOH (0.178 mL) was added 1M aq. NaOH (30 μL, 0.030 mmol) and the reaction mixture was stirred at room temperature. After 1 h, the reaction was concentrated in vacuo. The residue was acidified with 1M aq. HCl and then reconcentrated in vacuo. The residue was purified by preparative HPLC (Column: Phenomenex Luna AXIA 5μ C18 21.2×100 mm, 5-μm particles; Mobile Phase A: 10:90 MeOH:H₂O with 0.1% TFA; Mobile Phase B: 90:10 MeOH:H₂O with 0.1% TFA; Gradient: 5-100% B over 10 minutes, then a 2-minute hold at 100% B; Flow: 20 mL/min) to afford Example 45, ditrifluoroacetic acid salt (1.4 mg, 2.0 μmol, 34% yield) as an off-white solid. LCMS (ES): m/z 422.6 [M+H]⁺. ¹H NMR (500 MHz, CD₃OD) δ 7.71 (d, J=2.5 Hz, 1H), 7.66 (d, J=2.2 Hz, 1H), 7.61-7.44 (m, 2H), 6.59 (d, J=1.2 Hz, 1H), 6.49 (d, J=9.4 Hz, 1H), 6.13 (d, J=2.5 Hz, 1H), 5.67-5.58 (m, 1H), 3.54 (s, 3H), 3.52-3.46 (m, 2H), 3.43-3.33 (m, 1H), 3.14 (dd, J=16.5, 6.1 Hz, 1H), 2.81 (br t, J=6.2 Hz, 2H), 2.68 (dt, J=11.8, 7.4 Hz, 4H), 2.01-1.88 (m, 4H). Human αVβ6 IC50 (nM)=1.6; Human αVβ3 IC50 (nM)=1.6; and Human αVβ8 IC50 (nM)=3020.

Example 46

(±)-3-(6-Methoxypyridin-3-yl)-3-(3-(3-(5,6,7,8-tetrahydro-1,8-naphthyridin-2-yl)phenyl)-1H-pyrazol-1-yl)propanoic acid

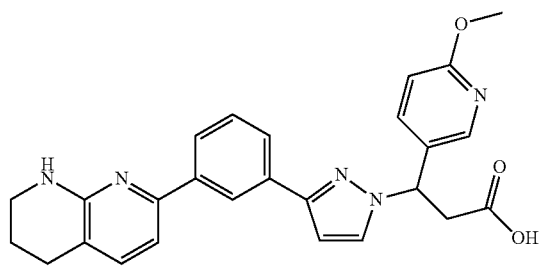

Example 46

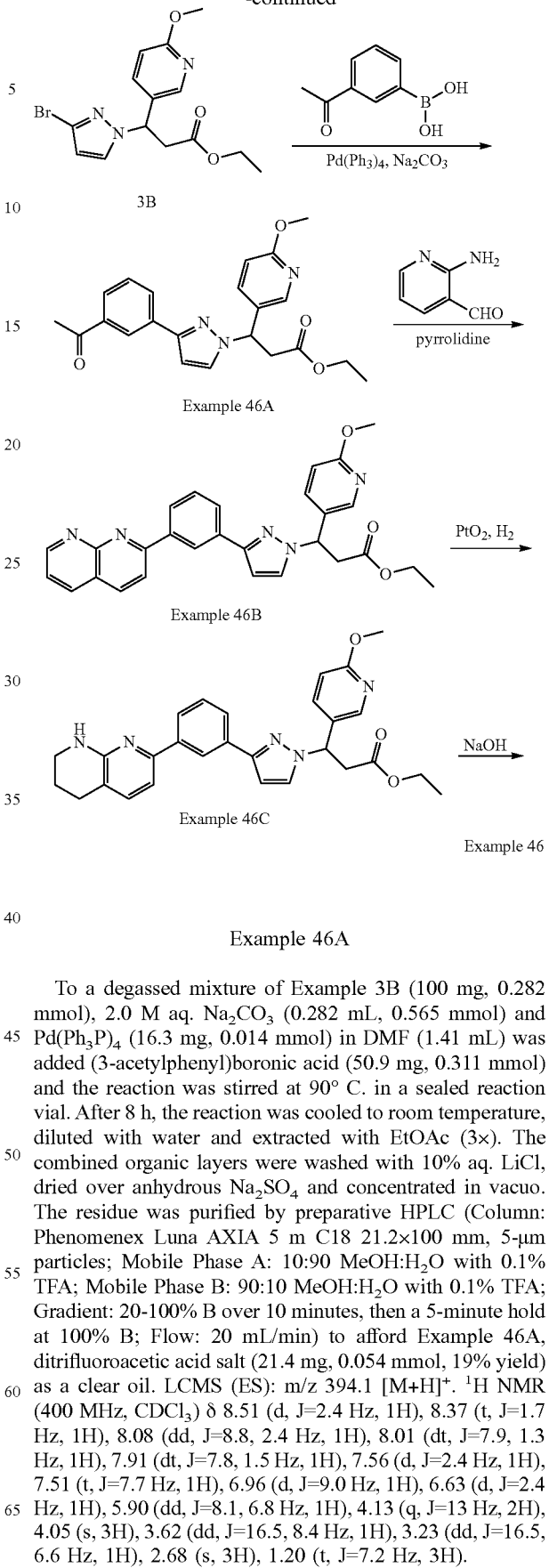

Example 46A

To a degassed mixture of Example 3B (100 mg, 0.282 mmol), 2.0 M aq. Na₂CO₃ (0.282 mL, 0.565 mmol) and Pd(Ph₃P)₄ (16.3 mg, 0.014 mmol) in DMF (1.41 mL) was added (3-acetylphenyl)boronic acid (50.9 mg, 0.311 mmol) and the reaction was stirred at 90° C. in a sealed reaction vial. After 8 h, the reaction was cooled to room temperature, diluted with water and extracted with EtOAc (3×). The combined organic layers were washed with 10% aq. LiCl, dried over anhydrous Na₂SO₄ and concentrated in vacuo. The residue was purified by preparative HPLC (Column: Phenomenex Luna AXIA 5 m C18 21.2×100 mm, 5-μm particles; Mobile Phase A: 10:90 MeOH:H₂O with 0.1% TFA; Mobile Phase B: 90:10 MeOH:H₂O with 0.1% TFA; Gradient: 20-100% B over 10 minutes, then a 5-minute hold at 100% B; Flow: 20 mL/min) to afford Example 46A, ditrifluoroacetic acid salt (21.4 mg, 0.054 mmol, 19% yield) as a clear oil. LCMS (ES): m/z 394.1 [M+H]⁺. ¹H NMR (400 MHz, CDCl₃) δ 8.51 (d, J=2.4 Hz, 1H), 8.37 (t, J=1.7 Hz, 1H), 8.08 (dd, J=8.8, 2.4 Hz, 1H), 8.01 (dt, J=7.9, 1.3 Hz, 1H), 7.91 (dd, J=7.8, 1.5 Hz, 1H), 7.56 (d, J=2.4 Hz, 1H), 7.51 (t, J=7.7 Hz, 1H), 6.96 (d, J=9.0 Hz, 1H), 6.63 (d, J=2.4 Hz, 1H), 5.90 (dd, J=8.1, 6.8 Hz, 1H), 4.13 (q, J=13 Hz, 2H), 4.05 (s, 3H), 3.62 (dd, J=16.5, 8.4 Hz, 1H), 3.23 (dd, J=16.5, 6.6 Hz, 1H), 2.68 (s, 3H), 1.20 (t, J=7.2 Hz, 3H).

Example 46B

The title compound was synthesized according to the method described for the synthesis of Example 10G, using Example 46A as the starting material: (12.5 mg, 0.026 mmol, 48% yield, orange oil). LCMS (ES): m/z 480.1 [M+H]$^+$. $^1$H NMR (400 MHz, CD$_3$OD) δ 9.10-9.06 (m, 1H), 8.76 (t, J=1.7 Hz, 1H), 8.50 (d, J=8.6 Hz, 1H), 8.46 (dd, J=8.1, 2.0 Hz, 1H), 8.26-8.21 (m, 2H), 7.84 (dd, J=8.8, 2.6 Hz, 1H), 7.81 (d, J=2.4 Hz, 1H), 7.69-7.54 (m, 4H), 6.80 (dd, J=5.6, 3.2 Hz, 2H), 5.95 (dd, J=9.0, 6.4 Hz, 1H), 4.10 (q, J=7.1 Hz, 2H), 3.90 (s, 3H), 3.65 (dd, J=16.2, 9.1 Hz, 1H), 3.32-3.26 (m, 1H), 1.16 (t, J=7.2 Hz, 3H).

Example 46C

The title compound was synthesized according to the method described for the synthesis of Example 10H, using Example 46B as the starting material: (12.0 mg, 0.025 mmol, 95% yield, orange oil). LCMS (ES): m/z 484.1 [M+H]$^+$. $^1$H NMR (400 MHz, CD$_3$OD) δ 8.25 (t, J=1.5 Hz, 1H), 8.19 (d, J=2.6 Hz, 1H), 7.83-7.70 (m, 4H), 7.43 (t, J=7.9 Hz, 1H), 7.28-7.23 (m, 1H), 6.95 (d, J=7.5 Hz, 1H), 6.78 (d, J=8.6 Hz, 1H), 6.68 (d, J=2.4 Hz, 1H), 5.91 (dd, J=9.0, 6.4 Hz, 1H), 4.08 (q, J=7.3 Hz, 2H), 3.88 (s, 3H), 3.59 (dd, J=16.2, 9.1 Hz, 1H), 3.42 (dd, J=10.8, 5.3 Hz, 2H), 3.26 (dd, J=16.2, 6.3 Hz, 1H), 2.77 (t, J=6.3 Hz, 2H), 1.98-1.85 (m, 2H), 1.14 (t, J=7.2 Hz, 3H).

Example 46

To a solution of Example 46C (12 mg, 0.025 mmol) in EtOH (0.730 mL) was added 1M aq. NaOH (74 μL, 0.074 mmol) and the reaction mixture was stirred at room temperature. After 5 h, the reaction was concentrated in vacuo. The residue was acidified with 1M aq. HCl and then reconcentrated in vacuo. The residue was purified by preparative HPLC (Column: XBridge C18, 19×200 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 16-56% B over 20 minutes, then a 4-minute hold at 100% B; Flow: 20 mL/min) to afford Example 46 (7.8 mg, 0.017 mmol, 67% yield). LCMS (ES): m/z 456.3 [M+H]$^+$. $^1$H NMR (500 MHz, CD$_3$OD) δ 8.25 (s, 1H), 8.17 (d, J=2.1 Hz, 1H), 7.84-7.65 (m, 4H), 7.43 (t, J=7.7 Hz, 1H), 7.33 (d, J=7.4 Hz, 1H), 6.96 (d, J=7.5 Hz, 1H), 6.76 (d, J=8.7 Hz, 1H), 6.67 (d, J=2.2 Hz, 1H), 5.89 (t, J=7.5 Hz, 1H), 3.88 (s, 3H), 3.50 (dd, J=16.0, 8.5 Hz, 1H), 3.47-3.39 (m, 2H), 3.19 (dd, J=16.0, 6.5 Hz, 1H), 2.79 (t, J=6.3 Hz, 2H), 1.96-1.86 (m, 2H). Human αVβ6 IC50 (nM)=28 Human αVβ3 IC50 (nM)=14; Human αVβ5 IC50 (nM)=11; and Human αVβ8 IC50 (nM)=8200.

Example 47

Ethyl (S)-3-(6-methoxypyridin-3-yl)-3-(3-(3-(5,6,7,8-tetrahydro-1,8-naphthyridin-2-yl)propyl)-1H-pyrazol-1-yl)propanoate

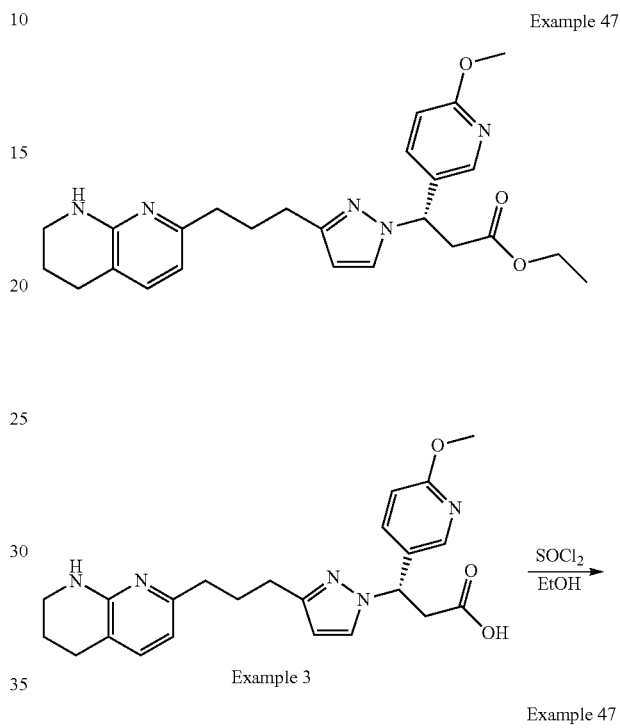

Example 47: SOCl$_2$ (0.066 mL, 0.906 mmol) was added dropwise to a room temperature solution of Example 2 (0.166 g, 0.394 mmol) in EtOH (3.94 mL). After stirring at room temperature overnight, the solvent was removed in vacuo to give Example 47, trichloridric acid salt (251 mg, 0.449 mmol) as a crude yellow-brown solid which was used in the next step without purification. 15 mg of this crude material was further purified by preparative HPLC (Column: XBridge C18, 19×200 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 21-61% B over 20 minutes, then a 4-minute hold at 100% B; Flow: 20 mL/min) to afford Example 47 (11.9 mg, 0.025 mmol). LCMS (ES): m/z 450.3 [M+H]$^+$. $^1$H NMR (500 MHz, CD$_3$OD) δ 8.07 (d, J=2.4 Hz, 1H), 7.65 (dd, J=8.7, 2.5 Hz, 1H), 7.61 (d, J=2.3 Hz, 1H), 7.49 (d, J=7.3 Hz, 1H), 6.74 (d, J=8.7 Hz, 1H), 6.54 (d, J=7.3 Hz, 1H), 6.11 (d, J=2.3 Hz, 1H), 5.79 (dd, J=9.0, 6.4 Hz, 1H), 4.06 (qd, J=7.1, 1.9 Hz, 2H), 3.88 (s, 3H), 3.51-3.46 (m, 2H), 3.46-3.41 (m, 1H), 3.20 (dd, J=16.0, 6.3 Hz, 1H), 2.79 (t, J=6.2 Hz, 2H), 2.72-2.52 (m, 4H), 2.06-1.86 (m, 4H), 1.14 (t, J=7.1 Hz, 3H). Human αVβ6 IC50 (nM)=11; Human αVβ3 IC50 (nM)=1120; and Human αVβ5 IC50 (nM)=270.

Example 48

(±)-3-(6-Methoxypyridin-3-yl)-3-(3-(3-(5,6,7,8-tetrahydro-1,8-naphthyridin-2-yl)propoxy)-1H-pyrazol-1-yl)propanoic acid

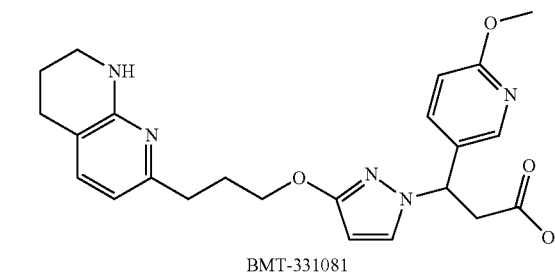

BMT-331081

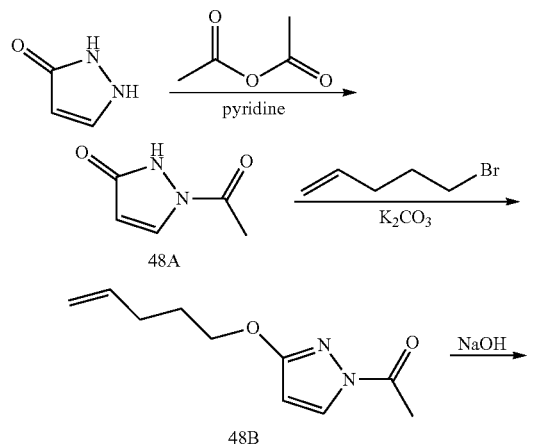

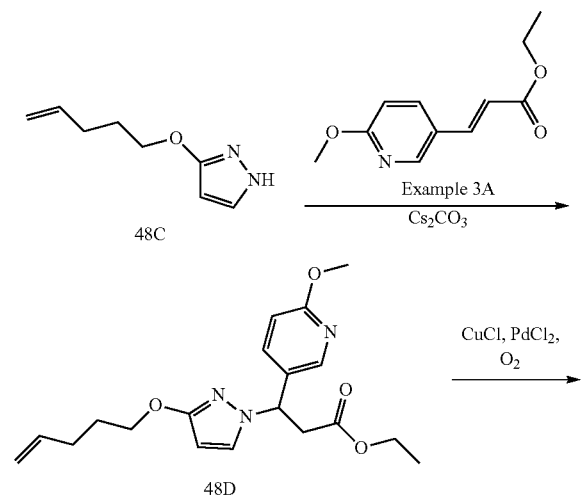

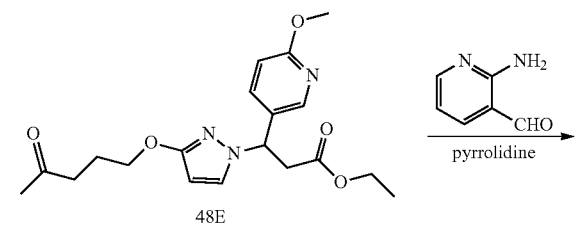

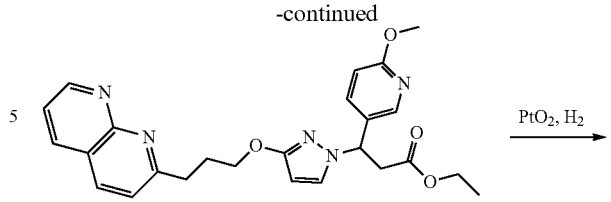

48F

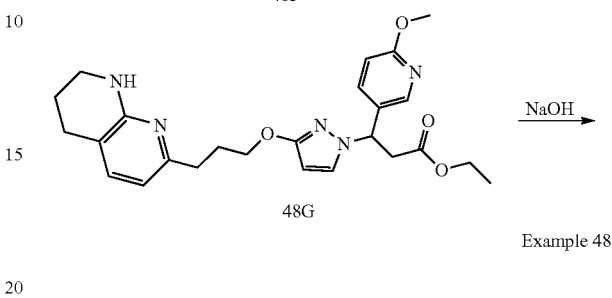

48G

Example 48A

The title compound was synthesized according to the method described in Patent WO 2011026937: (549 mg, 4.35 mmol, 73% yield, white solid). LCMS (ES): m/z 127.3 [M+H]⁺. ¹H NMR (400 MHz, DMSO-d₆) δ 11.12-10.87 (m, 1H), 8.15-8.10 (m, 1H), 6.00 (d, J=3.1 Hz, 1H), 2.47 (s, 3H).

Example 48B

A suspension of Example 48A (50 mg, 0.396 mmol), commercially available 5-bromopent-1-ene (0.063 mL, 0.528 mmol) and K₂CO₃ (60.3 mg, 0.436 mmol) in DMF (1.32 mL) was stirred at room temperature. After 24 h, the reaction mixture was diluted water and extracted with EtOAc (2×). The combined organic layers were dried over anhydrous Na₂SO₄ and concentrated in vacuo. The crude product was purified by flash chromatography (0 to 25% EtOAc/hexanes) to afford Example 48B (61 mg, 0.314 mmol, 79% yield) as a clear oil. LCMS (ES): m/z 195.2 [M+H]⁺. ¹H NMR (400 MHz, CDCl₃) δ 8.06 (d, J=3.1 Hz, 1H), 5.96 (d, J=3.1 Hz, 1H), 5.92-5.67 (m, 1H), 5.16-4.95 (m, 2H), 4.25 (t, J=6.5 Hz, 2H), 2.59 (s, 3H), 2.31-2.13 (m, 2H), 1.95-1.80 (m, 2H).

Example 48C

To a solution of Example 48B (61 mg, 0.314 mmol) in MeOH (0.785 mL) was added 6M aq. NaOH (0.052 mL, 0.314 mmol) and the reaction was stirred at room temperature. After 1 h, the volatiles were removed in vacuo and the residue was dissolved in EtOAc and washed with water (2×). The aqueous layer was back-extracted with EtOAc (2×) and the combined organic layers were dried over anhydrous Na₂SO₄ and concentrated in vacuo to afford Example 48C (48.7 mg, 0.320 mmol) as a crude yellow oil which was used in the next step without further purification. LCMS (ES): m/z 153.2 [M+H]⁺. ¹H NMR (500 MHz, CDCl₃) δ 9.78-8.45 (m, 1H), 7.37 (d, J=2.5 Hz, 1H), 5.86 (ddt, J=17.0, 10.2, 6.6 Hz, 1H), 5.74 (d, J=2.2 Hz, 1H), 5.12-5.04 (m, 1H), 5.00 (dd, J=10.3, 1.5 Hz, 1H), 4.17 (t, J=6.6 Hz, 2H), 2.28-2.17 (m, 2H), 1.94-1.83 (m, 2H).

Example 48D

A mixture of Example 48C (48.7 mg, 0.320 mmol) and Cs$_2$CO$_3$ (313 mg, 0.960 mmol) in CH$_3$CN (2.13 mL) was stirred at room temperature. After 5 min., Example 3A (66.3 mg, 0.320 mmol) was added and the reaction was heated at 80° C. for 5 h. Upon cooling to room temperature, the reaction was filtered and the filtrate concentrated in vacuo. The crude product was purified by flash chromatography (0 to 50% EtOAc/hexanes) to afford Example 48D (35.6 mg, 0.099 mmol, 31% yield) as a light yellow oil. LCMS (ES): m/z 360.1 [M+H]$^+$. $^1$H NMR (500 MHz, CDCl$_3$) δ 8.14 (d, J=2.5 Hz, 1H), 7.64 (dd, J=8.5, 2.5 Hz, 1H), 7.19 (d, J=2.2 Hz, 1H), 6.71 (d, J=8.5 Hz, 1H), 5.93-5.77 (m, 1H), 5.61 (d, J=2.2 Hz, 1H), 5.53 (dd, J=8.4, 6.5 Hz, 1H), 5.06 (dd, J=17.1, 1.7 Hz, 1H), 4.99 (dd, J=10.2, 1.7 Hz, 1H), 4.17-4.04 (m, 4H), 3.92 (s, 3H), 3.50 (dd, J=16.2, 8.5 Hz, 1H), 3.01 (dd, J=16.2, 6.6 Hz, 1H), 2.29-2.15 (m, 2H), 1.93-1.76 (m, 2H), 1.19 (t, J=7.2 Hz, 3H).

Example 48E

A solution of Example 48D (35.6 mg, 0.099 mmol), CuCl (29.4 mg, 0.297 mmol) and PdCl$_2$ (17.6 mg, 0.099 mmol) in DMF (2.03 mL) and water (0.508 mL) was stirred under an O$_2$ atmosphere (1 atm, balloon) at room temperature. After 7 h, the reaction was filtered through a Celite® pad and the filtrate was concentrated in vacuo. The residue was purified by preparative HPLC (Column: Phenomenex Luna AXIA 5u C18 21.2×100 mm; Mobile Phase A: 10:90 MeOH:H$_2$O with 0.1% TFA; Mobile Phase B: 90:10 MeOH:H$_2$O with 0.1% TFA; Gradient: 5-100% B over 10 minutes, then a 2-minute hold at 100% B; Flow: 20 mL/min) to afford Example 48E, ditrifluoroacetic acid salt (19.9 mg, 0.033 mmol, 33% yield) as a brown oil. LCMS (ES): m/z 376.1 [M+H]$^+$.

Example 48F

The title compound was synthesized according to the method described for the synthesis of Example 10G, using Example 48E as the starting material: (15.2 mg, 0.033 mmol, 100% yield, orange oil). LCMS (ES): m/z 462.2.

Example 48G

The title compound was synthesized according to the method described for the synthesis of Example 10H, using Example 48F as the starting material: (15.4 mg, 0.033 mmol, 100% yield, brown oil). LCMS (ES): m/z 466.2.

Example 48

To a solution of Example 48G (15.4 mg, 0.033 mmol) in EtOH (0.599 mL) was added 1M aq. NaOH (0.099 mL, 0.099 mmol) and the reaction mixture was stirred at room temperature. After 1 h, the reaction was concentrated in vacuo. The residue was acidified with 1M aq. HCl and then reconcentrated in vacuo. The residue was purified by preparative HPLC (Column: XBridge C18, 19×200 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 10-50% B over 20 minutes, then a 4-minute hold at 100% B; Flow: 20 mL/min) to afford Example 48 (4.6 mg, 0.010 mmol, 31% yield). LCMS (ES): m/z 438.2 [M+H]$^+$. $^1$H NMR (500 MHz, CD$_3$OD) δ 8.08 (s, 1H), 7.66 (dd, J=8.7, 2.4 Hz, 1H), 7.44-7.33 (m, 2H), 6.74 (d, J=8.7 Hz, 1H), 6.51 (br d, J=6.8 Hz, 1H), 5.62 (br dd, J=9.4, 4.8 Hz, 1H), 5.54 (s, 1H), 4.38-4.25 (m, 1H), 4.17-4.07 (m, 1H), 3.88 (s, 3H), 3.48-3.39 (m, 2H), 3.35 (br s, 1H), 3.01-2.88 (m, 1H), 2.80-2.71 (m, 4H), 2.17 (br dd, J=13.5, 6.8 Hz, 1H), 2.09 (br dd, J=13.3, 6.9 Hz, 1H), 1.91 (quin, J=6.0 Hz, 2H). Human αVβ6 IC50 (nM)=29; Human αVβ3 IC50 (nM)=7.5; and Human αVβ5 IC50 (nM)=2.7.

| Example | Structure & Name | Analytical Data | Method |
|---|---|---|---|
| 49 | 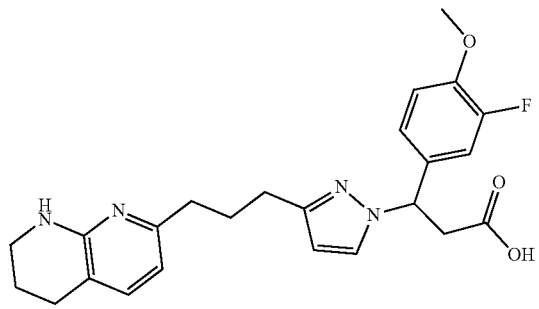 [SMILES: COc1ccc(C(CC(=O)O)n2ccc(CCCc3ccc4c(n3)NCCC4)n2)cc1F]<br>(±)-3-(3-Fluoro-4-methoxyphenyl)-3-(3-(3-(5,6,7,8-tetrahydro-1,8-naphthyridin-2-yl)propyl)-1H-pyrazol-1-yl)propanoic acid | $^1$H NMR (500 MHz, DMSO-d$_6$) δ 8.48 (d, J = 1.5 Hz, 1H), 7.94 (br d, J = 11.9 Hz, 1H), 7.90-7.86 (m, 2H), 7.84 (br d, J = 7.3 Hz, 1H), 7.04 (d, J = 7.3 Hz, 1H), 6.83 (d, J = 1.8 Hz, 1H), 6.50-6.41 (m, 1H), 4.03 (br s, 3H), 3.90-3.81 (m, 1H), 3.39 (br t, J = 6.0 Hz, 2H), 3.35 (s, 3H), 3.29-3.25 (m, 2H), 3.22 (br t, J = 7.5 Hz, 2H), 2.66-2.58 (m, 2H), 2.57-2.48 (m, 2H). LCMS (ES): m/z 439.1 [M + H]$^+$. Human αVβ6 IC50 (nM) = 24. | Example 22 |

| Example | Structure & Name | Analytical Data | Method |
|---|---|---|---|
| 50 | 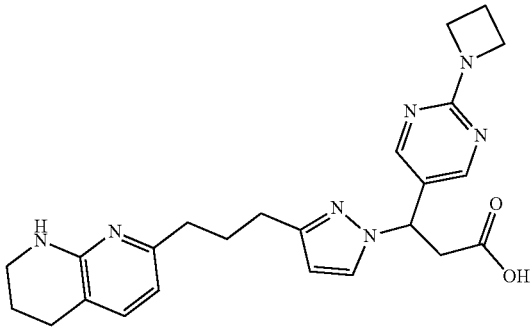 [SMILES: O=C(O)CC(c1cnc(N2CCC2)nc1)n1ccc(CCCc2ccc3c(n2)NCCC3)n1]<br>(±)-3-(2-(Azetidin-1-yl)pyrimidin-5-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 8.30 (s, 2H), 7.68 (s, 1H), 7.03 (br d, J = 7.3 Hz, 1H), 6.24 (d, J = 7.0 Hz, 1H), 6.02 (s, 1H), 5.58 (br t, J = 7.5 Hz, 1H), 3.98 (br t, J = 7.5 Hz, 4H), 3.28-3.20 (m, 3H), 3.05 (br dd, J = 15.9, 7.0 Hz, 1H), 2.59 (br t, J = 6.0 Hz, 2H), 2.47 (br t, J = 7.5 Hz, 2H), 2.44-2.37 (m, 2H), 2.27 (quin, J = 7.4 Hz, 2H), 1.86-1.76 (m, 2H), 1.73 (br d, J = 5.5 Hz, 2H). ). LCMS (ES): m/z 448.4 [M + H]$^+$. Human αVβ6 IC50 (nM) = 6.4. | Example 22 |
| 51 | 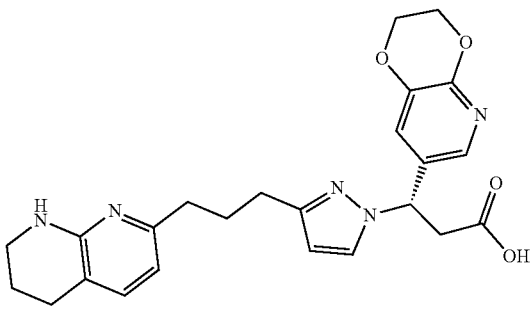 [SMILES: O=C(O)C[C@@H](c1cnc2c(c1)OCCO2)n1ccc(CCCc2ccc3c(n2)NCCC3)n1]<br>(S)-3-(2,3-Dihydro-[1,4]dioxino[2,3-b]pyridin-7-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 7.70 (br d, J = 12.6 Hz, 2H), 7.23 (br s, 1H), 7.05 (br d, J = 7.0 Hz, 1H), 6.25 (br d, J = 7.2 Hz, 1H), 6.03 (s, 1H), 5.67 (br s, 1H), 4.34 (br s, 2H), 4.19 (br s, 2H), 3.31-3.19 (m, 1H), 3.16 (s, 1H), 2.59 (br s, 2H), 2.49-2.44 (m, 2H), 2.41 (br s, 2H), 1.95-1.85 (m, 2H), 1.85-1.76 (m, 2H), 1.73 (br s, 2H). LCMS (ES): m/z 450.1 [M + H]$^+$. Human αVβ6 IC50 (nM) = 4.9. | Example 22 & 8 |
| 52 | 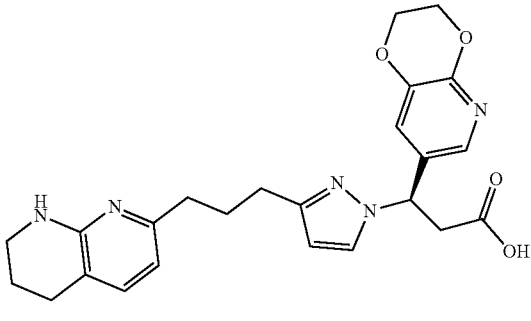 [SMILES: O=C(O)C[C@H](c1cnc2c(c1)OCCO2)n1ccc(CCCc2ccc3c(n2)NCCC3)n1]<br>(R)-3-(2,3-Dihydro-[1,4]dioxino[2,3-b]pyridin-7-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 7.70 (br d, J = 12.6 Hz, 2H), 7.23 (br s, 1H), 7.05 (br d, J = 7.0 Hz, 1H), 6.25 (br d, J = 7.2 Hz, 1H), 6.03 (s, 1H), 5.67 (br s, 1H), 4.34 (br s, 2H), 4.19 (br s, 2H), 3.31-3.19 (m, 1H), 3.16 (s, 1H), 2.59 (br s, 2H), 2.49-2.44 (m, 2H), 2.41 (br s, 2H), 1.95-1.85 (m, 2H), 1.85-1.76 (m, 2H), 1.73 (br s, 2H). LCMS (ES): m/z 450.1 [M + H]$^+$. Human αVβ6 IC50 (nM) = 730. | Example 22 & 9 |

| Example | Structure & Name | Analytical Data | Method |
|---|---|---|---|
| 53 | 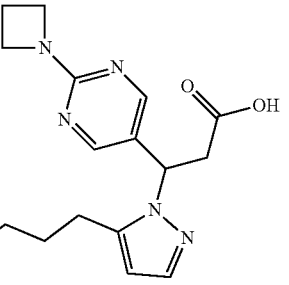<br>(±)-3-(2-(Azetidin-1-yl)pyrimidin-5-yl)-3-(5-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 8.23 (s, 2H), 7.55 (br d, J = 7.3 Hz, 1H), 7.48-7.37 (m, 1H), 6.56 (br d, J = 7.6 Hz, 1H), 6.13-6.03 (m, 1H), 5.75-5.56 (m, 1H), 3.98 (br t, J = 7.5 Hz, 4H), 3.40 (br d, J = 5.5 Hz, 2H), 3.30-3.13 (m, 1H), 3.05 (br dd, J = 16.8, 5.2 Hz, 1H), 2.81-2.60 (m, 6H), 2.28 (br t, J = 7.3 Hz, 2H), 2.07-1.86 (m, 2H), 1.82 (br s, 2H). LCMS (ES): m/z 448.4 [M + H]$^+$. Human αVβ6 IC50 (nM) = 140. | Example 22 |
| 54 | 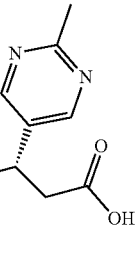<br>(S)-3-(2-Methylpyrimidin-5-yl)-3-(3-(3-(5,6,7,8-tetrahydro-1,8-naphthyridin-2-yl)propyl)-1H-pyrazol-1-yl)propanoic acid | $^1$H NMR (500 MHz, CD$_3$OD) δ 8.64 (s, 2H), 7.74 (d, J = 2.2 Hz, 1H), 7.57 (d, J = 7.4 Hz, 1H), 6.59 (d, J = 7.4 Hz, 1H), 6.16 (d, J = 2.2 Hz, 1H), 5.90 (dd, J = 8.9, 6.2 Hz, 1H), 3.58-3.39 (m, 2H), 3.31-3.24 (m, 2H), 2.81 (br t, J = 6.1 Hz, 2H), 2.69 (q, J = 7.2 Hz, 4H), 2.66 (s, 3H), 2.07-1.98 (m, 2H), 1.98-1.92 (m, 2H). LCMS (ES): m/z 407.0 [M + H]$^+$. Human αVβ6 IC50 (nM) = 18; Human αVβ3 IC50 (nM) = 7.3; and Human αVβ5 IC50 (nM) = 0.99. | Example 22 & 8 |
| 55 | 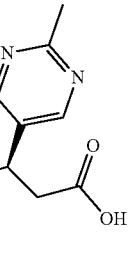<br>(R)-3-(2-Methylpyrimidin-5-yl)-3-(3-(3-(5,6,7,8-tetrahydro-1,8-naphthyridin-2-yl)propyl)-1H-pyrazol-1-yl)propanoic acid | $^1$H NMR (500 MHz, CD$_3$OD) δ 8.64 (s, 2H), 7.74 (d, J = 2.2 Hz, 1H), 7.57 (d, J = 7.4 Hz, 1H), 6.59 (d, J = 7.4 Hz, 1H), 6.16 (d, J = 2.2 Hz, 1H), 5.90 (dd, J = 8.9, 6.2 Hz, 1H), 3.58-3.39 (m, 2H), 3.31-3.24 (m, 2H), 2.81 (br t, J = 6.1 Hz, 2H), 2.69 (q, J = 7.2 Hz, 4H), 2.66 (s, 3H), 2.07-1.98 (m, 2H), 1.98-1.92 (m, 2H). ). LCMS (ES): m/z 407.0 [M + H]$^+$. Human αVβ6 IC50 (nM) = 900. | Example 22 & 9 |
| 56 | 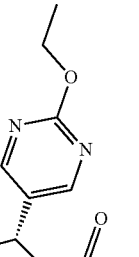<br>(S)-3-(2-Ethoxypyrimidin-5-yl)-3-(3-(3-(5,6,7,8-tetrahydro-1,8-naphthyridin-2-yl)propyl)-1H-pyrazol-1-yl)propanoic acid | $^1$H NMR (500 MHz, CD$_3$OD) δ 8.53 (s, 2H), 7.71 (d, J = 2.2 Hz, 1H), 7.56 (d, J = 7.4 Hz, 1H), 6.58 (d, J = 7.4 Hz, 1H), 6.14 (d, J = 2.2 Hz, 1H), 4.41 (q, J = 7.1 Hz, 2H), 3.52-3.46 (m, 2H), 3.46-3.42 (m, 1H), 3.25 (dd, J = 16.5, 6.3 Hz, 1H), 2.81 (br t, J = 6.2 Hz, 2H), 2.68 (q, J = 7.2 Hz, 4H), 2.04 (s, 1H), 2.03-1.98 (m, 2H), 1.98-1.90 (m, 2H), 1.38 (t, J = 7.0 Hz, 3H). ). LCMS (ES): m/z 437.1 [M + H]$^+$. Human αVβ6 IC50 (nM) = 7.1. | Example 22 & 8 |

| Example | Structure & Name | Analytical Data | Method |
|---|---|---|---|
| 57 | 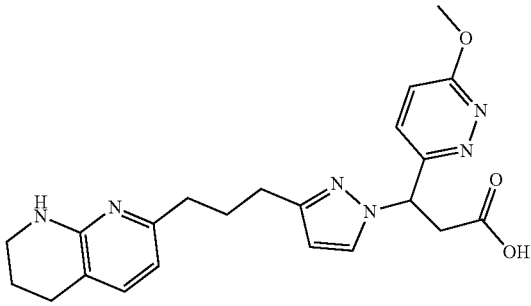 [SMILES: COc1ccc(C(CC(=O)O)n2ccc(CCCc3ccc4c(n3)NCCC4)n2)nn1]<br>(±)-3-(6-Methoxypyridazin-3-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 7.75-7.70 (m, 1H), 7.32 (d, J = 9.2 Hz, 1H), 7.14 (d, J = 9.2 Hz, 1H), 7.01 (d, J = 7.2 Hz, 1H), 6.22 (d, J = 7.2 Hz, 1H), 6.06 (d, J = 1.9 Hz, 1H), 5.94 (t, J = 7.4 Hz, 1H), 4.01 (s, 3H), 3.29-3.20 (m, 2H), 2.59 (br t, J = 6.2 Hz, 2H), 2.49-2.44 (m, 2H), 2.44-2.38 (m, 2H), 1.87-1.78 (m, 2H), 1.74 (quin, J = 5.9 Hz, 2H), 1.23 (s, 2H). LCMS (ES): m/z 422.9 [M + H]$^+$. Human αVβ6 IC50 (nM) = 51. | Example 22 |
| 58 | 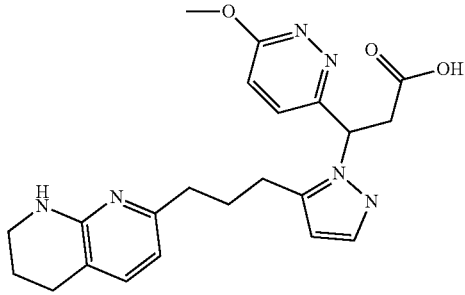<br>(±)-3-(6-Methoxypyridazin-3-yl)-3-(5-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 7.38 (s, 1H), 7.21 (d, = 9.2 Hz, 1H), 7.13 (d, J = 9.3 Hz, 1H), 7.02 (d, J = 7.2 Hz, 1H), 6.24 (d, J = 7.2 Hz, 1H), 6.07 (s, 1H), 6.00 (br dd, J = 8.4, 6.0 Hz, 1H), 4.01 (s, 3H), 3.32-3.20 (m, 2H), 2.72 (qt, J = 15.4, 7.9 Hz, 2H), 2.60 (br t, J = 6.2 Hz, 2H), 2.48-2.43 (m, 2H), 1.95-1.83 (m, 2H), 1.75 (quin, J = 5.8 Hz, 2H), 1.24 (s, 2H). LCMS (ES): m/z 423.0 [M + H]$^+$. Human αVβ6 IC50 (nM) = 2100.. | Example 22 |
| 59 | 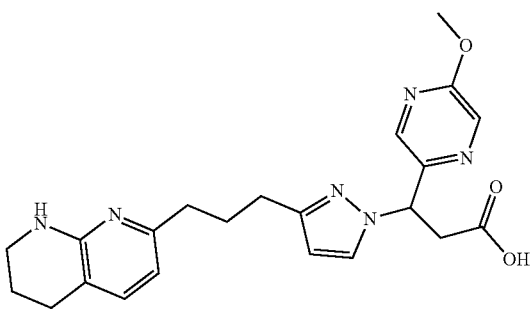 [SMILES: COc1cnc(C(CC(=O)O)n2ccc(CCCc3ccc4c(n3)NCCC4)n2)cn1]<br>(±)-3-(5-Methoxypyrazin-2-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 7.98 (s, 1H), 7.68 (s, 1H), 7.02 (d, J = 7.2 Hz, 1H), 6.22 (s, 1H), 6.05 (d, J = 2.1 Hz, 1H), 5.82 (t, J = 7.4 Hz, 1H), 3.89 (s, 3H), 3.25 (br s, 2H), 2.62-2.56 (m, 2H), 2.49-2.46 (m, 2H), 2.46-2.36 (m, 2H), 1.88-1.70 (m, 5H), 1.24 (s, 2H LCMS (ES): m/z 423.1 [M + H]$^+$. Human αVβ6 IC50 (nM) = 110. | Example 22 |
| 60 | 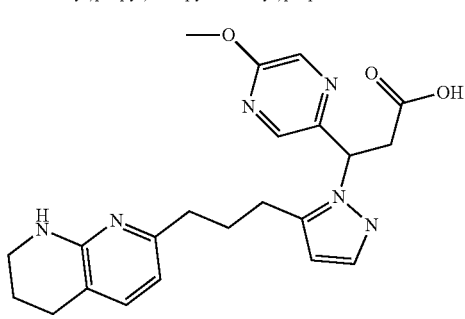<br>(±)-3-(5-Methoxypyrazin-2-yl)-3-(5-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 8.22 (s, 1H), 7.77 (s, 1H), 7.55-7.42 (m, 1H), 7.39 (s, 1H), 6.51 (br d, J = 7.3 Hz, 1H), 6.11 (s, 1H), 5.80 (dd, J = 9.5, 4.9 Hz, 1H), 3.90-3.77 (m, 3H), 3.35 (br d, J = 5.2 Hz, 1H), 3.33-3.21 (m, 1H), 3.21-3.10 (m, 1H), 2.79-2.58 (m, 7H), 1.98-1.85 (m, 2H), 1.85-1.72 (m, 2H). LCMS (ES): m/z 423.0 [M + H]$^+$. Human αVβ6 IC50 (nM) = 500. | Example 22 |

| Example | Structure & Name | Analytical Data | Method |
|---|---|---|---|
| 61 | 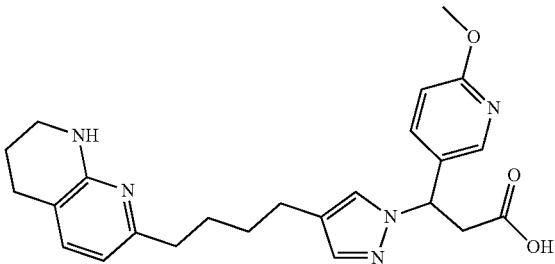 [SMILES: COc1ccc(C(CC(=O)O)n2cc(CCCCc3ccc4c(n3)NCCC4)cn2)cn1]<br>(±)-3-(6-Methoxypyridin-3-yl)-3-(4-(4-(5,6,7,8-tetrahydro-1,8-naphthyridin-2-yl)butyl)-1H-pyrazol-1-yl)propanoic acid | $^1$H NMR (500 MHz, DMSO-$d_6$) δ 8.11 (d, J = 1.8 Hz, 1H), 7.65 (s, 1H), 7.63-7.56 (m, 1H), 7.50 (br d, J = 7.3 Hz, 1H), 7.27 (s, 1H), 6.75 (d, J = 8.5 Hz, 1H), 6.52 (d, J = 7.3 Hz, 1H), 5.71 (br dd, J = 8.4, 6.6 Hz, 1H), 3.80 (s, 2H), 3.40-3.31 (m, 1H), 3.10 (dd, J = 16.3, 6.3 Hz, 1H), 2.70 (br t, J = 5.8 Hz, 2H), 2.60 (br t, J = 7.3 Hz, 2H), 2.54 (s, 3H), 2.37 (br t, J = 7.3 Hz, 2H), 1.86-1.73 (m, 2H), 1.63-1.53 (m, 2H), 1.53-1.42 (m, 2H). LCMS (ES): m/z 436.1 [M + H]$^+$. Human αVβ6 IC50 (nM) = 56. | Example 22 |
| 62 | 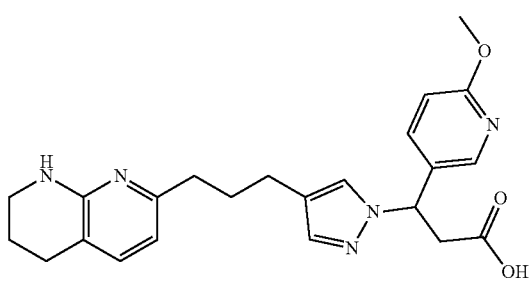 [SMILES: COc1ccc(C(CC(=O)O)n2cc(CCCc3ccc4c(n3)NCCC4)cn2)cn1]<br>(±)-3-(6-Methoxypyridin-3-yl)-3-(4-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 8.12 (s, 1H), 7.67 (br d, J = 8.5 Hz, 1H), 7.64-7.61 (m, 1H), 7.28 (s, 1H), 7.02 (d, J = 7.3 Hz, 1H), 6.76 (d, J = 8.5 Hz, 1H), 6.24 (d, J = 7.3 Hz, 1H), 5.72 (br t, J = 7.6 Hz, 1H), 3.81 (s, 3H), 3.36-3.20 (m, 2H), 3.20-3.03 (m, 2H), 2.60 (br t, J = 6.1 Hz, 2H), 2.46-2.33 (m, 4H), 1.81-1.70 (m, 4H). LCMS (ES): m/z 422.1 [M + H]$^+$. Human αVβ6 IC50 (nM) = 170. | Example 22 |

Example 63 3-(5-methoxypyridin-3-yl)-3-(5-(3-(5,6,7,8-tetrahydro-1,8-naphthyridin-2-yl)propyl)-1H-pyrazol-1-yl)propanoic acid (Racemic, N1 Pyrazole Regioisomer)

Example 64 3-(5-methoxypyridin-3-yl)-3-(3-(3-(5,6,7,8-tetrahydro-1,8-naphthyridin-2-yl)propyl)-1H-pyrazol-1-yl)propanoic acid (Enantiomer A, N2 Pyrazole Regioisomer)

Example 65 3-(5-methoxypyridin-3-yl)-3-(3-(3-(5,6,7,8-tetrahydro-1,8-naphthyridin-2-yl)propyl)-1H-pyrazol-1-yl)propanoic acid (Enantiomer B, N2 Pyrazole Regioisomer)

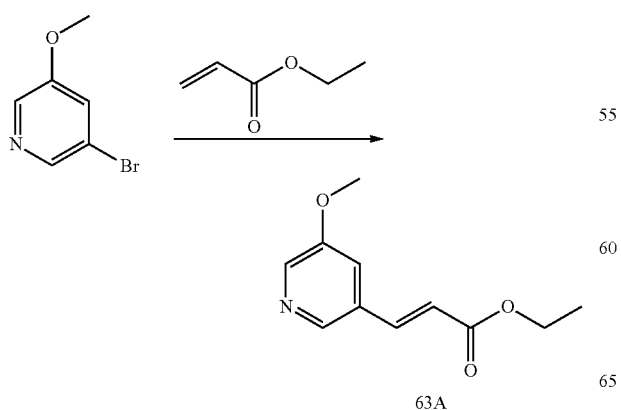

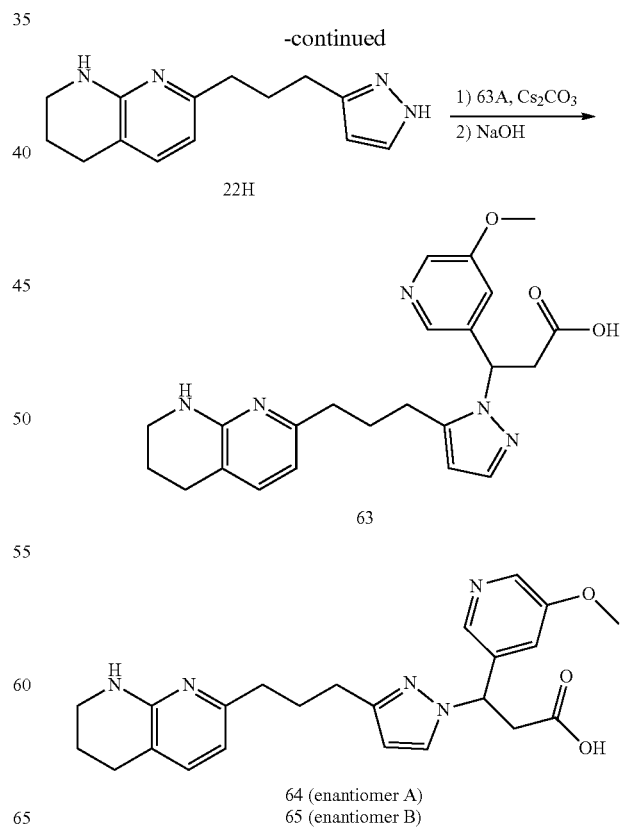

Example 63A

To a solution of 3-bromo-5-methoxypyridine (2.0 g, 10.64 mmol), ethyl acrylate (4.03 ml, 37.2 mmol), triethylamine (4.00 ml, 28.7 mmol) and tri-o-tolylphosphine (0.54 g, 1.769 mmol) in ACN (13.30 ml) that was degassed with nitrogen for 10 min was added palladium(II) acetate (0.27 g, 1.20 mmol). The vial was then heated at 90° C. for 8 h, then allowed to stir at room temperature overnight. The reaction was diluted with water and extracted with EtOAc. The organic layers were combined, dried with $MgSO_4$, filtered and concentrated under reduced pressure. The crude product was purified by flash chromatography (0-75% EtOAc/Hex) to give Example 63A (1.83 g, 8.83 mmol, 83% yield) as a light yellow solid. LCMS (ESI) m/z 208.0 (M+H)$^+$. $^1$H NMR (500 MHz, METHANOL-$d_4$) δ 8.39-8.31 (m, 1H), 8.26 (d, J=2.8 Hz, 1H), 7.77-7.59 (m, 2H), 6.71 (d, J=16.0 Hz, 1H), 4.28 (q, J=7.0 Hz, 2H), 3.93 (s, 3H), 1.35 (t, J=1.2 Hz, 3H).

To a solution of Example 22H (0.35 g, 1.44 mmol) and Example 63A (0.30 g, 1.44 mmol) in acetonitrile (2 mL) was added cesium carbonate (1.41 g, 4.33 mmol) and the vial was heated to 80° C. for 16 hours. The reaction was concentrated under a stream of nitrogen. The crude material [LCMS (ESI) m/z 450.4 and 422.3 (M+H)$^+$] was dissolved in MeOH (7.33 mL) and treated with 1M NaOH (1.466 mL, 1.466 mmol). The reaction mixture was allowed to stir at room temperature for 2 hours. The reaction was filtered through diatomaceous earth and concentrated under reduced pressure. The crude product was purified by reverse phase HPLC (Start % B=10, Final % B=90, Gradient time=10 min, Flow rate=40 mL/min, Wavelength=220, Solvent A=10% MeOH—90% water—0.1% TFA, Solvent B=90% MeOH—10% water-0.1% TFA, Phenominex Luna 5u C18 100×30 MM) to give 324 mg of a yellow oil. The material was further separated by chiral SFC separation (Chromegachiral CC4, 21×250 mm, 5 micron, 43% MeOH/ACN (0.1% NH$_4$OH)/57% CO$_2$, 45 mL/min, 120 Bar, 40° C., 220 nm) to give Example 63 (racemate), Example 64 (enantiomer A), and Example 65 (enantiomer B). Example 63 (racemate, N1 pyrazole regioisomer, 31.6 mg, 9.8% yield): LCMS (ESI) m/z 422.3 (M+H)$^+$. $^1$H NMR (500 MHz, METHANOL-$d_4$) δ 8.19-8.04 (m, 1H), 8.02-7.84 (m, 1H), 7.42 (d, J=1.2 Hz, 1H), 7.32-7.22 (m, 2H), 6.41 (d, J=1.1 Hz, 1H), 6.06 (d, J=1.0 Hz, 1H), 5.97 (br dd, J=8.8, 5.1 Hz, 1H), 3.82 (s, 3H), 3.53-3.35 (m, 3H), 3.08-2.97 (m, 1H), 2.82 (br d, J=6.8 Hz, 1H), 2.73 (br t, J=5.9 Hz, 3H), 2.58 (t, J=7.6 Hz, 2H), 2.17 (brd, J=6.8 Hz, 1H), 2.06-1.94 (m, 1H), 1.94-1.84 (m, 2H). Human αVβ6 IC50 (nM)=13; Human αVβ3 IC50 (nM)=8.0; Human αVβ5 IC50 (nM)=0.87; and Human αVβ8 IC50 (nM)=770.

Example 64 (enantiomer A, N2 pyrazole regioisomer, 52 mg, 16% yield)): LCMS (ESI) m/z 422.3 (M+H)$^+$. $^1$H NMR (500 MHz, METHANOL-$d_4$) δ 8.50-7.87 (m, 2H), 1 FI (s, 1H), 7.39 (d, J=7.3 Hz, 1H), 7.34 (s, 1H), 6.47 (brd, J=7.3 Hz, 1H), 6.11 (d, J=1.5 Hz, 1H), 5.91 (br s, 1H), 3.83 (s, 3H), 3.45-3.39 (m, 2H), 3.31 (dt, J=3.2, 1.7 Hz, 1H), 3.09-2.99 (m, 1H), 2.74 (t, J=6.1 Hz, 2H), 2.66-2.54 (m, 4H), 2.05-1.84 (m, 4H). Human αVβ6 IC50 (nM)=19; Human αVβ3 IC50 (nM)=3.8 and Human αVβ8 IC50 (nM)=110.

Example 65 (enantiomer B, N2 pyrazole regioisomer, 55.5 mg, 17% yield): LCMS (ESI) m/z 422.3 (M+H)$^+$. 1H NMR (600 MHz, METHANOL-d4) Shift 8.24-8.12 (m, 1H), 8.08 (br s, 1H), 7.64 (s, 1H), 7.52 (br d, J=7.2 Hz, 1H), 7.38 (br s, 1H), 6.59 (br d, J=7.2 Hz, 1H), 6.14 (d, J=1.8 Hz, 1H), 5.91 (br dd, J=10.9, 4.3 Hz, 1H), 3.88 (s, 3H), 3.49 (t, J=5.4 Hz, 2H), 3.04 (br dd, J=14.6, 4.3 Hz, 1H), 2.81 (br t, J=5.9 Hz, 2H), 2.72-2.53 (m, 4H), 2.16-2.03 (m, 2H), 2.01-1.89 (m, 3H). Human αVβ6 IC50 (nM)=410; Human αVβ3 IC50 (nM)=4.3; Human αVβ5 IC50 (nM)=1.1.

TABLE A

| Example | Structure & Name | Analytical Data | Method |
|---|---|---|---|
| 66 | 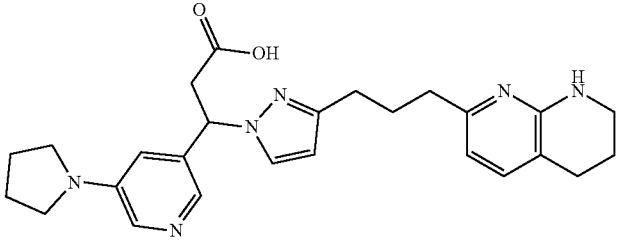 [SMILES: O=C(O)CC(c1cncc(N2CCCC2)c1)n1ccc(CCCc2ccc3c(n2)NCCC3)n1]<br>(±)-3-[5-(pyrrolidin-1-yl)pyridin-3-yl]-3-{3-[3-(5,6,7,8-tetrahydro-1,8-naphthyridin-2-yl)propyl]-1H-pyrazol-1-yl}propanoic acid | 1H NMR (600 MHz, DMSO-d6) δ 7.87-7.66 (m, 3H), 7.06 (br s, 1H), 6.77 (br s, 1H), 6.33-6.19 (m, 1H), 6.04 (d, J = 1.8 Hz, 1H), 5.69 (dd, J = 9.2, 5.9 Hz, 1H), 3.31-2.98 (m, 6H), 2.61 (br t, J = 6.1 Hz, 2H), 2.55 (s, 1H), 2.51 (br s, 2H), 2.45 (br t, J = 7.5 Hz, 2H), 1.95-1.87 (m, 7H), 1.87-1.80 (m, 2H), 1.79-1.70 (m, 2H) LC/MS [M + H]+ = 461.1. Human αVβ6 IC50 (nM) = 21 | Example 22 |
| 67 | 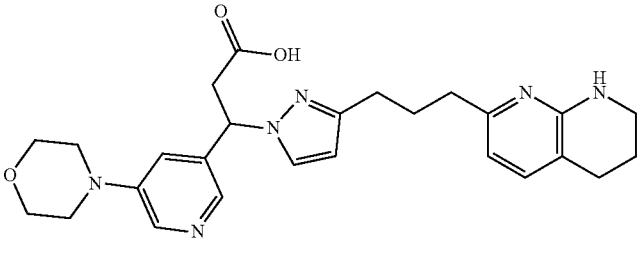 [SMILES: O=C(O)CC(c1cncc(N2CCOCC2)c1)n1ccc(CCCc2ccc3c(n2)NCCC3)n1]<br>3-[5-(morpholin-4-yl)pyridin-3-yl]-3-{3-[3-(5,6,7,8-tetrahydro-1,8-naphthyridin-2-yl)propyl]-1H-pyrazol-1-yl}propanoic acid<br>(Enantiomer A) | 1H NMR (500 MHz, METHANOL-d4) δ 8.25-8.06 (m, 1H), 7.93 (br s, 1H), 7.62 (d, J = 2.1 Hz, 1H), 7.47 (d, J = 7.3 Hz, 1H), 7.34 (s, 1H), 6.56 (d, J = 7.5 Hz, 1H), 6.13 (d, J = 2.3 Hz, 1H), 5.87 (dd, J = 10.8, 4.7 Hz, 1H), 3.89-3.75 (m, 4H), 3.52-3.43 (m, 2H), 3.24-3.15 (m, 5H), 3.01 (dd, J = 14.7, 4.8 Hz, 1H), 2.79 (t, J = 6.1 Hz, 2H), 2.72-2.53 (m, 5H), 2.15-1.82 (m, 4H) LC/MS [M + H]+ = 477.3 Human αVβ6 IC50 (nM) = 210. | Example 22, 8 |

TABLE A-continued

| Example | Structure & Name | Analytical Data | Method |
|---|---|---|---|
| 68 | 3-[5-(morpholin-4-yl)pyridin-3-yl]-3-{3-[3-(5,6,7,8-tetrahydro-1,8-naphthyridin-2-yl)propyl]-1H-pyrazol-1-yl}propanoic acid (Enantiomer B) | 1H NMR (500 MHz, METHANOL-d4) δ 8.25-8.09 (m, 1H), 7.93 (br s, 1H), 7.62 (d, J = 2.3 Hz, 1H), 7.48 (d, J = 7.3 Hz, 1H), 7.34 (d, J = 2.0 Hz, 1H), 6.57 (d, J = 7.3 Hz, 1H), 6.13 (d, J = 2.3 Hz, 1H), 5.87 (dd, J = 10.9, 4.7 Hz, 1H), 3.90-3.71 (m, 4H), 3.54-3.44 (m, 2H), 3.27 (s, 1H), 3.25-3.13 (m, 4H), 3.01 (dd, J = 14.6, 4.6 Hz, 1H), 2.80 (t, J = 6.2 Hz, 2H), 2.72-2.54 (m, 4H), 2.15-1.83 (m, 4H) LC/MS [M + H]+ = 477.3 Human αVβ6 IC50 (nM) = 2.8. | Example 22, 9 |
| 69 | 3-(5-methylpyridin-3-yl)-3-{3-[3-(5,6,7,8-tetrahydro-1,8-naphthyridin-2-yl)propyl]-1H-pyrazol-1-yl}propanoic acid (Enantiomer A) | 1H NMR (600 MHz, METHANOL-d4) Shift 8.35-8.21 (m, 2H), 7.68-7.55 (m, 2H), 7.47 (d, J = 7.3 Hz, 1H), 6.55 (d, J = 7.3 Hz, 1H), 6.12 (d, J = 1.9 Hz, 1H), 5.87 (dd, J = 10.8, 4.5 Hz, 1H), 3.46 (t, J = 5.6 Hz, 2H), 3.29-3.22 (m, 1H), 3.00 (dd, J = 14.6, 4.6 Hz, 1H), 2.78 (t, J = 6.2 Hz, 2H), 2.69-2.48 (m, 4H), 2.34 (s, 3H), 2.13-2.01 (m, 1H), 2.00-1.85 (m, 3H) LC/MS [M + H]+ = 406.3 Human αVβ6 IC50 (nM) = 15 | Example 22, 8 |
| 70 | 3-(5-methylpyridin-3-yl)-3-{3-[3-(5,6,7,8-tetrahydro-1,8-naphthyridin-2-yl)propyl]-1H-pyrazol-1-yl}propanoic acid (Enantiomer B) | 1H NMR (600 MHz, METHANOL-d4) Shift 8.28 (br d, J = 19.8 Hz, 2H), 7.68-7.54 (m, 2H), 7.46 (d, J = 7.3 Hz, 1H), 6.55 (d, J = 7.3 Hz, 1H), 6.11 (d, J = 1.9 Hz, 1H), 5.87 (dd, J = 10.8, 4.6 Hz, 1H), 3.46 (t, J = 5.6 Hz, 2H), 3.25 (s, 1H), 3.00 (dd, J = 14.6, 4.6 Hz, 1H), 2.78 (t, J = 6.2 Hz, 2H), 2.68-2.48 (m, 4H), 2.34 (s, 3H), 2.10-2.00 (m, 1H), 1.98-1.85 (m, 3H) LC/MS [M + H]+ = 406.3 Human αVβ6 IC50 (nM) = 4900 | Example 22, 9 |
| 71 | (±)-3-(3-fluoro-4-methoxyphenyl)-3-{5-[3-(5,6,7,8-tetrahydro-1,8-naphthyridin-2-yl)propyl]-1H-pyrazol-1-yl}propanoic acid | 1H NMR (500 MHz, DMSO-d6) δ 7.75-7.64 (m, 1H), 7.22-6.93 (m, 4H), 6.32-6.18 (m, 2H), 6.02 (s, 1H), 5.67 (br t, J = 7.3 Hz, 1H), 3.80 (s, 5H), 3.24 (br d, J = 4.6 Hz, 1H), 3.00 (br dd, J = 16.0, 6.3 Hz, 3H), 2.61 (br t, J = 6.3 Hz, 2H), 2.44 (br t, J = 7.6 Hz, 2H), 1.84 (br t, J = 7.9 Hz, 2H), 1.79-1.71 (m, 2H) LC/MS [M + H]+ = 439.2 Human αVβ6 IC50 (nM) = 15. | Example 22 |

| Example | Structure & Name | Analytical Data | Method |
|---|---|---|---|
| 72 | (±)-3-[5-(dimethylcarbamoyl)pyridin-3-yl]-3-{5-[3-(5,6,7,8-tetrahydro-1,8-naphthyridin-2-yl)propyl]-1H-pyrazol-1-yl}propanoic acid | 1H NMR (600 MHz, DMSO-d6) δ 7.60-7.49 (m, 1H), 7.27 (br d, J = 5.5 Hz, 1H), 7.20-6.98 (m, 4H), 6.28 (br d, J = 7.0 Hz, 1H), 5.94-5.78 (m, 1H), 5.54 (br dd, J = 8.8, 6.2 Hz, 1H), 3.01-2.85 (m, 1H), 2.71 (br s, 4H), 2.64-2.53 (m, 4H), 2.47 (br d, J = 5.9 Hz, 2H), 2.38 (br t, J = 7.3 Hz, 4H), 2.30 (br d, J = 7.3 Hz, 2H), 1.75-1.46 (m, 4H) LC/MS [M + H]+ = 463.2 Human αVβ6 IC50 (nM) = 24 | Example 22 |
| 73 | (±)-3-(2-methoxypyridin-4-yl)-3-{5-[3-(5,6,7,8-tetrahydro-1,8-naphthyridin-2-yl)propyl]-1H-pyrazol-1-yl}propanoic acid | 1H NMR (600 MHz, DMSO-d6) δ 8.15-7.98 (m, 1H), 7.75 (d, J = 1.8 Hz, 1H), 7.02 (d, J = 7.3 Hz, 1H), 6.81 (br d, J = 4.8 Hz, 1H), 6.53 (s, 1H), 6.24 (d, J = 7.3 Hz, 2H), 6.06 (s, 1H), 5.71 (dd, J = 8.8, 5.9 Hz, 1H), 3.80 (s, 3H), 3.09-2.96 (m, 1H), 2.60 (br t, J = 6.2 Hz, 3H), 2.49-2.48 (m, 1H), 2.43 (br t, J = 7.5 Hz, 3H), 1.83 (br t, J = 7.5 Hz, 3H), 1.79-1.66 (m, 3H) LC/MS [M + H]+ = 422.2 Human αVβ6 IC50 (nM) = 25 | Example 22 |
| 74 | (±)-3-[5-(dimethylcarbamoyl)pyridin-3-yl]-3-{3-[3-(5,6,7,8-tetrahydro-1,8-naphthyridin-2-yl)propyl]-1H-pyrazol-1-yl}propanoic acid | 1H NMR (600 MHz, DMSO-d6) δ 7.53 (d, J = 2.2 Hz, 1H), 7.19 (d, J = 1.1 Hz, 1H), 7.17-7.10 (m, 2H), 7.08-7.01 (m, 1H), 6.82-6.75 (m, 1H), 6.01 (d, J = 7.3 Hz, 1H), 5.82 (d, J = 1.8 Hz, 1H), 5.54 (br dd, J = 8.8, 6.2 Hz, 1H), 3.22-3.07 (m, 4H), 3.01 (br s, 3H), 2.92-2.80 (m, 2H), 2.72 (br s, 3H), 2.64-2.53 (m, 3H), 2.38 (br t, J = 6.1 Hz, 1H), 1.69 (s, 2H), 1.61 (br t, J = 7.5 Hz, 2H), 1.55-1.49 (m, 3H) LC/MS [M + H]+ = 463.1 Human αVβ6 IC50 (nM) = 13 | Example 22 |
| 75 | (±)-3-(3,5-dichlorophenyl)-3-{5-[3-(5,6,7,8-tetrahydro-1,8-naphthyridin-2-yl)propyl]-1H-pyrazol-1-yl}propanoic acid | 1H NMR (600 MHz, DMSO-d6) Shift 7.77 (br s, 1H), 7.49 (s, 1H), 7.31 (s, 2H), 7.02 (br d, J = 7.2 Hz, 1H), 6.24 (br s, 2H), 6.07 (s, 1H), 5.76 (br s, 1H), 3.28-3.16 (m, 2H), 3.18-3.05 (m, 2H), 2.60 (br t, J = 6.1 Hz, 2H), 2.49-2.47 (m, 2H), 2.41 (br d, J = 6.6 Hz, 2H), 1.87-1.79 (m, 2H), 1.78-1.70 (m, 2H) LC/MS [M + H]+ = 458.98 Human αVβ6 IC50 (nM) = 28 | Example 22 |

TABLE A-continued

| Example | Structure & Name | Analytical Data | Method |
|---|---|---|---|
| 76 | (±)-4-{[4-(2-carboxy-1-{3-[3-(5,6,7,8-tetrahydro-1,8-naphthyridin-2-yl)propyl]-1H-pyrazol-1-yl}ethyl)pyridin-2-yl]amino}butanoic acid | 1H NMR (600 MHz, DMSO-d6) Shift 7.91-7.77 (m, 1H), 7.70 (s, 1H), 7.05 (br d, J = 7.2 Hz, 1H), 6.53 (br s, 1H), 6.41-6.31 (m, 2H), 6.26 (d, J = 7.2 Hz, 1H), 6.22 (s, 1H), 6.13-6.03 (m, 1H), 5.53 (br dd, J = 9.1, 5.6 Hz, 1H), 3.23 (br s, 2H), 3.15 (br d, J = 5.9 Hz, 2H), 3.04 (br d, J = 5.5 Hz, 2H), 2.60 (br t, J = 6.0 Hz, 2H), 2.44 (br t, J = 7.5 Hz, 4H), 2.24 (br t, J = 7.4 Hz, 2H), 1.87-1.65 (m, 6H) LC/MS [M + H]+ = 493.2 Human αVβ6 IC50 (nM) = 55 | Example 22 |
| 77 | (±)-3-(5-fluoro-6-methoxypyridin-3-yl)-3-{5-[3-(5,6,7,8-tetrahydro-1,8-naphthyridin-2-yl)propyl]-1H-pyrazol-1-yl}propanoic acid | 1H NMR (500 MHz, DMSO-d6) δ 7.98-7.88 (m, 1H), 7.73 (s, 1H), 7.64 (br d, J = 11.6 Hz, 1H), 7.02 (d, J = 7.0 Hz, 1H), 6.34-6.17 (m, 2H), 6.03 (s, 1H), 5.75 (br t, J = 7.3 Hz, 1H), 3.91 (s, 3H), 3.29-3.13 (m, 4H), 3.02 (br dd, J = 16.3, 6.6 Hz, 2H), 2.60 (br t, J = 6.1 Hz, 2H), 2.43 (br t, J = 7.5 Hz, 2H), 1.84 (br t, J = 7.5 Hz, 2H), 1.78-1.68 (m, 2H) LC/MS [M + H]+ = 440.2 Human αVβ6 IC50 (nM) = 18 | Example 63 |
| 78 | (±)-3-(5-methylpyridin-3-yl)-3-{5-[3-(5,6,7,8-tetrahydro-1,8-naphthyridin-2-yl)propyl]-1H-pyrazol-1-yl}propanoic acid | 1H NMR (500 MHz, METHANOL-d4) Shift 8.31-8.21 (m, 1H), 8.15 (br s, 1H), 7.54 (s, 1H), 7.45-7.34 (m, 2H), 6.49 (d, J = 7.3 Hz, 1H), 6.03 (d, J = 1.7 Hz, 1H), 5.97 (dd, J = 10.5, 4.2 Hz, 1H), 3.55 (dd, J = 15.8, 10.4 Hz, 1H), 3.43 (t, J = 5.6 Hz, 2H), 2.99 (dd, J = 15.8, 4.3 Hz, 1H), 2.92-2.84 (m, 1H), 2.81-2.72 (m, 3H), 2.60 (t, J = 7.7 Hz, 2H), 2.31 (s, 4H), 2.04-1.95 (m, 1H), 1.94-1.87 (m, 2H) LC/MS [M + H]+ = 406.3 | Example 22 |
| 79 | (±)-4-{[4-(2-carboxy-1-{5-[3-(5,6,7,8-tetrahydro-1,8-naphthyridin-2-yl)propyl]-1H-pyrazol-1-yl}ethyl)pyridin-2-yl]amino}butanoic acid | 1H NMR (600 MHz, DMSO-d6) Shift 7.76-7.66 (m, 1H), 7.52 (d, J = 1.8 Hz, 1H), 7.09 (br d, J = 6.8 Hz, 1H), 6.31-6.25 (m, 1H), 6.20 (br d, J = 3.5 Hz, 1H), 6.14(s, 1H), 5.95 (s, 1H), 4.95 (br s, 1H), 3.29-3.03 (m, 3H), 2.61 (br t, J = 6.0 Hz, 3H), 2.48-2.39 (m, 5H), 2.22 (br t, J = 7.3 Hz, 3H), 1.82 (br t, J = 7.5 Hz, 3H), 1.78-1.72 (m, 3H), 1.66 (br t, J = 7.1 Hz, 3H) LC/MS [M + H]+ = 493.2 Human αVβ6 IC50 (nM) = 300 | Example 63 |

TABLE A-continued

| Example | Structure & Name | Analytical Data | Method |
|---|---|---|---|
| 80 | 3-(5-(2-methoxyethoxy)pyridin-3-yl)-3-(3-(3-(5,6,7,8-tetrahydro-1,8-naphthyridin-2-yl)propyl)-1H-pyrazol-1-yl)propanoic acid (Enantiomer A) | 1H NMR (400 MHz, METHANOL-d4) δ 8.24-8.12 (m, 1H), 8.08 (br s, 1H), 7.74 (d, J = 2.2 Hz, 1H), 7.35 (s, 1H), 7.12 (d, J = 7.3 Hz, 1H), 6.34 (d, J = 7.3 Hz, 1H), 6.16 (d, J = 2.2 Hz, 1H), 5.90 (t, J = 7.6 Hz, 1H), 4.18 (d, J = 4.2 Hz, 2H), 3.73 (t, J = 4.5 Hz, 2H), 3.40 (s, 3H), 3.37 (br s, 1H), 3.34 (dt, J = 3.2, 1.7 Hz, 1H), 3.29-3.15 (m, 1H), 3.14-3.01 (m, 1H), 2.70 (t, J = 6.3 Hz, 2H), 2.63 (t, J = 7.6 Hz, 2H), 2.58-2.49 (m, 2H), 2.01-1.84 (m, 4H) LC/MS [M + H]+ = 466.4 Human αVβ6 IC50 (nM) = 1.8 | Example 63 |
| 81 | (R)-3-(2-ethoxypyrimidin-5-yl)-3-(3-(3-(5,6,7,8-tetrahydro-1,8-naphthyridin-2-yl)propyl)-1H-pyrazol-1-yl)propanoic acid | The isomers were separated using a preparative chiral SFC equipped with Chiralpak AD-H (30 x 250 mm, δ μm) using an isocratic method of 20% MeOH/0.1% DEA in CO$_2$, 150 bar at 35° C. with a flow rate of 70 mL/min and momtored @ 220 nm, $^1$H NMR (400 MHz, DMSO-d$_6$ δ 8.56 (s, 2H), 7.75 (d, J = 2.2 Hz, 1H), 7.01 (d, J = 7.1 Hz, 1H), 6.28 (br s, 1H), 6.23 (d, J = 7.3 Hz, 1H), 6.04 (d, J = 2.2 Hz, 1H), 5.77 (dd, J = 8.2, 6.2 Hz, 1H), 4.32 (q, J = 6.9 Hz, 2H), 3.26-3 .20 (m, 3H), 3.18-3.10 (m, 1H), 2.60 (br t, J = 6.4 Hz, 2H), 2.47 (m, 2H), 2.42 (br t, J = 7.5 Hz, 2H), 1.88-1.69 (m, 4H), 1.30 (t, J = 7.0 Hz, 3H), MS (ESI): (m/z): 437.13 (M + H)$^+$. Human αVβ6 IC50 (nM) = 480 | Example 22 |
| 82 | (S)-3-(2-methoxypyrimidin-5-yl)-3-(3-(3-(5,6,7,8-tetrahydro-1,8-naphthyridin-2-yl)propyl)-1H-pyrazol-1-yl)propanoic acid | The isomers were separated using a preparative chiral SFC equipped with Chiralpak AD-H (30 x 250 mm, δ μm), The separations were performed using an isocratic method of 20% MeOH/0.1% DEA in CO$_2$. 150 bar at 35° C. with a flow rate of 70 mL/min and momtored @ 220 nm, $^1$H NMR (400 MHz, METHANOL-d$_4$) δ 8.59-8.51 (m, 2H), 7.66 (d, J = 2.0 Hz, 1H), 7.42 (d, J = 1.1 Hz, 1H), 6.53 (d, J = 7.1 Hz, 1H), 6.13 (d, J = 2.0 Hz, 1H), 5.85 (dd, J = 9.7, 5.3 Hz, 1H), 4.01 (s, 3H), 3.49-3.43 (m, 2H), 3.25 (dd, J = 14.7, 9.8 Hz, 1H), 3.04 (dd, J = 14.5, 5.7 Hz, 1H), 2.78 (t, J = 6.1 Hz, 2H), 2.68-2.52 (m, 4H), 2.12-1.86 (m, 4H), MS (ESI) (m/z) 423.l9 (M + H)$^+$. Human αVβ6 IC50 (nM) = 8.5 | Example 22 |
| 83 | (R)-3-(2-methoxypyrimidin-5-yl)-3-(3-(3-(5,6,7,8-tetrahydro-1,8-naphthyridin-2-yl)propyl)-1H-pyrazol-1-yl)propanoic acid | $^1$H NMR (400 MHz, ACETONITRILE-d$_3$) δ 8.52 (s, 2H), 7.57 (d, J = 2.2 Hz, 1H), 7.50-7.43 (m, 1H), 6.50 (d, J = 7.3 Hz, 1H), 6.13-6.08 (m, 1H), 5.76 (dd, J = 9.5, 5.4 Hz, 1H), 3.96 (s, 3H), 3.48-3 .44 (m, 2H), 3.21-3.11 (m, 2H), 2.77 (br t, J = 6.1 Hz, 2H), 2.71-2.62 (m, 4H), 2.06-2.00 (m, 2H), 1.94-1.87 (m, 2H), MS (ESI): (m/z): 423.10 (M + H)$^+$. Human αVβ6 IC50 (nM) = 310 | Example 22 |

TABLE A-continued

| Example | Structure & Name | Analytical Data | Method |
|---|---|---|---|
| 84 | 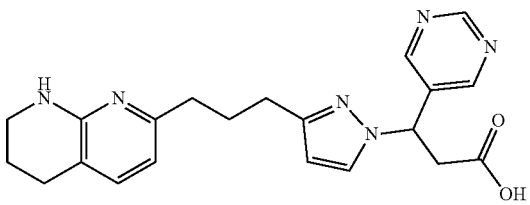 [SMILES: O=C(O)CC(c1cncnc1)n1ccc(CCCc2ccc3c(n2)NCCC3)n1]<br>3-(pyrimidin-5-yl)-3-(3-(3-(5,6,7,8-tetrahydro-1,8-naphthyridin-2-yl)propyl)-1H-pyrazol-1-yl)propanoic acid | $^1$H NMR (500 MHz, DMSO-$d_6$) δ 9.14-9.04 (m, 1H), 8.73 (s, 2H), 7.83-7.77 (m, 1H), 7.01 (d, J = 7.3 Hz, 1H), 6.34-6.26 (m, 1H), 6.22 (d, J = 7.0 Hz, 1H), 6.06 (d, J = 2.1 Hz, 1H), 5.84 (br t, J = 7.5 Hz, 1H), 3.31-3.20 (m, 2H), 3.16 (br dd, J = 16.2, 6.4 Hz, 2H), 2.60 (br t, J = 6.0 Hz, 2H), 2.48 (m, 2H), 2.42 (br t, J = 7.3 Hz, 2H), 1.88-1.79 (m, 2H), 1.78-1.70 (m, 2H), MS (ESI) (m/z): 393.2 (M + H)$^+$ Human αVβ6 IC50 (nM) = 110 | Example 22 |

Example 85

Example 85: (S)-3-(2-hydroxypyrimidin-5-yl)-3-(3-(3-(5,6,7,8-tetrahydro-1,8-naphthyridin-2-yl)propyl)-1H-pyrazol-1-yl)propanoic acid

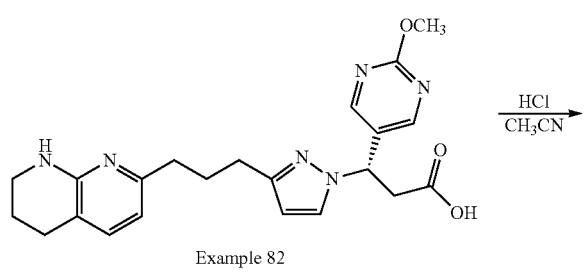

Example 82

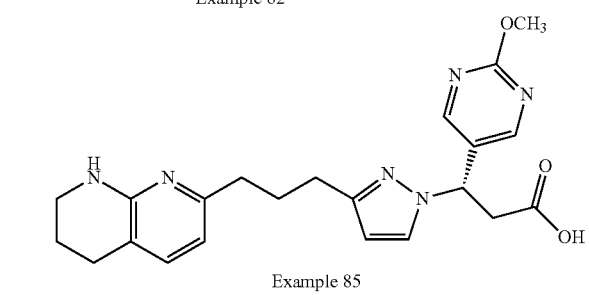

Example 85

To (S)-3-(2-methoxypyrimidin-5-yl)-3-(3-(3-(5,6,7,8-tetrahydro-1,8-naphthyridin-2-yl)propyl)-1H-pyrazol-1-yl)propanoic acid (Example 82, 21 mg, 0.050 mmol) in acetonitrile (1 mL) was added HCl, 1M (0.045 mL, 1.491 mmol). The reaction mixture was stirred at rt for 5 mins. The sample was concentrated and then lyophilyzed to give (S)-3-(2-hydroxypyrimidin-5-yl)-3-(3-(3-(5,6,7,8-tetrahydro-1,8-naphthyridin-2-yl)propyl)-1H-pyrazol-1-yl)propanoic acid, 3 TFA Example 85 (10 mg, 0.013 mmol, 25.5% yield). $^1$H NMR (400 MHz, DEUTERIUM OXIDE) δ 8.32-8.28 (m, 2H), 7.69-7.65 (m, 1H), 7.41-7.34 (m, 1H), 6.44-6.35 (m, 1H), 6.17-6.11 (m, 1H), 5.79-5.69 (m, 1H), 3.42-3.36 (m, 2H), 3.33-3.17 (m, 2H), 2.70-2.64 (m, 2H), 2.63-2.54 (m, 4H), 2.00-1.91 (m, 2H), 1.87-1.78 (m, 2H). MS (ESI) (m/z): 409.12 (M+H)$^+$. Human αVβ6 IC50 (nM)= 52

Example 86 and Example 87

(S)-3-(2-methylpyrimidin-5-yl)-3-(3-(3-((S)-1,2,3,4-tetrahydro-1,8-naphthyridin-2-yl)propyl)-1H-pyrazol-1-yl)propanoic acid (Example 86)

3-(2-methylpyrimidin-5-yl)-3-(5-(3-((S)-1,2,3,4-tetrahydro-1,8-naphthyridin-2-yl)propyl)-1H-pyrazol-1-yl)propanoic acid (Example 87)

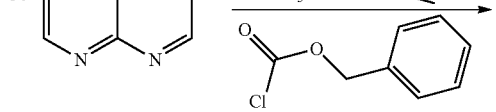

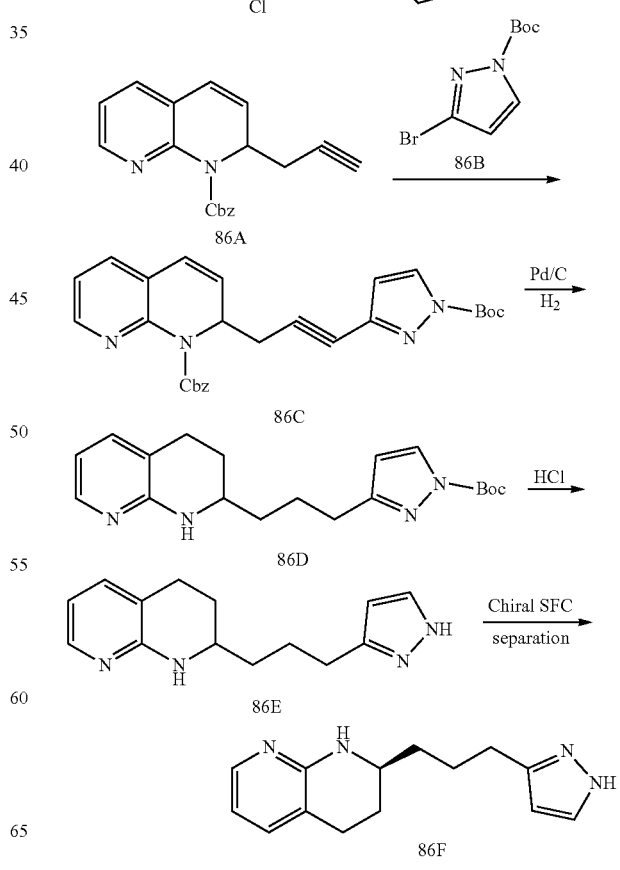

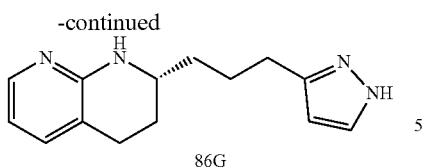

86G

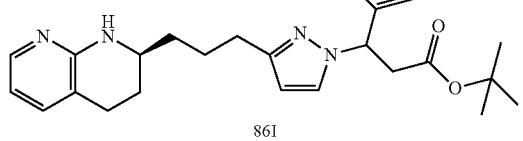

86F → 86H →

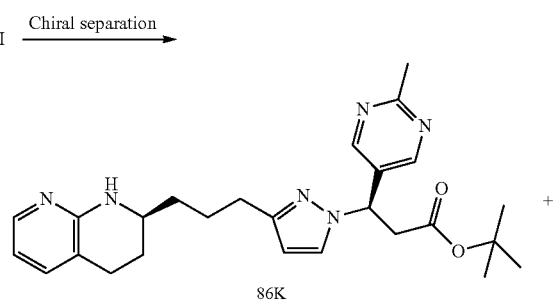

86I

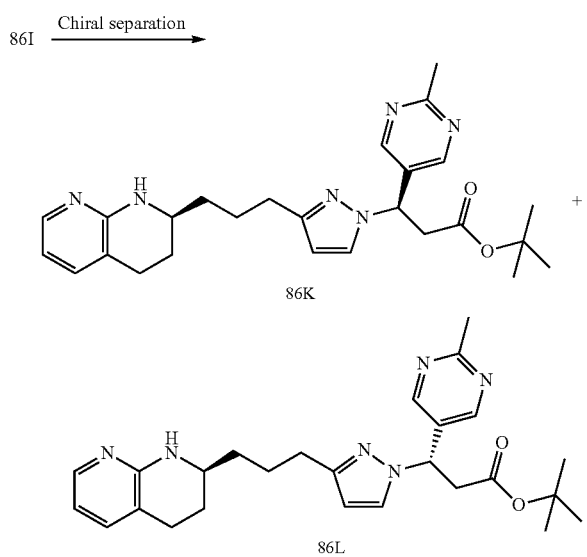

86J

86I —Chiral separation→

86K +

86L

86L —TFA//DCM→

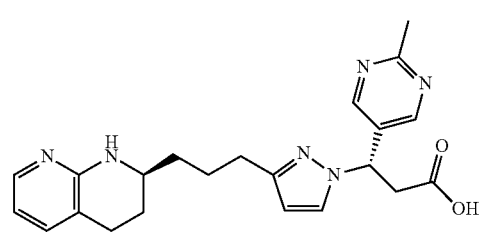

Example 86

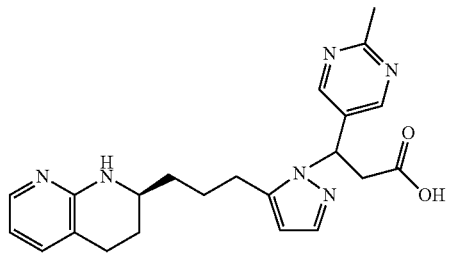

86J —TFA/□/DCM→

Example 87

Benzyl 2-(prop-2-yn-1-yl)-1,8-naphthyridine-1(2H)-carboxylate (86A)

A solution of 1,8-naphthyridine (1.30 g, 9.99 mmol) and freshly prepared tributyl(propa-1,2-dien-1-yl)stannane (3.90 g, 9.49 mmol) in DCM (35 mL) at 0° C. (ice water bath) was treated with benzyl carbonochloridate (2.045 g, 11.99 mmol) dropwise. After 1 hr at 0° C. the ice bath was removed and stirring was continued at RT ON. The rxn was concentrated and purified directly by Biotage (40 g col, 10-35% EtOAc/Hexanes, 16 CV) to give desired product 86A (2.0 g, elutes around 25% ETOAc/hexanes) as a clear wax. $^1$H NMR (400 MHz, CHLOROFORM-d) δ 8.44-8.30 (m, 1H), 7.46-7.42 (m, 2H), 7.41-7.31 (m, 4H), 7.05 (dd, J=7.5, 4.8 Hz, 1H), 6.54 (d, J=9.5 Hz, 1H), 6.23 (dd, J=9.5, 5.8 Hz, 1H), 5.33 (d, J=5.5 Hz, 2H), 5.29-5.19 (m, 1H), 2.52-2.37 (m, 2H), 1.90 (t, J=2.5 Hz, 1H).

Tert-butyl 3-bromo-1H-pyrazole-1-carboxylate (86B)

To 3-bromo-1H-pyrazole (5 g, 34.0 mmol) and DIEA (17.83 ml, 102 mmol) in DCM (85 ml) at 0° C. was added BOC-anhydride (11.85 ml, 51.0 mmol) followed by DMAP (0.042 g, 0.340 mmol). The reaction mixture was allowed to warm to rt and then was stirred for 3 h at rt. Water was added and the layers were separated. The organic solvent layer was washed with brine and dried over sodium sulfate. The sample was filtered, concentrated, and the residue was dissolved in a small amount of dichloromethane and charged to a 80 g silica gel cartridge which was eluted with 0-30% ethyl acetate/hexanes over a period of 50 mins. The desired fractions were combined and dried in vacuo to give tert-butyl 3-bromo-1H-pyrazole-1-carboxylate 86B (8.2 g, 33.2 mmol, 98% yield). $^1$H NMR (400 MHz, CHLOROFORM-d) δ 8.05-7.96 (m, 1H), 6.43 (d, J=2.7 Hz, 1H), 1.67 (s, 9H). MS (ESI) (m/z): 190.77 (M+H−tBu)$^+$.

Benzyl 2-(3-(1-(tert-butoxycarbonyl)-1H-pyrazol-3-yl)prop-2-yn-1-yl)-1,8-naphthyridine-1(2H)-carboxylate 86C A soln of tert-butyl 3-bromo-1H-pyrazole-1-carboxylate 86B (1.624 g, 6.57 mmol), benzyl 2-(prop-2-yn-1-yl)-1,8-naphthyridine-1(2H)-carboxylate 86A (2.0 g, 6.57 mmol), and TEA (3.21 mL, 23.00 mmol) in acetonitrile (30 mL) was purged with N2 bubble and sonication for 10 min. Solid copper(I) iodide (0.063 g, 0.329 mmol) and bis(triphenylphosphine)palladium(II) chloride (0.231 g, 0.329 mmol) were then added, the vial capped and then heated to 70° C. for 6 hrs (oil bath with timer). The reaction mixture was diluted with EtOAc, washed with H₂O, brine, dried (MgSO₄) and concentrated to give a dark wax. The wax was purified by Biotage (80 g col, 10-45% EtOAc/Hexanes, 14 CV) to give desired prod (1.50 g, yellow wax). MS (ESI) (m/z): 493.03 (M+Na)

Tert-butyl 3-(3-(1,2,3,4-tetrahydro-1,8-naphthyridin-2-yl)propyl)-1H-pyrazole-1-carboxylate (86D)

A suspension of benzyl 2-(3-(1-(tert-butoxycarbonyl)-1H-pyrazol-3-yl)prop-2-yn-1-yl)-1,8-naphthyridine-1(2H)-carboxylate 86C (1.5 g, 3.19 mmol), and Pd—C (100 mg, 0.094 mmol) in ethanol (25 mL) was hydrogenated (PARR) at 45 psi for 5 hrs. Crude LCMS and NMR show that the triple bond is reduced but most of the material is still Cbz protected. The rxn was then re-subjected to the same conditions, for 18 h longer (Ethanol, 100 mg 10% Pd/C, 45 psi). The reaction mixture was filtered through Celite and then concentrated to give the desired product (1.02 g, clear wax). MS (ESI) (m/z): 243.1 (M–Boc)

2-(3-(1H-pyrazol-3-yl)propyl)-1,2,3,4-tetrahydro-1,8-naphthyridine (86E)

To a soln of tert-butyl 3-(3-(1,2,3,4-tetrahydro-1,8-naphthyridin-2-yl)propyl)-1H-pyrazole-1-carboxylate 86D (1.02 g, 2.98 mmol) at room temperature in DCM (1 mL) was added a soln of HCl (3 ml, 12.00 mmol) (4M in Dioxane) dropwise. The clear soln was stirred at rt for 2 h. The reaction mixture was concentrated and taken directly towards purification by Biotage, (40 g col, 0-10% MeOH/DCM, 12CV, then 10% MeOH/DCM, 6CV) to give desired product 86E (835 mg, white solid). The isomers were separated using a preparative chiral SFC equipped with Chiralcel OD-H (30×250 mm, 5 μm). The separations were performed using an isocratic method of 15% MeOH/0.1% DEA in CO₂, 150 bar at 35° C. with a flow rate of 70 mL/min and monitored @314 nm.

(S)-2-(3-(1H-pyrazol-3-yl)propyl)-1,2,3,4-tetrahydro-1,8-naphthyridine (86F)

¹H NMR (400 MHz, DMSO-d₆) δ 12.66-12.20 (m, 1H), 7.77 (d, J=5.1 Hz, 1H), 7.55-7.37 (m, 1H), 7.30 (br d, J=7.1 Hz, 1H), 6.95-6.79 (m, 1H), 6.54-6.47 (m, 1H), 6.05 (s, 1H), 3.40 (br d, J=3.4 Hz, 1H), 2.68 (br t, J=6.2 Hz, 2H), 2.61 (br t, J=7.3 Hz, 2H), 1.97-1.82 (m, 1H), 1.75-1.65 (m, 2H), 1.64-1.37 (m, 3H)

(R)-2-(3-(1H-Pyrazol-3-yl)propyl)-1,2,3,4-tetrahydro-1,8-naphthyridine (86G)

¹H NMR (400 MHz, DMSO-d₆) δ 12.66-12.25 (m, 1H), 7.84-7.69 (m, 1H), 7.52-7.39 (m, 1H), 7.33 (br d, J=6.8 Hz, 1H), 7.05-6.90 (m, 1H), 6.52 (t, J=6.2 Hz, 1H), 6.08-6.00 (m, 1H), 3.41 (brd, J=3.4 Hz, 1H), 2.69 (br t, J=6.2 Hz, 2H), 2.60 (br t, J=7.3 Hz, 2H), 1.93-1.83 (m, 1H), 1.77-1.65 (m, 2H), 1.63-1.40 (m, 3H)

Tert-butyl (E)-3-(2-methylpyrimidin-5-yl)acrylate (86H)

To a mixture of 2-methylpyrimidine-5-carbaldehyde (5.0 g, 40.9 mmol), tert-butyl diethylphosphonoacetate (11.58 mL, 49.1 mmol), and molecular sieves (4A) (20 g, 189 mmol) in THF (100 mL) was added lithium hydroxide (1.176 g, 49.1 mmol). The mixture was stirred at rt for 72 h and then filtered. The filter cake washed with THF. The combined organic layers were concentrated in vacuo and the residue was dissolved in EtOAc and washed with H2O. The combined organic layers were dried over Na₂SO₄, filtered, concentrated, and the residue subjected to flash column chromatography (ethyl acetate/hexanes 1:1) to afford tert-butyl (E)-3-(2-methylpyrimidin-5-yl)acrylate 86H (7.04 g, 32.0 mmol, 78% yield) as a white solid. ¹H NMR (400 MHz, CHLOROFORM-d) δ 8.75 (br s, 2H), 7.48 (br d, J=16.1 Hz, 1H), 6.47 (br d, J=16.1 Hz, 1H), 2.75 (br s, 3H), 1.53 (br s, 9H). MS (ESI) (m/z): 221.08 (M+H)⁺.

Tert-butyl 3-(2-methylpyrimidin-5-yl)-3-(3-(3-((S)-1,2,3,4-tetrahydro-1,8-naphthyridin-2-yl)propyl)-1H-pyrazol-1-yl)propanoate (86I) and tert-butyl 3-(2-methylpyrimidin-5-yl)-3-(5-(3-((S)-1,2,3,4-tetrahydro-1,8-naphthyridin-2-yl)propyl)-1H-pyrazol-1-yl)propanoate (86J)

The title compounds were prepared using a method analogous to Example 22A by reaction of (S)-2-(3-(1H-pyrazol-3-yl)propyl)-1,2,3,4-tetrahydro-1,8-naphthyridine (86F) with acrylate (86H). The crude product was dissolved in a small amount of dichloromethane and charged to a 24 g gold silica gel cartridge. The column was eluted with 0-8% dichloromethane/methanol over a period of 60 mins. TLC using 2.5-5% MeOH/DCM eluted 3× showed the separated regioisomers. The desired fractions were combined and dried in vacuo to give tert-butyl 3-(2-methylpyrimidin-5-yl)-3-(3-(3-(1,2,3,4-tetrahydro-1,8-naphthyridin-2-yl)propyl)-1H-pyrazol-1-yl)propanoate (86I) (124.9 mg, 0.270 mmol, 32.7% yield, 2nd eluting peak of regioisomers) and tert-butyl 3-(2-methylpyrimidin-5-yl)-3-(5-(3-(1,2,3,4-tetrahydro-1,8-naphthyridin-2-yl)propyl)-1H-pyrazol-1-yl)propanoate (86J) (14.9 mg, 0.032 mmol, 3.90% yield, 1st eluting peak of the regioisomers). For 86I: ¹H NMR (400 MHz, CHLOROFORM-d) δ 8.62 (s, 2H), 7.87 (d, J=4.9 Hz, 1H), 7.38 (d, J=1.7 Hz, 1H), 7.16 (br d, J=7.1 Hz, 1H), 6.54-6.45 (m, 1H), 6.07 (d, J=1.2 Hz, 1H), 5.67 (t, J=7.5 Hz, 1H), 4.88 (br s, 1H), 3.43 (br dd, J=15.9, 8.3 Hz, 2H), 3.11 (dd, J=16.1, 6.8 Hz, 1H), 2.73 (s, 5H), 2.68 (t, J=1.5 Hz, 2H), 2.01-1.91 (m, 1H), 1.82-1.72 (m, 2H), 1.64-1.57 (m, 3H), 1.37 (s, 9H). MS (ESI) (m/z) 463.33 (M+H)⁺. NOE-at 7.38 ppm—shows NOE with C-alpha H, pyrimidine H, pyrazole H4 and t-butyl group. For 86J: ¹H NMR (400 MHz, CHLOROFORM-d) δ 8.57 (s, 2H), 7.86 (br d, J=4.6 Hz, 1H), 7.50 (s, 1H), 7.17 (br d, J=6.8 Hz, 1H), 6.51 (t, J=6.2 Hz, 1H), 6.06 (s, 1H), 5.69 (dd, J=8.6, 6.1 Hz, 1H), 4.94-4.81 (m, 1H), 3.57 (dd, J=16.1, 9.0 Hz, 1H), 3.47-3.38 (m, 1H), 3.06 (dd, J=16.4, 5.9 Hz, 1H), 2.82-2.69 (m, 6H), 2.60 (dt, J=15.3, 7.6 Hz, 1H), 1.99-1.86 (m, 1H), 1.84-1.70 (m, 2H), 1.68-1.44 (m, 3H), 1.36 (s, 9H). NOE-at 7.5 ppm—shows NOE with pyrazole H4 (6.06) and tBu.

Tert-butyl (R)-3-(2-methylpyrimidin-5-yl)-3-(3-(3-((S)-1,2,3,4-tetrahydro-1,8-naphthyridin-2-yl)propyl)-1H-pyrazol-1-yl)propanoate (86K) and toy-butyl (S)-3-(2-methylpyrimidin-5-yl)-3-(3-(3-((S)-1,2,3,4-tetrahydro-1,8-naphthyridin-2-yl)propyl)-1H-pyrazol-1-yl)propanoate (86L)

The diastereomers of toy-butyl 3-(2-methylpyrimidin-5-yl)-3-(3-(3-((S)-1,2,3,4-tetrahydro-1,8-naphthyridin-2-yl)propyl)-1H-pyrazol-1-yl)propanoate 86I were separated using a preparative chiral SFC equipped with Chiralpak AD-H (30×250 mm, 5 μm). The separations were performed using an isocratic method of 25% MeOH/0.1% DEA in CO₂, 150 bar at 35° C. with a flow rate of 70 mL/min. For 86K: ¹H NMR (500 MHz, CHLOROFORM-d) δ 8.62 (s, 2H), 7.89-7.82 (m, 1H), 7.38 (d, J=23 Hz, 1H), 7.16 (d, J=1.2 Hz, 1H), 6.49 (dd, J=1.2, 5.0 Hz, 1H), 6.06 (d, J=2.3 Hz, 1H), 5.66 (t, J=7.6 Hz, 1H), 4.90-4.81 (m, 1H), 3.48-3.36 (m, 2H), 3.17-3.06 (m, 1H), 2.73 (s, 3H), 2.67 (t, J=7.6 Hz, 2H), 1.99-1.92 (m, 1H), 1.85-1.71 (m, 2H), 1.57-1.52 (m, 3H), 1.37 (s, 9H). MS (ESI) (m/z): 463.3 (M+H)⁺. For 86L. ¹H NMR (500 MHz, CHLOROFORM-d) δ 8.62 (s, 2H), 7.86 (d, J=3.7 Hz, 1H), 7.38 (d, J=2.3 Hz, 1H), 7.16 (d, J=7.2 Hz, 1H), 6.49 (dd, J=7.2, 5.0 Hz, 1H), 6.07 (d, J=2.3 Hz, 1H), 5.71-5.62 (m, 1H), 4.98-4.85 (m, 1H), 3.48-3.37 (m, 2H), 3.16-3.05 (m, 1H), 2.73 (s, 3H), 2.67 (t, J=7.6 Hz, 2H), 2.00-1.91 (m, 1H), 1.83-1.71 (m, 2H), 1.58-1.53 (m, 3H), 1.37 (s, 9H). MS (ESI) (m/z): 463.29 (M+H)⁺.

Example 86

(S)-3-(2-Methylpyrimidin-5-yl)-3-(3-(3-((S)-1,2,3,4-tetrahydro-1,8-naphthyridin-2-yl)propyl)-1H-pyrazol-1-yl)propanoic acid To tert-butyl (S)-3-(2-methylpyrimidin-5-yl)-3-(3-(3-((S)-1,2,3,4-tetrahydro-1,8-naphthyridin-2-yl)propyl)-1H-pyrazol-1-yl)propanoate 86L (50 mg, 0.108 mmol) in CH₂Cl₂ (1.5 mF) was added TFA (0.4 mF, 5.19 mmol). The reaction mixture was stirred at rt overnight. The sample was concentrated and dried. The sample was desalted using a Sep-Pak plus cartridge: Solvent A: 95:5 (water/acetonitrile) with 0.1% NH4OH; Solvent B: acetonitrile with 0.1% NH4OH. Preparation of Sep-Pak plus long (820 mg/1.6 ml): added 20 mF of methanol to wet the material and then washed with solvent A (20 mF). Loading: sample in solvent A was loaded unto column then washed with solvent A (15 mF). Elution: acetonitrile with 0.1% NH4OH (10 mF) was added to elute product followed by a final wash with Methanol (6 mF). TEC was utilized to detect product elution on each fraction. The desired fractions were combined and lyophilized to give desired product, Example 86. ¹H NMR (400 MHz, METHANOL-d₄) δ 8.62 (s, 2H), 7.70 (s, 1H), 7.69-7.66 (m, 1H), 7.52 (d, J=7.4 Hz, 1H), 6.67 (t, J=6.6 Hz, 1H), 6.17 (s, 1H), 5.90 (dd, J=9.5, 5.6 Hz, 1H), 3.54 (br d, J=4.9 Hz, 1H), 3.43-3.35 (m, 1H), 3.16-3.09 (m, 1H), 2.86-2.69 (m, 3H), 2.66 (s, 4H), 2.03-1.94 (m, 1H), 1.85-1.76 (m, 2H), 1.70-1.56 (m, 3H). MS (ESI) (m/z): 407.2 (M+H)⁺. Human αVβ6 IC50 (nM)=270

Example 87

3-(2-Methylpyrimidin-5-yl)-3-(5-(3-((S)-1,2,3,4-tetrahydro-1,8-naphthyridin-2-yl)propyl)-1H-pyrazol-1-yl)propanoic acid Sample was prepared using methods analogous to Example 86. ¹H NMR shows a mixture of diastereomers. MS (ESI) (m/z): 407.2 (M+H)⁺. Human αVβ6 IC50 (nM)= 1382

| Example | Structure & Name | Analytical Data | Method |
| --- | --- | --- | --- |
| 88 | 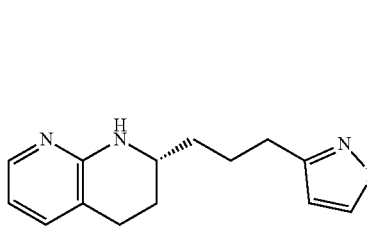<br>(S)-3-(2-methylpyrimidin-5-yl)-3-(3-(3-((R)-1,2,3,4-tetrahydro-1,8-naphthyridin-2-yl)propyl)-1H-pyrazol-1-yl)propanoic acid | 1H NMR (400 MHz, METHANOL-d₄) δ 8.69-8.59 (m, 2H), 7.68 (s, 1H), 7.67 (s, 1H), 7.57-7.50 (m, 1H), 6.72-6.64 (m, 1H), 6.15 (d, J = 2.0 Hz, 1H), 5.94-5.86 (m, 1H), 3.65-3.51 (m, 1H), 3.40-3.35 (m, 1H), 3.18-3.06 (m, 1H), 2.90-2.75 (m, 2H), 2.74-2.68 (m, 2H), 2.67 (s, 3H), 2.07-1.95 (m, 1H), 1.86-1.74 (m, 2H), 1.68-1.53 (m, 3H), MS (ESI) (m/z): 407.18 (M + H)⁺. Human αVβ6 IC50 (nM) = 170 | Example 86 (using 86G) |
| 89 | 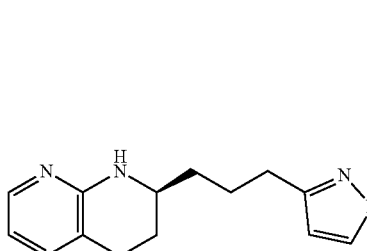<br>(S)-3-(2-methoxypyrimidin-5-yl)-3-(3-(3-((S)-1,2,3,4-tetrahydro-1,8-naphthyridin-2-yl)propyl)-1H-pyrazol-1-yl)propanoic acid | ¹H NMR (400 MHz, METHANOL-d₄) δ 8.52 (s, 2H), 7.68 (m, 2H), 7.49 (d, J = 6.8 Hz, 1H), 6.66 (t, J = 6.4 Hz, 1H), 6.15 (d, J = 2.0 Hz, 1H), 5.86 (dd, J = 9.4, 6.0 Hz, 1H), 3.99 (s, 3H), 3.58-3.52 (m, 1H), 3.45-3.36 (m, 1H), 3.09 (dd, J = 15.7, 5.9 Hz, 1H), 2.85-2.77 (m, 2H), 2.75-2.58 (m, 2H), 1.98 (br d, J = 9.0 Hz, 1H), 1.84-1.76 (m, 2H), 1.69-1.56 (m, 3H), MS (ESI) (m/z): 423.18 (M + H)⁺. Human αVβ6 IC50 (nM) = 100 | Example 86 |

| Example | Structure & Name | Analytical Data | Method |
| --- | --- | --- | --- |
| 90 | 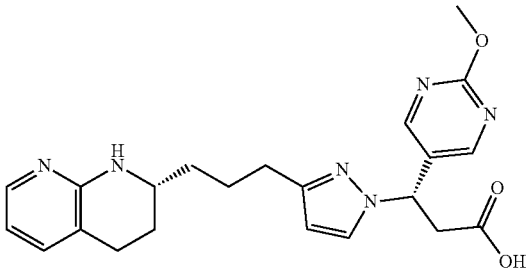 [SMILES: COc1ncc([C@H](CC(=O)O)n2ccc(CCC[C@@H]3CCc4cccnc4N3)n2)cn1]<br>(S)-3-(2-methoxypyrimidin-5-yl)-3-(3-(3-((R)-1,2,3,4-tetrahydro-1,8-naphthyridin-2-yl)propyl)-1H-pyrazol-1-yl)propanoic acid | $^1$H NMR (500 MHz, METHANOL-$d_4$) δ 8.54 (s, 2H), 7.71-7.64 (m, 2H), 7.46 (dd, J = 7.2, 1.0 Hz, 1H), 6.63 (dd, J = 7.1, 5.9 Hz, 1H), 6.14 (d, J = 2.3 Hz, 1H), 5.85 (dd, J = 9.5, 6.0 Hz, 1H), 4.00 (s, 3H), 3.56-3.53 (m, 1H), 3.31-3.26 (m, 1H), 3.12-3.05 (m, 1H), 2.83-2.77 (m, 2H), 2.70-2.64 (m, 2H), 2.02-1.94 (m, 1H), 1.84-1.75 (m, 2H), 1.66-1.56 (m, 3H), MS (ESI) (m/z): 423.21 (M + H)$^+$. Human αVβ6 IC50 (nM) = 220 | 86 (using 86G) |
| 91 | 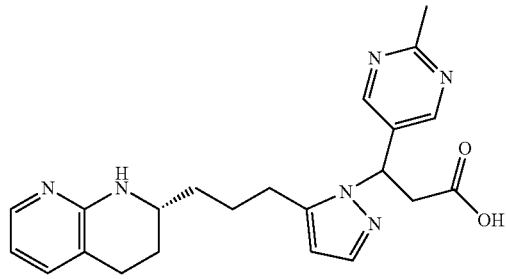 [SMILES: Cc1ncc(C(CC(=O)O)n2nccc2CCC[C@@H]2CCc3cccnc3N2)cn1]<br>3-(2-methylpyrimidin-5-yl)-3-(5-(3-((R)-1,2,3,4-tetrahydro-1,8-naphthyridin-2-yl)propyl)-1H-pyrazol-1-yl)propanoic acid | $^1$H NMR shows a mixture of diastereomers, MS (ESI) (m/z): 407.2 (M + H), Human αVβ6 IC50 (nM) = 1400 | Example 87 |
| 92 | 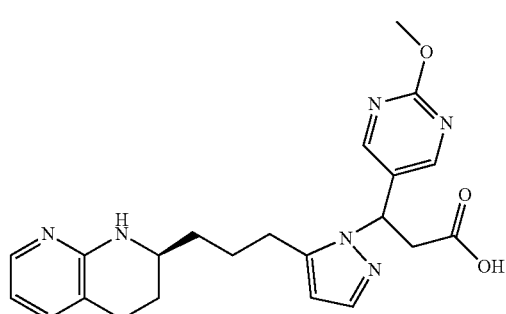<br>3-(2-methoxypyrimidin-5-yl)-3-(5-(3-((S)-1,2,3,4-tetrahydro-1,8-naphthyridin-2-yl)propyl)-1H-pyrazol-1-yl)propanoic acid. | $^1$H NMR shows a mixture of diastereomers, MS (ESI) (m/z): 423.2 (M + H) Human αVβ6 IC50 (nM) = 6700 | Example 87 |

| Example | Structure & Name | Analytical Data | Method |
|---|---|---|---|
| 93 | 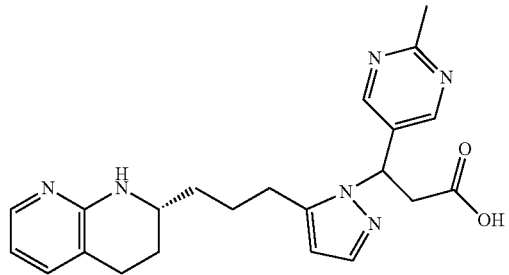<br>3-(2-methoxypyrimidin-5-yl)-3-(5-(3-((R)-1,2,3,4-tetrahydro-1,8-naphthyridin-2-yl)propyl)-1H-pyrazol-1-yl)propanoic acid. | $^1$H NMR shows a mixture of diastereomers, MS (ESI) (m/z): 423.15 (M + H) Human αVβ6 IC50 (nM) = 1030 | Example 87 |
| 94 | 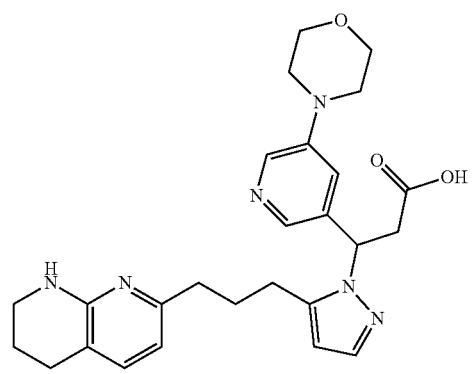<br>3-(5-morpholinopyridin-3-yl)-3-(5-(3-(5,6,7,8-tetrahydro-1,8-naphthyridin-2-yl)propyl)-1H-pyrazol-1-yl)propanoic acid<br>(Enantiomer 1) | $^1$H NMR (500 MHz, METHANOL-d$_4$) δ 8.13-8.02 (m, 1H), 7.82 (s, 1H), 7.43 (d, J = 1.7 Hz, 1H), 7.26 (t, J = 2.1 Hz, 1H), 7.07 (d, J = 7.3 Hz, 1H), 6.24 (d, J = 7.3 Hz, 1H), 6.11 (d, J = 1.7 Hz, 1H), 5.92 (t, J = 7.2 Hz, 1H), 3.86-3.73 (m, 4H), 3.40-3.33 (m, 2H), 3.27 (dd, J = 15.4, 7.3 Hz, 1H), 3.17-3.11 (m, 4H), 3.04 (dd, J = 15.4, 7.1 Hz, 1H), 2.81-2.65 (m, 4H), 2.58-2.48 (m, 2H), 1.92-1.82 (m, 4H) LC/MS [M + H]+ = 477.3 Human αVβ6 IC50 (nM) = 19 | Example 22 |
| 95 | 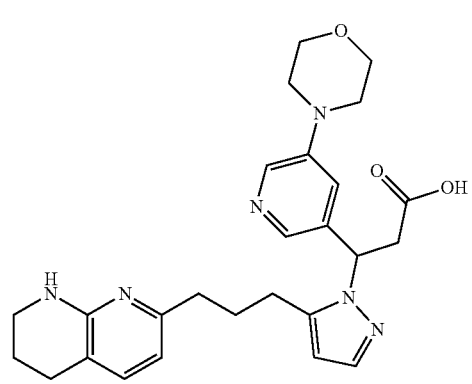<br>3-(5-morpholinopyridin-3-yl)-3-(5-(3-(5,6,7,8-tetrahydro-1,8-naphthyridin-2-yl)propyl)-1H-pyrazol-1-yl)propanoic acid<br>(Enantiomer 2) | $^1$H NMR (500 MHz, METHANOL-d$_4$) δ 8.13-8.02 (m, 1H), 7.82 (s, 1H), 7.43 (d, J = 1.7 Hz, 1H), 7.26 (t, J = 2.1 Hz, 1H), 7.07 (d, J = 7.3 Hz, 1H), 6.24 (d, J = 7.3 Hz, 1H), 6.11 (d, J = 1.7 Hz, 1H), 5.92 (t, J = 7.2 Hz, 1H), 3.86-3.73 (m, 4H), 3.40-3.33 (m, 2H), 3.27 (dd, J = 15.4, 7.3 Hz, 1H), 3.17-3.11 (m, 4H), 3.04 (dd, J = 15.4, 7.1 Hz, 1H), 2.81-2.65 (m, 4H), 2.58-2.48 (m, 2H), 1.92-1.82 (m, 4H) LC/MS [M + H]+ = 477.3 Human αVβ6 IC50 (nM) = 230 | Example 22 |

Example 96, Example 97, and Example 98
(±)-3-(2-methylpyrimidin-5-yl)-3-(3-(3-(6,7,8,9-tetrahydro-5H-pyrido[2,3-b]azepin-2-yl)propyl)-1H-pyrazol-1-yl)propanoic acid (Example 96)
Example 97
Enantiomer 1 from Example 96
Example 98
Enantiomer 2 from Example 96
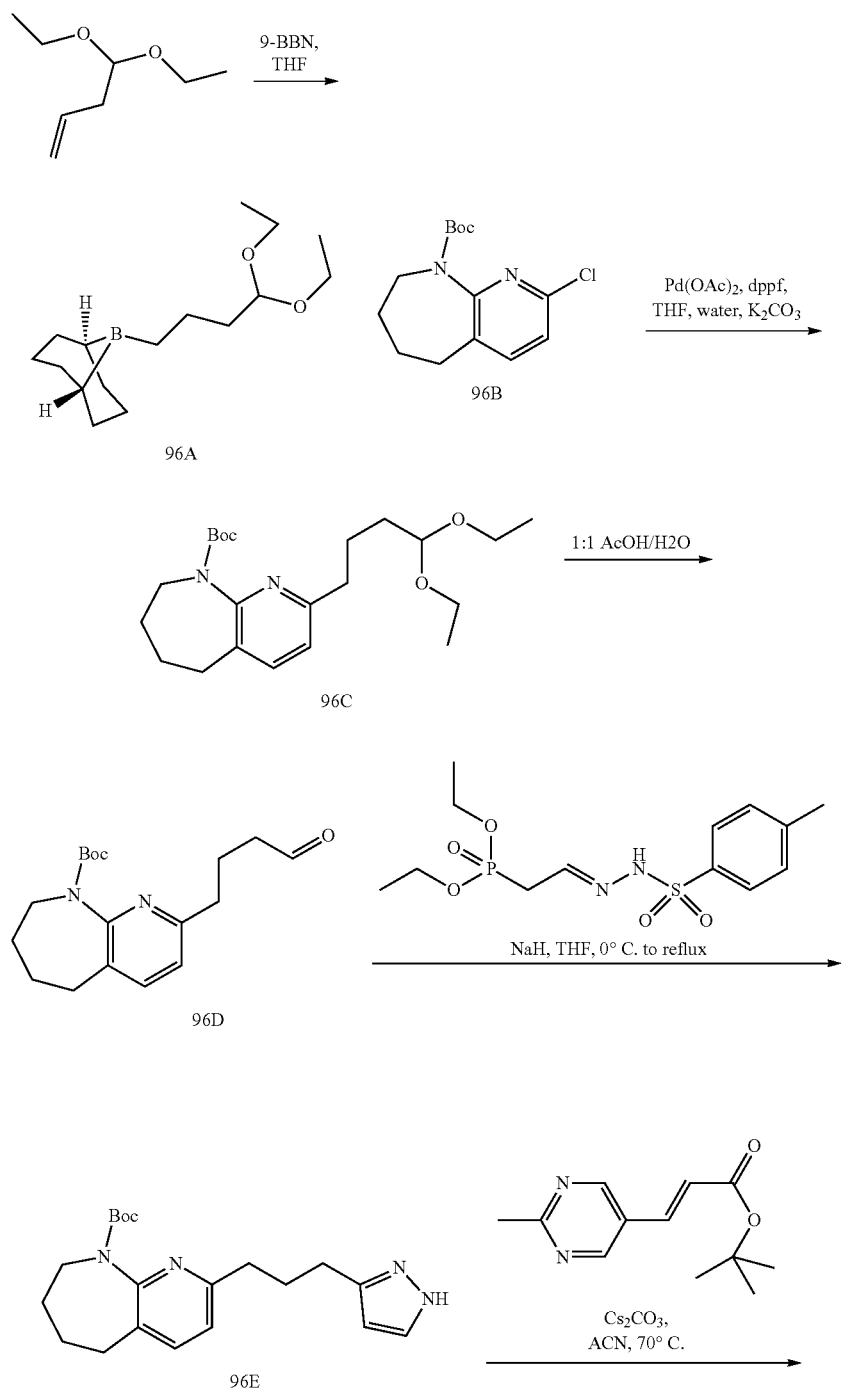

-continued
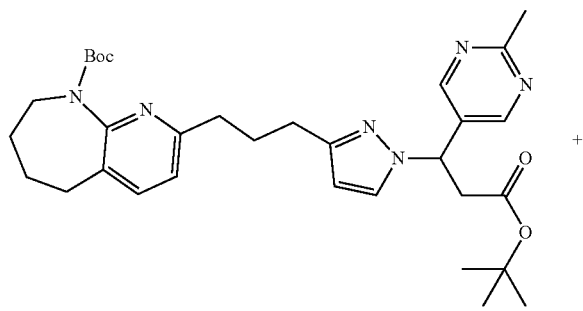
96F
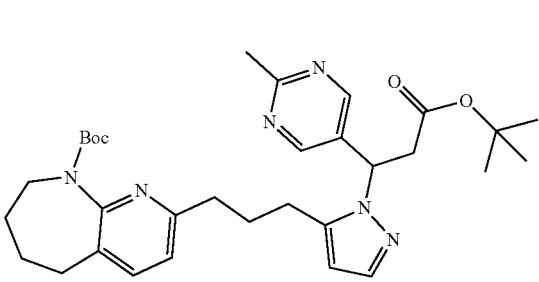
96G
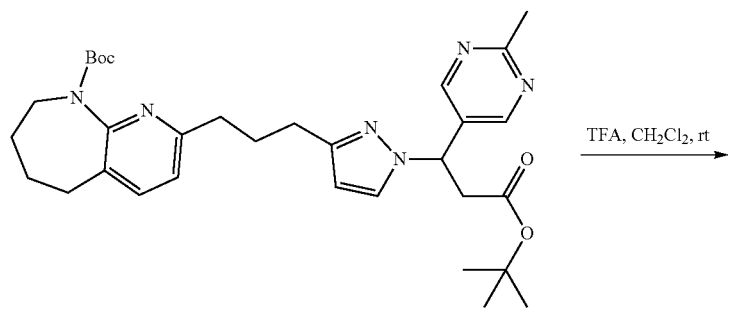
96F
TFA, CH₂Cl₂, rt →
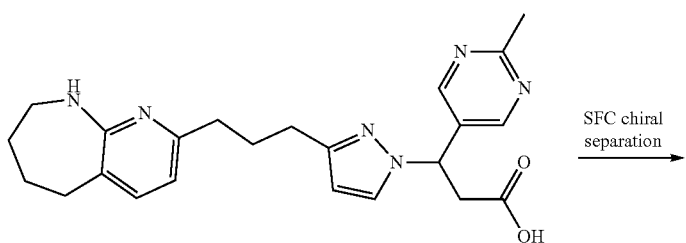
Example 96 (racemic)
SFC chiral separation →
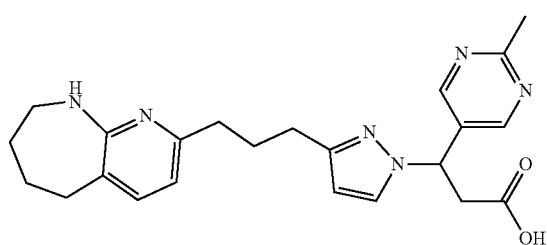
Example 97 (Enantiomer 1 from Example 96)

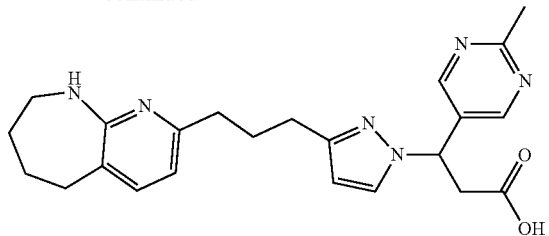

Example 98 (Enantiomer 2 from Example 96)

(1s,5s)-9-(4,4-diethoxybutyl)-9-borabicyclo[3.3.1] nonane (96A)

The title compound 96A was prepared as described in *Journal of Organic Chemistry* (2005) 70, 1771-1779 Keen et al.

Tert-butyl 2-chloro-5,6,7,8-tetrahydro-9H-pyrido[2,3-b]azepine-9-carboxylate (96B)

The title compound 96B was prepared following the procedure described in WO 2011/059839.

Tert-butyl 2-(4,4-diethoxybutyl)-5,6,7,8-tetrahydro-9H-pyrido[2,3-b]azepine-9-carboxylate (96C)

The title compound was prepared as described in *Journal of Organic Chemistry* (2005) 70, 1771-1779 Keen et al. with the exception that degassed water was added to the reaction mixture. Potassium carbonate (1.741 g, 12.60 mmol), palladium(II) acetate (0.094 g, 0.420 mmol), DPPF (0.233 g, 0.420 mmol), and tert-butyl 2-chloro-5,6,7,8-tetrahydro-9H-pyrido[2,3-b]azepine-9-carboxylate 96B (1.188 g, 4.20 mmol) were placed in a Schlenk flask. The flask was sealed and the contents were flushed with nitrogen. To the contents of the Schlenk flask was added a mixture of THF (50 mL) and water (5 mL) which had been degassed by passing a stream of nitrogen through it. The reaction mixture was again degassed by alternating vacuum and nitrogen (3 times). Then, the solution of (1s,5s)-9-(4,4-diethoxybutyl)-9-borabicyclo[3.3.1]nonane 96A (12.61 mmol) in THF (35 mL) was added. The contents of the Schlenk flask were degassed once more and then the mixture was heated at 80° C. for 18 h under sealed nitrogen atmosphere. The cooled mixture was diluted with water and extracted with EtOAc. The organic layer was washed with brine, dried over MgSO4, filtered and evaporated. Purification of the resulting residue by silica gel flash column chromatography (5-95% EtOAc in hexanes) gave tert-butyl 2-(4,4-diethoxybutyl)-5,6,7,8-tetrahydro-9H-pyrido[2,3-b]azepine-9-carboxylate 96C (1.34 g, 3.42 mmol, 81% yield). LCMS (ESI): m/z 393 [M+H]+. 1H NMR (400 MHz, CHLOROFORM-d) δ 7.45 (d, J=7.6 Hz, 1H), 6.98 (d, J=7.6 Hz, 1H), 4.52 (t, J=5.5 Hz, 1H), 3.90-3.72 (m, 1H), 3.70-3.40 (m, 6H, overlapping multiplets), 2.78 (t, J=7.6 Hz, 2H), 2.70 (br t, J=5.5 Hz, 2H), 1.94-1.62 (m, 8H), 1.42 (br s, 9H), 1.25-1.04 (m, 6H).

Tert-butyl 2-(4-oxobutyl)-5,6,7,8-tetrahydro-9H-pyrido[2,3-b]azepine-9-carboxylate (96D)

In a round bottom flask, tert-butyl 2-(4,4-diethoxybutyl)-5,6,7,8-tetrahydro-9H-pyrido[2,3-b]azepine-9-carboxylate 96C (500 mg, 1.274 mmol) was stirred at rt in a mixture of 1:1 AcOH (5 mL)/water (5 mL) for 18 h. The solvent was evaporated to remove as much AcOH as possible. The mixture was diluted with water and adjusted to pH 8 by addition of sat'd aq. sodium bicarbonate solution. The aqueous layer was extracted with EtOAc and the combined organic extracts were dried over MgSO4, filtered and evaporated. Purification by silica gel flash column chromatography (10-100% EtOAc in hexanes) gave tert-butyl 2-(4-oxobutyl)-5,6,7,8-tetrahydro-9H-pyrido[2,3-b]azepine-9-carboxylate 96D (295 mg, 0.926 mmol, 72.7% yield). LCMS (ESI): m/z 319 [M+H]+. 1H NMR (400 MHz, CHLOROFORM-d) δ 9.79 (s, 1H), 7.48 (d, J=7.6 Hz, 1H), 6.98 (d, J=7.6 Hz, 1H), 3.06-2.85 (m, 1H), 2.81 (t, J=7.6 Hz, 1H), 2.76-2.62 (m, 2H), 2.51 (t, J=7.3 Hz, 2H), 2.15-1.98 (m, 2H), 1.93-1.82 (m, 2H), 1.59 (br s, 2H), 1.80-1.52 (m, 4H), 1.43 (s, 9H).

tert-butyl 2-(3-(1H-pyrazol-3-yl)propyl)-5,6,7,8-tetrahydro-9H-pyrido[2,3-b]azepine-9-carboxylate (96E)

In a round bottom flask, a solution of diethyl (E)-(2-(2-tosylhydrazono)ethyl)phosphonate (1.15 g, 3.30 mmol, prepared as described in WO 2007/073503) in THF (6 mL) was slowly added to a suspension of 60% NaH as dispersion in mineral oil (264 mg, 6.60 mmol) in THF (6 mL) while cooling at 0° C. This mixture was stirred at 0° C. for 30 min during which the mixture became a yellow suspension. A solution of toy-butyl 2-(4-oxobutyl)-5,6,7,8-tetrahydro-9H-pyrido[2,3-b]azepine-9-carboxylate 96D (700 mg, 2.198 mmol) in THF was added to the suspension at 0° C. after which the ice bath was removed. After stirring at rt for 1 h, the mixture was heated at reflux 82° C. for 5.5 h followed by stirring at rt for 14 h. The mixture was diluted with sat'd aq. ammonium chloride and extracted with EtOAc. The combined organic extracts were dried over MgSO4, filtered and evaporated. Purification of the residue by silica gel flash column chromatography (30-100% EtOAc in hexanes) gave the title compound that was still considerably impure. Purification by preparative HPLC (XBridge C18 19×100 mm Flow rate: 20 mL/min. Wavelength: 220 nM. Solvent A: 0.1% TFA in 95:5 H2O/CH3CN. Solvent B: 0.1% TFA in 5:95 H2O/CH3CN) followed by passing the desired fractions through a Solid Phase Extraction carbonate cartridge (Agilent Technologies PL-HCO3 MP SPE) to remove TFA and evaporation gave the title compound toy-butyl 2-(3-(1H-pyrazol-3-yl)propyl)-5,6,7,8-tetrahydro-9H-pyrido[2,3-b]azepine-9-carboxylate 96E (255 mg, 0.715 mmol, 32.5% yield). LCMS (ESI): m/z 357 [M+H]+. 1H NMR (400 MHz, CHLOROFORM-d) δ 7.56-7.38 (m, 2H), 7.00 (d, J=7.6 Hz, 1H), 6.08 (s, 1H), 2.83-2.75 (m, 2H), 2.75-2.70 (m, 2H), 2.65 (br t, J=6.7 Hz, 2H), 2.61-2.13 (m, 2H), 2.05 (quin, J=7.0 Hz, 2H), 1.94-1.77 (m, 2H), 1.77-1.49 (m, 2H), 1.49-1.24 (br s, 9H).

tert-butyl 2-(3-(1-(3-(toy-butoxy)-1-(2-methylpyrimidin-5-yl)-3-oxopropyl)-1H-pyrazol-3-yl)propyl)-5,6,7,8-tetrahydro-9H-pyrido[2,3-b]azepine-9-carboxylate (96F) and tert-butyl 2-(3-(1-(3-(tert-butoxy)-1-(2-methylpyrimidin-5-yl)-3-oxopropyl)-1H-pyrazol-5-yl)propyl)-5,6,7,8-tetrahydro-9H-pyrido[2,3-b]azepine-9-carboxylate (96G)

In a small pressure vessel, tert-butyl 2-(3-(1H-pyrazol-3-yl)propyl)-5,6,7,8-tetrahydro-9H-pyrido[2,3-b]azepine-9-carboxylate 96E (93 mg, 0.261 mmol), tert-butyl (E)-3-(2-methylpyrimidin-5-yl)acrylate (86 mg, 0.391 mmol), and cesium carbonate (255 mg, 0.783 mmol) were stirred and heated at 70° C. in CH$_3$CN (3 mL) for 5 h, after which stirring was continued at rt for 16 h. The reaction mixture was filtered to remove cesium carbonate, the solid was rinsed with CH$_3$CN, and the filtrate was evaporated. Purification by silica gel flash column chromatography (1% to 10% MeOH in CH$_2$Cl$_2$) enabled separation of the products and the acrylate starting material. The fractions containing the two regioisomers were purified by preparative HPLC (XBridge C18 19×100 mm, flow rate: 20 mL/min, wavelength: 220 nM, 20 min gradient, 25 min run, 0% to 100% Solvent A: 0.1% TFA in 95:5 H$_2$O/CH$_3$CN. Solvent B: 0.1% TFA in 5:95 H$_2$O/CH$_3$CN). The fractions containing separated isomers were passed through SPE carbonate cartridges (Agilent Technologies PL-HCO3 MP SPE) to remove TFA and were evaporated to give (tert-butyl 2-(3-(1-(3-(tert-butoxy)-1-(2-methylpyrimidin-5-yl)-3-oxopropyl)-1H-pyrazol-3-yl)propyl)-5,6,7,8-tetrahydro-9H-pyrido[2,3-b]azepine-9-carboxylate 96F (55 mg, 0.095 mmol, 36.6% yield) and tert-butyl 2-(3-(1-(3-(tert-butoxy)-1-(2-methylpyrimidin-5-yl)-3-oxopropyl)-1H-pyrazol-5-yl)propyl)-5,6,7,8-tetrahydro-9H-pyrido[2,3-b]azepine-9-carboxylate 96G (14 mg, 0.024 mmol, 9.30% yield). For 96F: LCMS (ESI): m/z 577 [M+H]$^+$. $^1$H NMR (500 MHz, CHLOROFORM-d) δ 8.62 (s, 2H), 7.49-7.44 (m, 1H), 7.38-7.30 (m, 2H), 6.96 (d, J=7.6 Hz, 1H), 6.08 (d, J=2.3 Hz, 1H), 5.66 (t, J=7.6 Hz, 1H), 3.42 (dd, J=16.0, 8.4 Hz, 1H), 3.09 (dd, J=16.1, 6.9 Hz, 1H), 2.80 (br d, J=15.4 Hz, 2H), 2.73 (s, 3H), 2.73-2.52 (m, 6H), 2.09-2.02 (m, 1H), 2.15-1.96 (m, 2H), 1.94-1.82 (m, 2H), 1.63-1.41 (m, 1H), 1.40 (br s, 9H), 1.36 (s, 9H). For 96G: LCMS (ESI): m/z 577 [M+H]$^+$. 1H NMR (400 MHz, CHLOROFORM-d) δ 8.55 (s, 2H), 7.49 (s, 1H), 7.46 (d, J=7.6 Hz, 1H), 6.92 (d, J=7.8 Hz, 1H), 6.07 (s, 1H), 5.68 (dd, J=8.9, 6.2 Hz, 1H), 3.53 (dd, J=16.0, 8.7 Hz, 1H), 3.07 (dd, J=16.4, 5.9 Hz, 1H), 2.81 (br t, J=7.1 Hz, 2H), 2.77-2.67 (m, 3H), 2.72 (s, 3H), 2.66-2.50 (m, 1H), 2.18-1.96 (m, 3H), 1.88 (br s, 3H), 1.78-1.64 (m, 2H), 1.40 (br s, 9H), 1.36 (br s, 9H).

Example 96 (Racemic)

(±)-3-(2-methylpyrimidin-5-yl)-3-(3-(3-(6,7,8,9-tetrahydro-5H-pyrido[2,3-b]azepin-2-yl)propyl)-1H-pyrazol-1-yl)propanoic acid Tert-butyl 2-(3-(1-(3-(tert-butoxy)-1-(2-methylpyrimidin-5-yl)-3-oxopropyl)-1H-pyrazol-3-yl)propyl)-5,6,7,8-tetrahydro-977-pyrido[2,3-b]azepine-9-carboxylate 96F (55 mg, 0.095 mmol) and TFA (0.2 mL, 2.60 mmol) were stirred in CH$_2$Cl$_2$ (1 mL) for 18 h. The solvent was evaporated and the residue was dried in vacuo to give (±)-3-(2-methylpyrimidin-5-yl)-3-(3-(3-(6,7,8,9-tetrahydro-5H-pyrido[2,3-b]azepin-2-yl)propyl)-1H-pyrazol-1-yl)propanoic acid, 3 TFA (Example 96, 68 mg, 0.089 mmol, 86% yield). LCMS (ESI): m/z 421 [M+H]$^+$. $^1$H NMR (400 MHz, ACETONITRILE-d$_3$) δ 8.72 (s, 2H), 7.61 (d, J=2.2 Hz, 1H), 7.57 (d, J=7.6 Hz, 1H), 6.60 (d, J=7.3 Hz, 1H), 6.14 (d, J=2.2 Hz, 1H), 5.85 (dd, J=9.3, 5.4 Hz, 1H), 3.56 (br t, J=5.0 Hz, 2H), 3.49 (dd, J=16.8, 9.4 Hz, 1H), 3.22 (dd, J=16.6, 5.4 Hz, 1H), 2.91 (br t, J=5.4 Hz, 2H), 2.74-2.62 (m, 4H), 2.69 (s, 3H), 2.07-1.85 (m, 6H). Human αVβ6 IC50 (nM)=17.

Example 97 (Enantiomer 1) and Example 98 (Enantiomer 2)

Enantiomer 1 of 3-(2-methylpyrimidin-5-yl)-3-(3-(3-(6,7,8,9-tetrahydro-5H-pyrido[2,3-b]azepin-2-yl)propyl)-1H-pyrazol-1-yl)propanoic acid (97)

Enantiomer 2 of 3-(2-methylpyrimidin-5-yl)-3-(3-(3-(6,7,8,9-tetrahydro-5H-pyrido[2,3-b]azepin-2-yl)propyl)-1H-pyrazol-1-yl)propanoic acid (98)

(±)-3-(2-methylpyrimidin-5-yl)-3-(3-(3-(6,7,8,9-tetrahydro-5H-pyrido[2,3-b]azepin-2-yl)propyl)-1H-pyrazol-1-yl)propanoic acid 96 was separated into individual enantiomers by chiral SFC (Chiralpak AD-H, 30×250 mm, 5 μm, 20% MeOH/0.1% NH$_4$OH in CO$_2$ (150 bar), 35° C., 70 mL/min, 28 min, λ 220 nm) to give Example 97 (first eluting enantiomer, 12 mg, 32% yield) as a white solid. LCMS (ESI): m/z 421 [M+H]$^+$. $^1$H NMR (400 MHz, METHANOL-d$_4$) δ 8.65 (s, 2H), 7.70 (s, 1H), 7.50 (d, J=7.6 Hz, 1H), 6.65 (d, J=7.3 Hz, 1H), 6.14 (s, 1H), 5.89 (br dd, J=9.2, 6.0 Hz, 1H), 3.43-3.24 (m, 3H), 3.18-3.01 (m, 1H), 2.89-2.74 (m, 2H), 2.71-2.51 (m, 4H), 2.67 (s, 3H), 2.14-1.62 (m, 6H). Human αVβ6 IC50 (nM)=45. Example 98 (second eluting enantiomer, 14 mg, 35% yield) was also isolated as a white solid. LCMS (ESI): m/z 421 [M+H]$^+$. $^1$H NMR (400 MHz, METHANOL-d$_4$) δ 8.64 (s, 2H), 7.71 (s, 1H), 7.46 (d, J=7.3 Hz, 1H), 6.63 (d, J=7.3 Hz, 1H), 6.14 (s, 1H), 5.93-5.83 (m, 1H), 3.38-3.34 (m, 2H), 3.27 (br d, J=9.0 Hz, 1H), 3.15 (br d, J=6.4 Hz, 1H), 2.85-2.75 (m, 2H), 2.71-2.53 (m, 4H), 2.67 (s, 3H), 2.11-1.75 (m, 6H). Human αVβ6 IC$_{50}$ (nM)=595.

Example 99

(±)-3-(2-methylpyrimidin-5-yl)-3-(5-(3-(6,7,8,9-tetrahydro-5/Z-pyrido[2,3-b]azepin-2-yl)propyl)-1H-pyrazol-1-yl)propanoic acid

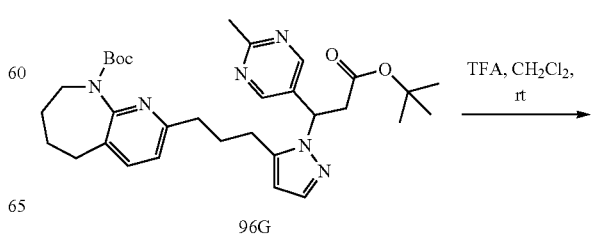

96G

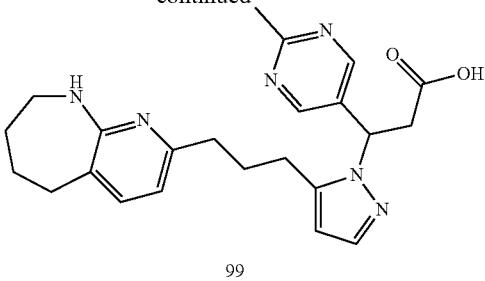

99

The title compound was prepared from 96G using the same method as described for Example 96 to give (±)-3-(2-methylpyrimidin-5-yl)-3-(5-(3-(6,7,8,9-tetrahydro-5H-pyrido[2,3-b]azepin-2-yl)propyl)-1H-pyrazol-1-yl)propanoic acid Example 99, 3 TFA (14 mg, 69% yield). LCMS (ESI): m/z 421 [M+H]$^+$. $^1$H NMR (400 MHz, ACETONITRILE-d$_3$) δ 8.55 (s, 2H), 7.54 (d, J=7.6 Hz, 1H), 7.49 (s, 1H), 6.55 (d, J=7.6 Hz, 1H), 6.16 (s, 1H), 5.81 (dd, J=10.1, 4.3 Hz, 1H), 3.69-3.50 (m, 3H), 3.16 (dd, J=16.9, 4.4 Hz, 1H), 2.91 (br s, 2H), 2.86-2.65 (m, 4H), 2.64 (s, 3H), 2.15-1.74 (m, 6H). Human αVβ6 IC$_{50}$ (nM)=410.

| Example | Structure & Name | Analytical Data | Method |
|---|---|---|---|
| 100 | 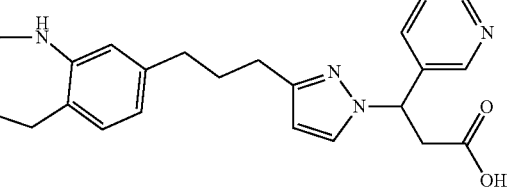<br>(±)-3-(6-methoxypyridin-3-yl)-3-(3-(3-(6,7,8,9-tetrahydro-5H-pyrido[2,3-b]azepin-2-yl)propyl)-1H-pyrazol-1-yl)propanoic acid, 3 TFA | $^1$H NMR (500 MHz, CHLOROFORM-d) δ 8.29 (d, J = 2.1 Hz, 1H), 7.80 (dd, J = 8.9, 2.4 Hz, 1H), 7.48-7.40 (m, 2H), 6.92 (d, J = 8.9 Hz, 1H), 6.50 (d, J = 7.5 Hz, 1H), 6.18 (d, J = 2.3 Hz, 1H), 5.97-5.85 (m, 1H), 4.03 (s, 3H), 3.64-3.42 (m, 3H), 3.25-3.10 (m, 1H), 2.96-2.84 (m, 2H), 2.79 (td, J = 6.8, 2.8 Hz, 2H), 2.71-2.66 (m, 2H), 2.19-1.85 (m, 6H), LCMS (ESI): m/z 436 [M + H]$^+$. αVβ6 IC$_{50}$ (nM) = 6.4. | Example 96 |
| 101 | 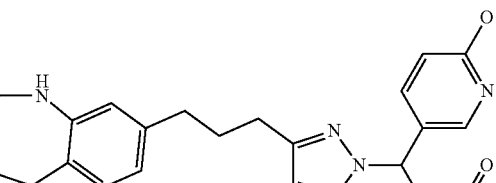<br>3-(6-methoxypyridin-3-yl)-3-(3-(3-(6,7,8,9-tetrahydro-5H-pyrido[2,3-b]azepin-2-yl)propyl)-1H-pyrazol-1-yl)propanoic acid (Enantiomer 1) | $^1$H NMR (400 MHz, METHANOL-d$_4$) δ 8.10 (d, J = 1.7 Hz, 1H), 7.68 (dd, J = 8.7, 2.1 Hz, 1H), 7.59 (d, J = 1.5 Hz, 1H), 7.52 (d, J = 7.3 Hz, 1H), 6.78 (d, J = 8.8 Hz, 1H), 6.65 (d, J = 7.3 Hz, 1H), 6.11 (d, J = 1.5 Hz, 1H), 5.82 (dd, J = 10.0, 5.1 Hz, 1H), 3.90 (s, 3H), 3.44-3.35 (m, 2H), 3.32-3.23 (m, 1H), 3.04 (dd, J = 15.0, 5.3 Hz, 1H), 2.90-2.74 (m, 2H), 2.62 (br t, J = 6.5 Hz, 3H), 2.15-1.77 (m, 6H), LCMS (ESI): m/z 436 [M + H]$^+$. Human αVβ6 IC$_{50}$ (nM) = 4.3. | Example 97 |
| 102 | 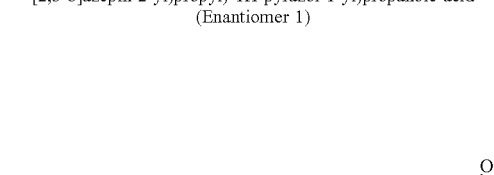<br>3-(6-methoxypyridin-3-yl)-3-(3-(3-(6,7,8,9-tetrahydro-5H-pyrido[2,3-b]azepin-2-yl)propyl)-1H-pyrazol-1-yl)propanoic acid (Enantiomer 2) | $^1$H NMR (400 MHz, METHANOL-d$_4$) δ 8.10 (d, J = 2.0 Hz, 1H), 7.68 (dd, J = 8.7, 2.3 Hz, 1H), 7.59 (s, 1H), 7.51 (d, J = 7.3 Hz, 1H), 6.78 (d, J = 8.6 Hz, 1H), 6.65 (d, J = 7.3 Hz, 1H), 6.11 (d, J = 1.5 Hz, 1H), 5.82 (dd, J = 10.0, 5.1 Hz, 1H), 3.90 (s, 3H), 3.44-3.35 (m, 2H), 3.31-3.21 (m, 1H), 3.04 (dd, J = 14.9, 5.1 Hz, 1H), 2.91-2.79 (m, 2H), 2.62 (br t, J = 6.4 Hz, 4H), 2.18-1.76 (m, 6H), LCMS (ES): m/z 436 [M + H]$^+$. Human αVβ6 IC$_{50}$ (nM) = 150. | Example 98 |

| Example | Structure & Name | Analytical Data | Method |
|---|---|---|---|
| 103 | 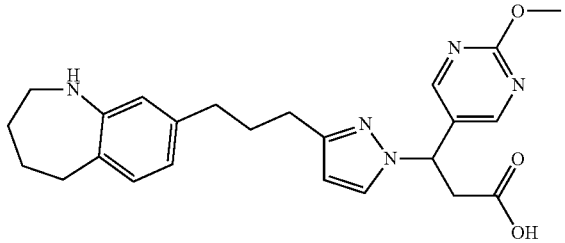 [SMILES: COc1ncc(C(CC(=O)O)n2ccc(CCCc3ccc4c(c3)NCCCC4)n2)cn1]<br>(±)-3-(2-methoxypyrimidm-5-yl)-3-(3-(3-(6,7,8,9-tetrahydro-5H-pyrido[2,3-b]azepin-2-yl)propyl)-1H-pyrazol-1-yl)propanoic acid, 3 TFA | $^1$H NMR (400 MHz, CHLOROFORM-d) δ 8.56 (s, 2H), 7.44 (d, J = 7.6 Hz, 1H), 7.40 (d, J = 1.7 Hz, 1H), 7.09-7.09 (m, 1H), 6.48 (d, J = 7.3 Hz, 1H), 6.13 (d, J = 1.7 Hz, 1H), 5.80 (dd, J = 10.3, 4.6 Hz, 1H), 4.05 (s, 3H), 3.66-3.41 (m, 3H), 3.13 (dd, J = 15.7, 4.6 Hz, 1H), 2.90 (br d, J = 5.6 Hz, 2H), 2.76 (br t, J = 6.5 Hz, 2H), 2.70 (br t, J = 7.8 Hz, 2H), 2.02 (br d, J = 5.9 Hz, 4H), LCMS (ES): m/z 437 [M + H]$^+$. Human αVβ6 IC$_{50}$ (nM) = 30. | Example 96 |
| 104 | 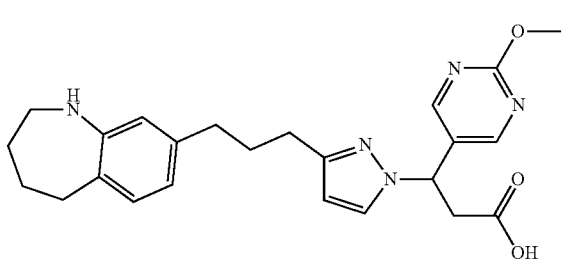 [SMILES: COc1ncc(C(CC(=O)O)n2ccc(CCCc3ccc4c(c3)NCCCC4)n2)cn1]<br>3-(2-methoxypyrimidin-5-yl)-3-(3-(3-(6,7,8,9-tetrahydro-5H-pyrido[2,3-b]azepin-2-yl)propyl)-1H-pyrazol-1-yl)propanoic acid (Enantiomer 1) | $^1$H NMR (400 MHz, METHANOL-d$_4$) δ 8.56 (s, 2H), 7.67 (s, 1H), 7.51 (d, J = 7.6 Hz, 1H), 6.66 (br d, J = 7.6 Hz, 1H), 6.13 (s, 1H), 5.93-5.70 (m, 1H), 4.01 (s, 3H), 3.37 (m, 3H) 3.19-3.00 (m, 1H), 2.89-2.74 (m, 2H), 2.64 (br t, J = 7.0 Hz, 4H), 2.20-1.64 (m, 6H), LCMS (ESI): m/z 437 [M + H]$^+$. Human αVβ6 IC$_{50}$ (nM) = 10. | Example 97 |
| 105 | 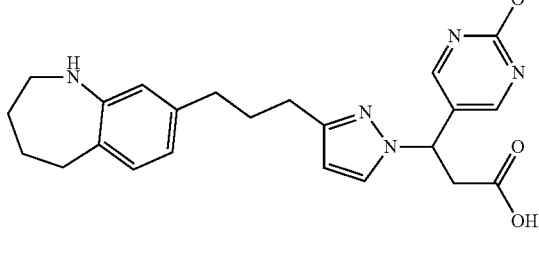<br>3-(2-methoxypyrimidin-5-yl)-3-(3-(3-(6,7,8,9-tetrahydro-5H-pyrido[2,3-b]azepin-2-yl(propyl)-1H-pyrazol-1-yl)propanoic acid (Enantiomer 2) | $^1$H NMR (400 MHz, METHANOL-d$_4$) δ 8.55 (s, 2H), 7.68 (s, 1H), 7.50 (d, J = 7.6 Hz, 1H), 6.65 (d, J = 7.3 Hz, 1H), 6.13 (s, 1H), 5.92-5.71 (m, 1H), 4.01 (s, 3H), 3.50-3.25 (s,3H), 3.23-2.97 (m, 1H), 2.92-2.74 (m, 2H), 2.64 (br t, J = 7.0 Hz, 4H), 2.20-1.66 (m, 6H), LCMS (ESI): m/z 437 [M + H]$^+$. Human αVβ6 IC$_{50}$ (nM) = 470. | Example 98 |
| 106 | 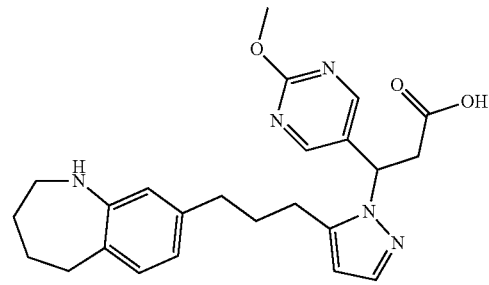 [SMILES: COc1ncc(C(CC(=O)O)n2nccc2CCCc2ccc3c(c2)NCCCC3)cn1]<br>(±)-3-(2-methoxypyrimidin-5-yl)-3-(5-(3-(6,7,8,9-tetrahydro-5H-pyrido[2,3-b]azepin-2-yl)propyl)-1H-pyrazol-1-yl) propanoic acid, 3 TFA | $^1$H NMR (400 MHz, CHLOROFORM-d) δ 8.52 (br s, 2H), 7.56 (s, 1H), 7.43 (d, J = 7.3 Hz, 1H), 6.44 (d, J = 7.3 Hz, 1H), 6.10 (s, 1H), 5.80 (dd, J = 10.3, 2.9 Hz, 1H), 4.03 (s,3H), 3.76 (dd, J = 16.0, 10.6 Hz, 1H), 3.62 (br s, 2H), 3.09 (dd, J = 16.0, 3.3 Hz, 1H), 2.94-2.67 (m, 6H), 2.27-1.90 (m, 6H), LCMS (ESI): m/z 437 [M + H]$^+$. Human αVβ6 IC50 (nM) = 820. | Example 99 |

-continued

| Example | Structure & Name | Analytical Data | Method |
|---|---|---|---|
| 107 | (±)-3-(5-methoxypyridin-3-yl)-3-(3-(3-(6,7,8,9-tetrahydro-5H-pyrido[2,3-b]azepin-2-yl)propyl)-1H-pyrazol-1-yl)propanoic acid, 3 TFA | $^1$H NMR (400 MHz, CHLOROFORM-d) δ 8.55-8.40 (m, 2H), 7.84 (br s, 1H), 7.51 (br s, 1H), 7.47 (d, J = 7.6 Hz, 1H), 6.51 (d, J = 7.3 Hz, 1H), 6.17 (br s, 1H), 6.06-5.92 (m, 1H), 4.00 (s, 3H), 3.63-3.52 (m, 3H), 3.25 (br d, J = 14.2 Hz, 1H), 2.91 (br d, J = 5.6 Hz, 2H), 2.77 (br s, 2H), 2.70(br t, J = 7.2 Hz, 2H), 2.22-1.92 (m, 6H), LCMS (ESI): m/z 436 [M + H]$^+$. Human αVβ6 IC$_{50}$ (nM) = 4.9. | Example 96 |
| 108 | (±)-3-(5-methoxypyridin-3-yl)-3-(5-(3-(6,7,8,9-tetrahydro-5H-pyrido[2,3-b]azepin-2-yl)propyl)-1H-pyrazol-1-yl)propanoic acid, 3 TFA | $^1$H NMR (400 MHz, CHLOROFORM-d) δ 8.43 (br s, 1H), 8.38 (br s, 1H), 7.90 (s, 1H), 7.57 (s, 1H), 7.44 (d, J = 7.1 Hz, 1H), 6.46 (d, J = 6.8 Hz, 1H), 6.13 (s, 1H), 6.00 (br d, J = 5.1 Hz, 1H), 3.98 (s, 3H), 3.74 (br dd, J = 16.4, 9.0 Hz, 1H) 3.61 (br s, 2H), 3.23-3.11 (m, 1H), 2.97-2.87 (m, 2H), 2.86-2.75 (m, 2H), 2.75-2.64 (m, 2H), 2.21-1.89 (m, 6H), LCMS (ESI): m/z 436 [M + H]$^+$. Human αVβ6 IC$_{50}$ (nM) = 170. | Example 99 |

Example 109

(S)-3-(1-benzyl-6-oxo-1,6-dihydropyridin-3-yl)-3-(3-(3-(5,6,7,8-tetrahydro-1,8-naphthyridin-2-yl)propyl)-1H-pyrazol-1-yl)propanoic acid

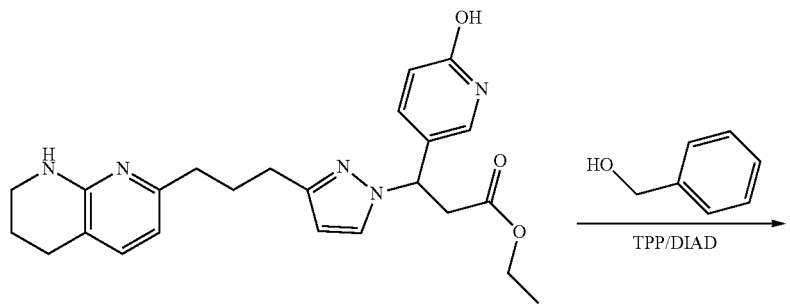

Example 12

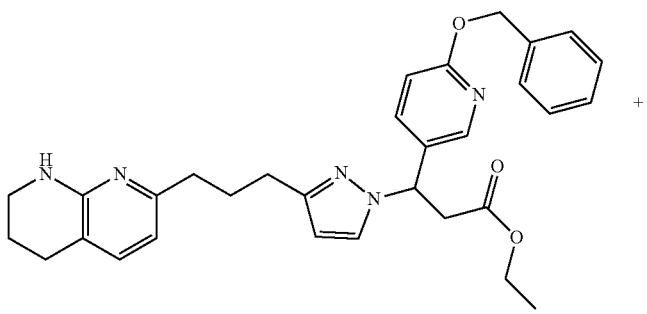

109A

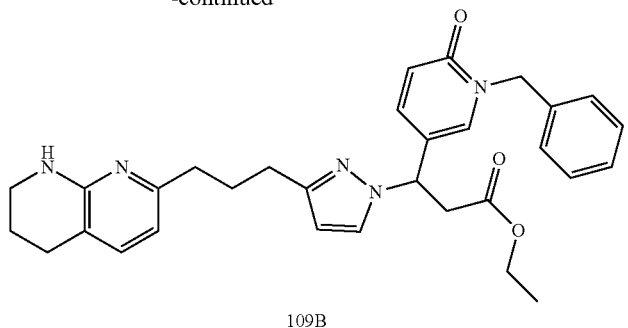

109B

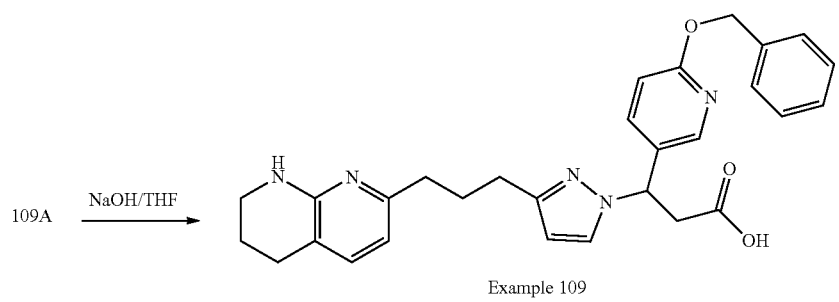

Example 109

Ethyl (S)-3-(6-(benzyloxy)pyridin-3-yl)-3-(3-(3-(5,6,7,8-tetrahydro-1,8-naphthyridin-2-yl)propyl)-1H-pyrazol-1-yl)propanoate (109A) and ethyl (S)-3-(1-benzyl-6-oxo-1,6-dihydropyridin-3-yl)-3-(3-(3-(5,6,7,8-tetrahydro-1,8-naphthyridin-2-yl)propyl)-1H-pyrazol-1-yl)propanoate (109B)

A cold (0° C.) solution of ethyl (S)-3-(6-hydroxypyridin-3-yl)-3-(3-(3-(5,6,7,8-tetrahydro-1,8-naphthyridin-2-yl)propyl)-1H-pyrazol-1-yl)propanoate (Example 12; 817 mg, 1.876 mmol) benzyl alcohol (0.195 mL, 1.876 mmol) and triphenylphosphine (590 mg, 2.251 mmol) in DCM (35 mL) was treated with diisopropyl azodicarboxylate (0.438 mL, 2.251 mmol) dropwise. After min the ice bath was removed and stirring was continued at room temperature overnight. The reaction was diluted with DCM and washed with H2O, brine, dried (MgSO4) and concentrated. The resulting yellow wax was purified by Biotage (40 g col, 10-80% EtOAc/DCM, 13CV) to remove reagents. The column was then run with (0-8% MeOH/DCM, 12CV) to give the 1st band, O-alkylated product, ethyl (S)-3-(6-(benzyloxy)pyridin-3-yl)-3-(3-(3-(5,6,7,8-tetrahydro-1,8-naphthyridin-2-yl)propyl)-1H-pyrazol-1-yl)propanoate (109A), 330 mg (30% yield). LCMS (ES): ret. time=0.88 min, m/z 526.07 [M+H]$^+$, along with the 2nd band, N-alkylated product, ethyl (S)-3-(1-benzyl-6-oxo-1,6-dihydropyridin-3-yl)-3-(3-(3-(5,6,7,8-tetrahydro-1,8-naphthyridin-2-yl)propyl)-1H-pyrazol-1-yl)propanoate (109B) 690 mg (70% yield). LCMS (ES): ret. time=0.73 min, m/z 526.07 [M+H]$^+$.

Example 109: (S)-3-(1-benzyl-6-oxo-1,6-dihydropyridin-3-yl)-3-(3-(3-(5,6,7,8-tetrahydro-1,8-naphthyridin-2-yl)propyl)-1H-pyrazol-1-yl)propanoic acid A solution of ethyl (S)-3-(1-benzyl-6-oxo-1,6-dihydropyridin-3-yl)-3-(3-(3-(5,6,7,8-tetrahydro-1,8-naphthyridin-2-yl)propyl)-1H-pyrazol-1-yl)propanoate 109A (600 mg, 1.141 mmol) in MeOH (6 mL) was treated in one portion with a solution of 1N aqueous NaOH (3.42 mL, 3.42 mmol). The suspension was stirred at room temperature for 30 min. The reaction was concentrated and then the solution was diluted with H2O, made slightly acidic with 1N HCl, and extracted with DCM (5×). The organic layers were combined, dried (MgSO$_4$) and conc, to give a 556 mg of a white solid. A portion (15 mg) of the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 6-46% B over 20 minutes, then a 4-minute hold at 100% B; Flow: 20 mL/min to give (S)-3-(1-benzyl-6-oxo-1,6-dihydropyridin-3-yl)-3-(3-(3-(5,6,7,8-tetrahydro-1,8-naphthyridin-2-yl)propyl)-1H-pyrazol-1-yl)propanoic acid (Example 109), 7.9 mg. LCMS (ES): m/z 498.19[M+H]$^+$. $^1$H NMR (500 MHz, DMSO-d$_6$) δ 7.86 (s, 1H), 7.66 (d, J=1.8 Hz, 1H), 7.44 (dd, J=9.5, 2.4 Hz, 1H), 7.31-7.24 (m, 5H), 7.02 (d, J=7.3 Hz, 1H), 6.36 (d, J=9.2 Hz, 1H), 6.24 (d, J=7.3 Hz, 1H), 6.00 (d, J=1.8 Hz, 1H), 5.50 (t, J=7.5 Hz, 1H), 5.09-4.99 (m, 2H), 3.91 (s, 1H), 3.58-3.35 (m, 2H), 3.20-3.04 (m, 2H), 2.94 (br d, J=6.4 Hz, 1H), 2.90 (s, 1H), 2.74 (s, 1H), 2.65-2.60 (m, 1H), 2.43 (s, 1H), 1.90 (s, 2H), 1.82 (br t, J=7.5 Hz, 2H), 1.78-1.69 (m, 2H). Human αVβ6 IC$_{50}$ (nM)=4.2

Example 110

Ethyl (S)-3-(6-(benzyloxy)pyridin-3-yl)-3-(3-(3-(5,6,7,8-tetrahydro-1,8-naphthyridin-2-yl)propyl)-1H-pyrazol-1-yl)propanoate

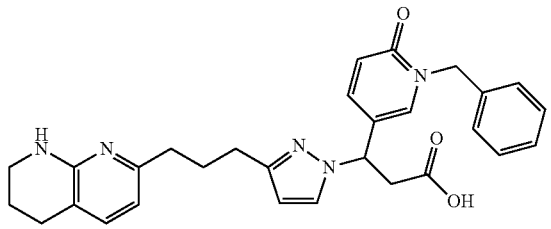

In a similar manner as for the preparation of Example 109, ethyl (S)-3-(6-(benzyloxy)pyridin-3-yl)-3-(3-(3-(5,6,7,8-tetrahydro-1,8-naphthyridin-2-yl)propyl)-1H-pyrazol-1-yl)propanoate 109B was saponified to give (S)-3-(6-(benzyloxy)pyridin-3-yl)-3-(3-(3-(5,6,7,8-tetrahydro-1,8-naphthyridin-2-yl)propyl)-1H-pyrazol-1-yl)propanoic acid (Example 110), 8.2 mg. LCMS (ES): m/z 498.2[M+H]$^+$, $^1$H NMR (500 MHz, DMSO-d$_6$) δ 8.10 (s, 1H), 7.74-7.65 (m, 2H), 7.43-7.29 (m, 5H), 7.02 (br d, J=7.0 Hz, 1H), 6.82 (d, J=8.5 Hz, 1H), 6.30 (br s, 1H), 6.23 (d, J=7.0 Hz, 1H), 6.03-6.00 (m, 1H), 5.72 (br t, J=7.5 Hz, 1H), 5.31 (s, 2H), 3.68 (br s, 2H), 3.32-3.25 (m, 2H), 3.20-3.11 (m, 1H), 3.02 (br dd, J=16.0, 6.6 Hz, 2H), 2.90 (s, 1H), 2.74 (s, 1H), 2.60 (br s, 1H), 2.50-2.42 (m, 1H), 1.87-1.79 (m, 2H), 1.78-1.71 (m, 2H). Human αVβ6 IC$_{50}$ (nM)=9.3

Example 111

(S)-3-(1-(cyclopropylmethyl)-6-oxo-1,6-dihydropyridin-3-yl)-3-(3-(3-(5,6,7,8-tetrahydro-1,8-naphthyridin-2-yl)propyl)-1H-pyrazol-1-yl)propanoic acid

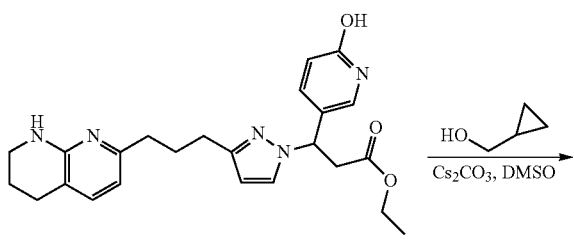

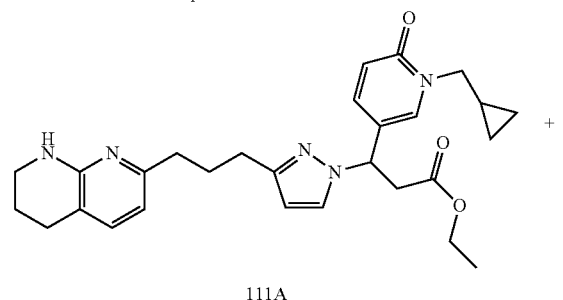

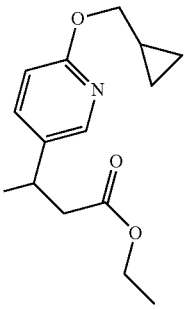

Ethyl (S)-3-(1-(cyclopropylmethyl)-6-oxo-1,6-dihydropyridin-3-yl)-3-(3-(3-(5,6,7,8-tetrahydro-1,8-naphthyridin-2-yl)propyl)-1H-pyrazol-1-yl)propanoate (111A) and ethyl (S)-3-(6-(cyclopropylmethoxy)pyridin-3-yl)-3-(3-(3-(5,6,7,8-tetrahydro-1,8-naphthyridin-2-yl)propyl)-1H-pyrazol-1-yl)propanoate (111B)

To a room temperature solution of ethyl (S)-3-(6-hydroxypyridin-3-yl)-3-(3-(3-(5,6,7,8-tetrahydro-1,8-naphthyridin-2-yl)propyl)-1H-pyrazol-1-yl)propanoate (Example 12) (100 mg, 0.230 mmol) in DMSO (2 mL) was added Cs2CO3 (135 mg, 0.413 mmol) followed by (bromomethyl)cyclopropane (31.0 mg, 0.230 mmol). The reaction mixture was stirred overnight. The reaction was diluted with ice/H2O, then extracted with EtOAc. The organic layers were combined, dried (MgSO4) and concentrated. The residue was then purified by Prep. HPLC (30×100 Luna col, 5-80% MeCN/H2O, 10 mmol NH4OAc, 35 ml/min, 16 min grad.) to give N-alkylated material, ethyl (S)-3-(1-(cyclopropylmethyl)-6-oxo-1,6-dihydropyridin-3-yl)-3-(3-(3-(5,6,7,8-tetrahydro-1,8-naphthyridin-2-yl)propyl)-1H-pyrazol-1-yl)propanoate 111A, 48 mg (42% yield), LCMS (ES): ret. time=0.69 min, m/z 490.08 [M+H]$^+$, along with the O-alkylated, ethyl (S)-3-(6-(cyclopropylmethoxy)pyridin-3-yl)-3-(3-(3-(5,6,7,8-tetrahydro-1,8-naphthyridin-2-yl)propyl)-1H-pyrazol-1-yl)propanoate 111B, 17 mg (15% yield), LCMS (ES): ret. time=0.74 min, m/z 490.11 [M+H]$^+$.

(S)-3-(1-(cyclopropylmethyl)-6-oxo-1,6-dihydropyridin-3-yl)-3-(3-(3-(5,6,7,8-tetrahydro-1,8-naphthyridin-2-yl)propyl)-1H-pyrazol-1-yl)propanoic acid (Example 111)

(S)-3-(1-(cyclopropylmethyl)-6-oxo-1,6-dihydropyridin-3-yl)-3-(3-(3-(5,6,7,8-tetrahydro-1,8-naphthyridin-2-yl)propyl)-1H-pyrazol-1-yl)propanoic acid was prepared and purified in a similar manor using the procedure from Example 109 using ethyl (S)-3-(1-(cyclopropylmethyl)-6-oxo-1,6-dihydropyridin-3-yl)-3-(3-(3-(5,6,7,8-tetrahydro-1,8-naphthyridin-2-yl)propyl)-1H-pyrazol-1-yl)propanoate (111A) to give Example 111, 16.5 mg, LCMS (ES): m/z 462.22[M+H]$^+$, $^1$H NMR (500 MHz, DMSO-d$_6$) δ 7.76 (s, 1H), 7.68 (s, 1H), 7.44 (br d, J=9.5 Hz, 1H), 7.02 (br d, J=7.0 Hz, 1H), 6.35 (d, J=9.2 Hz, 1H), 6.30-6.22 (m, 1H), 6.03 (s, 1H), 5.54-5.48 (m, 1H), 3.69 (br dd, J=10.1, 7.3 Hz, 2H), 3.23 (br s, 2H), 3.17 (s, 1H), 2.63-2.54 (m, 2H), 2.49-2.40 (m, 2H), 1.91 (s, 2H), 1.83 (br t, J=7.5 Hz, 2H), 1.79-1.70 (m, 2H), 1.24 (s, 2H), 1.15 (br dd, J=7.5, 4.1 Hz, 1H), 0.43 (br d, J=7.9 Hz, 2H), 0.34 (br d, J=3.7 Hz, 2H). Human αVβ6 IC$_{50}$ (nM)=19

Example 112

(S)-3-(6-(cyclopropylmethoxy)pyridin-3-yl)-3-(3-(3-(5,6,7,8-tetrahydro-1,8-naphthyridin-2-yl)propyl)-1H-pyrazol-1-yl)propanoic acid

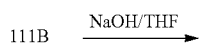

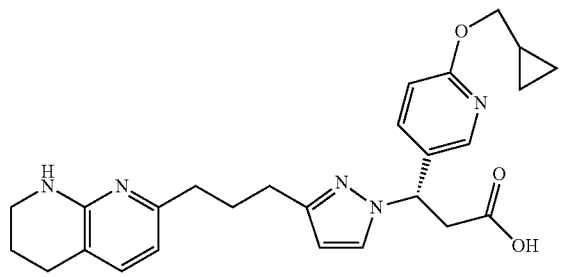

Example 112

(S)-3-(6-(cyclopropylmethoxy)pyridin-3-yl)-3-(3-(3-(5,6,7,8-tetrahydro-1,8-naphthyridin-2-yl)propyl)-1H-pyrazol-1-yl)propanoic acid was prepared and purified in a similar manor using the procedure from Example 109 using ethyl (S)-3-(6-(cyclopropylmethoxy)pyridin-3-yl)-3-(3-(3-(5,6,7,8-tetrahydro-1,8-naphthyridin-2-yl)propyl)-1H-pyrazol-1-yl)propanoate (111B) to give Example 112, 1.5 mg, LCMS (ES): m/z 462.22[M+H]$^+$, $^1$H NMR (500 MHz, DMSO-d$_6$) δ 7.76 (s, 1H), 7.68 (s, 1H), 7.44 (br d, J=9.5 Hz, 1H), 7.02 (br d, J=7.0 Hz, 1H), 6.35 (d, J=9.2 Hz, 1H), 6.30-6.22 (m, 2H), 6.03 (s, 1H), 5.54-5.48 (m, 1H), 3.69 (br dd, J=10.1, 7.3 Hz, 2H), 3.23 (br s, 2H), 3.05 (br d, J=6.1 Hz, 1H), 2.63-2.54 (m, 2H), 2.49-2.40 (m, 2H), 1.91 (s, 2H), 1.83 (br t, J=7.5 Hz, 2H), 1.79-1.70 (m, 2H), 1.24 (s, 2H), 1.15 (br d, J=3.4 Hz, 1H), 0.43 (br d, J=1.9 Hz, 2H), 0.34 (br d, J=3.7 Hz, 2H). Human αVβ6 IC$_{50}$ (nM)=3.5

Example 113

3-(6-methoxypyridin-3-yl)-3-(1-(3-(5,6,7,8-tetrahydro-1,8-naphthyridin-2-yl)propyl)-1H-pyrazol-3-yl)propanoic acid

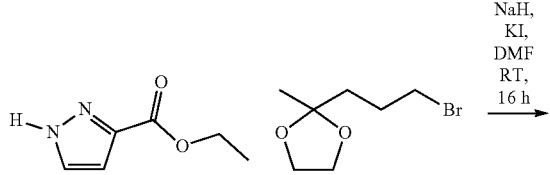

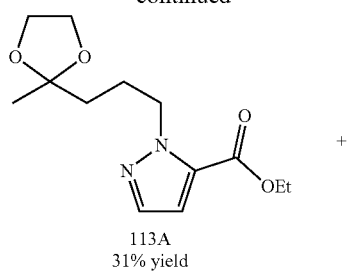

113A
31% yield

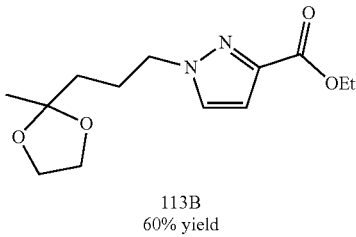

113B
60% yield

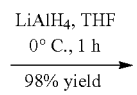

 113B

LiAlH$_4$, THF
0° C., 1 h
98% yield

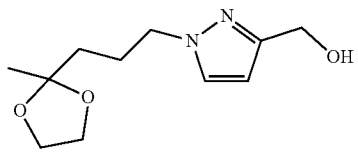 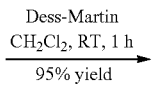

113C

Dess-Martin
CH$_2$Cl$_2$, RT, 1 h
95% yield

 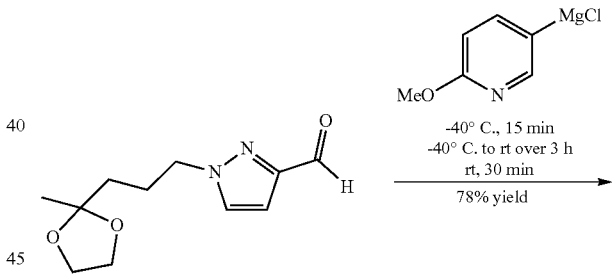

113D

-40° C., 15 min
-40° C. to rt over 3 h
rt, 30 min
78% yield

 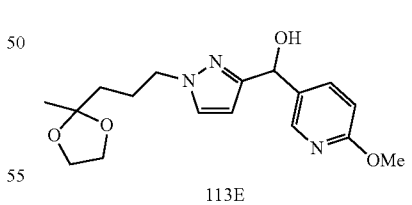 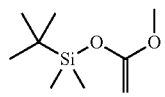

113E

TiCl$_4$, CH$_2$Cl$_2$
0° C., 10 min,
then 1 h
5.1% yield

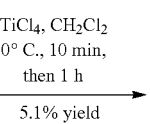

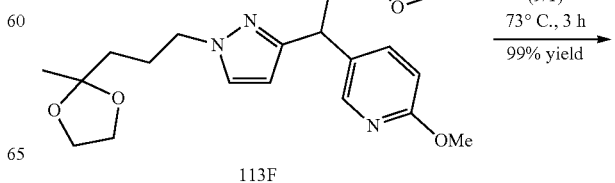

113F

PPTS
acetone/H$_2$O
(9/1)
73° C., 3 h
99% yield

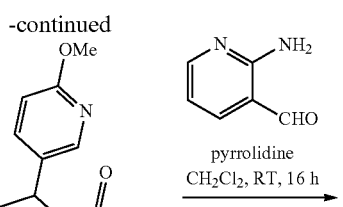

Example 113

Ethyl 1-(3-(2-methyl-1,3-dioxolan-2-yl)propyl)-1H-pyrazole-3-carboxylate (113B

DMF (40 mL) was added to a flask containing ethyl 1H-pyrazole-3-carboxylate (1.5 g, 10.70 mmol), sodium hydride (0.514 g, 12.84 mmol, 60% dispersion in mineral oil) at 0° C. After 15 min at 0° C., the reaction mixture was allowed to warm up to RT and stirred at RT for 30 min. The reaction mixture was cooled to 0° C. and a solution of 2-(3-bromopropyl)-2-methyl-1,3-dioxolane (2.69 g, 12.84 mmol), and potassium iodide (0.355 g, 2.141 mmol) in DMF (20 mL) was added. The reaction mixture was stirred at 0° C. for 15 min, then allowed to warm up to RT and stirred at RT for 16 h. After cooling to 0° C., the reaction mixture was quenched with aq NH₄Cl (30 mL), and all DMF was removed under high vacuum. The residue was diluted with EtOAc (200 mL), washed with brine, dried over Na₂SO₄, filtered, and concentrated. Flash chromatography (EtOAc/hexanes) afforded Example 113A (0.881 g, 3.28 mmol, 31% yield) and Example 113B (1.724 g, 6.43 mmol, 60% yield). LCMS (ES): m/z 269.10 [M+H]⁺. Example 113A: ¹H NMR (400 MHz, CDCl₃) δ 7.43 (d, J=1.7 Hz, 1H), 6.79 (d, J=2.0 Hz, 1H), 4.55 (t, J=7.3 Hz, 2H), 4.30 (q, J=7.1 Hz, 2H), 3.88 (br d, J=2.9 Hz, 4H), 1.97-1.84 (m, 2H), 1.71-1.57 (m, 2H), 1.34 (t, J=7.1 Hz, 3H), 1.26 (s, 3H). Example 113B: ¹H NMR (400 MHz, CDCl₃) δ 7.38 (d, J=1.7 Hz, 1H), 6.74 (d, J=1.7 Hz, 1H), 4.34 (q, J=7.1 Hz, 2H), 4.17 (br t, J=7.2 Hz, 2H), 3.98-3.69 (m, 4H), 2.02-1.90 (m, 2H), 1.67-1.52 (m, 2H), 1.34 (t, J=7.1 Hz, 3H), 1.24 (s, 3H).

(1-(3-(2-Methyl-1,3-dioxolan-2-yl)propyl)-1H-pyrazol-3-yl)methanol (113C)

LiAlH₄ (3.21 mL, 6.41 mmol, 2 M in THF) was added at 0° C. to a solution of 113B (1.72 g, 6.41 mmol) in THF (50 mL) After 1 h at 0° C., the following were added sequentially at 0° C.: H₂O (1.1 mL), 1 N NaOH (1.1 mL), and H₂O (3.3 mL). The resulting suspension was stirred at 0° C. for 15 min and RT for 15 min, and then filtered through a pad of Celite. After the filtrate was concentrated and dried under high vacuum, CH₂Cl₂ (100 mL) was added. The resulting light white suspension was stirred over Na₂SO₄ for 30 min. It was filtered through a pad of Celite, concentrated and dried under high vacuum to afford Example 113C (1.42 g, 6.26 mmol, 98% yield) as a colorless liquid, which was used directly without further purification. LCMS (ES): m/z 227.10 [M+H]⁺. ¹H NMR (400 MHz, CDCl₃) δ 7.35 (d, J=2.0 Hz, 1H), 6.23 (d, J=2.2 Hz, 1H), 4.69 (s, 2H), 4.12 (t, J=7.2 Hz, 2H), 4.03-3.80 (m, 4H), 2.45-2.23 (m, 1H), 2.06-1.92 (m, 2H), 1.72-1.61 (m, 2H), 1.32 (s, 3H).

1-(3-(2-Methyl-1,3-dioxolan-2-yl)propyl)-1H-pyrazole-3-carbaldehyde (113D)

Dess-Martin periodinane (3.17 g, 7.48 mmol) was added at RT to a solution of 113C (1.41 g, 6.23 mmol) in CH₂Cl₂ (50 mL). After stirring at RT for 1 h, the reaction mixture was concentrated and the residue subjected to flash chromatography (EtOAc/hexanes) to afford Example 113D (1.33 g, 5.93 mmol, 95% yield) as a very light tan liquid. LCMS (ES): m/z 225.09 [M+H]⁺. ¹H NMR (400 MHz, CDCl₃) δ 9.89 (s, 1H), 7.42 (d, J=2.2 Hz, 1H), 6.72 (d, J=2.4 Hz, 1H), 4.19 (t, J=7.2 Hz, 2H), 3.94-3.73 (m, 4H), 2.15-1.80 (m, 2H), 1.69-1.46 (m, 2H), 1.24 (s, 3H).

(6-Methoxypyridin-3-yl)(1-(3-(2-methyl-1,3-dioxolan-2-yl)propyl)-1H-pyrazol-3-yl)methanol (113E)

(6-methoxypyridin-3-yl)magnesium chloride (21.4 mL, 3.85 mmol) was added dropwise to a solution of 113D (0.665 g, 2.97 mmol) in THF (10 mL) at −40° C. The reaction mixture was warmed up to 10° C. over 3 h with the original cooling bath still on. The cooling bath was removed and the reaction mixture was stirred at RT for 1 h. After being cooled to 0° C., the reaction mixture was quenched with aq NH₄Cl, and all THF was removed under vacuum. The residue was extracted with EtOAc (3×) and brine in the presence of solid NaCl. The combined organic layers were dried over Na₂SO₄, filtered, and concentrated. Flash chromatography (MeOH/CH₂Cl₂) gave 113E (0.774 g, 2.32 mmol, 78% yield). LCMS (ES): m/z 334.21 [M+H]⁺. ¹H NMR (400 MHz, CDCl$_3$) δ 8.16 (d, J=2.0 Hz, 1H), 7.62 (dd, J=8.6, 2.2 Hz, 1H), 7.28 (d, J=2.0 Hz, 1H), 6.68 (d, J=8.6 Hz, 1H), 6.00 (d, J=2.0 Hz, 1H), 5.81 (d, J=2.2 Hz, 1H), 4.06 (t, J=1.2 Hz, 2H), 3.92-3.83 (m, 5H), 3.89 (s, 3H), 1.98-1.84 (m, 2H), 1.66-1.54 (m, 2H), 1.26 (s, 3H).

Methyl 3-(6-methoxypyridin-3-yl)-3-(1-(3-(2-methyl-1,3-dioxolan-2-yl)propyl)-1H-pyrazol-3-yl)propanoate (113F)

TiCl$_4$ (1.0 M in CH$_2$Cl$_2$, 0.774 mL, 0.774 mmol) was added at 0° C. to a solution of 113E (258 mg, 0.774 mmol) in CH$_2$Cl$_2$ (7 mL). After stirring at 0° C. for 30 min, 1-(tert-butyldimethylsilyloxy)-1-methoxyethene (0.338 mL, 1.548 mmol) was added dropwise. The reaction mixture was stirred at 0° C. for 1 h, and quenched by addition of saturated NaHCO$_3$ solution and extracted with CH$_2$Cl$_2$ (3×). The combined organic layers were dried over Na$_2$SO$_4$, filtered, and concentrated. Flash chromatography (MeOH/CH$_2$Cl$_2$) afforded a mixture containing the desired product. It was further purified by pre-HPLC with the following conditions: Column: SunFire Prep 19×55 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 10 minutes, then a 2-minute hold at 100% B; Flow: 20 mL/min to give 113F (15.5 mg, 5.1% yield). LCMS (ES): m/z 390.11 [M+H]$^+$. $^1$H NMR (400 MHz, CDCl$_3$) δ 8.11 (d, J=2.4 Hz, 1H), 7.51 (dd, J=8.7, 2.3 Hz, 1H), 7.27 (d, J=8.6 Hz, 1H), 6.68 (d, J=8.6 Hz, 1H), 5.95 (d, J=2.2 Hz, 1H), 4.53 (t, J=7.8 Hz, 1H), 4.09 (t, J=7.4 Hz, 2H), 3.97-3.88 (m, 4H), 3.92 (s, 3H), 3.62 (s, 3H), 3.22 (dd, J=15.8, 7.2 Hz, 1H), 2.91 (dd, J=15.8, 8.4 Hz, 1H), 2.02-1.87 (m, 2H), 1.73-1.53 (m, 2H), 1.31 (s, 3H).

Methyl 3-(6-methoxypyridin-3-yl)-3-(1-(4-oxopentyl)-1H-pyrazol-3-yl)propanoate (113G)

A mixture of 113F (24.5 mg, 0.063 mmol) and pyridinium p-toluenesulfonate (22 mg, 0.088 mmol) in acetone (9 mL) and water (1 mL) was heated at 73° C. for 3 h. Acetone was removed under vacuum. The residue was extracted with EtOAc (3×) and washed with brine in the presence of solid NaCl. The combined organic layers were dried over Na$_2$SO$_4$, filtered, concentrated and dried under high vacuum to afford 113G (21.7 mg, 0.063 mmol, 100% yield), which was used directly for the next step without further purification. LCMS (ES): m/z 346.12 [M+H]$^+$. $^1$H NMR (400 MHz, CDCl$_3$) δ 8.10 (d, J=2.0 Hz, 1H), 7.51 (dd, J=8.6, 2.4 Hz, 1H), 7.24 (d, J=2.0 Hz, 1H), 6.68 (d, J=8.6 Hz, 1H), 5.96 (d, J=2.2 Hz, 1H), 4.52 (t, J=7.8 Hz, 1H), 4.09 (t, J=8.0 Hz, 2H), 3.92 (s, 3H), 3.62 (s, 3H), 3.20 (dd, J=15.8, 7.5 Hz, 1H), 2.90 (dd, J=15.9, 8.3 Hz, 1H), 2.39 (t, J=7.0 Hz, 2H), 2.11 (s, 3H), 2.10-2.06 (m, 2H).

Methyl 3-(1-(3-(1,8-naphthyridin-2-yl)propyl)-1H-pyrazol-3-yl)-3-(6-methoxypyridin-3-yl)propanoate (113H)

Pyrrolidine (0.056 mL, 0.677 mmol) was added to a solution of 113G and 2-aminonicotinaldehyde (46.0 mg, 0.376 mmol) in CH$_2$Cl$_2$ (4 mL). After the reaction mixture was stirred at RT overnight, all volatiles were removed and the residue subjected to flash chromatography (MeOH/CH$_2$Cl$_2$) to afford a mixture containing 113H (60 mg). LCMS (ES): m/z 432.08 [M+H]$^+$. It was used directly for the next step without further purification.

Methyl 3-(6-methoxypyridin-3-yl)-3-(1-(3-(5,6,7,8-tetrahydro-1,8-naphthyridin-2-yl)propyl)-1H-pyrazol-3-yl)propanoate (113I)

The mixture of 113H (60 mg, used crude) and platinum (IV) oxide (16.74 mg, 0.074 mmol) in MeOH (15 mL) was subjected to hydrogenation under a balloon of H$_2$ overnight at RT. The reaction mixture was filtered through a pad of Celite and the filter cake washed twice with MeOH. The combined filtrates were concentrated, the residue subjected to Prep-HPLC with the following conditions: Column: SunFire Prep 19×55 mm, 5-(un particles; Mobile Phase A: 5:95 acetonitrile:water with 10-mM ammonium acetate; Mobile Phase B: 95:5 acetonitrile:water with 10-mM ammonium acetate; Gradient: 20-100% B over 10 minutes, then a 2-minute hold at 100% B; Flow: 20 mL/min to give 113I (14.3 mg, 0.033 mmol, 44.6% yield over two steps). LCMS (ES): m/z 436.12 [M+H]$^+$. $^1$H NMR (400 MHz, CDCl$_3$) δ 8.11 (d, J=2.0 Hz, 1H), 7.52 (dd, J=8.6, 2.2 Hz, 1H), 7.30 (d, J=2.2 Hz, 1H), 7.11 (d, J=7.3 Hz, 1H), 6.68 (d, J=8.6 Hz, 1H), 6.26 (d, J=1.1 Hz, 1H), 5.95 (d, J=2.0 Hz, 1H), 4.53 (t, J=7.8 Hz, 1H), 4.10 (t, J=7.0 Hz, 2H), 4.05 (br s, 1H), 3.92 (s, 3H), 3.62 (s, 3H), 3.43 (br t, J=5.5 Hz, 2H), 3.22 (dd, J=15.8, 7.2 Hz, 1H), 2.91 (dd, J=15.8, 8.4 Hz, 1H), 2.70 (br t, J=6.1 Hz, 2H), 2.57 (t, J=7.5 Hz, 2H), 2.21 (quin, J=7.2 Hz, 2H), 1.91 (quin, J=5.9 Hz, 2H).

Example 113: 3-(6-Methoxypyridin-3-yl)-3-(1-(3-(5,6,7,8-tetrahydro-1,8-naphthyridin-2-yl)propyl)-1H-pyrazol-3-yl)propanoic acid A solution of lithium hydroxide monohydrate (6.39 µl, 0.230 mmol) in water (1 mL) was added at RT to a solution of 113I (14.3 mg, 0.033 mmol) in MeOH (1 mL) and THF (1 mL). After the resulting clear solution was stirred at RT overnight, all volatiles were removed under high vacuum. Water (2 mL) was added, followed by HCl (1N, 0.23 mL, 0.23 mmol). The mixture was concentrated and dried under high vacuum. The residue was dissolved in DMF (1.5 mL), filtered and subjected to preparative LC/MS using the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 2-42% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-32% B over 30 minutes, then a 5-minute hold at 100% B; Flow: 20 mL/min. Fractions containing the desired product were combined and dried via centrifugal evaporation to give 3-(6-methoxypyridin-3-yl)-3-(1-(3-(5,6,7,8-tetrahydro-1,8-naphthyridin-2-yl)propyl)-1H-pyrazol-3-yl)propanoic acid (Example 113 (13.4 mg, 97% yield). LCMS (ES): m/z 422.08 [M+H]$^+$. $^1$H NMR (500 MHz, DMSO-d$_6$) δ 8.05 (s, 1H), 7.59 (br s, 2H), 7.03 (br d, J=7.0 Hz, 1H), 6.72 (d, J=8.5 Hz, 1H), 6.23 (br d, J=7.0 Hz, 1H), 6.05 (s, 1H), 4.35 (br t, J=7.6 Hz, 1H), 4.02 (br t, J=7.0 Hz, 2H), 3.81 (s, 3H), 3.25-3.17 (m, 2H), 3.00 (br dd, J=15.7, 7.2 Hz, 1H), 2.86-

2.73 (m, 1H), 2.61 (br t, J=5.5 Hz, 2H), 2.36 (br t, J=7.3 Hz, 2H), 2.07-1.95 (m, 2H), 1.81-1.67 (m, 2H). Human αVβ6 IC50 (nM)=35.

Example 114

(R)-3-(4-fluoro-3-(3-(5,6,7,8-tetrahydro-1,8-naphthyridin-2-yl)propyl)-1H-pyrazol-1-yl)-3-(2-methylpyrimidin-5-yl)propanoic acid (Example 114)

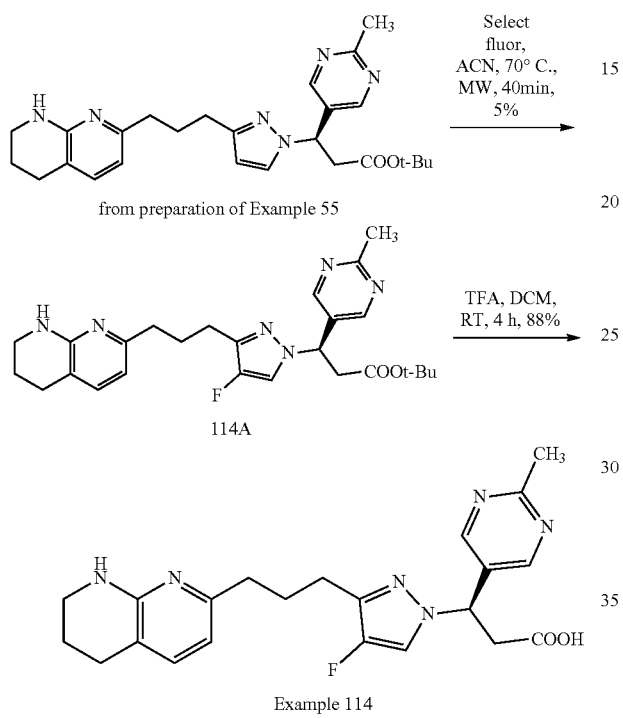

Tert-butyl (R)-3-(4-fluoro-3-(3-(5,6,7,8-tetrahydro-1,8-naphthyridin-2-yl)propyl)-1H-pyrazol-1-yl)-3-(2-methylpyrimidin-5-yl)propanoate (114A)

To a stirred solution of tert-butyl (R)-3-(2-methylpyrimidin-5-yl)-3-(3-(3-(5,6,7,8-tetrahydro-1,8-naphthyridin-2-yl)propyl)-1H-pyrazol-1-yl)propanoate (366 mg, 0.791 mmol) in ACN (2.5 mL) under nitrogen atmosphere was added Selectfluor (280 mg, 0.791 mmol). Resulting solution was kept under microwave conditions at 70° C. for 30 min. Selectfluor (280 mg, 0.791 mmol) was added again to ensure the maximum product formation and the reaction was continued to stir at the same conditions for 1 h. The reaction mass was evaporated under vacuum to get the crude product. The crude product was purified by preparative HPLC (Sunfire OBD (250×30) mm; 5 micron column; Mobile Phase A: 0.1% TFA in water; Mobile Phase B: ACN, flow rate: 27.0 mL/min; time (min)/% B: 0/30, 18/70) to afford the title compound 114A (20 mg, 5%) as a colourless liquid. LC-MS retention time=2.63 min; m/z=481.4 [M+H]⁺ KINETIX XB-C18, (3×75) mm, 2.6 micron column; Mobile Phase A: 10 mM HCO₂NH₄ in 98% Water/2% ACN; Mobile Phase B: 10 mM HCO₂NH₄ in 2% Water/98% ACN; 20% B to 100% B over 4.6 min, then hold 0.5 min. at 20% B with flow rate 1 mL/min; Detection: UV at 220 nm.

(R)-3-(4-Fluoro-3-(3-(5,6,7,8-tetrahydro-1,8-naphthyridin-2-yl)propyl)-1H-pyrazol-1-yl)-3-(2-methylpyrimidin-5-yl)propanoic acid (Example 114)

To a stirred solution of tert-butyl (R)-3-(4-fluoro-3-(3-(5, 6,7,8-tetrahydro-1,8-naphthyridin-2-yl)propyl)-1H-pyrazol-1-yl)-3-(2-methylpyrimidin-5-yl)propanoate (114A) (20 mg, 0.042 mmol) in DCM (0.2 mL) was added TFA (0.2 mL, 2.60 mmol) and the resulting mixture was stirred at RT for 4 h. The reaction mixture was evaporated under reduced pressure to afford the desired product (22 mg, 88%) as a brown solid (as a TFA salt). LC-MS retention time=1.09 min; m/z=425.2 [M+H]⁺ KINETIX XB-C18, (3×75) mm, 2.6 micron column; Mobile Phase A: 10 mM HCO₂NH₄ in 98% Water/2% ACN; Mobile Phase B: 10 mM HCO₂NH₄ in 2% Water/98% ACN; 20% B to 100% B over 4.6 min, then hold 0.4 min. at 20% B with flow rate 1 mL/min; Detection: UV at 220 nm. ¹H NMR (400 MHz, CD₃OD) δ ppm 8.62 (s, 2H), 7.75 (d, J=4.40 Hz, 1H), 7.55 (d, J=7.20 Hz, 1H), 6.58 (d, J=7.20 Hz, 1H), 5.79 (dd, J=6.00, 9.00 Hz, 1H), 3.45-3.52 (m, 3H), 3.24 (dd, J=6.00, 16.40 Hz, 1H), 2.81 (m, 2H), 2.68-2.75 (m, 4H), 2.66 (s, 3H), 2.01-2.07 (m, 2H), 1.94-1.98 (m, 2H). Human αVβ6 IC50 (nM)=4800.

Example 115 and Example 116

Example 115: First eluting enantiomer of 3-(3-Fluoro-4-methoxyphenyl)-3-(5-(3-(5,6,7,8-tetrahydro-1,8-naphthyridin-2-yl)propyl)-1H-pyrazol-3-yl)propanoic acid Example 116: First eluting enantiomer of 3-(3-Fluoro-4-methoxyphenyl)-3-(5-(3-(5,6,7,8-tetrahydro-1,8-naphthyridin-2-yl)propyl)-1H-pyrazol-3-yl)propanoic acid

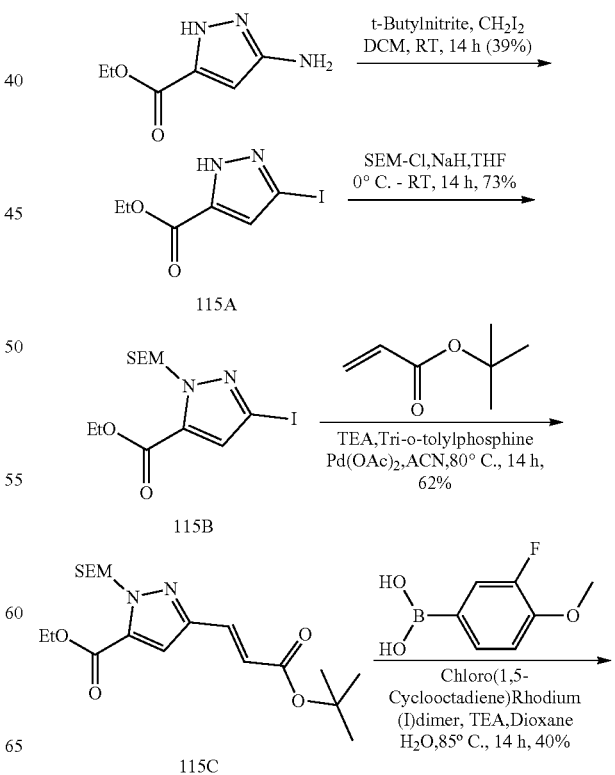

-continued

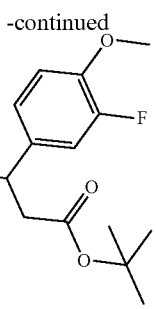
115D

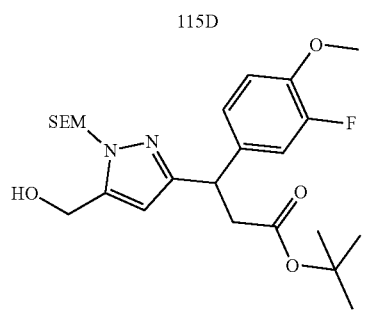
115E

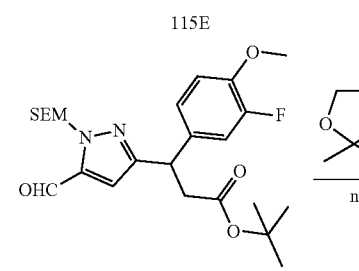
115F

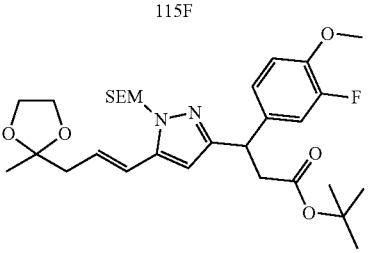
115G

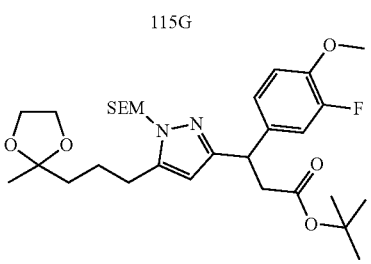
115H

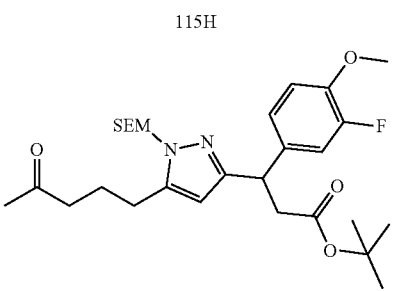
115I

-continued

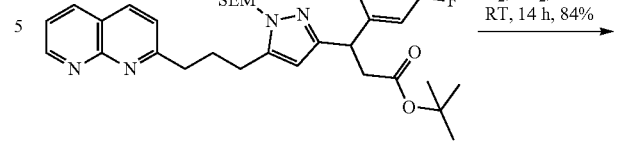
115J

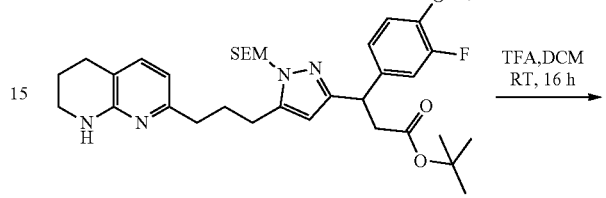
115K

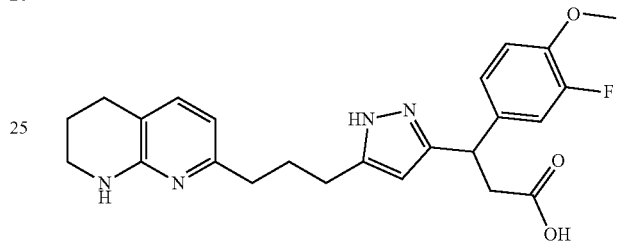

Example 115: first eluting enantiomer
Example 116: second eluting enantiomer

Ethyl 3-iodo-1H-pyrazole-5-carboxylate (115A)

To a stirred solution of ethyl 5-amino-1H-pyrazole-3-carboxylate (5 g, 32.2 mmol) in DCM (100 mL) under nitrogen atmosphere were added diiodomethane (4.54 mL, 56.4 mmol) followed by tert-butyl nitrite (5.80 mL, 48.3 mmol) and the reaction mixture was stirred at RT for 14 h. The reaction mixture was concentrated under reduced pressure to get crude compound. The crude compound was purified by flash silica gel column chromatography by using 0-50% ethyl acetate and pet-ether as mobile phase to afford the title compound 115A (3.4 g, 39%) as pale yellow solid. LC-MS retention time=1.651 min; m/z=265.0 [M−H]+ Column—KINETIX XB-C18, (3×75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, DMSO-$d_6$) δ ppm 14.28-13.94 (br. s., 1H), 7.00-6.89 (br. s., 1H), 4.28 (br. s., 2H), 1.28 (t, J=4.00 Hz, 3H).

Ethyl 3-iodo-1-((2-(trimethylsilyl)ethoxy)methyl)-1H-pyrazole-5-carboxylate (115B)

To a stirred solution of ethyl 5-iodo-1H-pyrazole-3-carboxylate 115A (3.4 g, 12.78 mmol) in THF (40 mL) under nitrogen atmosphere at 0° C. was added NaH (0.511 g, 12.78 mmol) as small portions and the reaction mixture was stirred at 0° C. for 1 h. SEM-Cl (2.267 mL, 12.78 mmol) was added to the above reaction mixture and stirred at RT for 14 h. Reaction mixture was quenched with saturated ammonium chloride (100 mL) and it was extracted with ethyl acetate (2×80 mL). The combined organic layer was washed with brine (100 mL), dried over anhydrous sodium sulphate, concentrated under reduced pressure to get crude compound. The crude product was purified by combiflash chromatography (40 g Redisep® SiO$_2$ column, eluting with 30% EtOAc in pet ether) to afford the title compound 115B (3.8 g, 74%) as off white solid. LC-MS retention time=3.667 min; m/z=397.0 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CDCl$_3$) δ ppm 7.05 (s, 1H), 5.60 (s, 2H), 4.43 (q, J=7.0 Hz, 2H), 3.66-3.60 (m, 2H), 1.41 (t, J=7.1 Hz, 3H), 0.95-0.89 (m, 2H), −0.01 (s, 9H).

Ethyl (E)-3-(3-(tert-butoxy)-3-oxoprop-1-en-1-yl)-1-((2-(trimethylsilyl)ethoxy)-methyl)-1H-pyrazole-5-carboxylate (115C)

In a sealed tube, ethyl 5-iodo-1-((2-(trimethylsilyl)ethoxy)methyl)-1H-pyrazole-3-carboxylate 115B (3.8 g, 9.59 mmol) in ACN (40 mL) was treated with tert-butyl acrylate (4.21 mL, 28.8 mmol) and the solution was degasified with argon gas for 5 min. TEA (4.01 mL, 28.8 mmol), tri-o-tolylphosphine (0.292 g, 0.959 mmol) followed by palladium(II) acetate (0.215 g, 0.959 mmol) were added and the reaction mixture was degasified with argon again for 5 min. The reaction mixture was then heated to 80° C. and stirred for 14 h. Reaction mixture was cooled, filtered through a pad of Celite and it was washed with DCM (4×20 mL). Filtrate was concentrated under reduced pressure to get crude compound. The crude product was purified by combiflash chromatography (40 g Redisep® SiO$_2$ column, eluting with 35% EtOAc in pet ether) to afford the title compound 115C (2.4 g, 62%) as pale yellow liquid. LC-MS retention time=3.836 min; m/z=397.2 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CDCl$_3$) δ ppm 7.63 (d, J=21.60 Hz, 1H), 7.14 (s, 1H), 6.43 (d, J=21.20 Hz, 1H), 5.65 (s, 2H), 4.46 (q, J=9.60 Hz, 2H), 3.62 (t, J=10.80 Hz, 2H), 1.57 (s, 9H), 1.44 (t, J=9.60 Hz, 3H), 0.93 (t, J=10.80 Hz, 2H), −0.01 (s, 9H).

Ethyl 3-(3-(tert-butoxy)-1-(3-fluoro-4-methoxyphenyl)-3-oxopropyl)-1-((2-(trimethylsilyl)ethoxy)methyl)-1H-pyrazole-5-carboxylate (115D)

A mixture of ethyl (E)-3-(3-(tert-butoxy)-3-oxoprop-1-en-1-yl)-1-((2-(trimethylsilyl)ethoxy)methyl)-1H-pyrazole-5-carboxylate 115C (2.4 g, 6.05 mmol) in 1,4-dioxane (40 mL) and water (10 mL) in a sealed tube was degassed with argon gas for 5 min. (3-fluoro-4-methoxyphenyl)boronic acid (1.543 g, 9.08 mmol) and TEA (1.687 mL, 12.10 mmol) were added and the reaction mixture was degassed with argon again for 5 min. Chloro(1,5-cyclooctadiene)rhodium (I) dimer (0.149 g, 0.303 mmol) was added, degassed with argon for 5 min more and the reaction mixture was stirred at 85° C. for 14 h. Reaction mixture was filtered through Celite and the collected solid was washed with DCM (4×15 mL). The combined filtrate was concentrated under reduced pressure to get crude compound. The crude product was purified by combiflash chromatography (24 g Redisep® SiO$_2$ column, eluting with 30% EtOAc in pet ether) to afford the title compound 115D (1.3 g, 40%) as colourless liquid. LC-MS retention time=3.94 min; m/z=323.4 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CDCl$_3$) δ ppm 7.03-6.95 (m, 3H), 6.89 (s, 1H), 5.53 (d, J=11.0 Hz, 1H), 5.37-5.28 (d, J=11.0 Hz, 1H), 4.72 (t, J=7.8 Hz, 1H), 4.47 (qd, J=7.2, 3.5 Hz, 2H), 3.91 (s, 3H), 3.47-3.38 (m, 2H), 2.98 (dd, J=15.6, 8.5 Hz, 1H), 2.85 (dd, J=15.6, 7.0 Hz, 1H), 1.46 (t, J=7.3 Hz, 3H), 1.40 (s, 9H), 0.91-0.74 (m, 2H), −0.01 (s, 9H).

tert-Butyl 3-(3-fluoro-4-methoxyphenyl)-3-(5-(hydroxymethyl)-1-((2-(trimethylsilyl)-ethoxy)methyl)-1H-pyrazol-3-yl)propanoate (115E)

To a stirred solution of ethyl 3-(3-(tert-butoxy)-1-(3-fluoro-4-methoxyphenyl)-3-oxopropyl)-1-((2-(trimethylsilyl)ethoxy)methyl)-1H-pyrazole-5-carboxylate 115E (1.1 g, 2.105 mmol) in THF (20 mL) under nitrogen atmosphere was added lithium borohydride (1.368 mL, 2 M in THF, 2.74 mmol) at 0° C. and the reaction mixture was stirred at RT for 48 h. Reaction mixture was quenched with water (50 mL) and it was extracted with ethyl acetate (2×40 mL). The combined organic layer was washed with brine (30 mL), dried over anhydrous sodium sulphate, concentrated under reduced pressure to get crude compound. The crude product was purified by combiflash chromatography (24 g Redisep® SiO$_2$ column, eluting with 70% EtOAc in pet ether) to afford the title compound 115E (0.750 g, 73%) as a colourless liquid. LC-MS retention time=3.517 min; m/z=481.2 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, DMSO-d$_6$) δ ppm 7.15-7.01 (m, 3H), 6.32 (s, 1H), 5.34 (d, J=1.0 Hz, 1H), 5.18 (d, J=11.0 Hz, 1H), 5.04 (t, J=5.8 Hz, 1H), 4.48 (t, J=8.0 Hz, 1H), 4.34 (d, J=6.0 Hz, 2H), 3.79 (s, 3H), 3.33-3.24 (m, 2H), 2.88 (dd, J=8.0, 4.0 Hz, 2H), 1.27 (s, 9H), 0.77-0.63 (m, 2H), −0.09 (s, 9H).

tert-Butyl 3-(3-fluoro-4-methoxyphenyl)-3-(5-formyl-1-((2-(trimethylsilyl)ethoxy)-methyl)-1H-pyrazol-3-yl)propanoate (115F)

To a stirred solution of tert-butyl 3-(3-fluoro-4-methoxyphenyl)-3-(5-(hydroxymethyl)-1-((2-(trimethylsilyl)ethoxy)methyl)-1H-pyrazol-3-yl)propanoate 115E (0.750 g, 1.560 mmol) in DCM (20 mL) under nitrogen atmosphere was added Dess-Martin Periodinane (0.993 g, 2.341 mmol) and the resulting solution was stirred at RT for 14 h. Reaction mixture was filtered through a pad of Celite and the same was washed with DCM (4×15 mL). The combined filtrate was concentrated under reduced pressure to get crude compound. The crude product was purified by combiflash chromatography (24 g Redisep® SiO$_2$ column, eluting with 40% EtOAc in pet ether) to afford the title compound 115F (0.750 g, 89%) as colourless liquid. LC-MS retention time=3.877 min; m/z=479.2 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN;

Mobile Phase B: 10 mM HCO₂NH₄ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CDCl₃) δ ppm 9.94 (s, 1H), 6.94-6.86 (m, 3H), 6.81 (s, 1H), 5.46 (d, J=11.0 Hz, 1H), 5.28 (d, J=11.0 Hz, 1H), 4.66 (t, J=7.9 Hz, 1H), 3.85 (s, 3H), 3.45 (ddd, J=10.6, 9.5, 6.1 Hz, 1H), 3.37 (ddd, J=10.8, 9.4, 6.0 Hz, 1H), 2.92 (dd, J=15.8, 8.8 Hz, 1H), 2.79 (dd, J=15.8, 7.3 Hz, 1H), 1.33 (s, 9H), 0.87-0.71 (m, 2H), −0.04 (s, 9H).

tert-Butyl (E)-3-(3-fluoro-4-methoxyphenyl)-3-(5-(3-(2-methyl-1,3-dioxolan-2-yl)prop-1-en-1-yl)-1-((2-(trimethylsilyl)ethoxy)methyl)-1H-pyrazol-3-yl)propanoate (115G)

To a stirred solution of bromo(2-(2-methyl-1,3-dioxolan-2-yl)ethyl)triphenyl-l5-phosphane (1.242 g, 2.72 mmol) in THF (4 mL) was added nBuLi (1.4 mL, 3.40 mmol, 2.5 M solution in hexane) at 0° C. and the resulting solution was stirred for 30 min. tert-Butyl 3-(3-fluoro-4-methoxyphenyl)-3-(5-formyl-1-((2-(trimethylsilyl)ethoxy)methyl)-1H-pyrazol-3-yl)propanoate 115F (0.650 g, 1.358 mmol) dissolved in THF (4 mL) was added to the above solution and stirred at RT for 2 h. Reaction mixture was quenched with saturated ammonium chloride (20 mL) and extracted with ethyl acetate (2×20 mL). The combined organic layer was washed with brine (10 mL), dried over anhydrous sodium sulphate, concentrated under reduced pressure to get crude compound. The crude product was purified by combiflash chromatography (24 g Redisep® SiO₂ column, eluting with 50% EtOAc in pet ether) to afford the title compound 115G (0.470 g, 60%) as pale yellow liquid. LC-MS retention time=4.090 min; m/z=577.4 [M+H]⁺ Column—KINETIX XB-C18, (3 10×75) mm, 2.6 micron column; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 50% B to 100% B over 4.6 min, then hold 0.4 min. at 50% B with flow rate 1.5 mL/min; Detection: UV at 220 nm.

tert-Butyl 3-(3-fluoro-4-methoxyphenyl)-3-(5-(3-(2-methyl-1,3-dioxolan-2-yl)propyl)-1-((2-(trimethylsilyl)ethoxy)methyl)-1H-pyrazol-3-yl)propanoate (115H)

To a stirred solution of tert-Butyl (E)-3-(3-fluoro-4-methoxyphenyl)-3-(5-(3-(2-methyl-1,3-dioxolan-2-yl)prop-1-en-1-yl)-1-((2-(trimethylsilyl)ethoxy)methyl)-1H-pyrazol-3-yl)propanoate 115G (0.470 g, 0.815 mmol) in ethanol (10 mL) was added palladium hydroxide on carbon (47 mg, 0.067 mmol) and the reaction mixture was stirred at RT under EL bladder for 14 h. Reaction mixture was filtered through a pad of Celite and the Celite was washed with MeOH (4×20 mL). The combined filtrate was concentrated under reduced pressure to afford the title compound 115H (0.430 g, 91%). LC-MS retention time=4.016 min; m/z=579.4 [M+H]⁺ Column-KINETIX XB-C18, (3×75) mm, 2.6 micron column; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CDCl₃) δ ppm 6.95-6.82 (m, 3H), 6.08 (s, 1H), 5.29 (d, J=1.3 Hz, 1H), 5.12 (d, J=11.3 Hz, 1H), 4.57 (t, J=7.9 Hz, 1H), 3.98-3.87 (m, 4H), 3.85 (s, 3H), 3.45-3.28 (m, 2H), 2.87 (dd, J=15.4, 8.1 Hz, 1H), 2.75 (dd, J=15.4, 7.9 Hz, 1H), 2.62-2.56 (m, 2H), 1.91 (td, J=7.6, 3.9 Hz, 1H), 1.83 (br. s., 1H), 1.76-1.65 (m, 2H), 1.56 (s, 3H), 1.31 (s, 9H), 0.84-0.68 (m, 2H), −0.07 (s, 9H).

tert-Butyl 3-(3-fluoro-4-methoxyphenyl)-3-(5-(4-oxopentyl)-1-((2-(trimethylsilyl)ethoxy)-methyl)-1H-pyrazol-3-yl)propanoate (115I)

To a stirred solution of tert-butyl 3-(3-fluoro-4-methoxyphenyl)-3-(5-(3-(2-methyl-1,3-dioxolan-2-yl)propyl)-1-((2-(trimethylsilyl)ethoxy)methyl)-1H-pyrazol-3-yl)propanoate 115H (0.430 g, 0.743 mmol) in THF (8 mL) was added HCl (0.991 mL, 1.486 mmol) and the reaction mixture was stirred at RT for 14 h. Reaction mixture was quenched with 10% sodium bicarbonate (50 mL) and it was extracted with ethyl acetate (2×50 mL). The combined organic layer was washed with brine (40 mL), dried over anhydrous sodium sulphate, concentrated under reduced pressure to get crude compound. The crude product was purified by combiflash chromatography (24 g Redisep® SiO₂ column, eluting with 60% EtOAc in pet ether) to afford the title compound 115I (0.300 g, 71%) as colourless liquid. LC-MS retention time=4.010 min; m/z=535.2 [M+H]⁺ Column-KINETIX XB-C18, (3×75) mm, 2.6 micron column; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CDCl₃) δ ppm 6.98-6.84 (m, 3H), 6.10 (s, 1H), 5.29 (d, J=11.0 Hz, 1H), 5.14 (d, J=11.0 Hz, 1H), 4.59 (t, J=7.7 Hz, 1H), 3.87 (s, 3H), 3.47-3.31 (m, 2H), 2.89 (dd, J=15.5, 8.2 Hz, 1H), 2.77 (dd, J=15.3, 7.7 Hz, 1H), 2.62 (t, J=7.6 Hz, 2H), 2.52-2.43 (m, 2H), 2.14 (s, 3H), 1.93 (m, 2H), 1.36 (s, 9H), 0.87-0.70 (m, 2H), −0.04 (s, 9H).

tert-Butyl 3-(5-(3-(1,8-naphthyridin-2-yl)propyl)-1-((2-(trimethylsilyl)ethoxy)-methyl)-1H-pyrazol-3-yl)-3-(3-fluoro-4-methoxyphenyl)propanoate (115J)

To a stirred solution of tert-butyl 3-(3-fluoro-4-methoxyphenyl)-3-(5-(4-oxopentyl)-1-((2-(trimethylsilyl)ethoxy)methyl)-1H-pyrazol-3-yl)propanoate 115I (0.300 g, 0.561 mmol) in ethanol (10 mL) under nitrogen atmosphere was added pyrrolidine (0.046 mL, 0.561 mmol) and the resulting mixture was stirred for 10 min at RT. To this solution was added 2-aminonicotinaldehyde (0.069 g, 0.561 mmol) and the reaction mixture was heated at 75° C. for 14 h. Reaction mixture was concentrated under reduced pressure to get crude compound. The crude product was purified by combiflash chromatography (24 g Redisep® SiO₂ column, eluting with 90% EtOAc in pet ether) to afford the title compound 115J (0.190 g, 50%) as a pale yellow liquid. LC-MS retention time=3.970 min; m/z=621.2 [M+H]⁺ Column—KINETIX XB-C18, (3×75) mm, 2.6 micron column; Flow rate: 1 mL/min; Mobile Phase A: 10 mM HCO₂NH₄ 98% Water/2% ACN; Mobile Phase B: 10 mM HCO₂NH₄ in 2% Water/98% ACN; 50% B to 100% B over 4.6 min, then hold 0.4 min. at 50% B with flow rate 1.5 mL/min; Detection: UV at 220 nm. $^1$H NMR (400 MHz, DMSO-d₆) δ ppm 9.03 (dd, J=4.5, 2.0 Hz, 1H), 8.42 (dd, J=8.0, 2.0 Hz, 1H), 8.37 (d, J=8.0 Hz, 1H), 7.58 (dd, J=8.0, 4.5 Hz, 1H), 7.52 (d, J=8.0 Hz, 1H), 7.15-7.01 (m, 3H), 6.28 (s, 1H), 5.32 (d, J=11.0 Hz, 1H), 5.17 (d, J=11.5 Hz, 1H), 4.51-4.42 (m, 1H), 3.78 (s, 3H), 3.35-3.45 (m, 2H), 3.03-2.95 (m, 2H), 2.90-2.84 (m, 2H), 2.63-2.56 (m, 2H), 2.13-2.06 (m, 2H), 1.25 (s, 9H), 0.71-0.59 (m, 2H), −0.13 (s, 9H).

tert-Butyl 3-(3-fluoro-4-methoxyphenyl)-3-(5-(3-(5,6,7,8-tetrahydro-1,8-naphthyridin-2-yl)propyl)-1-((2-(trimethylsilyl)ethoxy)methyl)-1H-pyrazol-3-yl)propanoate (115K)

To a stirred solution of tert-butyl 3-(5-(3-(1,8-naphthyridin-2-yl)propyl)-1-((2-(trimethylsilyl)ethoxy)methyl)-1H-pyrazol-3-yl)-3-(3-fluoro-4-methoxyphenyl)propanoate 115J (0.140 g, 0.226 mmol) in ethanol (5 mL) was added platinum(IV) oxide (14 mg, 0.062 mmol) and the reaction mixture was stirred at RT under $H_2$ bladder pressure for 14 h. Reaction mixture was filtered through a pad of Celite and the Celite was washed with MeOH (4×10 mL). The combined filtrate was concentrated under reduced pressure to afford the title compound 115K (0.130 g, 84%). LC-MS retention time=1.635 min; m/z=625.4 [M+H]$^+$ Column—KINETIX XB-C18, (3×75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 50% B to 100% B over 4.6 min, then hold 0.4 min. at 50% B with flow rate 1.5 mL/min; Detection: UV at 220 nm.

Example 115: First eluting enantiomer of 3-(3-Fluoro-4-methoxyphenyl)-3-(5-(3-(5,6,7,8-tetrahydro-1,8-naphthyridin-2-yl)propyl)-1H-pyrazol-3-yl)propanoic acid Example 116: First eluting enantiomer of 3-(3-Fluoro-4-methoxyphenyl)-3-(5-(3-(5,6,7,8-tetrahydro-1,8-naphthyridin-2-yl)propyl)-1H-pyrazol-3-yl)propanoic acid To a stirred solution of tert-butyl 3-(3-fluoro-4-methoxyphenyl)-3-(5-(3-(5,6,7,8-tetrahydro-1,8-naphthyridin-2-yl)propyl)-1-((2-(trimethylsilyl)ethoxy)methyl)-1H-pyrazol-3-yl)propanoate 115K (0.150 g, 0.240 mmol) in DCM (5 mL) was added TFA (1.5 mL, 19.47 mmol) under nitrogen atmosphere and stirred at RT for 14 h. The reaction mixture was concentrated under reduced pressure to get crude compound. The crude compound was purified by reverse phase HPLC (Sunfire C18 (150×21.2) mm, 5 micron; Mobile phase A: 10 mM Ammonium acetate in water, Mobile phase B: ACN; Flow: 18 mL/min, Time (min)/% B: 0/20, 2/20, 15/35, 16/100) to afford the racemate compound (50 mg). The individual enantiomers were separated by chiral HPLC (Column: Lux Cellulose C4 (250×21.2) mm; 5 micron; Mobile Phase: 0.4% DEA in ACN: MeOH (70:30); Flow: 20 mL/min). First eluting enantiomer Example 115 (Retention time 5.52 min., 25 mg, 23%) was isolated as a white solid. LC-MS retention time=1.29 min; m/z=439.2 [M+H]$^+$ Column—KINETIX XB-C18, (3×75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, $CD_3OD$) δ ppm 7.38 (d, J=7.0 Hz, 1H), 7.06-6.94 (m, 3H), 6.50 (d, J=1.5 Hz, 1H), 6.06 (s, 1H), 4.48 (t, J=8.0 Hz, 1H), 3.84 (s, 3H), 3.45 (J=5.6 Hz, 2H), 2.93 (dd, J=14.6, 9.0 Hz, 1H), 2.83 (dd, J=15.1, 7.0 Hz, 1H), 2.77 (t, J=6.0 Hz, 2H), 2.70-2.63 (m, 2H), 2.59 (t, J=7.5 Hz, 2H), 2.04-1.88 (m, 4H). Human αVβ6 IC50 (nM)=97. Second eluting enantiomer Example 116 (Retention time 7.77 min., 18 mg, 17%) was isolated as a white solid. LC-MS retention time=1.29 min; m/z=439.2 [M+H]$^+$ Column-KINETIX XB-C18, (3×75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, $CD_3OD$) δ ppm 7.38 (d, J=7.0 Hz, 1H), 7.06-6.94 (m, 3H), 6.50 (d, J=7.5 Hz, 1H), 6.06 (s, 1H), 4.48 (t, J=8.0 Hz, 1H), 3.84 (s, 3H), 3.45 (J=5.6 Hz, 2H), 2.93 (dd, J=14.6, 9.0 Hz, 1H), 2.83 (dd, J=15.1, 7.0 Hz, 1H), 2.77 (t, J=6.0 Hz, 2H), 2.70-2.63 (m, 2H), 2.59 (t, J=7.5 Hz, 2H), 2.04-1.88 (m, 4H). Human αVβ6 IC50 (nM)=47.

| Example | Structure | Prep-HPLC/SFC method, $^1$H NMR & LCMS | Method |
|---|---|---|---|
| 117 | 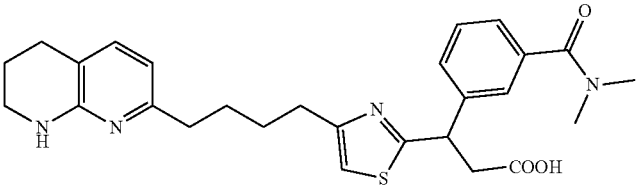 [SMILES: CN(C)C(=O)c1cccc(C(CC(=O)O)c2nc(CCCCc3ccc4c(n3)NCCC4)cs2)c1]<br>3-(3-(dimethylcarbamoyl)phenyl)-3-(4-(4-(5,6,7,8-tetrahydro-1,8-naphthyridin-2-yl)butyl)thiazol-2-yl)propanoic acid | Chiral Prep-HPLC: Retention time: 5.42 min. Column (Lux-cellulose C4 (250 × 21.2) mm 5 micron column: Mobile Phase: 0.1% DEA in MeOH: flow rate: 19.0 mL/min; Temperature: 35° C.; Detection: UV at 251 nm, $^1$H NMR (400 MHz, $CD_3OD$) δ ppm 7.50-7.52 (m, 1H), 7.41-7.45 (m, 3H), 7.31-7.33 (m, 1H), 6.96 (s, 1H), 6.46 (d, J = 7.20 Hz, 1H), 4.93 (dd, J = 11.60, 4.40 Hz, 1H), 3.45 (t, J = 5.60 Hz, 2H), 3.30 (m, 1H), 3.11 (s, 3H), 2.98 (s, 3H), 2.82-2.89 (m, 2H), 2.75-2.80 (m, 3H), 2.56-2.65 (m, 2H), 1.95-2.00 (m, 1H), 1.91-1.95 (m, 2H), 1.77-1.78 (m, 1H), 1.42-1.54 (m, 2H), LC-MS retention time = 1.22 min; m/z = 493.2 [M + H]$^+$ Column: KINETIX XB-C18, (3 × 75) mm, 2.6 micron column: Flow rate: 1 to 1.5 mL/min; Mobile Phase A: 10 mM $HCO_2NH_4$ in 98% Water/2% ACN; Mobile Phase B: 10 mM $HCO_2NH_4$ in 2% Water/98% ACN; 50% B to 100% B over 4.6 mm, then hold 0.4 mm, at | Example 13/14 |

| Example | Structure | Prep-HPLC/SFC method, ¹H NMR & LCMS | Method |
|---|---|---|---|
| | | 50% B with flow rate 1-1.5 mL/min; Detection: UV at 220 nm, Human αVβ6 IC50 (nM) = 76 | |
| 118 | 3-(3-(dimethylcarbamoyl)phenyl)-3-(4-(4-(5,6,7,8-tetrahydro-1,8-naphthyridin-2-yl)butyl)thiazol-2-yl)propanoic acid | Chiral Prep-HPLC: Retention time: 6.49 min, Column (Lux-cellulose C4 (250 × 21.2) mm 5 micron column; Mobile Phase: 0.1% DEA in MeOH; flow rate: 19.0 mL/min; Temperature: 35° C.; Detection: UV at 251 nm, ¹H NMR (400 MHz, CD₃OD) δ ppm 7.50-7.52 (m, 1H), 7.41-7.45 (m, 3H), 7.31-7.33 (m, 1H), 6.96 (s, 1H), 6.46 (d, J = 7.20 Hz, 1H), 4.93 (dd, J = 11.60, 4.40 Hz, 1H), 3.45 (t J = 5.60 Hz, 2H), 3.30 (m, 1H), 3.11 (s, 3H), 2.98 (s, 3H), 2.82-2.89 (m, 2H), 2.75-2.80 (m, 3H), 2.56-2.65 (m, 2H), 1.95-2.00 (m, 1H), 1.91-1.95 (m, 2H), 1.77-1.78 (m, 1H), 1.42-1.54 (m, 2H), LC-MS retention time = 1.22 min: m/z = 493.2 [M + H]⁺ Column: KINETIX XB-C18, (3 × 75) mm, 2.6 micron column; Flow rate: 1 to 1.5 mL/min; Mobile Phase A: 10 mM HCO₂NH₄ in 98% Water/2% ACN; Mobile Phase B: 10 mM HCO₂NH₄ in 2% Water/98% ACN; 50% B to 100% B over 4.6 mm, then hold 0.4 mm, at 50% B with flow rate 1-1.5 mL/min: Detection: UV at 220 nm, Human αVβ6 IC50 (nM) = 1.9 | Example 13/14 |
| 119 | 3-(quinoxalin-6-yl)-3-(4-(4-(5,6,7,8-tetrahydro-1,8-naphthyridin-2-yl)butyl)thiazol-2-yl)propanoic acid | Chiral Prep-HPLC: Retention time: 5.65 min, Column: Lux-cellulose C4 (250 × 21.2) mm 5 micron column; Mobile Phase: 0.1% DEA in MeOH; flow rate: 17 mL/min; Temperature: 35° C.; Detection: UV at 251 mm. ¹H NMR (400 MHz, CD₃OD) δ ppm 8.77 (d, J = 3.60 Hz, 2H), 7.96-7.99 (m, 2H), 7.82-7.85 (m, 1H), 7.28 (d, J = 7.20 Hz, 1H), 6.89 (s, 1H), 6.34 (d, J = 7.20 Hz, 1H), 5.04 (dd, J = 10.8, 5.2 Hz, 1H), 3.43-3.44 (m, 2H), 3.30 (m, 1H), 3.03 (dd, J = 14.8, 6.0 Hz, 1H), 2.73-2.83 (m, 2H), 2.73 (t, J = 6.4 Hz, 2H), 2.57-2.59 (m, 2H), 1.92-1.94 (m, 3H), 1.70-1.75 (m, 1H), 1.55-1.59 (m, 2H), LC-MS retention time = 1.42 min; m/z = 474.2 [M + H]⁺ Column: KINETIX XB-C18, (3 × 75) mm, 2.6 micron column; Flow rate: 1 to 1.5 mL/min; Mobile Phase A: 10 mM HCO₂NH₄ in 98% Water/2% ACN; Mobile Phase B: 10 mM HCO₂NH₄ in 2% Water/98% ACN; 50% B to 100% B over 4.6 mm, then hold 0.4 mm, at 50% B with flow rate 1-1.5 mL/min: Detection: UV at 220 nm, Human αVβ6 IC50 (nM) = 99 | Example 13/14 |

| Example | Structure | Prep-HPLC/SFC method, ¹H NMR & LCMS | Method |
|---|---|---|---|
| 120 | 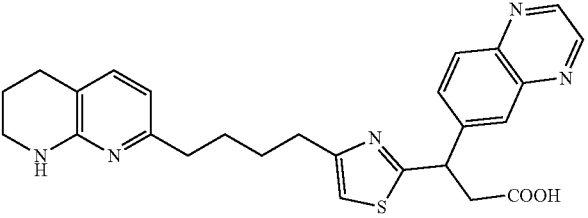 [SMILES: O=C(O)CC(c1ccc2nccnc2c1)c1nc(CCCCc2ccc3c(n2)NCCC3)cs1]<br>3-(quinoxalin-6-yl)-3-(4-(4-(5,6,7,8-tetrahydro-1,8-naphthyridin-2-yl)butyl)thiazol-2-yl)propanoic acid | Chiral Prep-HPLC: Retention time: 6.12 min, Column: Lux-cellulose C4 (250 × 21.2) mm 5 micron column; Mobile Phase: 0.1% DEA in MeOH; flow rate: 17 mL/min; Temperature: 35° C.; Detection: UV at 251 nm, ¹H NMR (400 MHz, CD$_3$OD) δ ppm 8.77 (d, J = 3.60 Hz, 2H), 7.96-7.99 (m, 2H), 7.82-7.85 (m, 1H), 7.28 (d, J = 7.20 Hz, 1H), 6.89 (s, 1H), 6.34 (d, J = 7.20 Hz, 1H), 5.04 (dd, J = 10.8, 5.2 Hz, 1H), 3.43-3.44 (m, 2H), 3.30 (m, 1H), 3.03 (dd, J = 14.8, 6.0 Hz, 1H), 2.73-2.83 (m, 2H), 2.73 (t, J = 6.4 Hz, 2H), 2.57-2.59 (m, 2H), 1.92-1.94 (m, 3H), 1.70-1.75 (m, 1H), 1.55-1.59 (m, 2H), LC-MS retention time = 1.42 min; m/z = 474.2 [M + H]$^+$ Column: KINETIX XB-C18, (3 × 75) mm, 2.6 micron column; Flow rate: 1 to 1.5 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 mm, then hold 0.4 mm, at 50% B with flow rate 1-1.5 mL/min; Detection: UV at 220 nm Human αVβ6 IC50 (nM) = 14 | Example 13/14 |
| 121 | 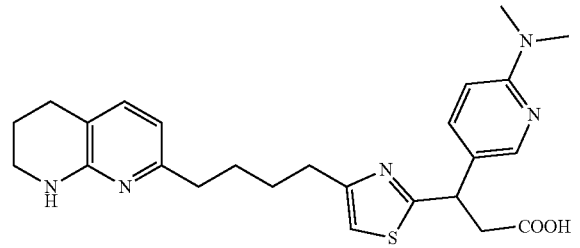 [SMILES: CN(C)c1ccc(C(CC(=O)O)c2nc(CCCCc3ccc4c(n3)NCCC4)cs2)cn1]<br>3-(6-(dimethylamino)pyridin-3-yl)-3-(4-(4-(5,6,7,8-tetrahydro-1,8-naphthyridin-2-yl)butyl)thiazol-2-yl)propanoic acid | Chiral Prep-HPLC: Retention time: 6.61 min, Column: Lux-cellulose C4 (250 × 21.2) mm 5 micron column: Mobile Phase: 0.1% DEA in MeOH: flow rate: 17 mL/min; Temperature: 35° C.; Detection: UV at 251 nm. ¹H NMR (400 MHz, CD$_3$OD) δ ppm 8.05 (d, J = 2.40 Hz, 1H), 7.57 (dd, J = 2.80, 9.80 Hz, 1H), 7.40 (d, J = 7.20 Hz, 1H), 6.94 (s, 1H), 6.66 (d, J = 8.80 Hz, 1H), 6.45 (d, J = 7.20 Hz, 1H), 4.78 (dd, J = 11.2, 5.2 Hz, 1H), 3.44 (t, J = 5.6 Hz, 2H), 3.22 (dd, J = 14.8, 11.2 Hz, 1H), 3.07 (s, 6H), 2.75-2.80 (m, 5H), 2.56-2.64 (m, 2H), 1.90-1.96 (m, 3H), 1.71-1.78 (m, 1H), 1.50-1.55 (m, 2H), LC-MS retention time = 1.45 min; m/z = 466.2 [M + H]$^+$ Column: KINETIX XB-C18, (3 × 75) mm, 2.6 micron column; Flow rate: 1 to 1.5 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 mm, then hold 0.4 mm, at 20% B with flow rate 1-1.5 mL/min; Detection: UV at 220 nm, Human αVβ6 IC50 (nM) = 170 | Example 13/14 |

| Example | Structure | Prep-HPLC/SFC method, $^1$H NMR & LCMS | Method |
|---|---|---|---|
| 122 | 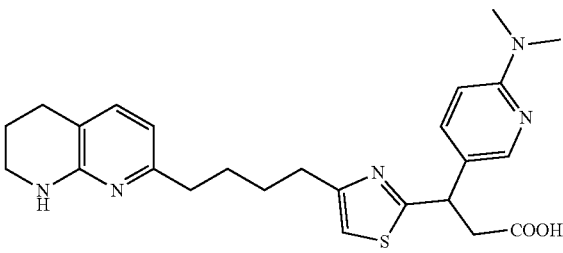 [SMILES: CN(C)c1ccc(C(CC(=O)O)c2nc(CCCCc3ccc4c(n3)NCCC4)cs2)cn1]<br>3-(6-(dimethylamino)pyridin-3-yl)-3-(4-(4-(5,6,7,8-tetrahydro-1,8-naphthyridin-2-yl)butyl)thiazol-2-yl)propanoic acid | Chiral Prep-HPLC: Retention time: 7.42 min, Column: Lux-cellulose C4 (250 × 21.2) mm 5 micron column; Mobile Phase: 0.1% DEA in MeOH; flow rate: 17 mL/min; Temperature: 35° C.; Detection: UV at 251 nm, $^1$H NMR (400 MHz, CD$_3$OD) δ ppm 8.05 (d, J = 2.40 Hz, 1H), 7.57 (dd, J = 2.80, 9.80 Hz, 1H), 7.40 (d, J = 7.20 Hz, 1H), 6.94 (s, 1H), 6.66 (d, J = 8.80 Hz, 1H), 6.45 (d, J = 7.20 Hz, 1H), 4.78 (dd, J = 11.2, 5.2 Hz, 1H), 3.44 (t, J = 5.6 Hz, 2H), 3.22 (dd, J = 14.8, 11.2 Hz, 1H), 3.07 (s, 6H), 2.75-2.80 (m 5H), 2.56-2.64 (m, 2H), 1.90-1.96 (m, 3H), 1.71-1.78 (m, 1H), 1.50-1.55 (m, 2H), LC-MS retention time = 1.45 min; m/z = 466.2 [M + H]$^+$ Column: KINETIX XB-C18, (3 × 75) mm, 2.6 micron column: Flow rate: 1 to 1.5 mL/min; Mobile Phase A: 10 mM HCO$_2$NH$_4$ in 98% Water/2% ACN: Mobile Phase B: 10 mM HCO$_2$NH$_4$ in 2% Water/98% ACN: 20% B to 100% B over 4.6 mm, then hold 0.4 mm, at 20% B with flow rate 1-1.5 mL/min: Detection: UV at 220 nm, Human αVβ6 IC50 (nM) = 3.5 | Example 13/14 |
| 123 | 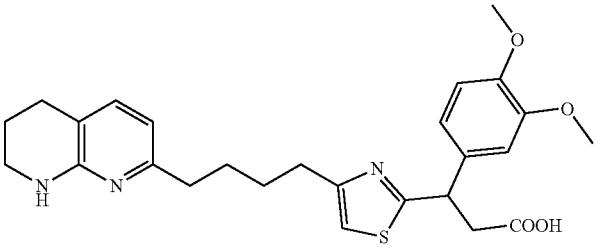 [SMILES: COc1ccc(C(CC(=O)O)c2nc(CCCCc3ccc4c(n3)NCCC4)cs2)cc1OC]<br>3-(3,4-dimethoxyphenyl)-3-(4-(4-(5,6,7,8-tetrahydro-1,8-naphthyridin-2-yl)butyl)thiazol-2-yl)propanoic acid | Chiral Prep-HPLC: Retention time: 5.90 min, Column: Lux-cellulose C4 (250 × 21.2) mm 5 micron column; Mobile Phase: 0.1% DEA in MeOH; flow rate: 17 mL/min; Temperature: 35° C.; Detection: UV at 251 nm, $^1$H NMR (400 MHz, CD$_3$OD) δ ppm 7.41 (d, J = 7.20 Hz, 1H), 7.00 (s, 1H), 6.92-6.93 (m, 3H), 6.45 (d, J = 7.20 Hz, 1H), 4.76-4.74 (m, 1H), 3.83 (s, 3H), 3.82 (s, 3H), 3.45 (t, J = 5.60 Hz, 2H), 3.22 (dd, J = 14.8, 11.2 Hz, 1H), 2.75-2.80 (m, 5H), 2.56-2.60 (m, 2H), 1.90-1.95 (m, 3H), 1.77-1.77 (m, 1H), 1.49-1.54 (m, 2H), LC-MS retention time = 1.54 min; m/z = 482.2 [M + H]$^+$ Column: KINETIX XB-C18, (3 × 75) mm, 2.6 micron column; Flow rate: 1 to 1.5 mL/min; Mobile Phase A: 10 mM HCO$_2$NH$_4$ in 98% Water/2% ACN; Mobile Phase B: 10 mM HCO$_2$NH$_4$ in 2% Water/98% ACN: 20% B to 100% B over 4.6 mm, then hold 0.4 mm, at 20% B with flow rate 1-1.5 mL/min; Detection: UV at 220 nm, Human αVβ6 IC50 (nM) = 180 | Example 13/14 |

| Example | Structure | Prep-HPLC/SFC method, $^1$H NMR & LCMS | Method |
|---|---|---|---|
| 124 | 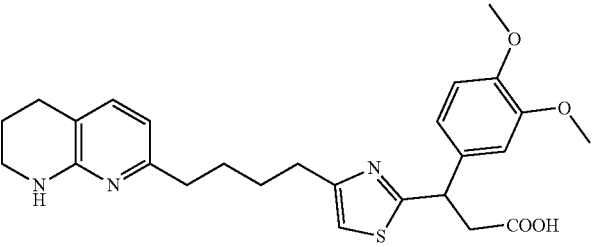 [SMILES: COc1ccc(C(CC(=O)O)c2nc(CCCCc3ccc4c(n3)NCCC4)cs2)cc1OC]<br>3-(3,4-dimethoxyphenyl)-3-(4-(4-(5,6,7,8-tetrahydro-1,8-naphthyridin-2-yl)butyl)thiazol-2-yl)propanoic acid | Chiral Prep-HPLC: Retention time: 7.03 min, Column: Lux-cellulose C4 (250 × 21.2) mm 5 micron column; Mobile Phase: 0.1% DEA in MeOH; flow rate: 17 mL/min; Temperature: 35° C.; Detection: UV at 251 nm, $^1$H NMR (400 MHz, CD$_3$OD) δ ppm 7.41 (d, J = 7.20 Hz, 1H), 7.00 (s, 1H), 6.92-6.93 (m, 3H), 6.45 (d, J = 7.20 Hz, 1H), 4.76-4.74 (m, 1H), 3.83 (s, 3H), 3.82 (s, 3H), 3.45 (t, J = 5.60 Hz, 2H), 3.22 (dd, J = 14.8, 11.2 Hz, 1H), 2.75-2.80 (m, 5H), 2.56-2.60 (m, 2H), 1.90-1.95 (m, 3H), 1.77-1.77 (m, 1H), 1.49-1.54 (m, 2H), LC-MS retention time = 1.54 min; m/z = 482.2 [M + H]$^+$ Column: KINETIX XB-C18, (3 × 75) mm, 2.6 micron column: Flow rate: 1 to 1.5 mL/min; Mobile Phase A: 10 mM HCO$_2$NH$_4$ in 98% Water/2% ACN: Mobile Phase B: 10 mM HCO$_2$NH$_4$ in 2% Water/98% ACN: 20% B to 100% B over 4.6 min, then hold 0.4 mm, at 20% B with flow rate 1-1.5 mL/min: Detection: UV at 220 nm, Human αVβ6 IC50 (nM) = 2.5 | Example 13/14 |
| 125 | 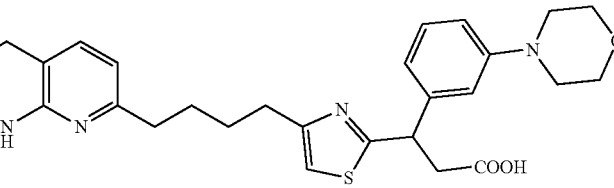<br>3-(3-morpholinophenyl)-3-(4-(4-(5,6,7,8-tetrahydro-1,8-naphthyridin-2-yl)butyl)thiazol-2-yl)propanoic acid | Chiral Prep-HPLC: Retention time: 6.83 min, Column: Lux-cellulose C4 (250 × 21.2) mm 5 micron column: Mobile Phase: 0.1% DEA in MeOH: flow rate: 19 mL/min; Temperature: 35° C.; Detection: UV at 251 nm. $^1$H NMR (400 MHz, CD$_3$OD) δ ppm 7.28 (d, J = 7.60 Hz, 1H), 7.08 (t, J = 8.0 Hz, 1H), 6.88 (d, J = 2.00 Hz, 1H), 6.88 (s, 1H), 6.73-6.78 (m, 2H), 6.33 (d, J = 7.20 Hz, 1H), 4.71-4.73 (m, 1H), 3.72 (t, J = 4.80 Hz, 4H), 3.33 (t, J = 5.60 Hz, 2H), 3.14 (dd, J = 14.6, 11.0 Hz, 1H), 3.02 (t, J = 4.80 Hz, 4H), 2.63-2.74 (m, 5H), 2.43-2.49 (m, 2H), 1.81-1.85 (m, 3H), 1.62-1.67 (m, 1H), 1.38-1.42 (m, 2H), LC-MS retention time = 1.68 min; m/z = 507.2 [M + H]$^+$ Column: KINETIX XB-C18, (3 × 75) mm, 2.6 micron column; Flow rate: 1 to 1.5 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 mm, then hold 0.4 mm, at 20% B with flow rate 1-1.5 mL/min; Detection: UV at 220 nm, Human αVβ6 IC50 (nM) = 180 | Example 13/14 |

| Example | Structure | Prep-HPLC/SFC method, ¹H NMR & LCMS | Method |
|---|---|---|---|
| 126 | 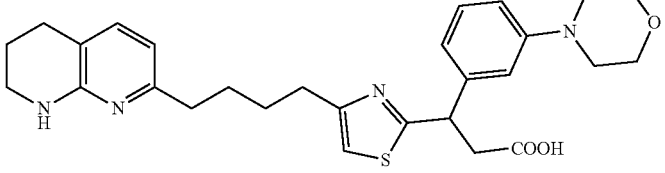<br>3-(3-morpholinophenyl)-3-(4-(4-(5,6,7,8-tetrahydro-1,8-naphthyridin-2-yl)butyl)thiazol-2-yl)propanoic acid | Chiral Prep-HPLC: Retention time: 8.53 min, Column: Lux-cellulose C4 (250 × 21.2) mm 5 micron column; Mobile Phase: 0.1% DEA in MeOH; flow rate: 19 mL/min; Temperature: 35° C.; Detection: UV at 251 nm, ¹H NMR (400 MHz, CD$_3$OD) δ ppm 7.28 (d, J = 7.60 Hz, 1H), 7.08 (t, J = 8.0 Hz, 1H), 6.88 (d, J = 2.00 Hz, 1H), 6.88 (s, 1H), 6.73-6.78 (m, 2H), 6.33 (d, J = 7.20 Hz, 1H), 4.71-4.73 (m, 1H), 3.72 (t, J = 4.80 Hz, 4H), 3.33 (t, J = 5.60 Hz, 2H), 3.14 (dd, J = 14.6, 11.0 Hz, 1H), 3.02 (t, J = 4.80 Hz, 4H), 2.63-2.74 (m, 5H), 2.43-2.49 (m, 2H), 1.81-1.85 (m, 3H), 1.62-1.67 (m, 1H), 1.38-1.42 (m, 2H), LC-MS retention time = 1.68 min; m/z = 507.2 [M + H]⁺ Column: KINETIX XB-C18, (3 × 75) mm, 2.6 micron column: Flow rate: 1 to 1.5 mL/min: Mobile Phase A: 10 mM HCO$_2$NH$_4$ in 98% Water/2% ACN: Mobile Phase B: 10 mM HCO$_2$NH$_4$ in 2% Water/98% ACN: 20% B to 100% B over 4.6 mm, then hold 0.4 mm, at 20% B with flow rate 1-1.5 mL/min: Detection: UV at 220 nm, Human αVβ6 IC50 (nM) = 6.0 | Example 13/14 |
| 127 | 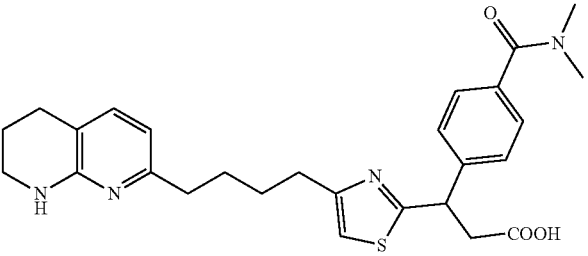 [SMILES: CN(C)C(=O)c1ccc(C(CC(=O)O)c2nc(CCCCc3ccc4c(n3)NCCC4)cs2)cc1]<br>3-(4-(dimethylcarbamoyl)phenyl)-3-(4-(4-(5,6,7,8-tetrahydro-1,8-naphthyridin-2-yl)butyl)thiazol-2-yl)propanoic acid | Chiral Prep-HPLC: Retention time: 6.2 min, Column: Lux-cellulose C4 (250 × 21.2) mm 5 micron column; Mobile Phase: 0.1% DEA in MeOH; flow rate: 19 mL/min; Temperature: 35° C.; Detection: UV at 251 nm, ¹H NMR (400 MHz, CD$_3$OD) δ ppm 7.49 (d, J = 8.40 Hz, 2H), 7.40-7.43 (m, 3H), 6.96 (s, 1H), 6.46 (d, J = 7.20 Hz, 1H), 4.92 (dd, J = 11.60, 4.40 Hz, 1H), 3.45 (t, J = 5.60 Hz, 2H), 3.21-3.23 (m, 1H), 3.11 (s, 3H), 3.01 (s, 3H), 2.88 (dd, J = 14.6, 4.0 Hz, 1H), 2.75-2.80 (m, 4H), 2.58-2.63 (m, 2H), 1.91-1.94 (m, 3H), 1.75-1.85 (m, 1H), 1.49-1.56 (m, 2H), LC-MS retention time = 1.35 min; m/z = 493.2 [M + H]⁺ Column: KINETIX XB-C18, (3 × 75) mm, 2.6 micron column: Flow rate: 1 to 1.5 mL/min: Mobile Phase A: 10 mM HCO$_2$NH$_4$ in 98% Water/2% ACN: Mobile Phase B: 10 mM HCO$_2$NH$_4$ in 2% Water/98% ACN: 20% B to 100% B over 4.6 mm, then hold 0.4 mm, at 20% B with flow rate 1-1.5 mL/min: Detection: UV at 220 nm, Human αVβ6 IC50 (nM) = 60 | Example 13/14 |

| Example | Structure | Prep-HPLC/SFC method, ¹H NMR & LCMS | Method |
|---|---|---|---|
| 128 | 3-(4-(dimethylcarbamoyl)phenyl)-3-(4-(4-(5,6,7,8-tetrahydro-1,8-naphthyridin-2-yl)butyl)thiazol-2-yl)propanoic acid | Chiral Prep-HPLC: Retention time: 7.14 min, Column: Lux-cellulose C4 (250 × 21.2) mm 5 micron column; Mobile Phase: 0.1% DEA in MeOH; flow rate: 19 mL/min; Temperature: 35° C.; Detection: UV at 251 nm, ¹H NMR (400 MHz, CD$_3$OD) δ ppm 7.49 (d, J = 8.40 Hz, 2H), 7.40-7.43 (m, 3H), 6.96 (s, 1H), 6.46 (d, J = 7.20 Hz, 1H), 4.92 (dd, J = 11.60, 4.40 Hz, 1H), 3.45 (t, J = 5.60 Hz, 2H), 3.21-3.23 (m, 1H), 3.11 (s, 3H), 3.01 (s, 3H), 2.88 (dd, J = 14.6, 4.0 Hz, 1H), 2.75-2.80 (m, 4H), 2.58-2.63 (m, 2H), 1.91-1.94 (m, 3H), 1.75-1.85 (m, 1H), 1.49-1.56 (m, 2H), LC-MS retention time = 1.35 min; m/z = 493.2 [M + H]$^+$ Column: KINETIX XB-C18, (3 × 75) mm, 2.6 micron column: Flow rate: 1 to 1.5 mL/min: Mobile Phase A: 10 mM HCO$_2$NH$_4$ in 98% Water/2% ACN: Mobile Phase B: 10 mM HCO$_2$NH$_4$ in 2% Water/98% ACN: 20% B to 100% B over 4.6 mm, then hold 0.4 mm, at 20% B with flow rate 1-1.5 mL/min: Detection: UV at 220 nm, Human αVβ6 IC50 (nM) = 4.3 | Example 13/14 |
| 129 | 3-(2-ethoxypyrimidin-5-yl)-3-(4-(4-(5,6,7,8-tetrahydro-1,8-naphthyridin-2-yl)butyl)thiazol-2-yl)propanoic acid | Chiral Prep-HPLC: Retention time: 5.42 min, Column: Lux-cellulose C4 (250 × 21.2) mm 5 micron column; Mobile Phase: 0.1% DEA in MeOH; flow rate: 19 mL/min; Temperature: 35° C.; Detection: UV at 251 nm, ¹H NMR (400 MHz, CD$_3$OD) δ ppm 8.59 (s, 2H), 7.38 (d, J = 7.20 Hz, 1H), 6.93 (s, 1H), 6.45 (d, J = 7.20 Hz, 1H), 4.79-4.82 (m, 1H), 4.44 (q, J = 6.80 Hz, 2H), 3.44 (t, J = 5.60 Hz, 2H), 3.21 (dd, J = 14.6, 11.0 Hz, 1H), 2.88 (dd, J = 14.4, 4.0 Hz, 1H), 2.75-2.80 (m, 4H), 2.59-2.60 (m, 2H), 1.90-1.95 (m, 3H), 1.70-1.79 (m, 1H), 1.52-1.59 (m, 2H), 1.41 (t, J = 7.20 Hz, 3H), LC-MS retention time = 1.54 min; m/z = 468.2 [M + H]$^+$ Column: KINETIX XB-C18, (3 × 75) mm, 2.6 micron column; Flow rate: 1 to 1.5 mL/min; Mobile Phase A: 10 mM HCO$_2$NH$_4$ in 98% Water/2% ACN: Mobile Phase B: 10 mM HCO$_2$NH$_4$ in 2% Water/98% ACN; 20% B to 100% B over 4.6 min then hold 0.4 mm, at 20% B with flow rate 1-1.5 mL/min: Detection: UV at 220 nm, Human αVβ6 IC50 (nM) = 28 | Example 13/14 |

| Example | Structure | Prep-HPLC/SFC method, ¹H NMR & LCMS | Method |
|---|---|---|---|
| 130 | 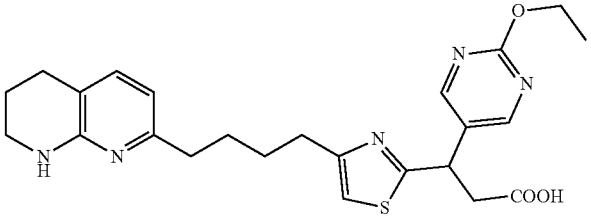 [SMILES: CCOc1ncc(C(CC(=O)O)c2nc(CCCCc3ccc4c(n3)NCCC4)cs2)cn1]<br>3-(2-ethoxypyrimidin-5-yl)-3-(4-(4-(5,6,7,8-tetrahydro-1,8-naphthyridin-2-yl)butyl)thiazol-2-yl)propanoic acid | Chiral Prep-HPLC: Retention time: 6.2 min, Column: Lux-cellulose C4 (250 × 21.2) mm 5 micron column: Mobile Phase: 0.1% DEA in MeOH: flow rate: 19 mL/min; Temperature: 35° C.; Detection: UV at 251 nm, ¹H NMR (400 MHz, CD$_3$OD) δ ppm 8.59 (s, 2H), 7.38 (d, J = 7.20 Hz, 1H), 6.93 (s, 1H), 6.45 (d, J = 7.20 Hz, 1H), 4.79-4.82 (m, 1H), 4.44 (q, J = 6.80 Hz, 2H), 3.44 (t, J = 5.60 Hz, 2H), 3.21 (dd, J = 14.6, 11.0 Hz, 1H), 2.88 (dd, J = 14.4, 4.0 Hz, 1H), 2.75-2.80 (m, 4H), 2.59-2.60 (m, 2H), 1.90-1.95 (m, 3H), 1.70-1.79 (m, 1H), 1.52-1.59 (m, 2H), 1.41 (t, J = 7.20 Hz, 3H), LC-MS retention time = 1.54 min; m/z = 468.2 [M + H]$^+$ Column: KINETIX XB-C18, (3 × 75) mm, 2.6 micron column; Flow rate: 1 to 1.5 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 mm, at 20% B with flow rate 1-1.5 mL/min; Detection: UV at 220 nm, Human αVβ6 IC50 (nM) = 2.9 | Example 13/14 |
| 131 | 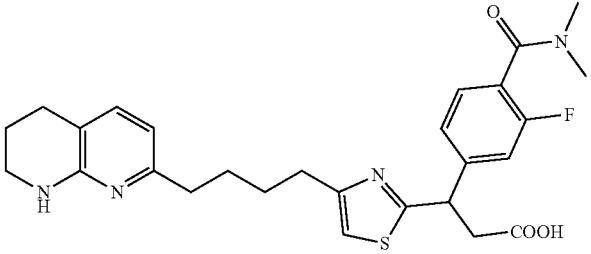<br>3-(4-(dimethylcarbamoyl)-3-fluorophenyl)-3-(4-(4-(5,6,7,8-tetrahydro-1,8-naphthyridin-2-yl)butyl)thiazol-2-yl)propanoic acid | Prep. Chiral SFC: Retention time: 3.5 min, Column Chiralpak AD-H (250 × 21) mm, 5 micron: Mobile phase: 55% of CO$_2$ and 45% of (0.2% NH$_4$OH in MeOH and ACN (1:1)); Total Flow: 70 g/min: Back Pressure: 100 bar: Temperature: 30° C.: Detection: UV at 240 nm, ¹H NMR (400 MHz, CD$_3$OD) δ ppm 7.35 (d, J = 7.20 Hz, 1H), 7.24-7.28 (m, 1H), 7.18-7.20 (m, 1H), 7.12 (d, J = 10.40 Hz, 1H), 6.95 (s, 1H), 6.44 (d, J = 7.60 Hz, 1H), 4.81-4.82 (m, 1H), 3.34 (t, J = 5.60 Hz, 2H), 3.10 (dd, J = 14.6, 11.0 Hz, 1H), 3.07 (s, 3H), 2.84 (s, 3H), 2.66-2.77 (m, 5H), 2.41-2.50 (m, 2H), 2.09-2.10 (m, 1H), 1.80-1.96 (m, 3H) 1.70-1.79 (m 1H), 1.52-1.59 (m, 2H), LC-MS retention time = 1.40 min; m/z = 497.2 [M + H]$^+$ Column: KINETIX XB-C18, (3× 75) mm, 2.6 micron column: Flow rate: 1 to 1.5 mL/min; Mobile Phase A: 10 mM HCO$_2$NH$_4$ in 98% Water/2% ACN: Mobile Phase B: 10 mM HCO$_2$NH$_4$ in 2% Water/98% ACN; 20% B to 100% B over 4.6 mm, then hold 0.4 mm, at 20% B with flow rate 1-1.5 mL/min; Detection: UV at 220 nm, Human αVβ6 IC50 (nM) = 2.3 | Example 13/14 |

| Example | Structure | Prep-HPLC/SFC method, $^1$H NMR & LCMS | Method |
|---|---|---|---|
| 132 | 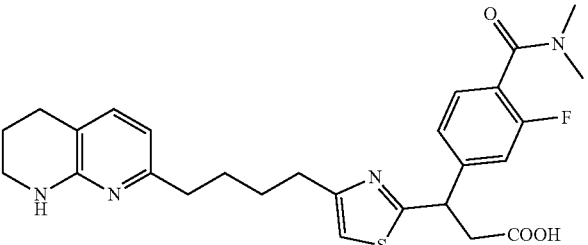<br>3-(4-(dimethylcarbamoyl)-3-fluorophenyl)-3-(4-(4-(5,6,7,8-tetrahydro-1,8-naphthyridin-2-yl)butyl)thiazol-2-yl)propanoic acid | Prep. Chiral SFC: Retention time: 7.0 min, Column: Chiralpak AD-H (250 × 21) mm, 5 micron: Mobile phase: 55% of $CO_2$ and 45% of (0.2% $NH_4OH$ in MeOH and ACN (1:1)); Total Flow: 70 g/min: Back Pressure: 100 bar: Temperature: 30° C.: Detection: UV at 240 nm, $^1$H NMR (400 MHz, $CD_3OD$) δ ppm 7.35 (d, J = 7.20 Hz, 1H), 7.24-7.28 (m, 1H), 7.18-7.20 (m, 1H), 7.12 (d, J = 10.40 Hz, 1H), 6.95 (s, 1H), 6.44 (d, J = 7.60 Hz, 1H), 4.81-4.82 (m, 1H), 3.34 (t, J = 5.60 Hz, 2H), 3.10 (dd, J = 14.6 11.0 Hz, 1H), 3.07 (s, 3H), 2.84 (s, 3H), 2.66-2.77 (m, 5H), 2.41-2.50 (m, 2H), 2.09-2.10 (m, 1H), 1.80-1.96 (m, 3H), 1.70-1.79 (m, 1H), 1.52-1.59 (m, 2H), LC-MS retention time = 1.40 min; m/z = 497.2 [M + H]$^+$ Column: KINETIX XB-C18, (3* 75) mm, 2.6 micron column: Flow rate: 1 to 1.5 mL/min; Mobile Phase A: 10 mM $HCO_2NH_4$ in 98% Water/2% ACN: Mobile Phase B: 10 mM $HCO_2NH_4$ in 2% Water/98% ACN: 20% B to 100% B over 4.6 mm, then hold 0.4 mm, at 20% B with flow rate 1-1.5 mL/min: Detection: UV at 220 nm, Human αVβ6 IC50 (nM) = 81 | Example 13/14 |
| 133 | 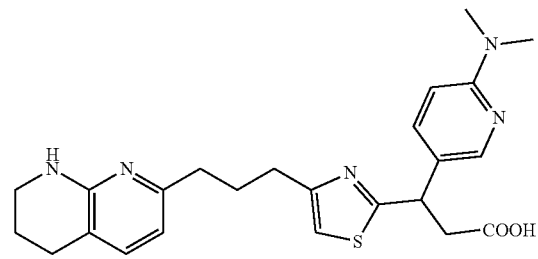 [SMILES: CN(C)c1ccc(C(CC(=O)O)c2nc(CCCc3ccc4c(n3)NCCC4)cs2)cn1]<br>3-(6-(dimethylamino)pyridin-3-yl)-3-(4-(3-(5,6,7,8-tetrahydro-1,8-naphthyridin-2-yl)propyl)thiazol-2-yl)propanoic acid | Chiral Prep-HPLC: Retention time: 6.0 min, Column: Lux-cellulose C4 (250 × 21.2) mm 5 micron column; Mobile Phase: 0.1% DEA in MeOH; flow rate: 19 mL/min; Temperature: 35° C.; Detection: UV at 251 nm, $^1$H NMR (400 MHz, $CD_3OD$) δ ppm 8.05 (d, J = 2.40 Hz 1H), 7.55 (dd, J = 2.40, 9.00 Hz, 1H), 7.38 (d, J = 7.20. Hz, 1H), 7.00 (s, 1H), 6.66 (d, J = 8.80 Hz, 1H), 6.51 (d, J = 7.60 Hz, 1H), 4.73 (dd, J = 11.60, 4.40 Hz, 1H), 3.45 (t, J = 5.60 Hz, 2H), 3.14 (dd, J = 14.6, 11.0 Hz, 1H), 3.07 (s, 6H), 2.80-2.83 (m, 5H), 2.57-2.60 (m, 2H), 2.03-2.10 (m, 2H), 1.90-1.96 (m, 2H), LC-MS retention time = 1.29 min; m/z = 452.2 [M + H]$^+$ Column: KINETIX XB-C18, (3 × 75) mm, 2.6 micron column: Flow rate: 1 to 1.5 mL/min; Mobile Phase A: 10 mM $HCO_2NH_4$ in 98% Water/2% ACN: Mobile Phase B: 10 mM $HCO_2NH_4$ in 2% Water/98% ACN; 20% B to 100% B over 4.6 mm, then hold 0.4 mm, at 20% B with flow rate 1-1.5 mL/min: Detection: UV at 220 nm, Human αVβ6 IC50 (nM) = 86 | Example 15/16 |

| Example | Structure | Prep-HPLC/SFC method, ¹H NMR & LCMS | Method |
|---|---|---|---|
| 134 | 3-(6-(dimethylamino)pyridin-3-yl)-3-(4-(3-(5,6,7,8-tetrahydro-1,8-naphthyridin-2-yl)propyl)thiazol-2-yl)propanoic acid | Chiral Prep-HPLC: Retention time: 6.7 min, Column: Lux-cellulose C4 (250 × 21.2) mm 5 micron column; Mobile Phase: 0.1% DEA in MeOH; flow rate: 19 mL/min; Temperature: 35° C.; Detection: UV at 251 nm, ¹H NMR (400 MHz, CD$_3$OD) δ ppm 8.05 (d, J = 2.40 Hz 1H), 7.55 (dd, J = 2.40, 9.00 Hz, 1H), 7.38 (d, J = 7.20. Hz, 1H), 7.00 (s, 1H), 6.66 (d, J = 8.80 Hz, 1H), 6.51 (d, J = 7.60 Hz, 1H), 4.73 (dd, J = 11.60, 4.40 Hz, 1H), 3.45 (t, J = 5.60 Hz, 2H), 3.14 (dd, J = 14.6, 11.0 Hz, 1H), 3.07 (s, 6H), 2.80-2.83 (m, 5H), 2.57-2.60 (m, 2H), 2.03-2.10 (m, 2H), 1.90-1.96(m, 2H), LC-MS retention time = 1.29 min; m/z = 452.2 [M + H]⁺ Column: KINETIX XB-C18, (3 × 75) mm, 2.6 micron column: Flow rate: 1 to 1.5 mL/min; Mobile Phase A: 10 mM HCO$_2$NH$_4$ in 98% Water/2% ACN: Mobile Phase B: 10 mM HCO$_2$NH$_4$ in 2% Water/98% ACN; 20% B to 100% B over 4.6 mm, then hold 0.4 mm, at 20% B with flow rate 1-1.5 mL/min: Detection: UV at 220 nm, Human αVβ6 IC50 (nM) = 1.8 | Example 15/16 |
| 135 | 3-(4-(dimethylcarbamoyl)-3-fluorophenyl)-3-(4-(3-(5,6,7,8-tetrahydro-1,8-naphthyridin-2-yl)propyl)thiazol-2-yl)propanoic acid | Prep. Chiral SFC: Retention time: 3.5 min, Column Chiralpak AD-H (250 × 21) mm, 5 micron; Mobile phase: 55% of CO$_2$ and 45% of (0.2% NH$_4$OH in MeOH and ACN (1:1): Total Flow: 70 g/min: Back Pressure: 100 bars: Temperature: 30° C.; Detection: UV at 240 nm, ¹H NMR (400 MHz, CD$_3$OD) δ ppm 7.35 (d, J = 7.20 Hz, 1H), 7.24-7.28 (m, 1H), 7.18-7.20 (m, 1H), 7.12 (d, J = 10.40 Hz, 1H), 6.95 (s, 1H), 6.44 (d, J = 7.60 Hz, 1H), 4.81-4.82 (m, 1H), 3.34 (t, J = 5.60 Hz, 2H), 3.10 (dd, J = 14.6, 11.0 Hz, 1H), 3.07 (s, 3H), 2.84 (s, 3H), 2.66-2.77 (m, 5H), 2.41-2.50 (m, 2H), 2.09-2.10 (m, 1H), 1.90-2.00 (m, 1H), 1.75-1.85 (m, 2H), LC-MS retention time = 1.40 min; m/z = 497.2 [M + H]⁺ Column: KINETIX XB-C18, (3 × 75) mm, 2.6 micron column; Flow rate: 1 to 1.5 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 mm, then hold 0.4 mm, at 20% B with flow rate 1-1.5 mL/min; Detection: UV at 220 nm, Human αVβ6 IC50 (nM) = 4.9 | Example 15/16 |

| Example | Structure | Prep-HPLC/SFC method, $^1$H NMR & LCMS | Method |
|---|---|---|---|
| 136 | 3-(4-(dimethylcarbamoyl)-3-fluorophenyl)-3-(4-(3-(5,6,7,8-tetrahydro-1,8-naphthyridin-2-yl)propyl)thiazol-2-yl)propanoic acid | Prep. Chiral SFC: Retention time: 7.0 min, Column Chiralpak AD-H (250 × 21) mm, 5 micron; Mobile phase: 55% of $CO_2$ and 45% of (0.2% $NH_4OH$ in MeOH and ACN (1:1)): Total Flow: 70 g/min: Back Pressure: 100 bars: Temperature: 30° C.; Detection: UV at 240 nm, $^1$H NMR (400 MHz, $CD_3OD$) δ ppm 7.35 (d, J = 7.20 Hz, 1H), 7.24-7.28 (m, 1H), 7.18-7.20 (m, 1H), 7.12 (d, J = 10.40 Hz, 1H), 6.95 (s, 1H), 6.44 (d, J = 7.60 Hz, 1H), 4.81-4.82 (m, 1H), 3.34 (t, J = 5.60 Hz, 2H), 3.10 (dd, J = 14.6, 11.0 Hz, 1H), 3.07 (s, 3H), 2.84 (s, 3H), 2.66-2.77 (m, 5H), 2.41-2.50 (m, 2H), 2.09-2.10 (m, 1H), 1.90-2.00 (m, 1H), 1.75-1.85 (m, 2H), LC-MS retention time = 1.40 min; m/z = 497.2 [M + H]$^+$ Column: KINETIX XB-C18, (3 × 75) mm, 2.6 micron column; Flow rate: 1 to 1.5 mL/min; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 mm, then hold 0.4 mm, at 20% B with flow rate 1-1.5 mL/min; Detection: UV at 220 nm, Human αVβ6 IC50 (nM) = 12 | Example 15/16 |

Example 137 and Example 138

Example 137: first eluting enantiomer of 3-(4-(dimethylcarbamoyl)phenyl)-3-(4-(3-(5,6,7,8-tetrahydro-1,8-naphthyridin-2-yl)propyl)thiazol-2-yl)propanoic acid Example 138: second eluting enantiomer of 3-(4-(dimethylcarbamoyl)phenyl)-3-(4-(3-(5,6,7,8-tetrahydro-1,8-naphthyridin-2-yl)propyl)thiazol-2-yl)propanoic acid

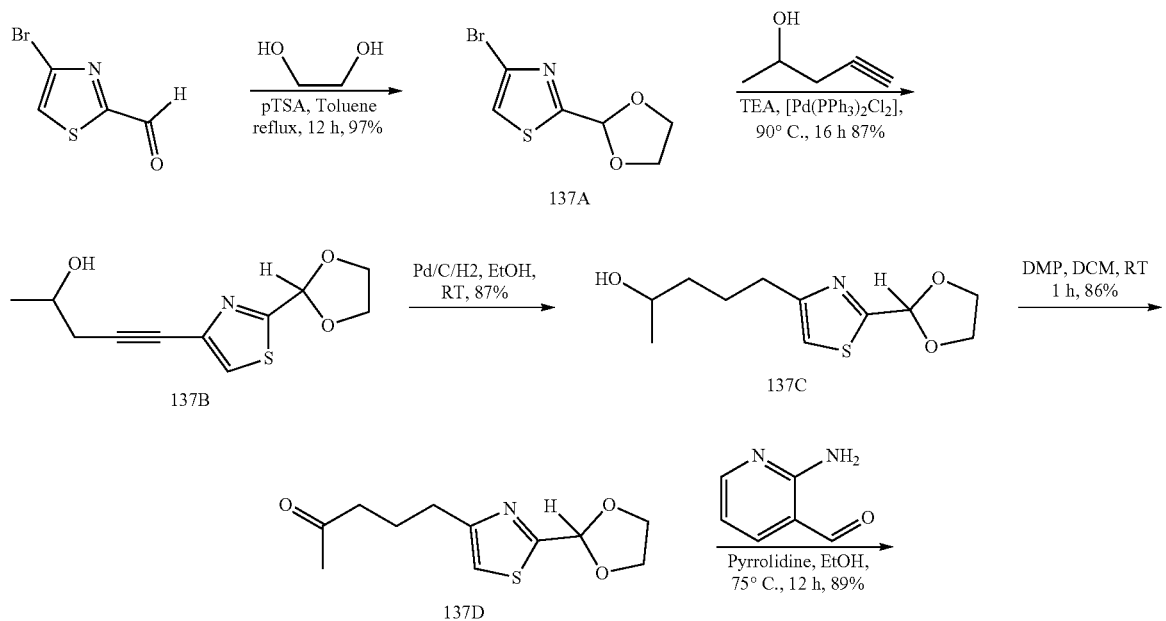

-continued

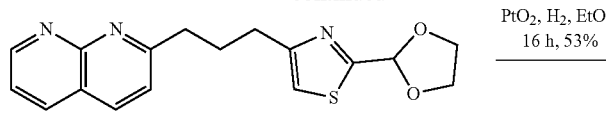
137E

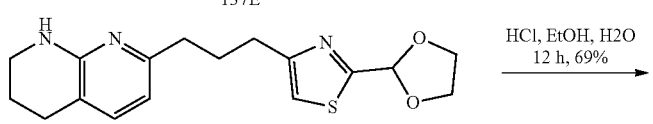
137F

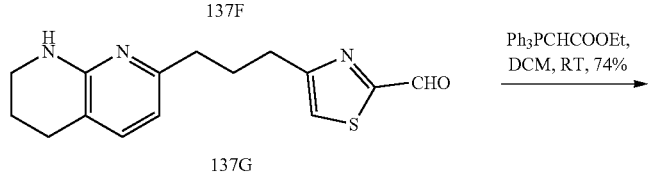
137G

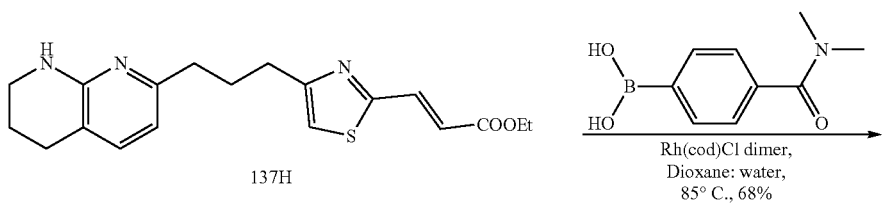
137H

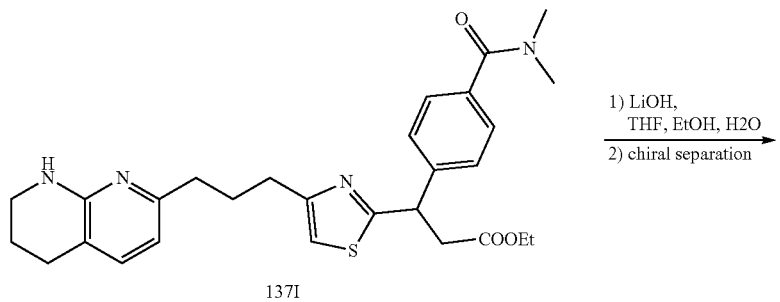
137I

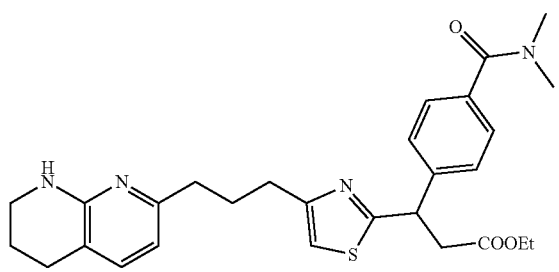 [SMILES: CN(C)C(=O)c1ccc(C(CC(=O)O)c2nc(CCCc3ccc4c(n3)NCCC4)cs2)cc1F]

Example 137: first eluting enantiomer:
Example 138: second eluting enantiomer 5-(2-(1,3-dioxolan-2-yl)thiazole (137A)

A toluene (120 mL) solution of 4-bromothiazole-2-carbaldehyde (7 g, 36.50 mmol) and ethylene glycol (2.72 g, 43.7 mmol) in a RB flask was added catalytic amount of pTsOH (0.347 g, 1.823 mmol). The RB flask was attached with Dean-Stark apparatus and reaction mixture was heated to reflux for 12 h. The mixture was cooled to RT, and was partitioned with saturated aqueous NaHCO₃ solution. The organic layer was separated, washed with saturated aqueous NaHCO₃ (2×120 mL) solution and then once with brine (100 mL). The organic layer was dried over anhydrous sodium sulphate, filtered and the filtrate concentrated under reduced pressure. The residue was purified by combiflash chromatography (40 g Redisep® SiO₂ column, eluting with 20% EtOAc in pet ether) to afford the title compound 137A (8 g, 97%) as a colourless liquid. LC-MS retention time=1.557 min; m/z=236.0 [M+2H]⁺ KINETIX XB-C18, (3×75) mm, 2.6 micron column; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 20% B to 100% B over 4.6 min, then hold 0.5 min. at 20% B with flow rate 1-1.5 mL/min; Detection: UV at 254 nm. ¹H NMR (400 MHz, DMSO-d6) δ 7.94 (s, 1H), 6.08 (s, 1H), 3.99-4.08 (m, 4H).

5-(2-(1,3-Dioxolan-2-yl)thiazol-4-yl)pent-4-yn-2-ol (137B)

To a stirred solution of 5-(2-(1,3-dioxolan-2-yl)thiazole 137A (5 g, 21.18 mmol), 4-pentyn-2-ol (2.67 g, 31.80 mmol)

in TEA (100 mL) under nitrogen atmosphere was added copper (I) iodide (0.282 g, 1.483 mmol) followed by bis (triphenylphosphine)palladium (II) dichloride (0.988 g, 1.483 mmol) and the reaction mixture was degassed with argon for 2 min. Then reaction mixture was then heated to 80° C. and stirred for 16 h. The reaction mixture cooled to RT and filtered through Celite pad. The Celite pad was washed with EtOAc (2×250 mL) and the combined filtrate was concentrated. The crude product was purified by combiflash chromatography (24 g Redisep® SiO$_2$ column, eluting with 90% EtOAc in pet ether) to afford the title compound 137B (4 g, 87%) as a colourless Liquid. LC-MS retention time=1.557 min; m/z=240.0 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. NMR (400 MHz, DMSO-d6) δ ppm 7.91 (s, 1H), 6.03 (s, 1H), 4.84 (d, J=4.8 Hz, 1H), 3.99-4.09 (m, 4H), 2.41 (d, J=6.8 Hz, 2H), 1.193 (d, J=7.2 Hz, 3H).

5-(2-(1,3-Dioxolan-2-yl) thiazol-4-yl) pentan-2-ol (137C)

To a degassed solution of 5-(2-(1,3-dioxolan-2-yl)thiazol-4-yl)pent-4-yn-2-ol 137B (4.0 g, 16.72 mmol) in EtOH (50 mL) was added 10% palladium on carbon (71 mg, 0.669 mmol) and the resulting reaction mixture was stirred under hydrogen bladder pressure at RT for 16 h. The reaction mixture was filtered through Celite pad and the Celite pad washed with EtOH (100 mL). The combined filtrate was concentrated to afford the crude title compound 137C (4.0 g, 87%) as a colourless liquid. LC-MS retention time=1.29 min; m/z=244.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 254 nm.

5-(2-(1,3-dioxolan-2-yl) thiazol-4-yl) pentan-2-ol (137D)

To a solution of 5-(2-(1,3-dioxolan-2-yl) thiazol-4-yl) pentan-2-ol 137C (7.5 g, 30.8 mmol) in DCM (150 mL) was added Dess-Martin periodinane (19.61 g, 42.2 mmol) at 0° C. The resulting reaction mixture was then stirred at RT for 60 min. The reaction mixture was diluted with DCM (200 mL), washed with 20% sodium bicarbonate solution (200 mL), brine solution (200 mL), dried over sodium sulfate, filtered and the filtrate concentrated. The crude product was purified by combiflash chromatography (24 g Redisep® SiO$_2$ column, eluting with 90% EtOAc in pet ether) to afford the title compound 137D (7.3 g, 86%) as a colourless Liquid. LC-MS retention time=1.33 min; m/z=242.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, DMSO-d6) δ ppm 7.36 (s, 1H), 6.00 (s, 1H), 3.96-4.08 (m, 4H), 2.68 (t, J=7.6 Hz, 2H), 2.44 (t, J=5.2 Hz, 2H), 2.19 (s, 3H), 1.79 (pent, J=7.2 Hz, 2H).

4-(3-(1,8-naphthyridin-2-yl)propyl)-2-(1,3-dioxolan-2-yl)thiazole (137E)

To a solution of 5-(2-(1,3-dioxolan-2-yl) thiazol-4-yl) pentan-2-ol 137D (4.0 g, 16.44 mmol) in ethanol (70 mL) was added pyrrolidine (1.268 mL, 15.33 mmol) under a nitrogen atm. and the solution was stirred for 10 min. 2-Aminonicotinaldehyde (2.06 g, 16.87 mmol) was then added and the resulting reaction mixture was stirred at 75° C. for overnight. The reaction mixture was concentrated and the crude product was purified by combiflash chromatography (24 g Redisep® SiO$_2$ column, eluting with 100% EtOAc to afford the title compound 137E (4.1 g, 89%) as a colourless liquid. LC-MS retention time=0.805 min; m/z=328.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 254 nm. $^1$H NMR (400 MHz, DMSO-d6) δ ppm 9.02-9.03 (dd, J=2.0, 1.6 Hz, 1H), 8.40-8.43 (m, 1H), 8.33-8.38 (d, J=8.4 Hz, 1H), 7.52-7.59 (m, 2H), 7.41 (s, 1H), 6.01 (s, 1H), 3.96-4.08 (m, 4H), 3.00-3.04 (t, J=7.6 Hz, 2H), 2.79-2.83 (t, J=7.2 Hz, 2H), 2.20 (m, 2H).

2-(1,3-dioxolan-2-yl)-4-(3-(5,6,7,8-tetrahydro-1,8-naphthyridin-2-yl)propyl)thiazole (137F)

To a stirred solution of 4-(3-(1,8-naphthyridin-2-yl)propyl)-2-(1,3-dioxolan-2-yl)thiazole 137E (0.3 g, 0.916 mmol) in ethanol (40 mL) was added platinum(IV) oxide (42 mg, 0.018 µmol) under nitrogen atmosphere. The reaction mixture then was degassed with hydrogen gas and stirred under hydrogen bladder pressure at RT for 16 h. The reaction mixture was filtered through Celite pad, Celite pad washed with EtOH (50 mL) and the combined filtrate concentrated to afford the title product 137F (270 mg, 53%) as a pale yellow oil. The crude product was taken for the next step without further purification. LC-MS retention time=1.705 min; m/z=332.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 254 nm.

4-(3-(5,6,7,8-tetrahydro-1,8-naphthyridin-2-yl)propyl)thiazole-2-carbaldehyde (137G)

To a solution of tert-butyl 7-(3-(2-(1,3-dioxolan-2-yl) thiazol-4-yl)propyl)-3,4-dihydro-1,8-naphthyridine-1 (2H)-carboxylate2-(1,3-dioxolan-2-yl)-4-(3-(5,6,7,8-tetrahydro-1,8-naphthyridin-2-yl)propyl)thiazole 137F (3.7 g, 11.16 mmol) in ethanol (25 mL) and H$_2$O (5 mL) was added conc. HCl (3.39 mL, 112 mmol) and resulting solution was stirred at RT for 12 h. The reaction mixture was concentrated and the residue quenched with sat. aqueous NaHCO$_3$ (100 mL) solution and extracted in ethyl acetate (2×250 mL). The combined organic layer was dried over Na$_2$SO$_4$, filtered, concentrated and crude desired product 137G (3.1 g, 69%) was used next step without purification. LC-MS retention time=1.474 min; m/z=288.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN;

20% B to 100% B over 4.6 min, then hold 0.5 min. at 20% B with flow rate 1-1.5 mL/min; Detection: UV at 254 nm.

Ethyl (E)-3-(4-(3-(5,6,7,8-tetrahydro-1,8-naphthyridin-2-yl)propyl)thiazol-2-yl)acrylate (137H)

To a stirred solution of 4-(3-(5,6,7,8-tetrahydro-1,8-naphthyridin-2-yl)propyl)thiazole-2-carbaldehyde 137G (0.14 g, 0.487 mmol) in dry DCM (7.0 mL) was added (carbethoxymethylene)triphenylphosphorane (0.204 g, 0.585 mmol) and resulting reaction mixture was stirred under nitrogen atmosphere at RT for 12 h. The reaction mixture was concentrated under vacuum and crude product was purified by combiflash chromatography (4.0 g Redisep® SiO$_2$ column, eluting with 0-100% EtOAc in n-hexanes) to afford the title compound 137H (0.11 g, 74%) as a semisolid. LC-MS retention time=1.507 min; m/z=358.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Ethyl 3-(4-(dimethylcarbamoyl)phenyl)-3-(4-(3-(5,6,7,8-tetrahydro-1,8-naphthyridin-2-yl)propyl)-thiazol-2-yl)propanoate (137I)

To a solution ethyl (E)-3-(4-(3-(5,6,7,8-tetrahydro-1,8-naphthyridin-2-yl)propyl)thiazol-2-yl)acrylate 137H (300 mg, 0.839 mmol)) in 1,4-dioxane (15.0 mL) and H$_2$O (2.5 mL) was added (4-(dimethylcarbamoyl)phenyl)boronic acid (16.20 mg, 0.084 mmol). The reaction mixture was degassed with argon for 5 min. Chloro(1,5-cyclooctadiene)rhodium(I) dimer (20.69 mg, 0.042 mmol) and TEA (0.234 mL, 1.678 mmol) were added and the resulting reaction mixture was heated to 85° C. and stirred for 16 h. The reaction mixture was cooled, poured into water (50 mL) and extracted with EtOAc (2×50 mL). The combined organic layer was washed with brine (50 mL), dried over anhydrous Na$_2$SO$_4$, filtered and concentrated under vacuum. The crude product was purified by combiflash chromatography (12 g Redisep® SiO$_2$ column, eluting with 0-20% MeOH in DCM) to afford the title compound 137I (290 mg, 68%) as a semisolid. The crude product was taken to the next step without further purification. LC-MS retention time=2.024 min; m/z=507.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 254 nm.

Example 137: first eluting enantiomer of 3-(4-(dimethylcarbamoyl)phenyl)-3-(4-(3-(5,6,7,8-tetrahydro-1,8-naphthyridin-2-yl)propyl)thiazol-2-yl)propanoic acid

Example 138: Second Eluting Enantiomer of 3-(4-(dimethylcarbamoyl)phenyl)-3-(4-(3-(5,6,7,8-tetrahydro-1,8-naphthyridin-2-yl)propyl)thiazol-2-yl) propanoic acid To a stirred solution of ethyl 3-(4-(dimethylcarbamoyl)phenyl)-3-(4-(3-(5,6,7,8-tetrahydro-1,8-naphthyridin-2-yl)propyl)thiazol-2-yl)propanoate 137I (0.29 g, 0.572 mmol) in THF (6.0 mL) and ethanol (4 mL) was added a solution of LiOH·H$_2$O (27 mg, 1.145 mmol) in water (2.0 mL) and the solution was stirred at RT for 12 h. Then, citric acid (50 mg) was added and stirred at RT for 1 h. The reaction mixture was concentrated and the crude product was purified by preparative reverse phase preparative HPLC (retention time=14.6 min, Column: INTERSIL ODS C18 (250×19) mm 5 micron; Mobile Phase A: 10 mM NH$_4$OAc in water; Mobile Phase B: ACN, flow rate: 17.0 mL/min; time (min)/% B: 0/20, 8/40, 14/60) to afford title compound (110 mg) as a racemic mixture. The individual enantiomers were then separated by preparative HPLC (Column: Lux-cellulose C4 (250×21.2) mm 5 micron column; flow rate: 19.0 mL/min; Mobile Phase B: 0.1% DEA in MeOH; time (min)/% B: 0/100, 20/100, temperature: 35° C.; Detection: UV at 220 nm). First eluting enantiomer Example 137 (Retention time 7.442 min., 24 mg, 9%) was isolated as a white solid. LC-MS retention time=1.192 min; m/z=479.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.47 (m, 3H), 7.43 (d, J=8.4 Hz, 2H), 7.04 (s, 1H), 6.56 (d, J=7.6 Hz, 1H), 4.92 (dd, J=1.17, 4.77 Hz, 1H), 3.48 (t, J=6.0 Hz, 2H), 3.23 (dd, J=14.53, 11.14 Hz, 1H), 3.11 (s, 3H), 3.01 (s, 3H), 2.88 (dd, J=14.4, 4.8 Hz, 1H), 2.74-2.90 (m, 4H), 2.48-2.66 (m, 2H), 1.91-2.01 (m, 1H), 1.31 (s, 1H), 1.92-1.97 (m, 2H). Human αVβ6 IC50 (nM)= 210. Second eluting enantiomer Example 138 (Retention time 8.044 min., 19.5 mg, 8%) was isolated as a white solid. LC-MS retention time=1.239; m/z=479.2 [M+H] KINETIX XB-C18, (3×75) mm, 2.6 micron column; Flow rate: 1 mL/min; Mobile Phase A: 10 mM HCO$_2$NH$_4$ in 98% Water/ 2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.47 (m, 3H), 7.43 (d, J=8.4 Hz, 2H), 7.04 (s, 1H), 6.56 (d, J=7.6 Hz, 1H), 4.92 (dd, J=1.17, 4.77 Hz, 1H), 3.48 (t, J=6.0 Hz, 2H), 3.23 (dd, J=14.53, 11.14 Hz, 1H), 3.11 (s, 3H), 3.01 (s, 3H), 2.88 (dd, J=14.4, 4.8 Hz, 1H), 2.74-2.90 (m, 4H), 2.48-2.66 (m, 2H), 1.91-2.01 (m, 1H), 1.31 (s, 1H), 1.92-1.97 (m, 2H). Human αVβ6 IC50 (nM)=4.0.

| Example | Structure | Preparative HPLC /SFC method, LCMS & $^1$H NMR | Method |
|---|---|---|---|
| 139 | 3-(3-(dimethylcarbamoyl)phenyl)-3-(4-(3-(5,6,7,8-tetrahydro-1,8-naphthyridin-2-yl)propyl)thiazol-2-yl)propanoic acid | Preparative SFC method: (retention time = 5.77 min), Chiralpak AD-H (250 × 21) mm, 5u; % $CO_2$: 60%; % Co solvent: 40% (0.2% DEA in MeOH); Total Flow: 70 g/min; Back Pressure: 100 bars; Temperature: 25° C.; Detection: UV at 254 nm, $^1$H NMR (400 MHz, $CD_3OD$) δ ppm 7.43-7.50 (m, 4H), 7.34 (d, J = 1.2 Hz, 1H), 7.04 (s, 1H), 6.57 (d, J = 7.6 Hz, 1H), 3.49 (t, J = 6.0, 2H), 3.23 (dd, J = 14.53, 11.14 Hz, 1H),, 3.10 (s, 3H), 2.98 (s, 3H), 2.89 (dd, J = 10.0, 4.8 Hz, 1H), 2.58-2.90 (m, 4H), 2.48-2.66 (m, 2H), 1.91-2.01 (m, 1H), 1.31 (s, 1H), 1.92-1.97 (m, 2H), LC-MS: retention time = 1.014 min; m/z = 479.2 [M + H]$^+$ KINETIX XB-C18, (3 × 75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm, Human αVβ6 IC50 (nM) = 34 | Example 137/138 |
| 140 | 3-(3-(dimethylcarbamoyl)phenyl)-3-(4-(3-(5,6,7,8-tetrahydro-1,8-naphthyridin-2-yl)propyl)thiazol-2-yl)propanoic acid | Preparative SFC method (retention time = 6.83), Chiralpak AD-H (250 X 21) mm, 5u; % $CO_2$: 60%; % Co solvent: 40% (0.2% DEA in MeOH); Total Flow: 70 g/min; Back Pressure: 100 bars; Temperature: 25° C.; Detection: UV at 254 nm, $^1$H NMR (400 MHz, $CD_3OD$) δ ppm 7.43-7.50 (m, 4H), 7.34 (d, J = 7.2 Hz, 1H), 7.04 (s, 1H), 6.57 (d, J = 7.6 Hz, 1H), 3.49 (t, J = 6.0, 2H), 3.23 (dd, J = 14.53, 11.14 Hz, 1H),, 3.10 (s, 3H), 2.98 (s, 3H), 2.89 (dd, J = 10.0, 4.8 Hz, 1H), 2.58-2.90 (m, 4H), 2.48-2.66 (m, 2H), 1.91-2.01 (m, 1H), 1.31 (s, 1H), 1.92-1.97 (m, 2H), LC-MS: retention time = 1.014 min; m/z = 479.2 [M + H]$^+$ KINETIX XB-C18, (3 × 75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm, Human αVβ6 IC50 (nM) = 3.7 | Example 137/138 |
| 141 | 3-(3, 4-dimethoxyphenyl)-3-(4-(3-(5,6,7,8-tetrahydro-1,8-naphthyridin-2-yl)propyl)thiazol-2-yl)propanoic acid | Preparative SFC method: (retention time = 3.62 min), Chiralpak AD-H (250 × 21) mm, 5u; % $CO_2$: 60%; % Co solvent: 40% (0.2% DEA in MeOH); Total Flow: 70 g/min; Back Pressure: 100 bar; Temperature: 25°C; Detection: UV at 245 nm, $^1$H NMR (400 MHz, $CD_3OD$) δ ppm 7.36 (d, J = 7.2 Hz, 1H), 6.90 (s, 1H), 6.92-6.96 (m, 3H), 6.56 (d, J = 7.2 Hz, 1H), 4.78-4.89 (dd, J = 6.4, 4.8 Hz, 1H), 3.83 (s, 3H), 3.82 (s, 3H), 3.49 (t, J = 5.2 Hz, 2H), 3.17 (dd, J = 11.2, 2.8 Hz, 1H), 2.72-2.86 (m, 5H), 2.43-2.48 (m, 2H), 1.83-1.87 (m, 2H), 1.80-1.81 (m, 2H), LC-MS: (retention time = 1.204 min), m/z = 468.2 [M + H]$^+$ KINETIX XB-C18, (3 × 75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% | Example 137/138 |

-continued

| Example | Structure | Preparative HPLC /SFC method, LCMS & ¹H NMR | Method |
|---|---|---|---|
| | | ACN: 20% B to 100% B over 4.6 min, then hold 0.5 min. at 20% B with flow rate 1-1.5 mL/min; Detection: UV at 220 nm, Human αVβ6 IC50 (nM) = 2.9 | |
| 142 | 3-(3, 4-dimethoxyphenyl)-3-(4-(3-(5,6,7,8-tetrahydro-1,8-naphthyridin-2-yl)propyl)thiazol-2-yl)propanoic acid | Preparative SFC method: (retention time = 4.07 min), Chiralpak AD-H (250 × 21) mm, 5u; % CO₂: 60%; % Co solvent: 40% (0.2% DEA in MeOH): Total Flow: 70 g/min: Back Pressure: 100 bar; Temperature: 25° C.; Detection: UV at 245 nm, ¹H NMR (400 MHz, CD₃OD) δ ppm 7.36 (d, J = 7.2 Hz, 1H), 6.90 (s, 1H), 6.92-6.96 (m, 3H), 6.56 (d, J = 12 Hz, 1H), 4.78-4.89 (dd, J = 6.4, 4.8 Hz, 1H), 3.83 (s, 3H), 3.82 (s, 3H), 3.49 (t, J = 5.2 Hz, 2H), 3.17 (dd, J = 11.2, 2.8 Hz, 1H), 2.12-2.86 (m, 5H), 2.43-2.48 (m, 2H), 1.83-1.87 (m, 2H), 1.80-1.81 (m, 2H), LC-MS: (retention time = 1.204 min), m/z = 468.2 [M + H]⁺ KINETIX XB-C18, (3 × 75) mm, 2.6 micron column; Flow rate: 1 mL/min; Mobile Phase A: 10 mM HCO₂NH₄ in 98% Water/2% ACN: Mobile Phase B: 10 mM HCO₂NH₄ in 2% Water/98% ACN: 20% B to 100% B over 4.6 min, then hold 0.5 min. at 20% B with flow rate 1-1.5 mL/min; Detection: UV at 220 nm, Human αVβ6 IC50 (nM) = 37 | Example 137/138 |

Example 143 and Example 144

Example 143: first eluting enantiomer of 3-(2-Methoxypyrimidin-5-yl)-3-(4-(4-(5,6,7,8-tetrahydro-1,8-naphthyridin-2-yl)butyl)thiazol-2-yl)propanoic acid Example 144: second eluting enantiomer of 3-(2-Methoxypyrimidin-5-yl)-3-(4-(4-(5,6,7,8-tetrahydro-1,8-naphthyridin-2-yl)butyl)thiazol-2-yl)propanoic acid

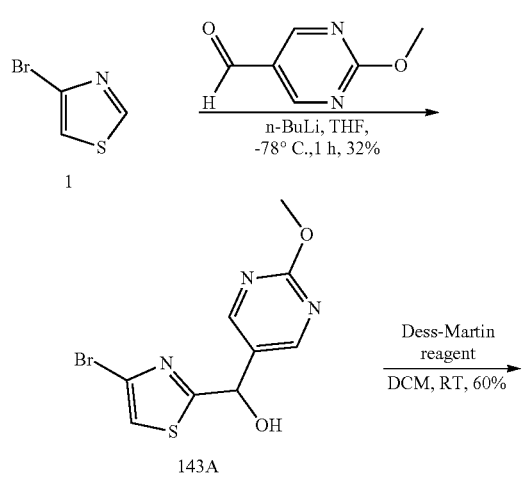

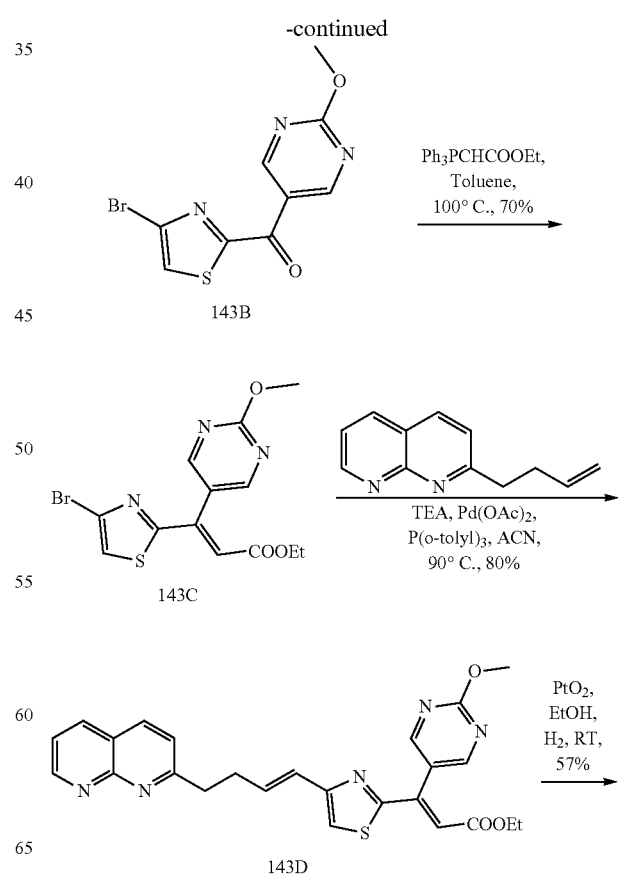

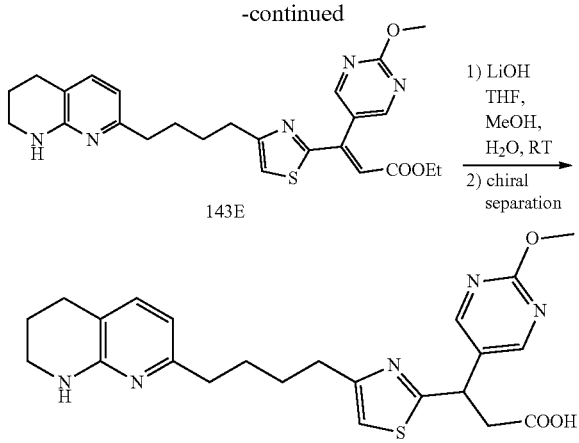

Example 143: first eluting enantiomer
Example 144: second eluting enantiomer

4-Bromothiazol-2-yl)(2-methoxypyrimidin-5-yl)
methanol (143A)

To a stirred solution of 4-bromothiazole (50.0 mg, 0.305 mmol) in THF (2 mL) under nitrogen atmosphere was added n-butyllithium (2.5 molar solution in hexane) (0.183 mL, 0.457 mmol) at −78° C. Resulting pale yellow solution was stirred at −78° C. for 30 min. Then, 2-methoxypyrimidine-5-carbaldehyde (37.9 mg, 0.274 mmol) in 0.5 mL THF was added and the reaction mixture was stirred at −78° C. for 1 h. Reaction was quenched with water (2 mL) and diluted with ethyl acetate (5 mL). The organic layer was separated, washed with brine, dried over anhydrous sodium sulphate and evaporated under vacuum to get the crude product. The crude product was purified by combiflash chromatography (4 g Redisep® SiO$_2$ column, eluting with 72% EtOAc in n-hexanes) to afford the title compound 143A (30 mg, 32%) as a pale yellow oil. LC-MS retention time=0.84 min; m/z=304.0 [M+H]$^+$ AQUITY UPLC BEH C18 (3.0×50 mm) 1.7 micron column; Mobile Phase A: 5 mM ammonium acetate in 95% Water/5% ACN; Mobile Phase B: 5 mM ammonium acetate in 5% Water/95% ACN; Gradient time 1.7 min. 20% B to 90% B over 1.7 min. Flow rate 0.7 mL/min; Detection: UV at 220 nm. $^1$H NMR (400 MHz, CD$_3$OD) δ ppm 8.63 (s, 2H), 7.55 (s, 1H), 6.05 (s, 1H), 4.03 (s, 3H).

4-Bromothiazol-2-yl)(2-methoxypyrimidin-5-yl)
methanone (143B)

To a stirred solution of (4-bromothiazol-2-yl)(2-methoxypyrimidin-5-yl)methanol 143A (200 mg, 0.662 mmol) in DCM (6 mL) under nitrogen atmosphere was added Dess-Martin periodinane (562 mg, 1.324 mmol) and the resulting mixture was stirred at RT for 16 h. The reaction mixture was concentrated under vacuum and the crude product obtained was purified by combiflash chromatography (12 g Redisep® SiO$_2$ column, eluting with 32% EtOAc in n-hexanes) to afford the title compound 143B (120 mg, 60%) as a pale yellow solid. LC-MS retention time=2.32 min; m/z=299.9 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CDCl$_3$) δ ppm 9.65 (s, 2H), 7.68 (s, 1H), 4.15 (s, 3H).

Ethyl (E)-3-(4-bromothiazol-2-yl)-3-(2-methoxypyrimidin-5-yl)acrylate (143C)

To a stirred solution of (4-bromothiazol-2-yl)(2-methoxypyrimidin-5-yl)methanone 143B (300 mg, 1.000 mmol) in toluene (10 mL) under nitrogen atmosphere was added (carbethoxymethylene)triphenylphosphorane (418 mg, 1.199 mmol) and the reaction mixture was stirred at 100° C. for 16 h. The reaction mixture was concentrated under reduced pressure to get the crude product. The crude product was then purified by combiflash chromatography (24 g Redisep® SiO$_2$ column, eluting with 33% EtOAc in n-hexanes) to afford the title compound 143C (260 mg, 70%, mixture of cis and trans isomers) as a white solid. LC-MS retention time=2.47 & 2.68 min; m/z=372.0 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Ethyl (E)-3-(4-((E)-4-(1,8-naphthyridin-2-yl)but-1-en-1-yl)thiazol-2-yl)-3-(2-methoxypyrimidin-5-yl)acrylate (143D)

To a stirred solution of ethyl (E)-3-(4-bromothiazol-2-yl)-3-(2-methoxypyrimidin-5-yl)acrylate 143C (30 mg, 0.081 mmol) in ACN (4 mL) under nitrogen atmosphere was added 2-(but-3-en-1-yl)-1,8-naphthyridine (14.9 mg, 0.081 mmol), tri-o-tolylphosphine (3.70 mg, 0.012 mmol), palladium(II) acetate (1.81 mg, 0.0081 mmol) and TEA (0.028 mL, 0.20 mmol). The reaction mixture was degassed with argon and stirred at 80° C. for 16 h. The reaction mixture was filtered, washed with EtOAc (5 mL) and the combined filtrate concentrated. The crude product was purified by combiflash chromatography (12 g Redisep® SiO$_2$ column, eluting with 3% MeOH in CHCl$_3$) to afford the title compound 143D (30 mg, 80%) as a brown oil. LC-MS retention time=2.3 & 2.5 min; m/z=474.2 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Ethyl 3-(2-methoxypyrimidin-5-yl)-3-(4-(4-(5,6,7,8-tetrahydro-1,8-naphthyridin-2-yl)butyl)thiazol-2-yl)propanoate (143E)

To a stirred solution of ethyl (E)-3-(4-((E)-4-(1,8-naphthyridin-2-yl)but-1-en-1-yl)thiazol-2-yl)-3-(2-methoxypyrimidin-5-yl)acrylate 143D (50 mg, 0.106 mmol) in ethanol (3 mL) was added platinum(IV) oxide (2 mg, 8.81 µmol) under nitrogen atmosphere. The reaction mixture was degassed with hydrogen and stirred under hydrogen bladder pressure at RT for 16 h. The reaction mixture was filtered through Celite, washed Celite with EtOH (5 mL) and the combined filtrate concentrated under reduced pressure to afford the title crude product 143E (150 mg, 57%) as a pale yellow oil. LC-MS retention time=1.28 min; m/z=482.3 [M+H]$^+$ AQUITY UPLC BEH C18 (3.0×50 mm) 1.7 micron column; Mobile Phase A: 5 mM ammonium acetate in 95% Water/5% ACN; Mobile Phase B: 5 mM ammonium acetate Example 143: first eluting enantiomer of 3-(2-Methoxypyrimidin-5-yl)-3-(4-(4-(5,6,7,8-tetrahydro-1,8-naphthyridin-2-yl)butyl)thiazol-2-yl)propanoic acid Example 144: second eluting enantiomer of 3-(2-Methoxypyrimidin-5-yl)-3-(4-(4-(5,6,7,8-tetrahydro-1,8-naphthyridin-2-yl)butyl)thiazol-2-yl)propanoic acid To a stirred solution of ethyl 3-(2-methoxypyrimidin-5-yl)-3-(4-(4-(5,6,7,8-tetrahydro-1,8-naphthyridin-2-yl)butyl)thiazol-2-yl)propanoate 143E (80 mg, 0.166 mmol) in THF (3 mL), MeOH (3 mL) and water (3 mL) was added LiOH·H$_2$O (7.96 mg, 0.332 mmol) and the resulting mixture was stirred at RT for 4 h. Then, citric acid (63.8 mg, 0.332 mmol) was added and stirred at RT for 10 min. The reaction mixture was filtered, concentrated under reduced pressure to get the crude product. The crude product was purified by preparative HPLC (YMC Trait (150 mm×20 mm ID) 5µ column. Mobile Phase A: 10 mM NH4OAc in water; Mobile Phase B: ACN: MeOH (1:1). Flow rate: 18.0 mL/min; time (min)/% B: 0/20, 02/30, 15/50, 15.5/100) to afford the pure compound as racemic mixture. Individual enantiomers was separated by chiral preparative SFC (Chiralpak AD-H (250× 21) mm, 5 micron column; % CO2: 50%; % Co solvent: 50%(0.2% DEA in IPA); Total Flow: 70 g/min; Back Pressure: 100 bars; Temperature: 30° C.; Detection: UV at 240 nm) to get first eluting isomer Example 143 (retention time: 4.2 min, 7 mg, 8.8%) as a white solid. LC-MS retention time=1.46 min; m/z=454.2 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 220 nm. $^1$H NMR (400 MHz, CD$_3$OD) δ ppm 8.61 (s, 2H), 7.42 (d, J=7.20 Hz, 1H), 7.08 (s, 1H), 6.53 (d, J=7.20 Hz, 1H), 4.80-4.83 (m, 1H), 4.01 (s, 3H), 3.45 (t, J=5.60 Hz, 2H), 3.17 (dd, J=14.6, 11.0 Hz, 1H), 2.91-2.96 (m, 1H), 2.76-2.84 (m, 4H), 2.54-2.62 (m, 2H), 1.92-1.96 (m, 3H), 1.70-1.78 (m, 1H), 1.51-1.59 (m, 2H). Human αVβ6 IC50 (nM)=88. Further eluting the same column furnished the second isomer, Example 144 (retention time: 6.5 min., 7 mg, 8.8%) as a white solid. LC-MS retention time=1.46 min; m/z=454.2 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 220 nm. $^1$H NMR (400 MHz, CD$_3$OD) δ ppm 8.61 (s, 2H), 7.42 (d, J=7.20 Hz, 1H), 7.08 (s, 1H), 6.53 (d, J=7.20 Hz, 1H), 4.80-4.83 (m, 1H), 4.01 (s, 3H), 3.45 (t, J=5.60 Hz, 2H), 3.17 (dd, J=14.6, 11.0 Hz, 1H), 2.91-2.96 (m, 1H), 2.76-2.84 (m, 4H), 2.54-2.62 (m, 2H), 1.92-1.96 (m, 3H), 1.70-1.78 (m, 1H), 1.51-1.59 (m, 2H). Human αVβ6 IC50 (nM)=7.0.

Example 145 and Example 146

Example 145: first eluting enantiomer of 3-(2-methoxypyrimidin-5-yl)-3-(4-(3-(5,6,7,8-tetrahydro-1,8-naphthyridin-2-yl)propyl)thiazol-2-yl)propanoic acid

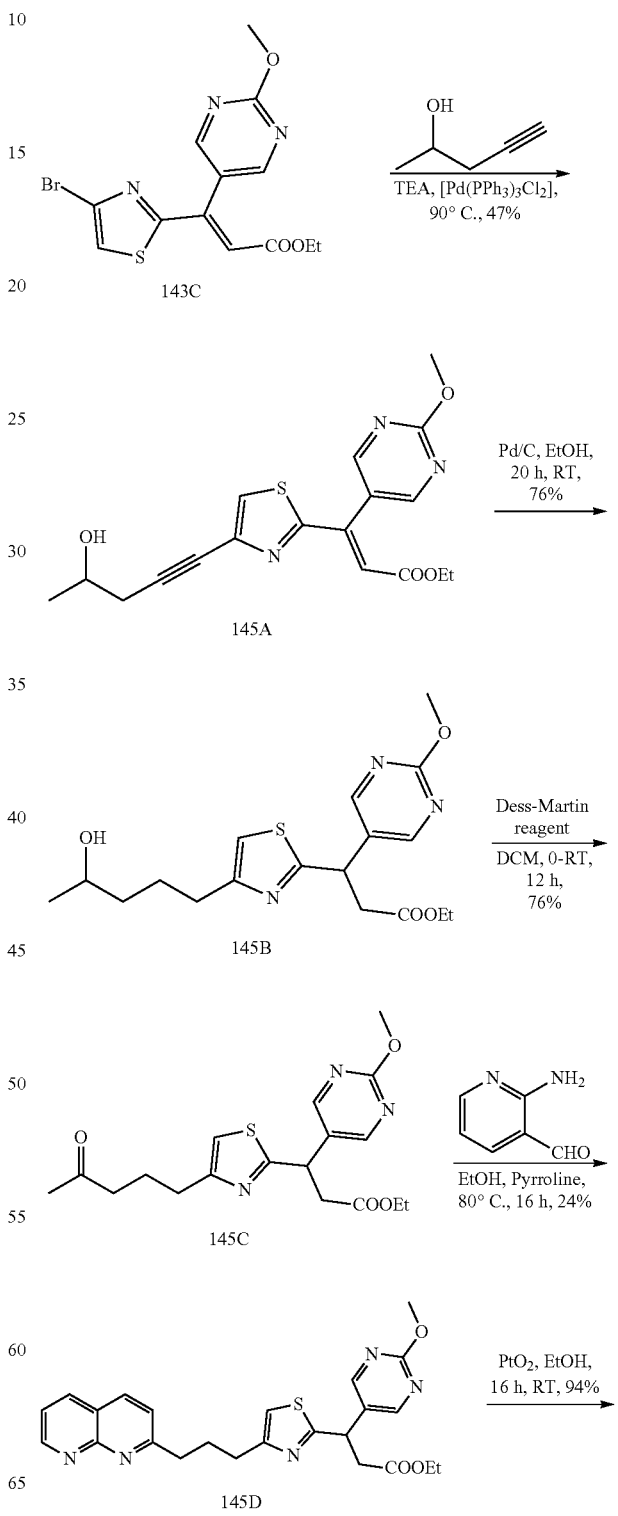

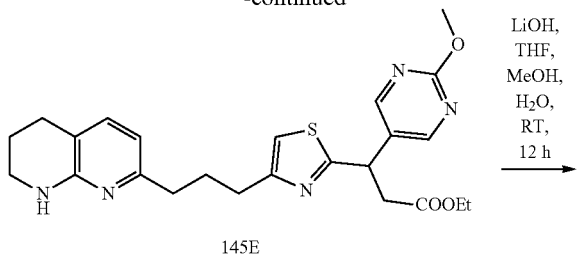

145E

Example 145: first eluting enantiomer
Example 146: second eluting enantiomer

Ethyl (E)-3-(4-(4-hydroxypent-1-yn-1-yl)thiazol-2-yl)-3-(2-methoxypyrimidin-5-yl)acrylate (145A)

To a stirred solution of ethyl (E)-3-(4-(4-bromothiazol-2-yl)-3-(2-methylpyrimidin-5-yl)acrylate 143C (100 mg, 0.282 mmol) and pent-4-yn-2-ol (23.75 mg, 0.282 mmol) in TEA (6 mL) under nitrogen atmosphere was added copper(I) iodide (2.69 mg, 0.014 mmol) followed by bis(triphenylphosphine)palladium (II) dichloride (9.9 mg, 0.014 mmol). Then, the reaction mixture was degassed with argon for 2 min and then heated at 80° C. for 16 h. After cooling to RT, the reaction mixture was filtered through Celite, Celite was washed with EtOAc (5 mL) and the combined filtrate concentrated under reduced pressure to give a brown colour crude oil. The crude product was purified by combiflash chromatography (12 g Redisep® SiO$_2$ column, eluting with 69% EtOAc in pet ether) to afford the title compound 145A (90 mg, 47%) as a pale yellow oil. LC-MS retention time=1.82 & 1.96 min; m/z=375.0 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Ethyl 3-(4-(4-hydroxypentyl)thiazol-2-yl)-3-(2-methoxypyrimidin-5-yl)propanoate (145B)

To a degassed solution of ethyl (E)-3-(4-(4-hydroxypent-1-yn-1-yl)thiazol-2-yl)-3-(2-methoxypyrimidin-5-yl)acrylate 145A (120 mg, 0.321 mmol) in EtOH (5 mL) was added 10% palladium on carbon (20 mg, 0.188 mmol). The resulting reaction mixture was stirred under hydrogen bladder pressure at RT for 16 h. The reaction mixture was filtered through Celite pad and the filtrate concentrated under vacuum to afford the crude title compound 145B (120 mg, 76%) as pale yellow oil. LC-MS retention time=1.90 min; m/z=380.0 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Ethyl 3-(2-methoxypyrimidin-5-yl)-3-(4-(4-oxopentyl)thiazol-2-yl)propanoate (145C)

To a solution of ethyl 3-(4-(4-hydroxypentyl)thiazol-2-yl)-3-(2-methoxypyrimidin-5-yl)propanoate 145B (120 mg, 0.316 mmol) in DCM (15 mL) was added Dess-Martin periodinane (268 mg, 0.632 mmol) at 0° C. and the resulting mixture was stirred at RT for 2 h. The reaction mass was diluted with DCM (20 mL), washed with 20% sodium bicarbonate solution (20 mL), brine solution (10 mL), dried over sodium sulfate and evaporated under reduced pressure to get white crude solid. The crude product was purified by combiflash chromatography (12 g Redisep® SiO$_2$ column, eluting with 41% EtOAc in pet ether) to afford the title compound 145C (100 mg, 76%) as a pale yellow oil. LC-MS retention time=1.44 min; m/z=378.2 [M+H]$^+$ LUNA 3.0 C18, (4×20) mm, 2.6 micron column; Mobile Phase A: 0.1% TLA in water. Mobile Phase B: 0.1% TFA in ACN; 20% B to 98% B over 2.7 min, then hold 0.3 min. at 20% B with flow rate 1-1.5 mL/min; Detection: UV at 220 nm.

Ethyl 3-(4-(3-(1,8-naphthyridin-2-yl)propyl)thiazol-2-yl)-3-(2-methoxypyrimidin-5-yl)propanoate (145D)

To a stirred solution of ethyl 3-(2-methoxypyrimidin-5-yl)-3-(4-(4-oxopentyl)thiazol-2-yl)propanoate 145C (130 mg, 0.344 mmol) and 2-aminonicotinaldehyde (50.6 mg, 0.414 mmol) in ethanol (5 mL) under nitrogen was added pyrrolidine (0.029 mL, 0.345 mmol) and the resulting reaction mixture was stirred at 70° C. for 4 h. The reaction mixture concentrated under the reduced pressure and the crude product was purified by combiflash chromatography (24 g Redisep® SiO$_2$ column, eluting with 100% EtOAc to afford the title compound 145D (75 mg, 42%) as a pale yellow liquid. LC-MS retention time=1.11 min; m/z=464.2 [M+H]$^+$ LUNA 3.0 C18, (4×20) mm, 2.6 micron column; Mobile Phase A: 0.1% TFA in water. Mobile Phase B: 0.1% TFA in ACN; 20% B to 98% B over 2.7 min, then hold 0.3 min. at 20% B with flow rate 1-1.5 mL/min; Detection: UV at 220 nm.

Ethyl 3-(2-methoxypyrimidin-5-yl)-3-(4-(3-(5,6,7,8-tetrahydro-1,8-naphthyridin-2-yl)propyl)thiazol-2-yl)propanoate (145E)

To a stirred solution of ethyl 3-(4-(3-(1,8-naphthyridin-2-yl)propyl)thiazol-2-yl)-3-(2-methoxypyrimidin-5-yl)propanoate 145D (180 mg, 0.388 mmol) in ethanol (8 mL) was added platinum(IV) oxide (2 mg, 8.81 µmol) under nitrogen atmosphere. The reaction mixture was degassed with hydrogen and stirred under hydrogen bladder pressure at RT for 16 h. The reaction mixture was filtered through the Celite, the Celite was washed with EtOH (5 mL) and the combined filtrate evaporated under reduced pressure to afford the title crude product 145E (150 mg, 94%) as a pale yellow oil. LC-MS retention time=1.11 min; m/z=468.3 [M+H]$^+$ AQUITY UPLC BEH C18 (3.0×50 mm) 1.7 micron column; Mobile Phase A: 5 mM ammonium acetate in 95% Water/5% ACN; Mobile Phase B: 5 mM ammonium acetate in 5% Water/95% ACN; Gradient time 1.7 min. 20% B to 90% B over 1.7 min. Flow rate 0.7 mL/min; Detection: UV at 220 nm.

Example 145: first eluting enantiomer of 3-(2-methoxypyrimidin-5-yl)-3-(4-(3-(5,6,7,8-tetrahydro-1,8-naphthyridin-2-yl)propyl)thiazol-2-yl)propanoic acid Example 146: second eluting enantiomer of 3-(2-methoxypyrimidin-5-yl)-3-(4-(3-(5,6,7,8-tetrahydro-1,8-naphthyridin-2-yl)propyl)thiazol-2-yl)propanoic acid To a stirred solution of ethyl 3-(2-methoxypyrimidin-5-yl)-3-(4-(3-(5,6,7,8-tetrahydro-1,8-naphthyridin-2-yl)propyl)thiazol-2-yl)propanoate 145E (100 mg, 0.214 mmol) in THF (3 mL), MeOH (3 mL) and water (3 mL) was added LiOH·H$_2$O (10 mg, 0.428 mmol) and the resulting mixture was stirred at RT for 4 h. Then, citric acid (82 mg, 0.428 mmol) was added and stirred at RT for 10 min. The reaction mixture was concentrated under reduced pressure to get the crude product. The crude product was purified by preparative HPLC (Sunfire OBD (250 mm×30 mm ID) 5μ. Mobile phase A: 10 mM NH$_4$OAc in water; Mobile phase B: ACN:MeOH (1:1); Flow rate: 18 mL/min; time (min)/% B: 0/20, 02/20, 15/60, 15.5/100) to afford the title compound as racemate. Individual enantiomers were separated by chiral SFC (Chiralpak AD-H (250×21) mm, 5 micron column; % CO2: 50%; % Co solvent: 45%(0.2% NH$_4$OH in MeOH and ACN (1:1); Total Flow: 70 g/min; Back Pressure: 100 bars; Temperature: 30° C.; Detection: UV at 245 nm) to afford Example 145 (retention time 4.5 min., 24 mg, 23%) as a white solid. LC-MS retention time=1.24 min; m/z=440.2 [M+H]$^+$ (KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 220 nm). $^1$H NMR (400 MHz, CD$_3$OD) δ ppm 8.61 (s, 2H), 7.42 (d, J=7.20 Hz, 1H), 7.08 (s, 1H), 6.53 (d, J=7.20 Hz, 1H), 4.80-4.83 (m, 1H), 4.01 (s, 3H), 3.45 (t, J=5.60 Hz, 2H), 3.17 (dd, J=14.6, 11.0 Hz, 1H), 2.91 (dd, J=14.6, 11.8 Hz, 1H), 2.76-2.84 (m, 4H), 2.54-2.62 (m, 2H), 2.12-2.14 (m, 1H), 2.02-2.26 (m, 1H), 1.92-1.96 (m, 2H). Human αVβ6 IC50 (nM)=4.5. Second eluting enantiomer, Example 146 (retention time 8.5 min, 22 mg, 23%) as a white solid. LC-MS retention time=1.24 min; m/z=440.2 [M+H]$^+$ (KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 220 nm). $^1$H NMR (400 MHz, CD$_3$OD) δ ppm 8.61 (s, 2H), 7.42 (d, J=7.20 Hz, 1H), 7.08 (s, 1H), 6.53 (d, J=7.20 Hz, 1H), 4.80-4.83 (m, 1H), 4.01 (s, 3H), 3.45 (t, J=5.60 Hz, 2H), 3.17 (dd, J=14.6, 11.0 Hz, 1H), 2.91 (dd, J=14.6, 11.8 Hz, 1H), 2.76-2.84 (m, 4H), 2.54-2.62 (m, 2H), 2.12-2.14 (m, 1H), 2.02-2.26 (m, 1H), 1.92-1.96 (m, 2H). Human αVβ6 IC50 (nM)=140.

| Example | Structure | Prep-HPLC/SFC conditions, $^1$H NMR and LC-MS data | Method |
| --- | --- | --- | --- |
| 147 | 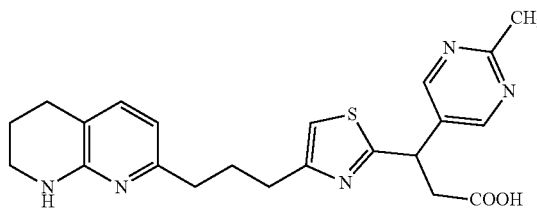<br>3-(2-methylpyrimidin-5-yl)-3-(4-(3-(5,6,7,8-tetrahydro-1,8-naphthyridin-2-yl)propyl)thiazol-2-yl)propanoic acid | Prep-HPLC: Retention time: 9.6 min. Sunfire C18 (250 x 30) mm; 5 micron; Mobile Phase A: 10 mM NH$_4$OAc in water; Mobile Phase B: ACN: MeOH (1:1), Flow rate: 17.0 mL/min; time (min)/% B: 0/20, 25/100. $^1$H NMR (400 MHz, CD$_3$OD) δ ppm 8.74 (s, 2H), 7.42 (d, J = 3.20 Hz, 1H), 7.08 (s, 1H), 6.53 (d, J = 7.20 Hz, 1H), 4.87-4.91 (m, 1H), 3.45 (t, J = 5.60 Hz, 2H), 3.17 (dd, J = 14.6, 11.0 Hz, 1H), 2.91 (dd, J = 14.0, 11.0 Hz, 1H), 2.76-2.87 (m, 4H), 2.68 (s, 3H), 2.55-2.61 (m, 2H), 2.12-2.18 (m, 1H), 2.00-2.07 (m, 1H), 1.90-1.98 (m, 2H), LC-MS retention time = 0.98 min; m/z = 424.2 [M + H]$^+$ KINETIX XB-C18, (3 x 75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 220 nm, Human αVβ6 IC50 (nM) = 1.9 | Example 145/146 |
| 148 | 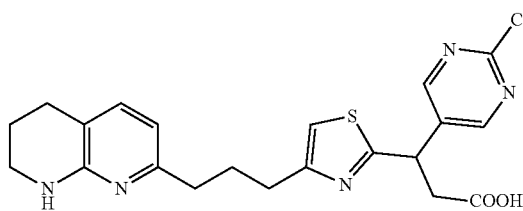 [SMILES: Cc1cncc(C(CC(=O)O)c2nc(CCCc3ccc4c(n3)NCCC4)cs2)c1]<br>3-(2-methylpyrimidin-5-yl)-3-(4-(3-(5,6,7,8-tetrahydro-1,8-naphthyridin-2-yl)propyl)thiazol-2-yl)propanoic acid | Chiral SFC: Retention time: 2.81 min. (Chiralpak AD-H (250 x 21) mm, 5 micron column; % CO2: 50%; % Co solvent: 45% (0.2% NH4OH in MeOH and ACN (1:1)); Total Flow: 70 g/min; Back Pressure: 100 bar; Temperature: 30° C.; Detection: UV at 245 nm), $^1$H NMR (400 MHz, CD$_3$OD) δ ppm 8.74 (s, 2H), 7.42 (d, J = 3.20 Hz, 1H), 7.08 (s, 1H), 6.53 (d, J = 7.20 Hz, 1H), 4.87-4.91 (m, 1H), 3.45 (t, J = 5.60 Hz, 2H), 3.17 (dd, J = 14.6, 11.0 Hz, 1H), 2.91 (dd, J = 14.0, 11.0 Hz, 1H), 2.76-2.87 (m, 4H), 2.68 (s, 3H), 2.55-2.61 (m, 2H), 2.12-2.18 (m, 1H), 2.00-2.07 (m, 1H), 1.90-1.98 (m, 2H), LC-MS retention time = 0.98 min; m/z = 424.2 | Example 145/146 |

| Example | Structure | Prep-HPLC/SFC conditions, $^1$H NMR and LC-MS data | Method |
|---|---|---|---|
| | | [M + H]$^+$ KINETIX XB-C18, (3 × 75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 220 nm, Human αVβ6 IC50 (nM) = 6.0 | |
| 149 | 3-(2-methylpyrimidin-5-yl)-3-(4-(3-(5,6,7,8-tetrahydro-1,8-naphthyridin-2-yl)propyl)thiazol-2-yl)propanoic acid | Chiral SFC: Retention time: 4.59 min. (Chiralpak AD-H (250 × 21) mm; 5 micron column; % CO$_2$: 50%; % Co solvent: 45% (0.2% NH$_4$OH in MeOH and ACN (1:1); Total Flow: 70 g/min; Back Pressure: 100 bar; Temperature: 30°C; Detection: UV at 245 nm), $^1$H NMR (400 MHz, CD$_3$OD) δ ppm 8.74 (s, 2H), 7.42 (d, J = 3.20 Hz, 1H), 7.08 (s, 1H), 6.53 (d, J = 7.20 Hz, 1H), 4.87-4.91 (m, 1H), 3.45 (t, J = 5.60 Hz, 2H), 3.17 (dd, J = 14.6, 11.0 Hz, 1H), 2.91 (dd, J = 14.0, 11.0 Hz, 1H), 2.76-2.87 (m, 4H), 2.68 (s, 3H), 2.55-2.61 (m, 2H), 2.12-2.18 (m, 1H), 2.00-2.07 (m, 1H), 1.90-1.98 (m, 2H), LC-MS retention time = 0.98 min; m/z = 424.2 [M + H]$^+$ KINETIX XB-C18, (3 × 75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min. then hold 0.4 min. at 20% B with flow rate 1-1.5 mL/min: Detection: UV at 220 nm, Human αVβ6 IC50 (nM) = 7.2 | Example 145/146 |
| 150 | 3-(5-methylpyridin-3-yl)-3-(4-(3-(5,6,7,8-tetrahydro-1,8-naphthyridin-2-yl)propyl)thiazol-2-yl)propanoic acid | Chiral SFC: Retention time: 4.54 min, Lux Cellulose C4 (250 x 21.2) mm; 5 micron: Mobile Phase: 0.4% DEA in ACN: MeOH (70:30), Flow: 25 mL/min. $^1$H NMR (400 MHz, CD$_3$OD) δ ppm 8.37 (s, 1H), 8.31 (s, 1H), 7.70 (s, 1H), 7.48 (d, J = 7.53 Hz, 1H), 7.07 (s, 1H), 6.57 (d, J = 7.03 Hz, 1H), 4.85-4.95 (m, 1H), 3.49 (t, J = 5.60 Hz, 2H), 3.24 (dd, J = 14.81, 10.79 Hz, 1H), 2.85-2.95 (m, 2H), 2.83 (t, J = 5.20 Hz, 2H), 2.75-2.83(m, 1H), 2.49-2.67 (m, 2H), 2.37 (s, 3H), 2.11-2.24 (m, 1H), 2.00-2.09 (m, 1H), 1.90-1.99 (m, 2H), LC-MS retention time = 1.14 min; m/z = 423.2 [M + H]$^+$ Column-KINETIX XB-C18, (3 × 75) mm; 2.6 micron column; Flow rate: 1 mL/min; Mobile Phase A: 10 mM HCO$_2$NH$_4$ in 98% Water/2% ACN: Mobile Phase B: 10 mM HCO$_2$NH$_4$ in 2% Water/98% ACN; 50% B to 100% B over 4.6 min. then hold 0.4 min. at 20% B with flow rate 1.5 mL/min: Detection: UV at 220 nm, Human αVβ6 IC50 (nM) = 87 | Example 145/146 |
| 151 | 3-(5-methylpyridin-3-yl)-3-(4-(3-(5,6,7,8-tetrahydro-1,8-naphthyridin-2-yl)propyl)thiazol-2-yl)propanoic acid | Chiral SFC: Retention time: 5.79 min, Lux Cellulose C4 (250 x 21.2) mm; 5 micron; Mobile Phase: 0.4% DEA in ACN: MeOH (70:30), Flow: 25 mL/min. $^1$H NMR (400 MHz, CD$_3$OD) δ ppm 8.37 (s, 1H), 8.31 (s, 1H), 7.70 (s, 1H), 7.48 (d, J = 7.53 Hz, 1H), 7.07 (s, 1H), 6.57 (d, J = 7.03 Hz, 1H), 4.85-4.95 (m, 1H), 3.49 (t, J = 5.60 Hz, 2H), 3.24 (dd, J = 14.81, 10.79 Hz, 1H), 2.85-2.95 (m, 2H), 2.83 (t, J = 5.20 Hz, 2H), 2.75-2.83 (m, 1H), 2.49-2.67 (m, 2H), 2.37 (s, 3H), 2.11-2.24 (m, 1H), 2.00-2.09 (m, 1H), 1.90-1.99 (m, 2H), LC-MS | Example 145/146 |

| Example | Structure | Prep-HPLC/SFC conditions, ¹H NMR and LC-MS data | Method |
|---------|-----------|---------------------------------------------------|--------|
|         |           | retention time = 1.15 min; m/z = 423.2 [M + H]⁺ Column-KINETIX XB-C18, (3 × 75) mm, 2.6 micron column; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 50% B to 100% B over 4.6 min, then hold 0.4 min. at 20% B with flow rate 1.5 mL/min; Detection: UV at 220 nm, Human αVβ6 IC50 (nM) = 2.6. |        |

Example 152 and Example 153

Example 152: first eluting enantiomer of 3-(3-fluoro-4-methoxyphenyl)-3-(2-(3-(5,6,7,8-tetrahydro-1,8-naphthyridin-2-yl)propyl)thiazol-4-yl) propanoic acid Example 153: second eluting enantiomer of 3-(3-fluoro-4-methoxyphenyl)-3-(2-(3-(5,6,7,8-tetrahydro-1,8-naphthyridin-2-yl)propyl)thiazol-4-yl) propanoic acid

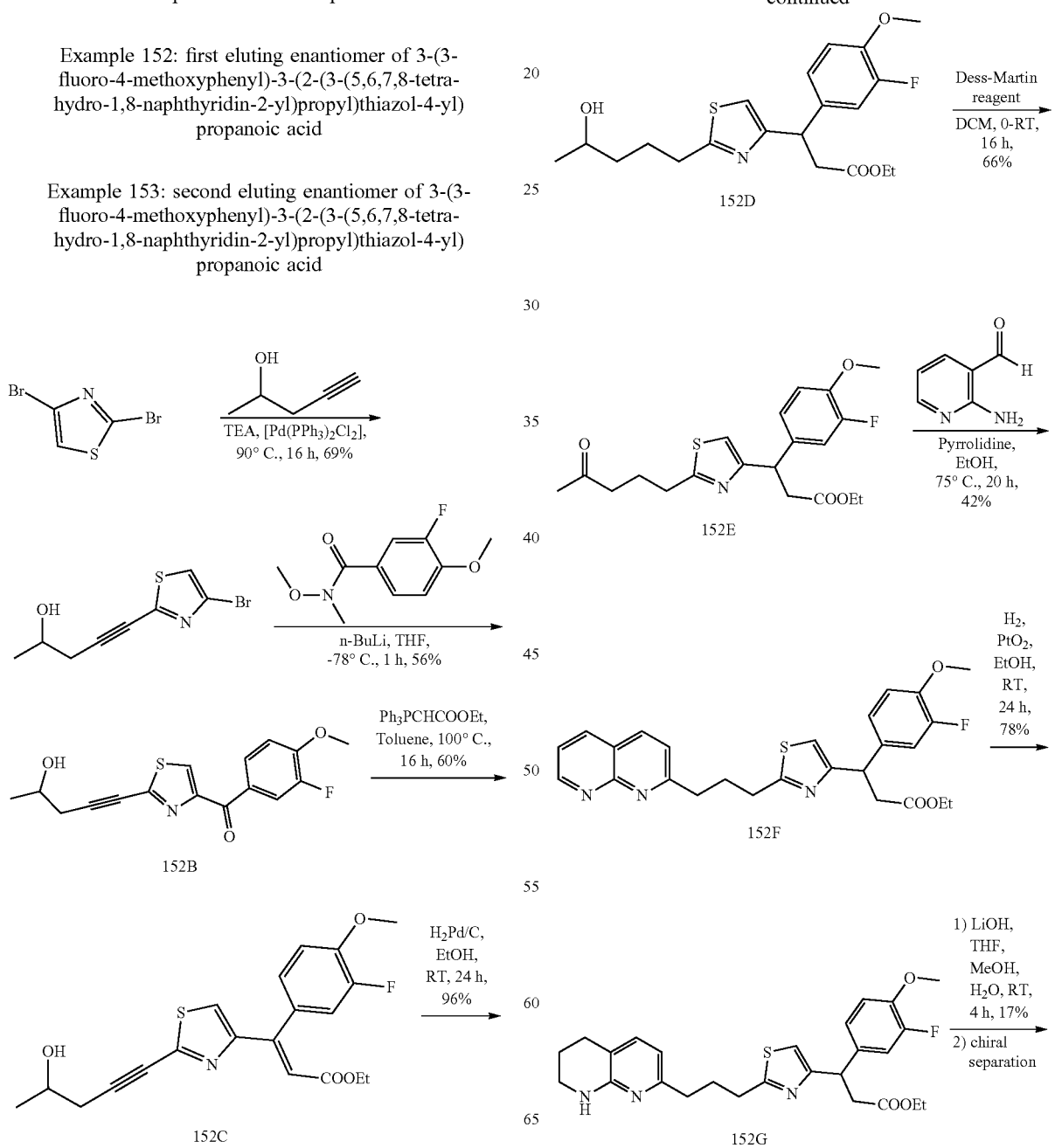

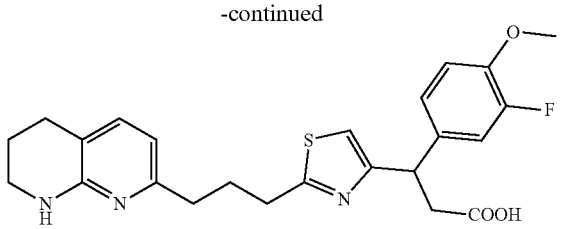

Example 152: first eluting enantiomer
Example 153: second eluting enantiomer

5-(4-Bromothiazol-2-yl)pent-4-yn-2-ol (152A)

To a solution of 2,4-dibromothiazole (500 mg, 2.058 mmol) and pent-4-yn-2-ol (208 mg, 2.47 mmol) in TEA (5 mL) was added copper(I) iodide (19.6 mg, 103.0 mmol) followed by bis(triphenylphosphine)palladium(II) dichloride (72.2 mg, 103 mmol) under nitrogen atmosphere. The reaction mixture was degassed with argon for 2 min and then stirred at 80° C. for 16 h. The reaction mixture was filtered and the filtrate concentrated under reduced pressure to get crude product as brown oil. The crude product was purified by combiflash chromatography (24 g Redisep® SiO$_2$ column, eluting with 52% EtOAc in pet ether) to afford the title compound 152A (350 mg, 69%) as a pale brown oil. LC-MS retention time=1.23 min; m/z=248.0 [M+H]$^+$ LUNA 3.0 C18, (4×20) mm, 2.6 micron column; Mobile Phase A: 0.1% TFA in water. Mobile Phase B: 0.1% TFA in ACN; 20% B to 98% B over 2.7 min, then hold 0.3 min. at 20% B with flow rate 1.0 mL/min; Detection: UV at 220 nm. $^1$H NMR (400 MHz, CDCl$_3$) δ ppm 7.26 (s, 1H), 4.11 (m, 1H), 2.64-2.67 (m, 2H), 1.98 (s, 1H), 1.34 (d, J=6.00 Hz, 3H).

(3-Fluoro-4-methoxyphenyl)(2-(4-hydroxypent-1-yn-1-yl)thiazol-4-yl)methanone (152B)

To a stirred solution of 5-(4-bromothiazol-2-yl)pent-4-yn-2-ol 152A (300 mg, 1.219 mmol) in THF (8 mL) under nitrogen atmosphere was added n-BuLi (0.731 mL, 2.5 molar solution in hexane, 1.82 mmol) at −78° C. and the resulting dark brown solution was stirred at the same temperature for 30 min. 3-Fluoro-N,4-dimethoxy-N-methylbenzamide (234 mg, 1.097 mmol) in 3.0 mL THF was added and the reaction was continued to stir at the same temperature for 1 h. Reaction was quenched with water (20 mL) and diluted with ethyl acetate (30 mL). The organic layer was separated, washed with brine, dried over anhydrous sodium sulphate and evaporated under vacuum to get the crude product. The crude product was purified by combiflash chromatography (24 g Redisep® SiO$_2$ column, eluting with 66% EtOAc in n-hexanes) to afford the title compound 152B (220 mg, 56%) as a pale yellow oil. LC-MS retention time=2.42 min; m/z=351.0 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1.0 mL/min; Detection: UV at 220 nm. $^1$H NMR (400 MHz, CDCl$_3$) δ ppm 8.20 (s, 1H), 7.65-7.72 (m, 2H), 7.6 (t, J=8.4 Hz, 1H), 4.14 (q, J=6.00 Hz, 1H), 3.99 (s, 3H), 2.70 (m, 2H), 2.04 (s, 1H), 1.35 (dd, J=4.00 Hz, 3H).

Ethyl (E)-3-(3-fluoro-4-methoxyphenyl)-3-(2-(4-hydroxypent-1-yn-1-yl)thiazol-4-yl)acrylate (152C)

To a stirred solution of (3-fluoro-4-methoxyphenyl)(2-(4-hydroxypent-1-yn-1-yl)thiazol-4-yl)methanone (200 mg, 0.626 mmol) 152B in toluene (10 mL) under nitrogen atmosphere was added (carbethoxymethylene)triphenylphosphorane (262 mg, 0.752 mmol) and the reaction mixture was stirred at 100° C. for 16 h. The reaction mixture was concentrated under reduced pressure to get the crude product. The crude product was purified by combiflash chromatography (12 g Redisep® SiO$_2$ column, eluting with 67% EtOAc in n-hexanes) to afford the title compound 152C (330 mg, 60%) as a white solid. LC-MS retention time=1.86 min, (m/z=390.2 [M+H]$^+$ AQUITY UPLC BEH C18 (3.0× 50) mm, 1.7 micron column; Mobile Phase A: 5 mM ammonium acetate in 95% Water/5% ACN; Mobile Phase B: 5 mM ammonium acetate in 5% Water/95% ACN; Gradient time 1.7 min. 20% B to 90% B over 1.7 min. Flow rate 0.7 mL/min; Detection: UV at 220 nm.

Ethyl 3-(3-fluoro-4-methoxyphenyl)-3-(2-(4-hydroxypentyl)thiazol-4-yl)propanoate (152D)

To a degassed solution of ethyl (E)-3-(3-fluoro-4-methoxyphenyl)-3-(2-(4-hydroxypent-1-yn-1-yl)thiazol-4-yl)acrylate 152C (200 mg, 0.506 mmol) in EtOH (5 mL) was added 10% palladium on carbon (20 mg, 0.303 mmol) and the resulting reaction mixture was stirred under hydrogen bladder pressure at RT for 16 h. The reaction mixture was filtered through Celite and the filtrate was concentrated under vacuum to afford the crude title compound 152D (180 mg, 96%) as pale yellow oil. LC-MS retention time=2.1 min; m/z=396.2 [M+H]$^+$ LUNA 3.0 C18, (4×20) mm, 2.6 micron column; Mobile Phase A: 0.1% TFA in water. Mobile Phase B: 0.1% TFA in ACN; 20% B to 98% B over 2.7 min, then hold 0.3 min. at 20% B with flow rate 1.0 mL/min; Detection: UV at 220 nm.

Ethyl 3-(3-fluoro-4-methoxyphenyl)-3-(2-(4-oxopentyl)thiazol-4-yl)propanoate (152E)

To a solution of ethyl 3-(3-fluoro-4-methoxyphenyl)-3-(2-(4-hydroxypentyl)thiazol-4-yl)propanoate 152D (180 mg, 0.458 mmol) in DCM (15 mL) was added Dess-Martin periodinane (324 mg, 0.916 mmol) at 0° C. and the resulting mixture was stirred at RT for 2 h. The reaction mass was diluted with DCM (20 mL), washed with 20% sodium bicarbonate solution (20 mL), brine solution (10 mL), dried over sodium sulfate, filtered and the filtrate evaporated under reduced pressure to get white crude product. The crude product was purified by combiflash chromatography (12 g Redisep® SiO$_2$ column, eluting with 91% EtOAc in pet ether) to afford the title compound 152E (100 mg, 66%) as a pale yellow solid. LC-MS retention time=1.24 min; m/z=394.3 [M+H]$^+$ AQUITY UPLC BEH C18 (3.0×50) mm; 1.7 micron column; Mobile Phase A: 5 mM ammonium acetate in 95% Water/5% ACN; Mobile Phase B: 5 mM ammonium acetate in 5% Water/95% ACN; Gradient time 1.7 min. 20% B to 90% B over 1.7 min. Flow rate 0.7 mL/min; Detection: UV at 220 nm.

Ethyl 3-(2-(3-(1,8-naphthyridin-2-yl)propyl)thiazol-4-yl)-3-(3-fluoro-4-methoxyphenyl)-propanoate (152F)

To a stirred solution of ethyl 3-(3-fluoro-4-methoxyphenyl)-3-(2-(4-oxopentyl)thiazol-4-yl)propanoate 152E (100 mg, 0.254 mmol) and 2-aminonicotinaldehyde (37.6 mg, 0.303 mmol) in ethanol (5 mL) under nitrogen was added pyrrolidine (0.03 mL, 0.504 mmol) and the mixture was stirred at 70° C. for 4 h. The reaction mixture concentrated to get the crude brown oil. The crude product was purified by combiflash chromatography (12 g Redisep® SiO2 column, eluting with 10% MeOH in chloroform to afford the title compound 152F (75 mg, 42%) as a pale yellow liquid. LC-MS retention time=1.24 min; m/z=480.4 [M+H]+ AQUITY UPLC BEH C18 (3.0×50 mm) 1.7 micron column; Mobile Phase A: 5 mM ammonium acetate in 95% Water/5% ACN; Mobile Phase B: 5 mM ammonium acetate in 5% Water/95% ACN; Gradient time 1.7 min. 20% B to 90% B over 1.7 min. Flow rate 0.7 mL/min; Detection: UV at 220 nm.

Ethyl 3-(3-fluoro-4-methoxyphenyl)-3-(2-(3-(5,6,7,8-tetrahydro-1,8-naphthyridin-2-yl)propyl)thiazol-4-yl)propanoate (152G)

To a stirred solution of ethyl 3-(2-(3-(1,8-naphthyridin-2-yl)propyl)thiazol-4-yl)-3-(3-fluoro-4-methoxyphenyl)propanoate 152F (75 mg, 0.154 mmol) in ethanol (8 mL) was added platinum(IV) oxide (2 mg, 6.61 μmol) under nitrogen atmosphere. The reaction mixture was degassed with hydrogen gas and stirred under hydrogen bladder pressure at RT for 16 h. The reaction mixture was filtered, washed with EtOH (5 mL), filtrate was evaporated under reduced pressure to afford the title crude product 152G (40 mg, 78%) as a pale yellow oil. LC-MS retention time=1.31 min; m/z=484.2 [M+H]+ LUNA 3.0 C18, (4×20) mm, 2.6 micron column; Mobile Phase A: 0.1% TFA in water. Mobile Phase B: 0.1% TFA in ACN; 20% B to 98% B over 2.7 min, then hold 0.3 min. at 20% B with flow rate 1.0 mL/min; Detection: UV at 220 nm.

Example 152: first eluting enantiomer of 3-(3-fluoro-4-methoxyphenyl)-3-(2-(3-(5,6,7,8-tetrahydro-1,8-naphthyridin-2-yl)propyl)thiazol-4-yl)propanoic acid Example 153: second eluting enantiomer of 3-(3-fluoro-4-methoxyphenyl)-3-(2-(3-(5,6,7,8-tetrahydro-1,8-naphthyridin-2-yl)propyl)thiazol-4-yl)propanoic acid To a stirred solution of ethyl 3-(3-fluoro-4-methoxyphenyl)-3-(2-(3-(5,6,7,8-tetrahydro-1,8-naphthyridin-2-yl)propyl)thiazol-4-yl)propanoate (40.0 mg, 0.083 mmol) 152G in THF (1 mL), MeOH (1 mL) and water (1 mL) was added LiOH·H2O (3.96 mg, 0.165 mmol) and the resulting mixture was stirred at RT for 4 h. Then, citric acid (32 mg, 0.165 mmol) was added and stirred at RT for 10 min. The reaction mixture was filtered, concentrated under reduced pressure to get the crude product. The crude product was purified by preparative HPLC (Sunfire OBD (250×30) mm; 5 micron; Mobile Phase A: 10 mM NH4OAc in water; Mobile Phase B: ACN:MeOH (1:1); Flow rate: 17.0 mL/min; time (min)/% B: 0/20, 02/20, 15/60, 15.5/100) to afford the pure racemate. Individual enantiomers were separated by chiral SFC (Chiralpak IG (250×4.6) mm, 5 micron column; % CO2: 50%; % Co solvent: 50% (0.2% NH4OH in MeOH and ACN (1:1); Total Flow: 4 g/min; Back Pressure: 100 bar; Temperature: 30° C.; Detection: UV at 245 nm). First eluting enantiomer, Example 152 (retention time 8.4 min., 3 mg, 7%) was isolated as a white solid. LC-MS retention time=1.92 min; m/z=456.2 [M+H]+ (KINETIX XB-C18, (3×75) mm, 2.6 micron column; Mobile Phase A: 10 mM HCO2NH4 in 98% Water/2% ACN; Mobile Phase B: 10 mM HCO2NH4 in 2% Water/98% ACN; 20% B to 100% B over 4.6 min, then hold 0.4 min. at 20% B with flow rate 1.0 mL/min; Detection: UV at 220 nm. 1H NMR (400 MHz, DMSO-d6) δ ppm 7.21 (dd, J=1.60, 12.00 Hz, 1H), 7.09-7.11 (m, 3H), 7.02 (dd, J=7.20, Hz, 1H), 6.27 (bs, 1H), 6.26 (dd, J=7.20, Hz, 1H), 4.68 (t, J=7.60 Hz, 1H), 3.80 (s, 3H), 3.23 (t, J=7.20 Hz, 2H), 3.18 (dd, J=7.60, Hz, 1H), 2.89 (dd, J=8.00, 16.00 Hz, 1H), 2.89 (dd, J=8.00, 16.00 Hz, 1H), 2.59-2.69 (m, 4H), 2.45 (m, 2H), 1.90-1.93 (m, 2H), 1.73-1.76 (m, 2H). Human αVβ6 IC50 (nM)=180. Second eluting enantiomer, Example 153 (retention time 11.0 min., 4 mg, 9%) as a white solid. LC-MS retention time=1.98 min; m/z=456.2 [M+H]+ KINETIX XB-C18, (3×75) mm, 2.6 micron column; Mobile Phase A: 10 mM HCO2NH4 in 98% Water/2% ACN; Mobile Phase B: 10 mM HCO2NH4 in 2% Water/98% ACN; 20% B to 100% B over 4.6 min, then hold 0.4 min. at 20% B with flow rate 1.0 mL/min; Detection: UV at 220 nm. 1H NMR (400 MHz, DMSO-d6) δ ppm 7.21 (dd, J=1.60, 12.00 Hz, 1H), 7.09-7.11 (m, 3H), 7.02 (dd, J=7.20, Hz, 1H), 6.27 (bs, 1H), 6.26 (dd, J=7.20, Hz, 1H), 4.68 (t, J=7.60 Hz, 1H), 3.80 (s, 3H), 3.23 (t, J=7.20 Hz, 2H), 3.18 (dd, J=7.60, Hz, 1H), 2.89 (dd, J=8.00, 16.00 Hz, 1H), 2.89 (dd, J=8.00, 16.00 Hz, 1H), 2.59-2.69 (m, 4H), 2.45 (m, 2H), 1.90-1.93 (m, 2H), 1.73-1.76 (m, 2H). Human αVβ6 IC50 (nM)=54.

Example 154, Example 155, Example 156, and Example 157

Example 154: first eluting diastereomer of 3-(6-methoxypyridin-3-yl)-3-(4-(3-(1,2,3,4-tetrahydro-1,8-naphthyridin-2-yl)propyl)thiazol-2-yl)propanoic acid Example 155: second eluting diastereomer of 3-(6-methoxypyridin-3-yl)-3-(4-(3-(1,2,3,4-tetrahydro-1,8-naphthyridin-2-yl)propyl)thiazol-2-yl)propanoic acid Example 156: second eluting diastereomer of 3-(6-methoxypyridin-3-yl)-3-(4-(3-(1,2,3,4-tetrahydro-1,8-naphthyridin-2-yl)propyl)thiazol-2-yl)propanoic acid Example 157: second eluting diastereomer of 3-(6-methoxypyridin-3-yl)-3-(4-(3-(1,2,3,4-tetrahydro-1,8-naphthyridin-2-yl)propyl)thiazol-2-yl)propanoic acid

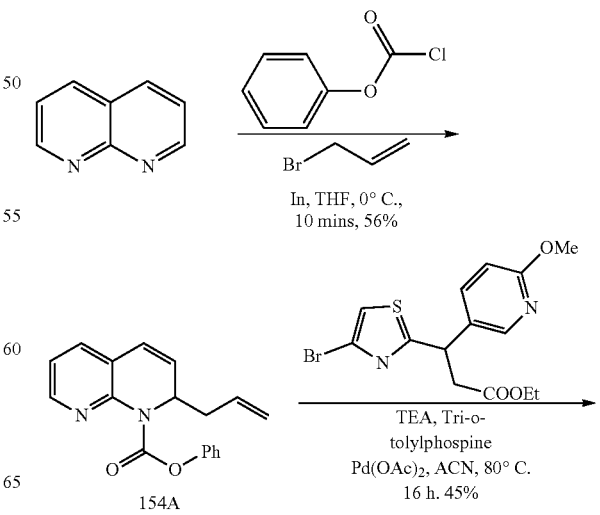

239

-continued

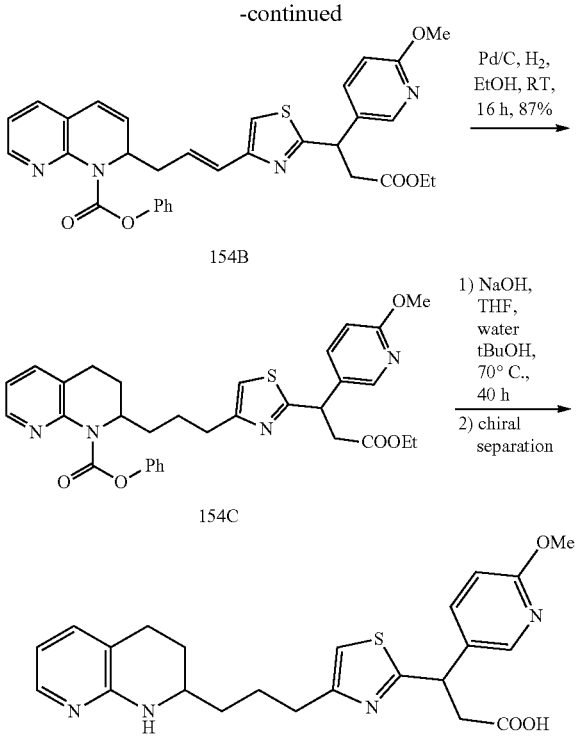

Example 154: first eluting diastereomer
Example 155: second eluting diastereomer
Example 156: third eluting diastereomer
Example 157: fourth eluting diastereomer Phenyl 2-allyl-1,8-naphthyridine-1(2H)-carboxylate (154A)

To a cooled solution of 1,8-naphthyridine (1 g, 7.68 mmol) in THF (35 mL) was added phenyl chloroformate (1.060 mL, 8.45 mmol) at 0° C. and the reaction mixture stirred at the same temperature for 30 min. Allyl indium bromide (prepared freshly by adding bromoprop-1-ene (1.992 mL, 23.05 mmol) dropwise to a suspension of indium (1.764 g, 15.37 mmol) in DMF (10 mL) at RT and stirring for 20 min) was added at 0° C. and stirred at the same temperature for 10 min. The reaction mixture diluted with water (50 mL) and extracted with ethyl acetate (2×50 mL). The combined organic layer was washed with water (2×50 mL), brine solution (50 mL), and dried over anhydrous sodium sulphate, filtered and then concentrated. The crude product was purified by combiflash chromatography (24 g Redisep® SiO$_2$ column, eluting with 20% ethyl acetate in n-hexane) to afford the title compound 154A (1.25 g, 56%) as an off white solid. LC-MS retention time=2.85 min; m/z=293.2 [M+H]$^+$ Column: KINETIX XB-C18, (3×75) mm; 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 20% B with flow rate 1.5 mL/min; Detection: UV at 220 nm. $^1$H NMR (400 MHz, DMSO-d$_6$) δ ppm 8.29 (dd, J=4.77, 1.76 Hz, 1H), 7.67 (dd, J=7.53, 2.01 Hz, 1H), 7.38-7.46 (m, 2H), 7.23-7.29 (m, 1H), 7.16-7.22 (m, 3H), 6.69 (d, J=9.54 Hz, 1H), 6.28 (dd, J=9.54, 6.02 Hz, 1H), 5.67-5.80 (m, 1H), 5.09 (dd, J=6.00, 13.20 Hz, 1H), 5.02 (s, 1H), 4.99 (d, J=5.02 Hz, 1H), 2.28-2.37 (m, 1H), 2.10-2.19 (m, 1H).

240

Phenyl (E)-2-(3-(2-(3-ethoxy-1-(6-methoxypyridin-3-yl)-3-oxopropyl)thiazol-4-yl)allyl)-1,8-naphthyridine-1(2H)-carboxylate (154B)

To a degassed solution of phenyl 2-allyl-1,8-naphthyridine-1(2H)-carboxylate 154A (331 mg, 1.131 mmol) in ACN (10 mL) was added ethyl 3-(4-bromothiazol-2-yl)-3-(6-methoxypyridin-3-yl)propanoate (350 mg, 0.943 mmol), TEA (0.263 mL, 1.886 mmol), tri-o-tolylphosphine (28.7 mg, 0.094 mmol) and palladium(II) acetate (21.17 mg, 0.094 mmol). The reaction mixture was then heated to 80° C. and stirred for 16 h. After completion of the reaction, the reaction mixture was filtered through Celite and the filtrate was concentrated. The crude product was purified by combiflash chromatography (12 g Redisep® SiO$_2$ column, eluting with 40% ethyl acetate in n-hexane) to afford the title compound 154B (250 mg, 45%) as a pale brown gummy liquid. LC-MS retention time=3.54 min; m/z=583.2 [M+H]$^+$ Column: KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 20% B with flow rate 1.5 mL/min; Detection: UV at 254 nm.

Phenyl 2-(3-(2-(3-ethoxy-1-(6-methoxypyridin-3-yl)-3-oxopropyl)thiazol-4-yl)propyl)-3,4-dihydro-1,8-naphthyridine-1(2H)-carboxylate (154C)

To a degassed solution of phenyl (E)-2-(3-(2-(3-ethoxy-1-(6-methoxypyridin-3-yl)-3-oxopropyl)thiazol-4-yl)allyl)-1,8-naphthyridine-1(2H)-carboxylate 154B (250 mg, 0.429 mmol) in ethanol (10 mL) was added palladium on carbon (50 mg, 0.047 mmol) and the reaction mixture was stirred under hydrogen balloon atmosphere at the RT for 16 h. The reaction mixture was filtered through Celite pad and the filtrate was concentrated to afford the title compound (220 mg, 87%) as a pale brown gummy liquid. The crude product 154C was taken to the next step without further purification. LC-MS retention time=1.90 min; m/z=587.2 [M+H]$^+$ Column: KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm.

Example 154: first eluting diastereomer of 3-(6-methoxypyridin-3-yl)-3-(4-(3-(1,2,3,4-tetrahydro-1,8-naphthyridin-2-yl)propyl)thiazol-2-yl)propanoic acid Example 155: second eluting diastereomer of 3-(6-methoxypyridin-3-yl)-3-(4-(3-(1,2,3,4-tetrahydro-1,8-naphthyridin-2-yl)propyl)thiazol-2-yl)propanoic acid Example 156: second eluting diastereomer of 3-(6-methoxypyridin-3-yl)-3-(4-(3-(1,2,3,4-tetrahydro-1,8-naphthyridin-2-yl)propyl)thiazol-2-yl)propanoic acid Example 157: second eluting diastereomer of 3-(6-methoxypyridin-3-yl)-3-(4-(3-(1,2,3,4-tetrahydro-1,8-naphthyridin-2-yl)propyl)thiazol-2-yl)propanoic acid To a solution of phenyl 2-(3-(2-(3-ethoxy-1-(6-methoxypyridin-3-yl)-3-oxopropyl)thiazol-4-yl)propyl)-3,4-dihydro-1,8-naphthyridine-1(2H)-carboxylate 154C (220 mg, 0.375 mmol) in THF (4 mL) and t-BuOH (4 mL) was added a solution of sodium hydroxide (75 mg, 1.875 mmol)) in water (2 mL) and the resulting reaction mixture was stirred at 70° C. for 40 h. After completion of the reaction, citric acid (216 mg, 1.125 mmol) was added and the reaction mixture was stirred at the RT for 10 min. The reaction mixture was concentrated and taken for purification as such. The crude product was purified by preparative reverse phase HPLC (SUNFIRE C18 (150×19) mm; 5 micron; Mobile Phase A: 10 mM ammonium acetate (pH=4.5); Mobile Phase B: ACN; flow rate: 15 mL/min; Time (min)/% B: 0/20, 25/60) afford the racemate of title compound (70 mg). Individual diastereomers of 3-(6-methoxypyridin-3-yl)-3-(4-(3-(1,2,3,4-tetrahydro-1,8-naphthyridin-2-yl)propyl)thiazol-2-yl)propanoic acid was separated by chiral SFC (Lux-cellulose-2 (250×30) mm; 5 micron; 50% CO$_2$ and 50% of 0.2% NH$_4$OH in MeOH+ACN (1:1) as co-solvent; Total Flow: 80 g/min; Back Pressure: 100 bar; Temperature: 30° C.; Detection: UV at 245 nM). First eluting diastereomer, Example 154 (Retention time 15.2 min., 7 mg, 4%) was isolated as an off white solid. LC-MS retention time=1.68 min; m/z=439.2 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CD$_3$OD) δ ppm 8.15 (d, J=2.01 Hz, 1H) 7.71 (dd, J=8.53, 2.51 Hz, 1H), 7.67 (d, J=6.02 Hz, 1H), 7.53 (d, J=7.03 Hz, 1H), 7.05 (s, 1H), 6.80 (d, J=8.53 Hz, 1H), 6.64 (t, J=6.53 Hz, 1H), 4.80-4.90 (m, 1H), 3.91 (s, 3H), 3.54-3.63 (m, 1H), 3.13-3.25 (m, 1H), 2.88 (dd, J=13.30, 4.77 Hz, 1H), 2.76-2.85 (m, 4H), 1.88-2.05 (m, 3H), 1.45-1.70 (m, 3H). Human αVβ6 IC50 (nM)=210. Second eluting diastereomer, Example 155 (Retention time 17.2 min., 6 mg, 3.6%) was isolated as an off white solid. LC-MS retention time J=1.69 min; m/z=439.2 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CD$_3$OD) δ ppm 8.12 (d, J=2.01 Hz, 1H), 7.68 (d, J=6.53 Hz, 1H), 7.64 (dd, J=8.53, 2.01 Hz, 1H), 7.52 (d, J=7.53 Hz, 1H), 7.03 (s, 1H), 6.78 (d, J=9.04 Hz, 1H), 6.67 (t, J=6.53 Hz, 1H), 4.82 (dd, J=10.29, 5.27 Hz, 1H), 3.91 (s, 3H), 3.58 (m, 1H), 3.29-3.33 (m, 1H), 2.70-2.95 (m, 5H), 1.93-2.05 (m, 2H), 1.77-1.88 (m, 1H), 1.56-1.74 (m, 2H), 1.43-1.54 (m, 1H). Human αVβ6 IC50 (nM)=8.1. Third eluting diastereomer, Example 156 (Retention time 19.3. min., 6 mg, 3.6%) was isolated as an off white solid, LC-MS retention time=1.37 min; m/z=439.2 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CD$_3$OD) δ ppm 8.12 (d, J=2.01 Hz, 1H), 7.68 (d, J=6.02 Hz, 1H), 7.65 (dd, J=8.53, 2.51 Hz, 1H), 7.50 (d, J=7.03 Hz, 1H), 7.03 (s, 1H), 6.78 (d, J=8.53 Hz, 1H), 6.65 (t, J=6.53 Hz, 1H), 4.83 (dd, J=9.79, 5.27 Hz, 1H), 3.90 (s, 3H), 3.53-3.62 (m, 1H), 3.29-3.33 (m, 1H), 2.68-2.95 (m, 5H), 1.91-2.04 (m, 2H), 1.76-1.88 (m, 1H), 1.56-1.73 (m, 2H), 1.41-1.55 (m, 1H). Human αVβ6 IC50 (nM)=260. Fourth eluting diastereomer, Example 157 (Retention time 23.1 min., 6 mg, 3.6%) was isolated as an off white solid. LC-MS retention time=1.37 min; m/z=439.2 [M+H]$^+$ Column—KINETIX XB-C18, (3×75) mm, 2.6 micron column; Flow rate: 1 mL/min; Mobile Phase A: 10 mM HCO$_2$NH$_4$ 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CD$_3$OD) δ ppm 8.15 (d, J=2.01 Hz, 1H), 7.71 (dd, J=8.53, 2.51 Hz, 1H), 7.66 (d, J=6.53 Hz, 1H), 7.54 (d, J=7.03 Hz, 1H), 7.05 (s, 1H), 6.80 (d, J=9.04 Hz, 1H), 6.67 (t, J=6.53 Hz, 1H), 4.85 (dd, J=13.20, 5.20 Hz, 1H), 3.91 (s, 3H) 3.55-3.63 (m, 1H), 3.14-3.25 (m, 1H), 2.88 (dd, J=13.80, 5.27 Hz, 1H), 2.77-2.85 (m, 4H), 1.89-2.05 (m, 3H), 1.46-1.70 (m, 3H). Human αVβ6 IC50 (nM)=27.

Example 158, Example 159, Example 160, and Example 161

Example 158: first eluting diastereomer of 3-(3-fluoro-4-methoxyphenyl)-3-(4-(3-(1,2,3,4-tetrahydro-1,8-naphthyridin-2-yl)propyl)thiazol-2-yl)propanoic acid Example 159: second eluting diastereomer of 3-(3-fluoro-4-methoxyphenyl)-3-(4-(3-(1,2,3,4-tetrahydro-1,8-naphthyridin-2-yl)propyl)thiazol-2-yl)propanoic acid Example 160: third eluting diastereomer of 3-(3-fluoro-4-methoxyphenyl)-3-(4-(3-(1,2,3,4-tetrahydro-1,8-naphthyridin-2-yl)propyl)thiazol-2-yl)propanoic acid Example 161: fourth eluting diastereomer of 3-(3-fluoro-4-methoxyphenyl)-3-(4-(3-(1,2,3,4-tetrahydro-1,8-naphthyridin-2-yl)propyl)thiazol-2-yl)propanoic acid

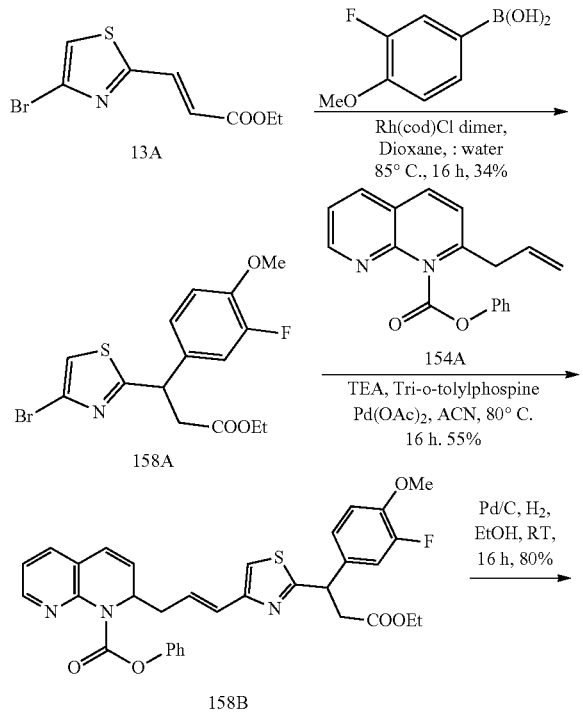

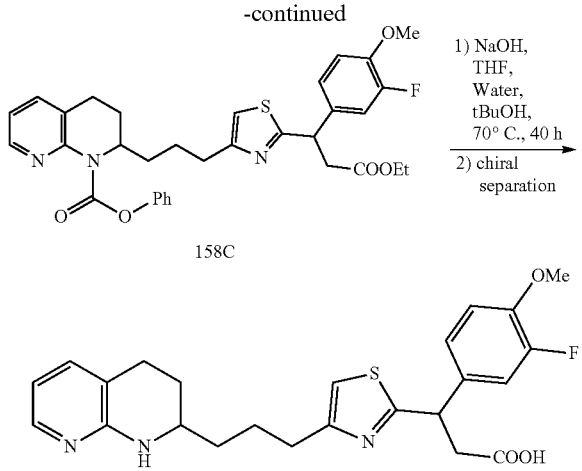

Example 158: first eluting diastereomer
Example 159: second eluting diastereomer
Example 160: third eluting diastereomer
Example 161: fourth eluting diastereomer Ethyl 3-(4-bromothiazol-2-yl)-3-(3-fluoro-4-methoxyphenyl)propanoate (158A)

Ethyl (E)-3-(4-bromothiazol-2-yl)acrylate 13A (1 g, 3.82 mmol) in 1,4-dioxane (35 mL) and water (5 mL) was purged with argon for 5 min. Chloro(1,5-cyclooctadiene)rhodium(I) dimer (0.094 g, 0.191 mmol), (3-fluoro-4-methoxyphenyl)boronic acid (0.973 g, 5.72 mmol) and TEA (1.064 mL, 7.63 mmol) were added and the resulting reaction mixture was stirred at 85° C. for 16 h. The reaction mixture was diluted with water (50 mL) and extracted with EtOAc (2×50 mL). The combined organic layer was washed with brine (50 mL), dried ($Na_2SO_4$), filtered and concentrated. The crude product was purified by combiflash chromatography (24 g Redisep® $SiO_2$ column, eluting with 25% EtOAc in n-hexanes) to afford the title compound 158A (500 mg, 34%) as a pale brown oil. LC-MS retention time=3.25 min; m/z=388.0 [M+2H]$^+$ (KINETIX XB-C18, (3×75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm). $^1$H NMR (400 MHz, $CDCl_3$) □ ppm 7.06-7.10 (m, 2H), 7.05 (s, 1H), 6.85-7.03 (m, 1H), 4.74 (t, J=10.00 Hz, 1H), 4.08 (dq, J=9.60, 6.40 Hz, 2H), 3.87 (s, 3H), 3.40 (dd, J=9.60, 20.80 Hz, H), 2.97 (dd, J=10.80, 22.00 Hz, H), 1.18 (t, J=9.60 Hz, 3H).

Phenyl (E)-2-(3-(2-(3-ethoxy-1-(3-fluoro-4-methoxyphenyl)-3-oxopropyl)thiazol-4-yl)allyl)-1,8-naphthyridine-1(2H)-carboxylate 158B To a degassed solution of phenyl 2-allyl-1,8-naphthyridine-1(2H)-carboxylate (316 mg, 1.082 mmol 158A in acetonitrile (10 mL) was added ethyl 3-(4-bromothiazol-2-yl)-3-(3-fluoro-4-methoxyphenyl)propanoate (350 mg, 0.901 mmol, TEA (0.251 mL, 1.803 mmol), tri-o-tolylphosphine (27.4 mg, 0.090 mmol) and palladium(II) acetate (20.24 mg, 0.090 mmol). The reaction mixture was then heated to 80° C. and stirred for 16 h. After completion of the reaction, the reaction mixture was filtered through Celite and the filtrate concentrated. The crude product was purified by combiflash chromatography (12 g Redisep® $SiO_2$ column, eluting with 40% ethyl acetate in n-hexane) to afford the title compound 158B (300 mg, 55%) as a pale brown gummy liquid. LC-MS retention time=3.73 min; m/z=600.2 [M+H]$^+$ Column: KINETIX XB-C18, (3×75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 50% B to 100% B over 4.6 min, then hold 0.4 min. at 20% B with flow rate 1.5 mL/min; Detection: UV at 254 nm.

Phenyl 2-(3-(2-(3-ethoxy-1-(3-fluoro-4-methoxyphenyl)-3-oxopropyl)thiazol-4-yl)propyl)-3,4-dihydro-1,8-naphthyridine-1(2H)-carboxylate (158C)

To a degassed solution of phenyl (E)-2-(3-(2-(3-ethoxy-1-(3-fluoro-4-methoxyphenyl)-3-oxopropyl)thiazol-4-yl)allyl)-1,8-naphthyridine-1(2H)-carboxylate 158B (300 mg, 0.500 mmol) in ethanol (10 mL) was added palladium on carbon (60 mg, 0.056 mmol) and the reaction mixture was stirred at RT under hydrogen balloon atmosphere for 16 h. The reaction mixture was filtered through Celite and the filtrate was concentrated to afford the title compound 158C (250 mg, 80%) as a pale brown gummy liquid. LC-MS retention time=3.66 min; m/z=604.2 [M+H]$^+$ Column: KINETIX XB-C18, (3×75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 50% B to 100% B over 4.6 min, then hold 0.4 min. at 50% B with flow rate 1.5 mL/min; Detection: UV at 220 nm.

Example 158: first eluting diastereomer of 3-(3-fluoro-4-methoxyphenyl)-3-(4-(3-(1,2,3,4-tetrahydro-1,8-naphthyridin-2-yl)propyl)thiazol-2-yl) propanoic acid Example 159: second eluting diastereomer of 3-(3-fluoro-4-methoxyphenyl)-3-(4-(3-(1,2,3,4-tetrahydro-1,8-naphthyridin-2-yl)propyl)thiazol-2-yl) propanoic acid Example 160: third eluting diastereomer of 3-(3-fluoro-4-methoxyphenyl)-3-(4-(3-(1,2,3,4-tetrahydro-1,8-naphthyridin-2-yl)propyl)thiazol-2-yl) propanoic acid Example 161: fourth eluting diastereomer of 3-(3-fluoro-4-methoxyphenyl)-3-(4-(3-(1,2,3,4-tetrahydro-1,8-naphthyridin-2-yl)propyl)thiazol-2-yl) propanoic acid To a stirred solution of phenyl 2-(3-(2-(3-ethoxy-1-(3-fluoro-4-methoxyphenyl)-3-oxopropyl)thiazol-4-yl)propyl)-3,4-dihydro-1,8-naphthyridine-1(2H)-carboxylate 158C (250 mg, 0.414 mmol) in THF (4 mL) and t-BuOH (4 mL), was added a solution of sodium hydroxide (83 mg, 2.071 mmol)) in water (2 mL) and the resulting reaction mixture was stirred at 70° C. for 40 h. After completion of the reaction, citric acid (239 mg, 1.242 mmol) was added and the reaction mixture was stirred at RT for 10 min. The reaction mixture was concentrated and crude product was purified by preparative reverse phase HPLC (SUNFIRE C18 (150×19) mm, 5 micron; Mobile Phase A: 10 mM ammonium acetate (pH=4.5); Mobile Phase B: Acetonitrile; flow rate: 15 mL/min; Time (min)/% B: 0/10, 10/40, 17/40) afford the title compound as diastereomeric mixture (70 mg). The individual diastereomers of the title compounds were separated by chiral SFC column: Luxcellulose-2 (250×30) mm; 5 micron; 50% CO$_2$ and 50% of 0.2% NH$_4$OH in Methanol+ACN (1:1) as co-solvent; Total Flow: 80 g/min; Back Pressure: 100 bar; Temperature: 30° C.; Detection: UV at 245 nM. First eluting diastereomer Example 158 (Retention time 15.2 min., 10 mg, 5%) was isolated as a white solid. LC-MS retention time=2.09 min; m/z=456.2 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CD$_3$OD) δ ppm 7.68 (d, J=5.02 Hz, 1H), 7.47 (d, J=7.03 Hz, 1H), 7.03-7.14 (m, 4H), 6.64 (t, J=6.40 Hz, 1H), 4.78 (dd, J=9.54, 5.52 Hz, 1H), 3.86 (s, 3H), 3.51-3.60 (m, 1H), 3.26 (dd, J=15.81, 10.29 Hz, 1H), 2.69-2.95 (m, 5H), 1.92-2.03 (m, 2H), 1.76-1.88 (m, 1H), 1.56-1.71 (m, 2H) 1.43-1.55 (m, 1H). Human αVβ6 IC50 (nM)=7.0. Second eluting diastereomer Example 159 (Retention time 17.2 min., 10 mg, 5%) was isolated as a white solid. LC-MS retention time=2.06 min; m/z=456.2 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CD$_3$OD) δ ppm 7.66 (br. s., 1H), 7.45 (d, J=7.03 Hz, 1H), 7.04-7.15 (m, 3H), 7.03 (s, 1H), 6.63 (br. s., 1H), 4.77-4.86 (m, 1H), 3.86 (s, 3H), 3.51-3.59 (m, 1H), 3.07-3.22 (m, 1H), 2.83-2.92 (m, 1H), 2.73-2.83 (m, 4H), 1.85-2.03 (m, 3H), 1.50-1.67 (m, 3H). Human αVβ6 IC50 (nM)=370. Third eluting diastereomer, Example 160 (Retention time 18.2. min., 7 mg, 4%) was isolated as a white solid. LC-MS retention time=2.07 min; m/z=456.2 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CD$_3$OD) δ ppm 7.68 (br. s., 1H), 7.52 (d, J=7.03 Hz, 1H), 7.03-7.10 (m, 3H), 7.02 (s, 1H), 6.68 (br. s., 1H), 4.78 (dd, J=10.54, 5.02 Hz, 1H), 3.86 (s, 3H), 3.51-3.59 (m, 1H), 3.23-3.31 (m, 1H), 2.68-2.96 (m, 5H), 1.93-2.03 (m, 2H), 1.76-1.88 (m, 1H), 1.56-1.73 (m, 2H), 1.43-1.54 (m, 1H). Human αVβ6 IC50 (nM)=195. Fourth eluting diastereomer, Example 161 (Retention time 22.3 min., 7 mg, 4%) was isolated as a white solid. LC-MS retention time=2.05 min; m/z=456.2 [M+H]$^+$ Column—KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1.5 mL/min; Detection: UV at 220 nm. $^1$H NMR (400 MHz, CD$_3$OD) δ ppm 7.66 (d, J=6.02 Hz, 1H), 7.52 (d, J=7.53 Hz, 1H), 7.04-7.15 (m, 3H), 7.04 (s, 1H), 6.67 (t, J=6.40 Hz, 1H), 4.81 (dd, J=11.04, 5.02 Hz, 1H), 3.86 (s, 3H), 3.55-3.63 (m, 1H), 3.10-3.19 (m, 1H), 2.76-2.90 (m, 5H), 1.89-2.04 (m, 3H), 1.46-1.69 (m, 3H). Human αVβ6 IC50 (nM)=12.

Example 162 and Example 163

Example 162: first eluting enantiomer of 3-(3,5-dimethyl-1H-pyrazol-1-yl)-3-(4-(3-(5,6,7,8-tetrahydro-1,8-naphthyridin-2-yl)propyl)thiazol-2-yl) propanoic acid Example 163: second eluting enantiomer of 3-(3,5-dimethyl-1H-pyrazol-1-yl)-3-(4-(3-(5,6,7,8-tetrahydro-1,8-naphthyridin-2-yl)propyl)thiazol-2-yl) propanoic acid

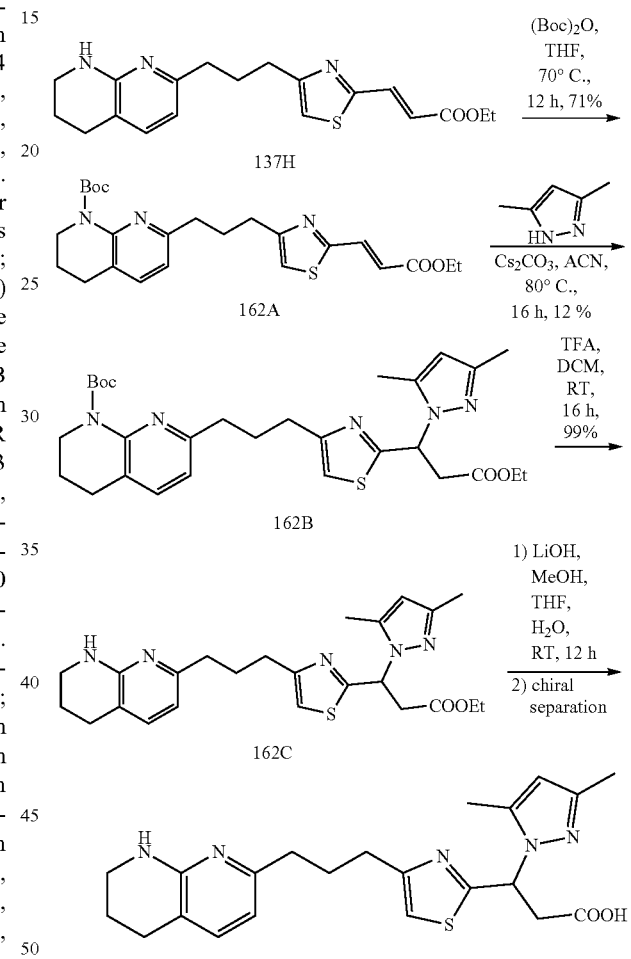

Tert-butyl (E)-7-(3-(2-(3-ethoxy-3-oxoprop-1-en-1-yl)thiazol-4-yl)propyl)-3,4-dihydro-1,8-naphthyridine-1(2H)-carboxylate (162A)

To a solution of ethyl (E)-3-(4-(3-(5,6,7,8-tetrahydro-1,8-naphthyridin-2-yl)propyl)thiazol-2-yl)acrylate 137H (300 mg, 0.839 mmol) in THF (5 mL) was added Boc$_2$O (1.5 mL, 6.46 mmol) and the reaction mixture was stirred at 70° C. for 12 h. After completion of the reaction, the reaction mixture was concentrated and the crude product was purified by combiflash chromatography (12 g Redisep® SiO$_2$ column, eluting with 90% ethyl acetate in Pet ether) to afford the title compound 162A (290 mg, 71%) as a pale brown gummy liquid. LC-MS retention time=3.2 and 3.4 min (cis & trans mixture); m/z=458.2 [M+2H]⁺ Column: KINETIX XB-C18, (3×75) mm, 2.6 micron column; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 50% B to 100% B over 4.6 min, then hold 0.4 min. at 20% B with flow rate 1.5 mL/min; Detection: UV at 220 nm.

Tert-butyl 7-(3-(2-(1-(3,5-dimethyl-1H-pyrazol-1-yl)-3-ethoxy-3-oxopropyl)thiazol-4-yl)propyl)-3,4-dihydro-1,8-naphthyridine-1(2H)-carboxylate (162B)

To a solution of tert-butyl (E)-7-(3-(2-(3-ethoxy-3-oxoprop-1-en-1-yl)thiazol-4-yl)propyl)-3,4-dihydro-1,8-naphthyridine-1(2H)-carboxylate 162A (200 mg, 0.437 mmol) in ACN was added 3,5-dimethyl-1H-pyrazole (42.0 mg, 0.437 mmol) and cesium carbonate (285 mg, 0.874 mmol). The reaction mixture was then heated at 80° C. and stirred for 16 h. The reaction mixture was cooled to RT and filtered through Celite. The filtrate was concentrated and the crude product was purified by preparative reverse phase HPLC (SYMMETRY C8 (300×19) mm; 7 micron; Mobile Phase A: 10 mM ammonium acetate; Mobile Phase B: Trifluoroethanol; flow rate: 18 mL/min; Time (min)/% B: 0/50, 27/100) to afford title compound 162B (30 mg, 12%) of required compound as an off white gummy liquid. LC-MS retention time=3.72 min; m/z=554.2 [M+H]⁺ Column: KINETIX XB-C18, (3×75) mm, 2.6 micron column; Flow rate: 1 mL/min; Mobile Phase A: 10 mM HCO₂NH₄ in 98% Water/ 2% ACN; Mobile Phase B: 10 mM HCO₂NH₄ in 2% Water/98% ACN; 50% B to 100% B over 4.6 min, then hold 0.4 min. at 20% B with flow rate 1.5 mL/min; Detection: UV at 220 nm.

Ethyl 3-(3,5-dimethyl-1H-pyrazol-1-yl)-3-(4-(3-(5,6,7,8-tetrahydro-1,8-naphthyridin-2-yl)propyl)thiazol-2-yl)propanoate (162C)

To a solution of tert-butyl 7-(3-(2-(1-(3,5-dimethyl-1H-pyrazol-1-yl)-3-ethoxy-3-oxopropyl)thiazol-4-yl)propyl)-3,4-dihydro-1,8-naphthyridine-1(2H)-carboxylate 162B (30 mg, 0.054 mmol) in DCM (10 mL) was added TFA (0.05 mL, 0.649 mmol) and stirred at the RT for 16 h. After the completion of the reaction, the reaction mixture was concentrated to afford the title compound 162C (24 mg, 99%) as a pale brown liquid. LC-MS retention time=2.87 min; m/z=454.3 [M+H]⁺ Column: KINETIX XB-C18, (3×75) mm, 2.6 micron column; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 50% B to 100% B over 4.6 min, then hold 0.4 min. at 20% B with flow rate 1.5 mL/min; Detection: UV at 220 nm.

Example 162: first eluting enantiomer of 3-(3,5-dimethyl-1H-pyrazol-1-yl)-3-(4-(3-(5,6,7,8-tetrahydro-1,8-naphthyridin-2-yl)propyl)thiazol-2-yl) propanoic acid Example 163: second eluting enantiomer of 3-(3,5-dimethyl-1H-pyrazol-1-yl)-3-(4-(3-(5,6,7,8-tetrahydro-1,8-naphthyridin-2-yl)propyl)thiazol-2-yl) propanoic acid To a solution of ethyl 3-(3,5-dimethyl-1H-pyrazol-1-yl)-3-(4-(3-(5,6,7,8-tetrahydro-1,8-naphthyridin-2-yl)propyl) thiazol-2-yl)propanoate 162C (24 mg, 0.055 mmol) in THF (1 mL) and MeOH (1 mL) was added a solution of lithium hydroxide monohydrate (6.94 mg, 0.165 mmol) in water (0.5 mL) and the resulting reaction mixture was stirred at RT for 16 h. After completion of the reaction, citric acid (21.18 mg, 0.110 mmol) was added and the reaction mixture was stirred at the RT for 10 min. The reaction mixture was concentrated and the crude product was purified by preparative reverse phase HPLC (SUNFIRE C18 (150×19) mm; 5 micron; Mobile Phase A: 10 mM ammonium acetate; Mobile Phase B: ACN; flow rate: 15 mL/min; Time (min)/% B: 0/20, 20/60) to afford the title compound (10 mg) as racemic mixture. The individual enantiomers of 3-(3,5-dimethyl-1H-pyrazol-1-yl)-3-(4-(3-(5,6,7,8-tetrahydro-1,8-naphthyridin-2-yl)propyl)thiazol-2-yl)propanoic acid were separated by chiral column (Lux Cellulose C2 (250×21.2) mm, 5 micron; Mobile phase: 0.1% DEA in ACN:Trifluoroethanol (70:30); flow: 25 mL/min). First eluting enantiomer, Example 162 (Retention time 5.01 min., 1.8 mg, 8%) was isolated as an off white solid. LC-MS retention time=1.22 min; m/z=426.2 [M+H]⁺ Column: KINETIX XB-C18, (3×75) mm, 2.6 micron column; Flow rate: 1 mL/min; Mobile Phase A: 10 mM HCO₂NH₄ in 98% Water/ 2% ACN; Mobile Phase B: 10 mM HCO₂NH₄ in 2% Water/98% ACN; 50% B to 100% B over 4.6 min, then hold 0.4 min. at 20% B with flow rate 1.5 mL/min; Detection: UV at 220 nm. ¹H NMR (400 MHz, CD₃OD) δ ppm 7.49 (d, J=7.20 Hz, 1H), 7.10 (s, 1H), 6.57 (d, J=7.20 Hz, 1H), 6.06 (dd, J=9.60, 5.20 Hz, 1H), 5.91 (s, 1H), 3.49 (m, 2H), 3.42 (dd, J=14.40, 9.60 Hz, 1H), 3.04 (dd, J=14.20, 5.60 Hz, 1H), 2.55-2.85 (m, 6H), 2.33 (s, 3H), 2.19 (s, 3H), 1.95-2.15 (m, 2H), 1.86-1.95 (m, 2H). Human αVβ6 IC50 (nM)=71. Second eluting enantiomer Example 163 (Retention time. 10.61 min., 2.2 mg, 9%) was isolated as an off white solid. LC-MS retention time=1.22 min; m/z=426.2 [M+H]⁺ Column: KINETIX XB-C18, (3×75) mm, 2.6 micron column; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 50% B to 100% B over 4.6 min, then hold 0.4 min. at 20% B with flow rate 1.5 mL/min; Detection: UV at 220 nm. ¹H NMR (400 MHz, CD₃OD) δ ppm 7.49 (d, J=7.20 Hz, 1H), 7.10 (s, 1H), 6.57 (d, J=7.20 Hz, 1H), 6.06 (dd, J=9.60, 5.20 Hz, 1H), 5.91 (s, 1H), 3.49 (m, 2H), 3.42 (dd, J=14.40, 9.60 Hz, 1H), 3.04 (dd, J=14.20, 5.60 Hz, 1H), 2.55-2.85 (m, 6H), 2.33 (s, 3H), 2.19 (s, 3H), 1.95-2.15 (m, 2H), 1.86-1.95 (m, 2H). Human αVβ6 IC50 (nM)=220.

Example 164 and Example 165

Example 164: first eluting enantiomer of 3-(6-methoxypyridin-3-yl)-3-(1-methyl-5-(4-(5,6,7,8-tetrahydro-1,8-naphthyridin-2-yl)butyl)-1H-imidazol-2-yl)propanoic acid Example 165: second eluting enantiomer of 3-(6-methoxypyridin-3-yl)-3-(1-methyl-5-(4-(5,6,7,8-tetrahydro-1,8-naphthyridin-2-yl)butyl)-1H-imidazol-2-yl)propanoic acid

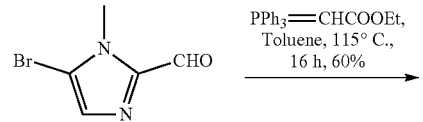

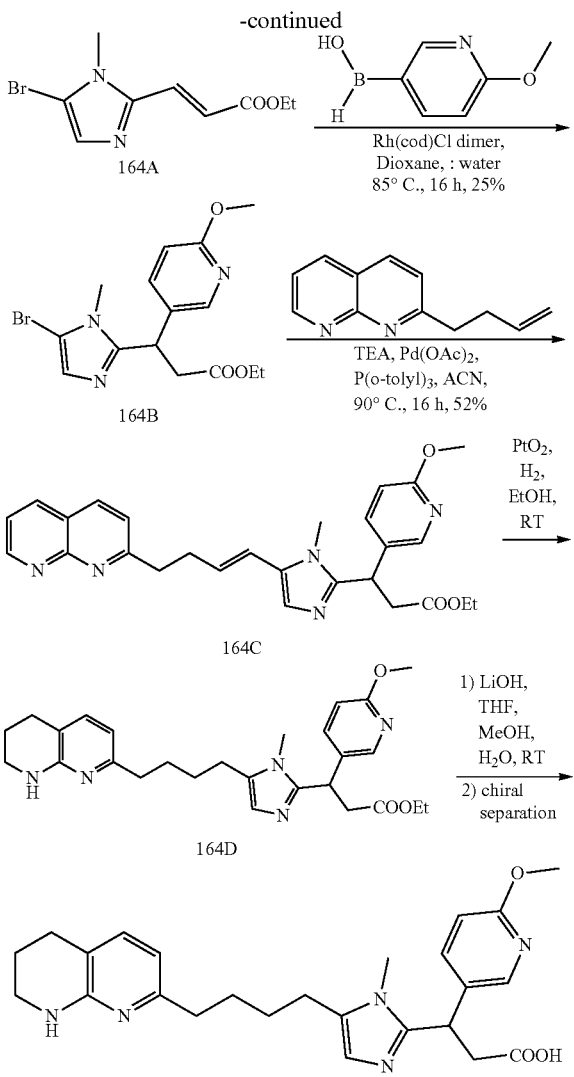

Example 164: first eluting enantiomer
Example 165: second eluting enantiomer

Ethyl (E)-3-(5-bromo-1-methyl-1H-imidazol-2-yl) acrylate (164A)

To a stirred solution of 5-bromo-1-methyl-1H-imidazole-2-carbaldehyde (2.5 g, 13.23 mmol) in toluene (50 mL) was added (carbethoxymethylene)triphenylphosphorane (6.91 g, 19.84 mmol) under nitrogen atmosphere. The resulting clear solution was heated to 110° C. and stirred for 16 h. After completion of the reaction, the reaction mixture was concentrated and the crude product was purified by combiflash chromatography (40 g Redisep® SiO$_2$ column, eluting with 30% ethyl acetate in n-hexanes) to afford the title compound 164A (2 g, 60%) as an off white solid. $^1$H NMR (400 MHz, DMSO-d$_6$) δ ppm 7.56 (d, J=15.56 Hz, 1H), 7.23 (s, 1H), 6.60 (d, J=15.56 Hz, 1H), 4.21 (q, J=7.03 Hz, 2H), 3.72 (s, 3H), 1.27 (t, J=7.03 Hz, 3H).

Ethyl 3-(5-bromo-1-methyl-1H-imidazol-2-yl)-3-(6-methoxypyridin-3-yl)propanoate (164B)

To a stirred solution of ethyl (E)-3-(5-bromo-1-methyl-1H-imidazol-2-yl)acrylate 164A (1 g, 3.86 mmol) in dioxane (30 mL) and water (10 mL) was added (6-methoxypyridin-3-yl)boronic acid (0.885 g, 5.79 mmol) and the reaction mixture was purged with argon gas for 10 min. TEA (1.076 mL, 7.72 mmol) and chloro(1,5-cyclooctadiene)rhodium(I) dimer (0.095 g, 0.193 mmol) were added and the reaction mixture was heated to 80° C. and stirred for 16 h. The reaction mixture was cooled to RT, diluted with water (50 mL) and extracted with ethyl acetate (2×50 mL). The combined organic layer was dried (Na$_2$SO$_4$), filtered and the filtrate concentrated. The crude product was purified by combiflash chromatography (40 g Redisep® SiO$_2$ column, eluting with 25% ethyl acetate in n-hexanes) to afford the title compound 164B (350 mg, 25%) as a pale brown gummy liquid. LC-MS retention time=2.23 min; m/z=370.1 [M+2H]$^+$ KINETIX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, CDCl$_3$) δ ppm 8.05 (d, J=2.51 Hz, 1H), 7.44 (dd, J=8.53, 2.51 Hz, 1H), 6.98 (s, 1H), 6.69 (d, J=8.53 Hz, 1H), 4.50 (dd, J=8.53, 6.53 Hz, 1H), 4.10 (q, J=7.03 Hz, 2H), 3.91 (s, 3H), 3.39 (s, 3H), 3.36-3.46 (m, 1H), 2.85 (dd, J=16.56, 6.53 Hz, 1H), 1.20 (t, J=7.03 Hz, 3H).

Ethyl (E)-3-(5-(4-(1,8-naphthyridin-2-yl)but-1-en-1-yl)-1-methyl-1H-imidazol-2-yl)-3-(6-methoxy-pyridin-3-yl)propanoate (164C)

To a stirred solution of ethyl 3-(5-bromo-1-methyl-1H-imidazol-2-yl)-3-(6-methoxypyridin-3-yl)propanoate 164B (300 mg, 0.815 mmol) in acetonitrile (15 mL) was added 2-(but-3-en-1-yl)-1,8-naphthyridine (225 mg, 1.22 mmol) and the reaction mixture was purged with nitrogen for 10 min. TEA (247 mg, 2.44 mmol), tri-o-tolylphosphane (24.80 mg, 0.081 mmol) and palladium acetate (18.3 mg, 0.081 mmol) were added and the reaction mixture was heated to 90° C. and stirred for 16 h. The reaction mixture was cooled to RT and filtered through Celite. The filtrate was diluted with water (5 mL) and extracted with DCM (2×10 mL). The combined organic layer was dried (Na$_2$SO$_4$), filtered and the filtrate concentrated. The crude product was purified by combiflash chromatography (4 g Redisep® SiO$_2$ column, eluting with 3% Methanol in Chloroform to afford the title compound 164C (200 mg, 52%) as a pale brown liquid. LC-MS retention time=2.15 min; m/z=472.4 [M+H]$^+$ KINETIX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.5 min. at 20% B with flow rate 1-1.5 mL/min; Detection: UV at 220 nm.

Ethyl 3-(6-methoxypyridin-3-yl)-3-(1-methyl-5-(4-(5,6,7,8-tetrahydro-1,8-naphthyridin-2-yl)butyl)-1H-imidazol-2-yl)propanoate (164D)

To a degassed solution of ethyl (E)-3-(5-(4-(1,8-naphthyridin-2-yl)but-1-en-1-yl)-1-methyl-1H-imidazol-2-yl)-3-(6-methoxypyridin-3-yl)propanoate 164C (200 mg, 0.424 mmol) in ethanol (20 mL) was added platinum(IV) oxide (20 mg, 0.088 mmol) and the reaction mixture was stirred at the RT under Hydrogen balloon atmosphere for 16 h. The reaction mixture was filtered through Celite pad, and the filtrate concentrated to afford the title compound 164D (200 mg, 99%) as a pale brown liquid. LC-MS retention time=1.17 min; m/z=478.7 [M+H]$^+$ AQUITY UPLC BEH C18 (3.0×50) mm; 1.7 micron; Mobile phase A: 10 mM NH$_4$COOCH$_3$:ACN (95:5) Mobile phase B: 10 mM NH$_4$COOCH$_3$:ACN (5:95) Method:% B: 0 min—20%:1.1 min—90%:1.7 min—90%.

Example 164: first eluting enantiomer of 3-(6-methoxypyridin-3-yl)-3-(1-methyl-5-(4-(5,6,7,8-tetrahydro-1,8-naphthyridin-2-yl)butyl)-1H-imidazol-2-yl)propanoic acid Example 165: second eluting enantiomer of 3-(6-methoxypyridin-3-yl)-3-(1-methyl-5-(4-(5,6,7,8-tetrahydro-1,8-naphthyridin-2-yl)butyl)-1H-imidazol-2-yl)propanoic acid To a stirred solution of ethyl ethyl 3-(6-methoxypyridin-3-yl)-3-(1-methyl-5-(4-(5,6,7,8-tetrahydro-1,8-naphthyridin-2-yl)butyl)-1H-imidazol-2-yl)propanoate 164D (200 mg, 0.419 mmol) in THF (4 mL) and MeOH (4 mL) was added a solution of LiOH·H$_2$O (12.22 mg, 0.291 mmol) in water (2 mL) and the resulting reaction mixture was stirred at RT for 16 h. After completion of the reaction, citric acid (241 mg, 1.256 mmol) was added and the reaction mixture was stirred at the RT for 10 min. The reaction mixture was concentrated and the crude product was purified by preparative reverse phase HPLC (Inersil ODS (250 mm×19 mm ID, 5u); Mobile Phase A: 10 mM ammonium acetate-pH-4.5; Mobile Phase B: Acetonitrile; flow rate: 17 mL/min; Time (min)/% B: 0/10, 7/22, 12.5/22) afford the title compound (50 mg) as racemic mixture. The individual enantiomers were then separated by chiral SFC (Chiralpak AD-H (250× 21) mm, 5u; 50% CO$_2$ and 50% of 0.2% NH$_4$OH in Methanol as co-solvent); Total Flow: 70 g/min; Back Pressure: 100 bar; Temperature: 30° C.; Detection: UV at 220 nM. First eluting enantiomer Example 164 (Retention time 3.40 min., 17 mg, 9%) was isolated as a white solid. LC-MS retention time=1.13 min; m/z=450.4 [M+H]$^+$ KINETIX XB-C18, (3×75) mm, 2.6 micron column; Flow rate: 1 mL/min; Mobile Phase A: 10 mM HCO$_2$NH$_4$ in 98% water/ 2% ACN; Mobile Phase B: 10 mM HCO$_2$NH$_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 8.04 (d, J=2.01 Hz, 1H), 7.62 (dd, J=8.53, 2.51 Hz, 1H), 7.28 (d, J=7.03 Hz, 1H), 6.67-6.78 (m, 2H), 6.39 (d, J=7.53 Hz, 1H), 4.63 (dd, J=9.54, 5.52 Hz, 1H), 3.87 (s, 3H), 3.52 (s, 3H), 3.39 (t, J=6.0 Hz, 2H), 3.19 (dd, J=16.0, 10.4 Hz, 1H), 2.84 (dd, J=16.0, 5.6 Hz, 1H), 2.56-2.76 (m, 4H), 2.42-2.56 (m, 1H), 2.21-2.39 (m, 1H), 1.81-1.96 (m, 2H), 1.42-1.79 (m, 4H). Human αVβ6 IC50 (nM)=460. Second eluting enantiomer Example 165 (Retention time 6.80 min., 18 mg, 9%) was isolated as a white solid. LC-MS retention time=1.13; m/z=450.4 [M+H]$^+$ KINETIX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 8.04 (d, J=2.01 Hz, 1H), 7.62 (dd, J=8.53, 2.51 Hz, 1H), 7.28 (d, J=7.03 Hz, 1H), 6.67-6.78 (m, 2H), 6.39 (d, J=7.53 Hz, 1H), 4.63 (dd, J=9.54, 5.52 Hz, 1H), 3.87 (s, 3H), 3.52 (s, 3H), 3.39 (t, J=6.0 Hz, 2H), 3.19 (dd, J=16.0, 10.4 Hz, 1H), 2.84 (dd, J=16.0, 5.6 Hz, 1H), 2.56-2.76 (m, 4H), 2.42-2.56 (m, 1H), 2.21-2.39 (m, 1H), 1.81-1.96 (m, 2H), 1.42-1.79 (m, 4H). Human αVβ6 IC50 (nM)=27.

| Example | Structure | Prep-HPLC/SFC conditions, LC-MS and $^1$H NMR | Method |
|---|---|---|---|
| 166 | 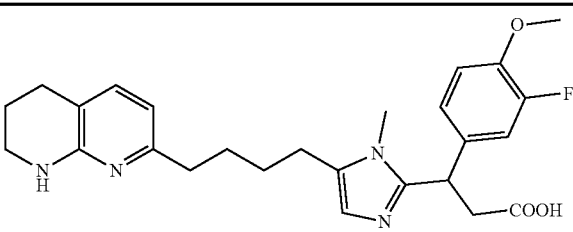  3-(3-fluoro-4-methoxyphenyl)-3-(1-methyl-5-(4-(5,6,7,8-tetrahydro-1,8-naphthyridin-2-yl)butyl)-1H-imidazol-2-yl)propanoic acid | Prep-SFC: Retention time 3.40 min. Chiralpak AD-H (250 × 21) mm, 5u; 50% CO$_2$ and 50% of 0.2% NH$_4$OH in Methanol as co-solvent); Total Flow: 70 g/min; Back Pressure: 100 bar; Temperature: 30° C.; Detection: UV at 220 nM. $^1$H NMR (400 MHz, CD$_3$OD) δ ppm 7.29 (d, J = 7.03 Hz, 1H), 6.96-7.06 (m, 3H), 6.76 (s, 1H), 6.39 (d, J = 7.03 Hz, 1H), 4.61 (dd, J = 10.54, 5.52 Hz, 1H), 3.84 (s, 3H), 3.51 (s, 3H), 3.41 (t, J = 5.2 Hz, 2H), 3.19 (dd, J = 16.0, 10.4 Hz, 1H), 2.84 (dd, J = 16.0, 5.6 Hz, 1H), 2.75 (t, J = 6.4 Hz, 2H), 2.64-2.70 (m, 2H), 2.42-2.55 (m, 1H), 2.21-2.38 (m, 1H), 1.83-1.92 (m, 2H), 1.49-1.82 (m, 4H), LC-MS retention time = 1.46 min; m/z = 467.2 [M + H]$^+$ KINETIX XB-C18, (3 × 75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$, in 2% water/98% ACN; 20% B to 100% B over 4.6 min, then hold 0.5 min. at 20% B with flow rate 1-1.5 mL/min; Detection: UV at 220 nm, Human αVβ6 IC50 (nM) = 280. | Example 164/165 |

| Example | Structure | Prep-HPLC/SFC conditions, LC-MS and ¹H NMR | Method |
|---|---|---|---|
| 167 | 3-(3-fluoro-4-methoxyphenyl)-3-(1-methyl-5-(4-(5,6,7,8-tetrahydro-1,8-naphthyridin-2-yl)butyl)-1H-imidazol-2-yl)propanoic acid | Prep-SFC: Retention time 6.80 min. Chiralpak AD-H (250 × 21) mm, 5u: 50% $CO_2$ and 50% of 0.2% $NH_4OH$ in Methanol as co-solvent); Total Flow: 70 g/min; Back Pressure: 100 bar; Temperature: 30° C.; Detection: UV at 220 nM. ¹H NMR (400 MHz, $CD_3OD$) δ ppm 7.29 (d, J = 7.03 Hz, 1H), 6.96-7.06 (m, 3H), 6.76 (s, 1H), 6.39 (d, J = 7.03 Hz, 1H), 4.61 (dd, J = 10.54, 5.52 Hz, 1H), 3.84 (s, 3H), 3.51 (s, 3H), 3.41 (t, J = 5.2 Hz, 2H), 3.19 (dd, J = 16.0, 10.4 Hz, 1H), 2.84 (dd, J = 16.0, 5.6 Hz, 1H), 2.75 (t, J = 6.4 Hz, 2H), 2.64-2.70 (m, 2H), 2.42-2.55 (m, 1H), 2.21-2.38 (m, 1H), 1.83-1.92 (m, 2H), 1.49-1.82 (m, 4H), LC-MS retention time = 1.47 min: m/z = 467.2 [M + H]⁺ KINETIX XB-C18, (3 × 75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm, Human αVβ6 IC50 (nM) = 27. | Example 164/165 |

Example 168 and Example 169

Example 168: first eluting enantiomer of 3-(3-fluoro-4-methoxyphenyl)-3-(1-methyl-4-(4-(5,6,7,8-tetrahydro-1,8-naphthyridin-2-yl)butyl)-1H-imidazol-2-yl)propanoic acid Example 169: second eluting enantiomer of 3-(3-fluoro-4-methoxyphenyl)-3-(1-methyl-4-(4-(5,6,7,8-tetrahydro-1,8-naphthyridin-2-yl)butyl)-1H-imidazol-2-yl)propanoic acid

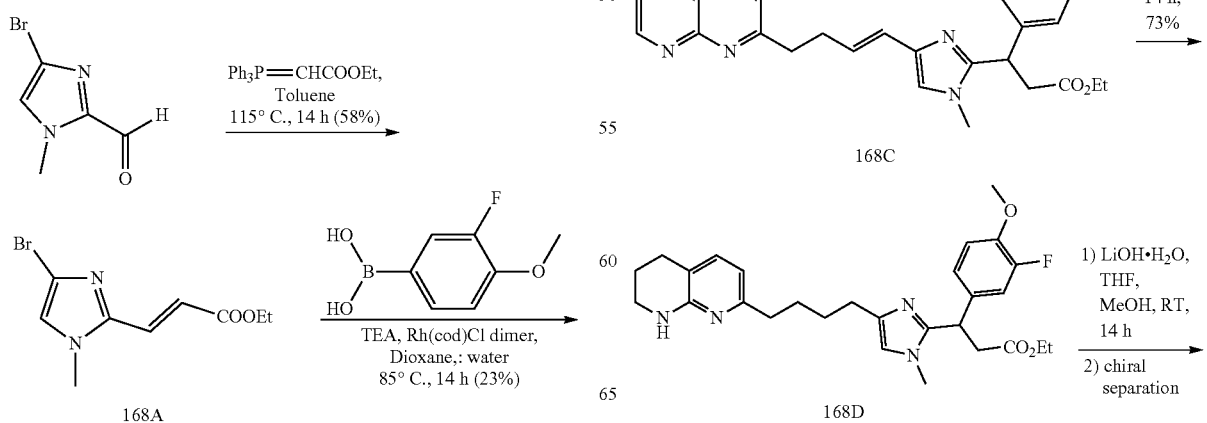

-continued

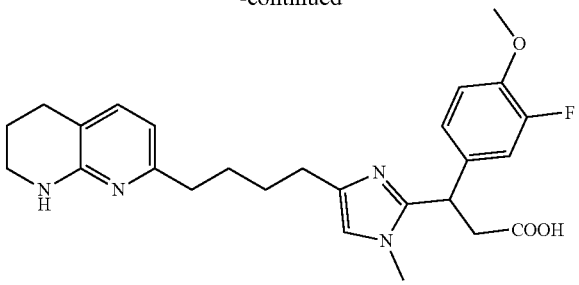

Example 168: first eluting enantiomer
Example 169: second eluting enantiomer

Ethyl (E)-3-(4-bromo-1-methyl-1H-imidazol-2-yl)acrylate (168A)

To a stirred solution of 4-bromo-1-methyl-1H-imidazole-2-carbaldehyde (2.4 g, 12.70 mmol) in toluene (25 mL) was added carbethoxymethylene)triphenylphosphorane (6.64 g, 19.05 mmol) under a nitrogen atmosphere and the resulting clear solution was heated to 110° C. and stirred for 16 h. After completion of the reaction, the reaction mixture was cooled to the RT and concentrated. The crude product was purified by combiflash chromatography (12 g Redisep® $SiO_2$ column, eluting with 25% ethyl acetate in n-hexanes) to afford the title compound 168A (2.3 g, 58%) as a colourless liquid. LC-MS retention time=1.85 min; m/z=261.0 $[M+2H]^+$ KINETIX XB-C18, (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, $CDCl_3$) δ ppm 7.50 (s, 1H), 7.44 (d, J=15.6 Hz, 1H), 6.51 (d, J=15.6 Hz, 1H), 4.18 (q, J=7.20 Hz, 2H) 3.76 (s, 3H), 1.25 (t, J=7.20 Hz, 3H).

Ethyl 3-(4-bromo-1-methyl-1H-imidazol-2-yl)-3-(3-fluoro-4-methoxyphenyl)-propanoate (168B)

To a stirred solution of ethyl (E)-3-(4-bromo-1-methyl-1H-imidazol-2-yl)acrylate 168A (0.700 g, 2.70 mmol) in 1,4-dioxane (10 mL) and water (2.5 mL) was added (3-fluoro-4-methoxyphenyl)boronic acid (0.689 g, 4.05 mmol) and the reaction mixture was purged with argon for 5 min. TEA (0.753 mL, 5.40 mmol) and chloro(1,5-cyclooctadiene)rhodium(i) dimer (0.067 g, 0.135 mmol) were added and the solution was heated to 85° C. and stirred for 14 h. The reaction mixture was cooled, filtered through a pad of Celite, The Celite pad was washed with dichloromethane (4×15 mL) and the combined filtrate was concentrated. The crude product was then purified by combiflash chromatography (40 g Redisep® $SiO_2$ column, eluting with 70% ethyl acetate in n-hexanes) to afford the title compound 168B (0.5 g, 23%) as a gummy liquid. LC-MS retention time=2.40 min; m/z=385.0 $[M+H]^+$ KINETIX XB-C18, (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm.

Ethyl (E)-3-(4-(4-(1,8-naphthyridin-2-yl)but-1-en-1-yl)-1-methyl-1H-imidazol-2-yl)-3-(3-fluoro-4-methoxyphenyl)propanoate (168C)

To a stirred solution of ethyl 3-(4-bromo-1-methyl-1H-imidazol-2-yl)-3-(3-fluoro-4-methoxyphenyl)propanoate 168B (0.5 g, 0.623 mmol) in acetonitrile (10 mL) was added 2-(but-3-en-1-yl)-1,8-naphthyridine (0.344 g, 1.869 mmol) and the reaction mixture was purged with argon for 5 min. TEA (0.261 mL, 1.869 mmol), tri-o-tolylphosphine (0.019 g, 0.062 mmol) and palladium(II) acetate (0.014 g, 0.062 mmol) were added and the solution was heated to 90° C. and stirred for 14 h. The reaction mixture was cooled, filtered through a pad of Celite and the pad was washed with dichloromethane (4×10 mL). The combined filtrate was concentrated and the crude product was purified by combiflash chromatography (24 g Redisep® $SiO_2$ column, eluting with 90% ethyl acetate in n-hexanes) to afford the title compound 168C (0.14 g, 35%) as a gummy liquid. LC-MS retention time=2.42 min; m/z=489.2 $[M+H]^+$ KINETIX XB-C18, (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm.

Ethyl 3-(3-fluoro-4-methoxyphenyl)-3-(1-methyl-4-(4-(5,6,7,8-tetrahydro-1,8-naphthyridin-2-yl)butyl)-1H-imidazol-2-yl)propanoate (168D)

To a degassed solution of ethyl (E)-3-(4-(4-(1,8-naphthyridin-2-yl)but-1-en-1-yl)-1-methyl-1H-imidazol-2-yl)-3-(3-fluoro-4-methoxyphenyl)propanoate 168C (0.140 g, 0.287 mmol) in ethanol (3 mL) was added platinum(IV) oxide (14 mg, 0.062 mmol) and the reaction mixture was stirred at the RT under hydrogen balloon atmosphere for 14 h. The reaction mixture was filtered through Celite pad and the filtrate concentrated to afford the title compound 168D (110 mg, 73%) as a gummy liquid. LC-MS retention time=2.69 min; m/z=495.2 $[M+H]^+$, KINETIX XB-C18, (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm.

Example 168: first eluting enantiomer of 3-(3-fluoro-4-methoxyphenyl)-3-(1-methyl-4-(4-(5,6,7,8-tetrahydro-1,8-naphthyridin-2-yl)butyl)-1H-imidazol-2-yl)propanoic acid

Example 169: second eluting enantiomer of 3-(3-fluoro-4-methoxyphenyl)-3-(1-methyl-4-(4-(5,6,7,8-tetrahydro-1,8-naphthyridin-2-yl)butyl)-1H-imidazol-2-yl)propanoic acid To a stirred solution of ethyl 3-(3-fluoro-4-methoxyphenyl)-3-(1-methyl-4-(4-(5,6,7,8-tetrahydro-1,8-naphthyridin-2-yl)butyl)-1H-imidazol-2-yl)propanoate 168D (0.110 g, 0.222 mmol) in THF (1 mL) and methanol (1 mL) was added a solution of $LiOH \cdot H_2O$ (0.037 g, 0.890 mmol) in water (1 mL) and the resulting reaction mixture was stirred at RT for 14 h. After completion of the reaction, citric acid (128 mg, 0.667 mmol) was added and the reaction mixture was stirred at the RT for 10 min. The reaction mixture was concentrated and the crude product was purified by preparative reverse phase HPLC to afford the racemate of title compound (90 mg). Individual enantiomers were separated by chiral preparative HPLC. Column: Lux-cellulose C4 (250×21.2) mm, 5 micron, Mobile Phase: ACN:MeOH (1:1), Flow: 19 mL/min, Time (min)/% B: 0/100, 20/100. First eluting enantiomer Example 168 (Retention time 3.86 min., 4 mg, 3%) was isolated as an off white solid. LC-MS retention time 1.60 min; m/z=467.2 [M+H]+ KINETIX XB-C18 (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, $CD_3OD$) δ ppm 7.38 (d, J=7.03 Hz, 1H), 7.06-6.99 (m, 3H), 6.79 (s, 1H), 6.45 (d, J=7.53 Hz, 1H), 4.63 (dd, J=10.79, 4.77 Hz, 1H), 3.84 (s, 3H), 3.54 (s, 3H), 3.42 (t, J=6.0 Hz, 2H), 3.18 (dd, J=14.81, 11.29 Hz, 1H), 2.83 (dd, J=14.81, 11.29 Hz, 1H), 2.73 (t, J=6.0 Hz, 2H), 2.68-2.54 (m, 4H), 1.93-1.87 (m, 3H), 1.61-1.53 (m, 3H). Human αVβ6 IC50 (nM)=91. Second eluting enantiomer Example 169 (Retention time 4.73 min., 4 mg, 3%) was isolated as a white solid. LC-MS retention time=1.60 min; m/z=467.2 [M+H]+ KINETIX XB-C18 (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, $CD_3OD$) δ ppm 7.38 (d, J=7.03 Hz, 1H), 7.06-6.99 (m, 3H), 6.79 (s, 1H), 6.45 (d, J=7.53 Hz, 1H), 4.63 (dd, J=10.79, 4.77 Hz, 1H), 3.84 (s, 3H), 3.54 (s, 3H), 3.42 (t, J=6.0 Hz, 2H), 3.18 (dd, J=14.81, 11.29 Hz, 1H), 2.83 (dd, J=14.81, 11.29 Hz, 1H), 2.73 (t, J=6.0 Hz, 2H), 2.68-2.54 (m, 4H), 1.93-1.87 (m, 3H), 1.61-1.53 (m, 3H). Human αVβ6 IC50 (nM)=67.

Example 170 and Example 171

Example 170: first eluting enantiomer of 3-(6-methoxypyridin-3-yl)-3-(4-(3-(5,6,7,8-tetrahydro-1,8-naphthyridin-2-yl)propyl)-2H-1,2,3-triazol-2-yl)propanoic acid Example 171: second eluting enantiomer of 3-(6-methoxypyridin-3-yl)-3-(4-(3-(5,6,7,8-tetrahydro-1,8-naphthyridin-2-yl)propyl)-2H-1,2,3-triazol-2-yl)propanoic acid

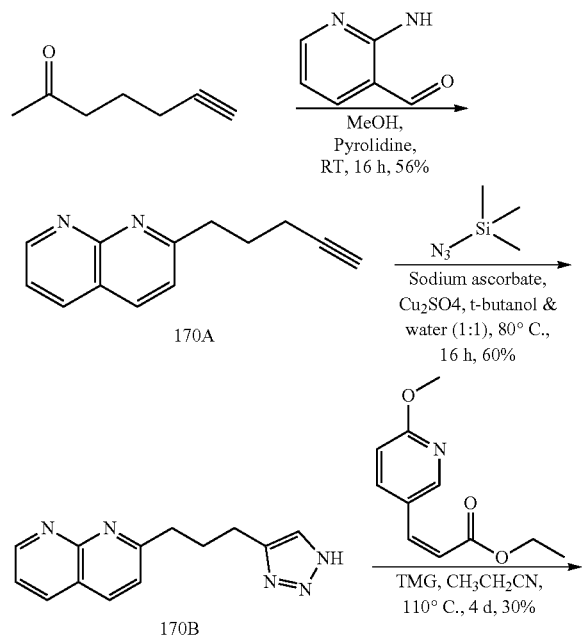

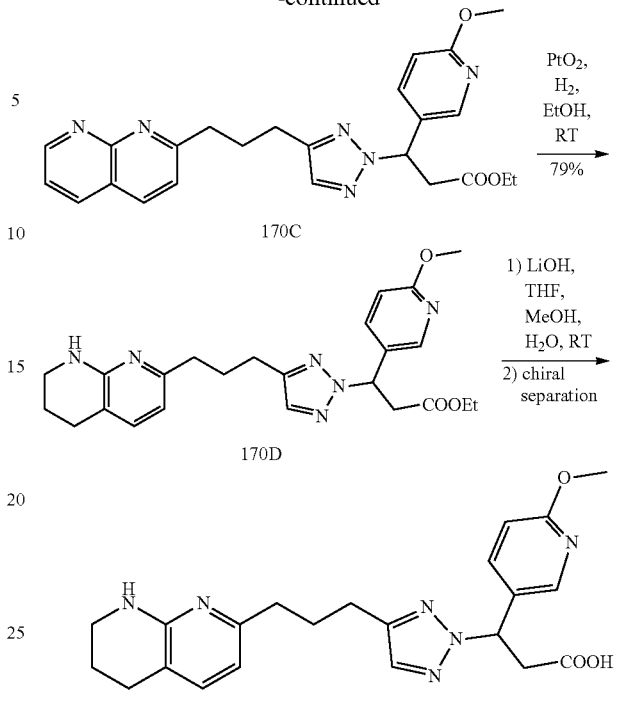

Example 170: first eluting enantiomer
Example 171: second eluting enantiomer 2-(pent-4-yn-1-yl)-1,8-naphthyridine (170A)

To a solution of hept-6-yn-2-one (1 g, 9.08 mmol) in MeOH (30 mL) was added pyrrolidine (0.751 mL, 9.08 mmol) and the solution was stirred at the RT for 10 min. under nitrogen atmosphere. 2-Aminonicotinaldehyde (1.164 g, 9.53 mmol) was added and the resulting reaction mixture was stirred at the RT for 16 h. After completion of the reaction, the reaction mixture was concentrated and the crude product was purified by combiflash chromatography (40 g Redisep® $SiO_2$ column, eluting with 60% ethyl acetate in n-hexanes) to afford the title compound 170A (1 g, 56%) as pale gummy liquid. LC-MS retention time=1.55 min; m/z=197.2 [M+H]+ KINETIX XB-C18, (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, $CDCl_3$) δ ppm 9.10 (dd, J=4.25, 2.00 Hz, 1H), 8.17 (dd, J=8.01, 2.00 Hz, 1H), 8.12 (d, J=8.51 Hz, 1H), 7.45 (dd, J=8.01, 2.00 Hz, 1H), 7.42 (d, J=8.2 Hz, 1H), 3.16-3.23 (t, J=7.6 Hz, 2H), 2.30-2.37 (m, 2H), 2.13-2.23 (m, 2H), 2.00 (t, J=2.63 Hz, 1H).

2-(3-(1H-1,2,3-triazol-4-yl)propyl)-1,8-naphthyridine (170B)

To a stirred solution of 2-(pent-4-yn-1-yl)-1,8-naphthyridine 170A (600 mg, 3.06 mmol) in t-butanol (10 mL) and water (10 mL) was added $TMSN_3$ (0.812 mL, 6.11 mmol), sodium ascorbate (1211 mg, 6.11 mmol) and copper(II) sulphate pentahydrate (229 mg, 0.917 mmol) at RT. The reaction mixture was then heated to 80° C. and stirred for 16 h. The reaction mixture was cooled RT, diluted with methanol (50 mL), filtered through Celite pad and the filtrate concentrated. The crude product was purified by combiflash chromatography (24 g Redisep® SiO$_2$ column, eluting with 8-10% methanol in chloroform) to afford the title compound 170B (0.47 g, 60%) as a brown gummy liquid. LC-MS retention time=0.80 min; m/z=240.1 [M+H]$^+$ Column-Kinetex XB-C18 (75×3 mm-2.6 μm), Mobile phase A: 0.1% TFA in water; Mobile phase B: ACN, Flow: 1 mL/min, Gradient B: 0 min—20%, 4 min—100%, $^1$H NMR (400 MHz, DMSO-d$_6$) δ ppm 9.04 (dd, J=4.52, 2.01 Hz, 1H), 8.34-8.47 (m, 1H), 8.37 (d, J=8.4 Hz, 1H), 7.53-7.65 (m, 3H), 3.03 (t, J=7.78 Hz, 2H), 2.65-2.75 (m, 2H), 2.09-2.23 (m, 2H).

Ethyl 3-(4-(3-(1,8-naphthyridin-2-yl)propyl)-2H-1,2,3-triazol-2-yl)-3-(6-methoxy-pyridin-3-yl)propanoate (170C)

In a sealed tube, to a stirred solution of 2-(3-(1H-1,2,3-triazol-4-yl)propyl)-1,8-naphthyridine 170B (270 mg, 1.128 mmol) in propionitrile (5 mL), ethyl (Z)-3-(6-methoxypyridin-3-yl)acrylate (351 mg, 1.693 mmol) and 1,1,3,3-tetramethylguanidine (0.425 mL, 3.39 mmol) were added. The reaction mixture was heated at 100° C. and stirred for 4 d. The reaction mixture was concentrated and the crude product was purified by combiflash chromatography (12 g Redisep® SiO$_2$ column, eluting with 3% methanol in chloroform) to afford the title compound 170C (150 mg, 30%) as a pale brown gummy liquid. LC-MS retention time=2.23 min; m/z=447.2 [M+H]$^+$ KINETIX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, DMSO-d$_6$) δ ppm 9.03 (dd, J=4.40, 1.96 Hz, 1H), 8.42 (dd, J=8.07, 1.96 Hz, 1H), 8.37 (d, J=8.31 Hz, 1H), 8.18 (d, J=2.69 Hz, 1H), 7.67 (dd, J=8.56, 2.69 Hz, 1H), 7.65 (s, 1H), 7.58 (dd, J=8.07, 4.16 Hz, 1H), 7.53 (d, J=8.07 Hz, 1H), 6.80 (d, J=8.80 Hz, 1H), 6.07 (dd, J=10.03, 5.38 Hz, 1H), 3.96-4.04 (m, 2H), 3.82 (s, 3H), 3.58 (dd, J=16.63, 10.03 Hz, 1H), 2.96-3.02 (m, 2H), 2.67-2.74 (m, 2H), 2.12 (quin, J=7.76 Hz, 2H), 1.06 (t, J=7.09 Hz, 3H).

Ethyl 3-(6-methoxypyridin-3-yl)-3-(4-(3-(5,6,7,8-tetrahydro-1,8-naphthyridin-2-yl)propyl)-2H-1,2,3-triazol-2-yl)propanoate (170D)

To a degassed solution of ethyl 3-(4-(3-(1,8-naphthyridin-2-yl)propyl)-2H-1,2,3-triazol-2-yl)-3-(6-methoxypyridin-3-yl)propanoate 170C (150 mg, 0.336 mmol) in ethanol (15 mL) was added platinum(IV) oxide (15 mg, 0.066 mmol). The reaction mixture was stirred at the RT under hydrogen balloon atmosphere for 16 h. The reaction mixture was filtered through Celite pad and the filtrate concentrated to afford the title compound 170D (120 mg, 79%) as a pale brown liquid. LC-MS retention time=2.60 min; m/z=451.4 [M+H]$^+$ KINETIX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.5 min. at 20% B with flow rate 1-1.5 mL/min; Detection: UV at 220 nm.

Example 170: first eluting enantiomer of 3-(6-methoxypyridin-3-yl)-3-(4-(3-(5,6,7,8-tetrahydro-1,8-naphthyridin-2-yl)propyl)-2H-1,2,3-triazol-2-yl)propanoic acid Example 171: second eluting enantiomer of 3-(6-methoxypyridin-3-yl)-3-(4-(3-(5,6,7,8-tetrahydro-1,8-naphthyridin-2-yl)propyl)-2H-1,2,3-triazol-2-yl)propanoic acid To a stirred solution of ethyl 3-(6-methoxypyridin-3-yl)-3-(4-(3-(5,6,7,8-tetrahydro-1,8-naphthyridin-2-yl)propyl)-2H-1,2,3-triazol-2-yl)propanoate 170D (200 mg, 0.444 mmol) in THF (5 mL), water (2 mL) and MeOH (5 mL), LiOH·H$_2$O (12.22 mg, 0.291 mmol) was added and the resulting reaction mixture was stirred at RT for 4 h. After completion of the reaction, citric acid (171 mg, 0.888 mmol) was added and the reaction mixture was stirred at the RT for 10 min. The reaction mixture was concentrated and the crude product was purified by preparative reverse phase preparative HPLC (Inersil ODS (250×19) mm; 5 micron; Mobile Phase A: 10 mM ammonium acetate (pH=4.5); Mobile Phase B: Acetonitrile; flow rate: 17 mL/min; Time (min)/% B: 0/10, 7/22, 12.5/22) afford the title compound (80 mg) as racemic mixture. The individual enantiomers were separated by chiral SFC (Luxcellulose-4 (250×21.5) mm; 5 micron; 50% CO$_2$ and 50% of 0.2% NH$_4$OH in Methanol and ACN (1:1) as co-solvent); Total Flow: 70 g/min; Back Pressure: 100 bar; Temperature: 30° C.; Detection: UV at 225 nM. The first eluting enantiomer, Example 170 (Retention time 7.0 min., 31 mg, 15%) was isolated as an off white solid. LC-MS retention time=1.19 min; m/z=423.2 [M+H]$^+$ KINETIX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 8.16 (d, J=2.51 Hz, 1H), 7.75 (dd, J=8.78, 2.76 Hz, 1H), 7.47 (s, 1H), 7.28 (d, J=8.03 Hz, 1H), 6.78 (d, J=8.53 Hz, 1H), 6.45 (d, J=7.03 Hz, 1H), 6.11 (dd, J=9.79, 5.77 Hz, 1H), 3.90 (s, 3H), 3.44 (t, J=5.6 Hz, 2H), 3.35 (dd, J=14.92, 10.2 Hz, 1H), 3.02 (dd, J=14.92, 4.16 Hz, 1H), 2.76 (t, J=6.27 Hz, 2H), 2.66-2.72 (m, 2H), 2.55-2.62 (m, 2H), 1.96-2.10 (m, 2H), 1.87-1.96 (m, 2H). Human αVβ6 IC50 (nM)=620. The second eluting enantiomer, Example 171 (Retention time. 8.50 min., 27 mg, 13%) was isolated as an off white solid, LC-MS retention time=1.19 min; m/z=423.2 [M+H]$^+$ KINETIX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 8.16 (d, J=2.51 Hz, 1H), 7.75 (dd, J=8.78, 2.76 Hz, 1H), 7.47 (s, 1H), 7.28 (d, J=8.03 Hz, 1H), 6.78 (d, J=8.53 Hz, 1H), 6.45 (d, J=7.03 Hz, 1H), 6.11 (dd, J=9.79, 5.77 Hz, 1H), 3.90 (s, 3H), 3.44 (t, J=5.6 Hz, 2H), 3.35 (dd, J=14.92, 10.2 Hz, 1H), 3.02 (dd, J=14.92, 4.16 Hz, 1H), 2.76 (t, J=6.27 Hz, 2H), 2.66-2.72 (m, 2H), 2.55-2.62 (m, 2H), 1.96-2.10 (m, 2H), 1.87-1.96 (m, 2H). Human αVβ6 IC50 (nM)=27.

| Example | Structure | Prep-HPLC/SFC conditions, 1H NMR and LC-MS data | Method |
|---|---|---|---|
| 172 | 3-(3-fluoro-4-methoxyphenyl)-3-(4-(3-(5,6,7,8-tetrahydro-1,8-naphthyridin-2-yl)propyl)-2H-1, 2, 3-triazol-2-yl)propanoic acid | Chiral SFC: RT = 8.37 min. Luxcellulose-4 (250 x 21.5) mm, 5u; 50% $CO_2$ and 50% of 0.2% $NH_4OH$ in Methanol and ACN (1:1) as co-solvent; Total Flow: 70 g/min: Back Pressure: 100 bar; Temperature: 30° C.; Detection: UV at 225 nM. $^1H$ NMR (400 MHz, $CD_3OD$) δ ppm 7.37 (s, 1H), 7.35 (d, J = 7.2 Hz, 1H), 6.90-7.05 (m, 3H), 6.44 (d, J = 7.34 Hz, 1H), 5.94 (dd, J = 11.37, 4.28 Hz, 1H), 3.75 (s, 3H), 3.35 (t, J = 6.0 Hz, 2H), 3.25-3.31 (m, 1H), 2.83 (dd, J = 14.92, 4.16 Hz, 1H), 2.67 (t, J = 6.2 Hz, 2H), 2.61-2.64 (m, 2H), 2.49 (t, J = 7.70 Hz, 2H), 1.75-2.01 (m, 4H), LC-MS: RT = 1.354 min., m/z = 440.2 [M + H]$^+$ KINETIX XB-C18, (3 x 75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min. then hold 0.5 min. at 20% B with flow rate 1-1.5 mL/min; Detection: UV at 220 nm, Human αVβ6 IC50 (nM) = 53 | Example 170/171 |
| 173 | 3-(3-fluoro-4-methoxyphenyl)-3-(4-(3-(5,6,7,8-tetrahydro-1,8-naphthyridin-2-yl)propyl)-2H-1, 2, 3-triazol-2-yl)propanoic acid | Chiral SFC: RT = 9.98 min. Luxcellulose-4 (250 x 21.5) mm, 5u; 50% $CO_2$ and 50% of 0.2% $NH_4OH$ in Methanol and ACN (1:1) as co-solvent; Total Flow: 70 g/min; Back Pressure: 100 bar; Temperature: 30° C.; Detection: UV at 225 nM. $^1H$ NMR (400 MHz, $CD_3OD$) δ ppm 7.37 (s, 1H), 7.35 (d, J = 7.2 Hz, 1H), 6.90-7.05 (m, 3H), 6.44 (d, J = 7.34 Hz, 1H), 5.94 (dd, J = 11.37, 4.28 Hz, 1H), 3.75 (s, 3H), 3.35 (t, J = 6.0 Hz, 2H), 3.25-3.31 (m, 1H), 2.83 (dd, J = 14.92, 4.16 Hz, 1H), 2.67 (t, J = 6.2 Hz, 2H), 2.61-2.64 (m, 2H), 2.49 (t, J = 7.70 Hz, 2H), 1.75-2.01 (m, 4H), LC-MS: RT = 1.354 min., m/z = 440.2 [M + H]$^+$ KINETIX XB-C18, (3 x 75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm, Human αVβ6 IC50 (nM) = 3.0 | Example 170/171 |
| 174 | 3-(quinolin-3-yl)-3-(4-(3-(5,6,7,8-tetrahydro-1,8-naphthyridin-2-yl)propyl)-2H-1, 2, 3-triazol-2-yl)propanoic acid | Chiral SFC: RT = 16 min, Luxcellulose-4 (250 x 21.5) mm, 5u; 50% $CO_2$ and 50% of 0.2% $NH_4OH$ in Methanol and ACN (1:1) as co-solvent; Total Flow: 70 g/min; Back Pressure: 100 bar; Temperature: 30° C.; Detection: UV at 230 nM. $^1H$ NMR (400 MHz, $CD_3OD$) δ ppm 8.78 (d, J = 2.01 Hz, 1H), 8.27 (d, J = 2.01 Hz, 1H), 7.91 (d, J = 8.03 Hz, 1H), 7.83 (d, J = 8.03 Hz, 1H), 7.67 (ddd, J = 8.53, 7.03, 1.51 Hz, 1H), 7.54-7.50 (m, 1H), 7.43 (s, 1H), 7.36 (d, J = 7.53 Hz, 1H), 6.45 (d, J = 7.53 Hz, 1H), 6.28 (dd, J = 11.04, 4.52 Hz, 1H), 3.42 (dd, J = 14.8, 11.2 Hz, 1H), 3.37 (t, J = 5.6 Hz, 2H), 3.05 (dd, J = 14.8, 4.4 Hz, 1H), 2.68-2.60 (m, 4H), 2.54-2.50 (m, 2H), 1.98-1.92 (m, 2H), 1.78-1.84 (m, 2H), LC-MS: RT = 1.359 min, m/z = 440.2 [M + H]$^+$ KINETIX XB-C18, (3 x 75) mm, 2.6 | Example 170/171 |

| Example | Structure | Prep-HPLC/SFC conditions, 1H NMR and LC-MS data | Method |
|---|---|---|---|
| | | micron column: Flow rate: 1 mL/min; Mobile Phase A: 10 mM HCO$_2$NH$_4$ in 98% water/2% ACN; Mobile Phase B: 10 mM HCO$_2$NH$_4$ in 2% water/ 98% ACN; 20% B to 100% B over 4.6 min, then hold 0.5 min. at 20% B with flow rate 1-1.5 mL/min; Detection: UV at 220 nm, Human αVβ6 IC50 (nM) = 170. | |
| 175 | 3-(quinolin-3-yl)-3-(4-(3-(5,6,7,8-tetrahydro-1,8-naphthyridin-2-yl)propyl)-2H-1, 2, 3-triazol-2-yl)propanoic acid | Chiral SFC: RT = 18.34 min. Luxcellulose-4 (250 x 21.5) mm, 5u; 50% CO$_2$ and 50% of 0.2% NH$_4$OH in Methanol and ACN (1:1) as co-solvent; Total Flow: 70 g/min; Back Pressure: 100 bar; Temperature: 30° C.; Detection: UV at 230 nM. $^1$H NMR (400 MHz, CD$_3$OD) δ ppm 8.78 (d, J = 2.01 Hz, 1H), 8.27 (d, J = 2.01 Hz, 1H), 7.91 (d, J = 8.03 Hz, 1H), 7.83 (d, J = 8.03 Hz, 1H), 7.67 (ddd, J = 8.53, 7.03, 1.51 Hz, 1H), 7.54-7.50 (m, 1H), 7.43 (s, 1H), 7.36 (d, J = 7.53 Hz, 1H), 6.45 (d, J = 7.53 Hz, 1H), 6.28 (dd, J = 11.04, 4.52 Hz, 1H), 3.42 (dd, J = 14.8, 11.2 Hz, 1H), 3.37 (t, J = 5.6 Hz, 2H), 3.05 (dd, J = 14.8, 4.4 Hz, 1H), 2.68-2.60 (m, 4H), 2.54-2.50 (m, 2H), 1.98-1.92 (m, 2H), 1.78-1.84 (m, 2H), LC-MS: RT = 1.359 min, m/z = 440.2 [M + H]$^+$ KINETIX XB-C18, (3 x 75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/ 98% ACN; 20% B to 100% B over 4.6 min, then hold 0.5 min. at 20% B with flow rate 1-1.5 mL/min; Detection: UV at 220 nm, Human αVβ6 IC50 (nM) = 4.3 | Example 170/171 |
| 176 | 3-(2-methoxypyrimidin-5-yl)-3-(4-(3-(5,6,7,8-tetrahydro-1,8-naphthyridin-2-yl)propyl)-2H-1, 2, 3-triazol-2-yl)propanoic acid | Chiral SFC: RT = 12.5 min (Chiralpak IC (250 x 21 mm, 5 u); 55% CO$_2$ and 45% of 0.2% NH$_4$OH in Methanol and ACN (1:1) as co-solvent; Total Flow: 70 g/min; Back Pressure: 100 bar; Temperature: 30° C.; Detection: UV at 220. $^1$H NMR (400 MHz, CD$_3$OD) δ ppm 8.66 (s, 2H), 7.54 (s, 1H), 7.50 (d, J = 7.34 Hz, 1H), 6.58 (d, J = 7.34 Hz, 1H), 6.15 (dd, J = 10.64, 4.77 Hz, 1H), 4.02 (s, 3H), 3.44-3.50 (m, 2H), 3.33-3.40 (m, 1H), 3.01 (dd, J = 14.55, 4.77 Hz, 1H), 2.79 (t, J = 6.24 Hz, 2H), 2.52-2.75 (m, 4H), 1.99-2.08 (m, 2H), 1.86-1.98 (m, 2H), LC-MS: RT = 1.079 min, m/z = 424.4 [M + H]$^+$ KINETIX XB-C18, (3 x 75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min. then hold 0.5 min. at 20% B with flow rate 1-1.5 mL/min; Detection: UV at 220 nm, Human αVβ6 IC50 (nM) = 43. | Example 170/171 |

| Example | Structure | Prep-HPLC/SFC conditions, 1H NMR and LC-MS data | Method |
|---|---|---|---|
| 177 | 3-(2-methoxypyrimidin-5-yl)-3-(4-(3-(5,6,7,8-tetrahydro-1,8-naphthyridin-2-yl)propyl)-2H-1, 2, 3-triazol-2-yl)propanoic acid | Chiral SFC: RT = 13.7 ruin (Chiralpak IC (250 x 21 mm, 5 u); 55% CO$_2$ and 45% of 0.2% NH$_4$OH in Methanol and ACN (1:1) as co-solvent; Total Flow: 70 g/min; Back Pressure: 100 bar: Temperature: 30° C.; Detection: UV at 220. $^1$H NMR (400 MHz, CD$_3$OD) δ ppm 8.66 (s, 2H), 7.54 (s, 1H), 7.50 (d, J = 7.34 Hz, 1H), 6.58 (d, J = 7.34 Hz, 1H), 6.15 (dd, J = 10.64, 4.77 Hz, 1H), 4.02 (s, 3H), 3.44-3.50 (m, 2H), 3.33-3.40 (m, 1H), 3.01 (dd, J = 14.55, 4.77 Hz, 1H), 2.79 (t, J = 6.24 Hz, 2H), 2.52-2.75 (m, 4H), 1.99-2.08 (m, 2H), 1.86-1.98 (m, 2H), LC-MS: RT = 1.079 min, m/z = 424.4 [M + H]$^+$ KINETIX XB-C18, (3 × 75) mm, 2.6 micron column: Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN: 20% B to 100% B over 4.6 min. then hold 0.5 min. at 20% B with flow rate 1-1.5 mL/min; Detection: UV at 220 nm, Human αVβ6 IC50 (nM) = 315. | Example 170/171 |

Example 178 and Example 179

Example 178: first eluting enantiomer of 3-(3-fluoro-4-methoxyphenyl)-3-(4-(3-(5,6,7,8-tetrahydro-1,8-naphthyridin-2-yl)propyl)oxazol-2-yl)propanoic acid

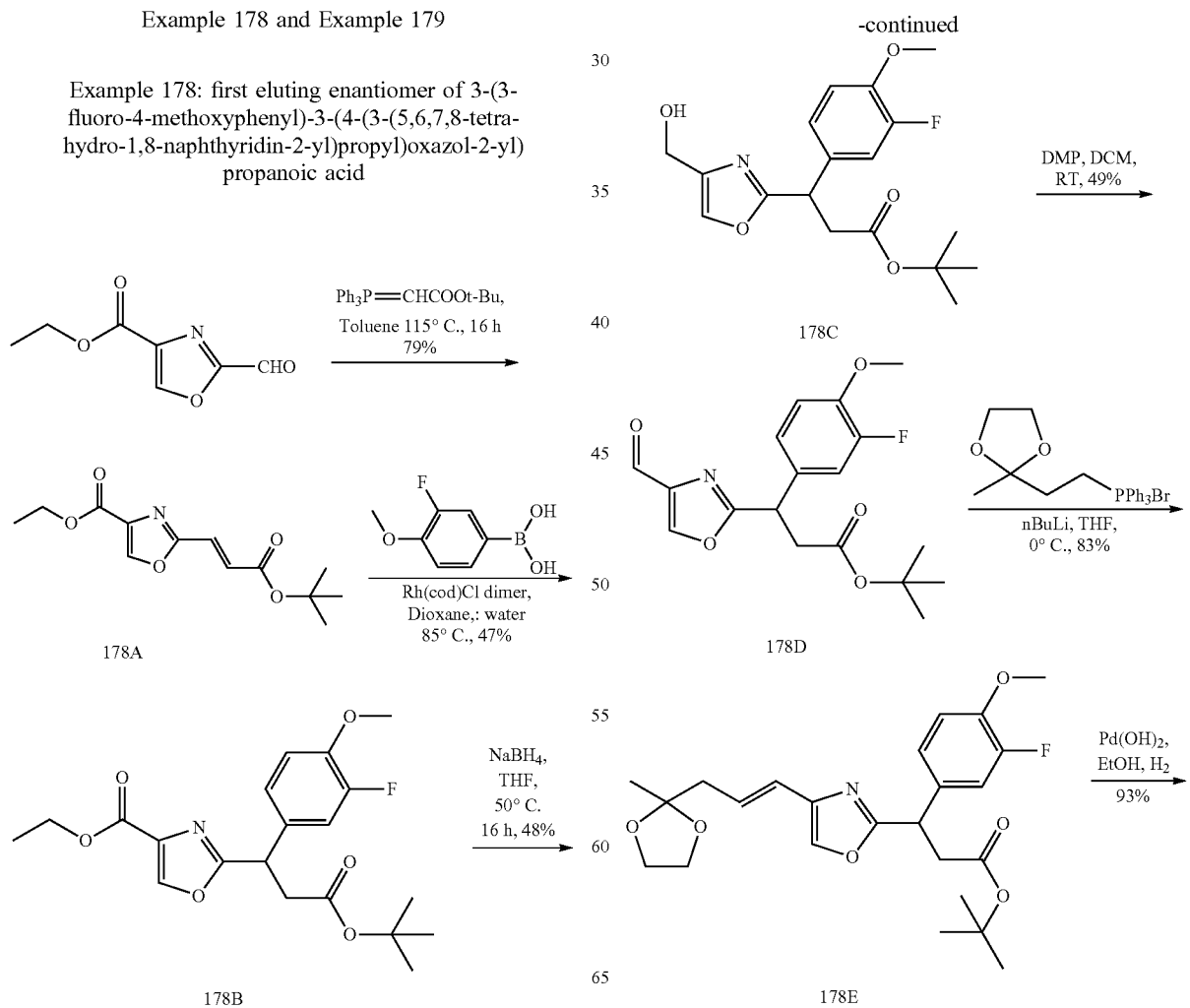

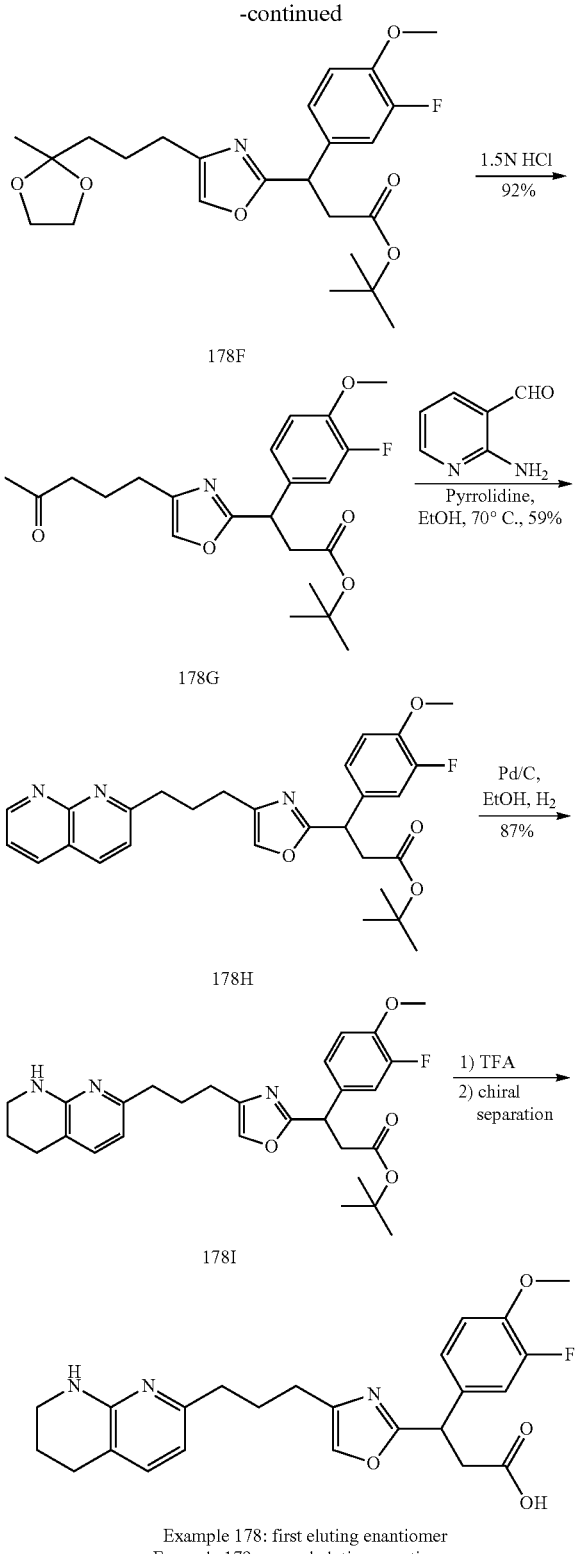

178F

178G

178H

178I

Example 178: first eluting enantiomer
Example 179: second eluting enantiomer

Ethyl (E)-2-(3-(tert-butoxy)-3-oxoprop-1-en-1-yl)oxazole-4-carboxylate (178A)

To a stirred solution of ethyl 2-formyloxazole-4-carboxylate (4 g, 23.65 mmol) in toluene (100 mL) was added tert-butyl 2-(triphenyl-15-phosphanylidene)acetate (13.35 g, 35.5 mmol) and the reaction mixture was heated to 110° C. and stirred for 16 h. After completion of the reaction, the reaction mixture was cooled and concentrated under vacuum. The crude product was purified by combiflash chromatography (40 g Redisep® $SiO_2$ column, eluting 45% ethyl acetate in pet ether) to afford the title compound 178A (5 g, 79%) as an off white solid. LC-MS retention time=2.77 min; m/z=268.2 [M+H]$^+$ KINETIX XB-C18, (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm. $^1$H NMR (400 MHz, $CDCl_3$) δ ppm 8.23 (s, 1H), 7.37 (d, J=16.01 Hz, 1H), 6.77 (d, J=16.01 Hz, 1H), 4.41 (q, J=7.00 Hz, 2H), 1.52 (s, 9H), 1.40 (t, J=7.13 Hz, 3H).

Ethyl 2-(3-(tert-butoxy)-1-(3-fluoro-4-methoxyphenyl)-3-oxopropyl)oxazole-4-carboxylate (178B)

To a stirred solution of ethyl (E)-2-(3-(tert-butoxy)-3-oxoprop-1-en-1-yl)oxazole-4-carboxylate 178A (1 g, 3.74 mmol) in dioxane (30 mL) and water (10 mL) was added (3-fluoro-4-methoxyphenyl)boronic acid (0.954 g, 5.61 mmol). The reaction mixture was purged with argon for 10 min and then TEA (1.043 mL, 7.48 mmol) and chloro(1,5-cyclooctadiene)rhodium(i) dimer (0.092 g, 0.187 mmol) were added. The reaction mixture was heated to 80° C. and stirred for 16 h. The reaction mixture was cooled to RT, diluted with water (50 mL) and extracted with ethyl acetate (2×50 mL). The combined organic layer was dried ($Na_2SO_4$), filtered and the filtrate concentrated. The crude product was purified by combiflash chromatography (40 g Redisep® $SiO_2$ column, eluting with 35% ethyl acetate in n-hexanes) to afford the title compound 178B (700 mg, 47%) as an off white gummy liquid. LC-MS retention time=3.13 min; m/z=338.1 [M−56+H]$^+$ KINETIX XB-C18, (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection: UV at 220 nm.

Tert-butyl 3-(3-fluoro-4-methoxyphenyl)-3-(4-(hydroxymethyl)oxazol-2-yl)propanoate (178C)

To a stirred solution of ethyl 2-(3-(tert-butoxy)-1-(3-fluoro-4-methoxyphenyl)-3-oxopropyl)oxazole-4-carboxylate carboxylate 178B (700 mg, 1.779 mmol) in THF (20 mL) and methanol (0.5 mL) was added $NaBH_4$ (202 mg, 5.34 mmol) under nitrogen atmosphere at RT. The reaction mixture was heated to 50° C. and stirred for 16 h. After completion of the reaction, the reaction mixture was quenched with ice cold water (15 mL) and extracted with ethyl acetate (2×30 mL). The combined organic layer was dried over anhydrous sodium sulphate, filtered and concentrated. The crude product was purified by combiflash chromatography (12 g Redisep® $SiO_2$ column, eluting with 45% ethyl acetate in n-hexanes) to afford the title compound 178C (300 mg, 48%) as an off white gummy liquid. LC-MS retention time=2.46 min; m/z=352.3 [M+H]$^+$ KINETIX XB-C18, (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.5 min. at 20% B with flow rate 1-1.5 mL/min; Detection:

UV at 220 nm. ¹H NMR (400 MHz, CDCl₃) δ ppm 7.50 (d, J=1.00 Hz, 1H), 6.98-7.09 (m, 2H), 6.85-6.94 (m, 1H), 4.58 (d, J=6.02 Hz, 2H), 4.52 (dd J=16.2, 8.03 Hz, 1H), 3.86 (s, 3H), 3.19 (dd, J=16.06, 8.53 Hz, 1H), 2.85 (dd, J=16.06, 7.53 Hz, 1H), 2.01 (t, J=6.02 Hz, 1H), 1.36 (s, 9H).

Tert-butyl 3-(3-fluoro-4-methoxyphenyl)-3-(4-formyloxazol-2-yl)propanoate (178D)

To a cooled solution of tert-butyl 3-(3-fluoro-4-methoxyphenyl)-3-(4-(hydroxymethyl)oxazol-2-yl)propanoate 178C (250 mg, 0.711 mmol) in DCM (5 mL) was added Dess-Martin periodinane (604 mg, 1.423 mmol) at 0° C. under nitrogen atmosphere. The reaction mixture was slowly warmed to RT and stirred at the same temperature for 16 h. After completion of the reaction, the reaction mixture was diluted with ethyl acetate (10 mL), washed with 10% sodium bicarbonate solution (2×5 mL), water (5 mL), brine solution (5 mL), dried over anhydrous sodium sulphate, filtered then concentrated. The crude product was purified by combiflash chromatography (4 g Redisep® SiO₂ column, eluting with 18% ethyl acetate in n-hexanes) to afford the title compound 178D (120 mg, 48%) as an off white gummy liquid. LC-MS retention time=2.76 min; m/z=350.2 [M+H]⁺ KINETIX XB-C18, (3×75) mm, 2.6 micron column; Flow rate: 1 mL/min; Mobile Phase A: 10 mM HCO₂NH₄ in 98% water/ 2% ACN; Mobile Phase B: 10 mM HCO₂NH₄ in 2% water/98% ACN; 20% B to 100% B over 4.6 min, then hold 0.5 min. at 20% B with flow rate 1-1.5 mL/min; Detection: UV at 220 nm. ¹H NMR (400 MHz, DMSO-d₆) δ ppm 9.83 (s, 1H), 8.90 (s, 1H), 7.23 (dd, J=12.55, 2.01 Hz, 1H), 7.03-7.16 (m, 2H), 4.60 (dd, J=9.29, 6.78 Hz, 1H), 3.82 (s, 3H), 3.18 (dd, J=16.31, 9.29 Hz, 1H), 2.90 (dd, J=16.06, 6.53 Hz, 1H), 1.29 (s, 9H).

Tert-butyl (E)-3-(3-fluoro-4-methoxyphenyl)-3-(4-(3-(2-methyl-1,3-dioxolan-2-yl)prop-1-en-1-yl)oxazol-2-yl)propanoate (178E)

To a cooled solution of bromo(2-(2-methyl-1,3-dioxolan-2-yl)ethyl)triphenyl-15-phosphane (785 mg, 1.717 mmol) in THF (25 mL) was added butyllithium (0.859 mL, 2.147 mmol, 2.5M solution in hexane) at 0° C. under nitrogen atmosphere by drop wise and stirred at the same temperature for 30 min. tert-Butyl 3-(3-fluoro-4-methoxyphenyl)-3-(4-formyloxazol-2-yl)propanoate 178D (300 mg, 0.859 mmol) in THF (25 mL) was added drop wise and the reaction mixture was stirred at the same temperature for 2 h. After completion of the reaction, the reaction mixture was quenched with saturated ammonium chloride solution (5 mL), extracted with ethyl acetate (2×10 mL). The combined organic layer was washed with water (10 mL), brine solution (10 mL), dried over anhydrous sodium sulphate, filtered and concentrated. The crude product was purified by combiflash chromatography (4 g Redisep® SiO₂ column, eluting with 18% ethyl acetate in n-hexanes) to afford the title compound 178E (320 mg, 83%) as an off white gummy liquid. LC-MS retention time=3.46 min; m/z=448.2 [M+H]⁺ KINETIX XB-C18, (3×75) mm, 2.6 micron column; Flow rate: 1 mL/min; Mobile Phase A: 10 mM HCO₂NH₄ in 98% water/ 2% ACN; Mobile Phase B: 10 mM HCO₂NH₄ in 2% water/98% ACN; 20% B to 100% B over 4.6 min, then hold 0.5 min. at 20% B with flow rate 1-1.5 mL/min; Detection: UV at 220 nm.

Tert-butyl 3-(3-fluoro-4-methoxyphenyl)-3-(4-(3-(2-methyl-1,3-dioxolan-2-yl)propyl)oxazol-2-yl)propanoate (178F)

To a degassed solution of tert-butyl (E)-3-(3-fluoro-4-methoxyphenyl)-3-(4-(3-(2-methyl-1,3-dioxolan-2-yl)prop-1-en-1-yl)oxazol-2-yl)propanoate 178E (320 mg, 0.715 mmol) in ethanol (10 mL) was added palladium hydroxide on carbon (30 mg, 0.043 mmol) and the reaction mixture was stirred at RT under hydrogen balloon atmosphere for 16 h. The reaction mixture was filtered through Celite pad and the filtrate concentrated to afford the title compound 178F (300 mg, 93%) as a pale brown liquid. LC-MS retention time=1.48 min; m/z=450.6 [M+H]⁺ AQUITY UPLC BEH C18 (3.0×50 mm, 1.7 μm, Mobile phase A: 10 mM NH₄COOCH₃:ACN (95:5) Mobile phase B: 10 mM NH₄COOCH₃:ACN (5:95), Method: % B: 0 min—20%:1.1 min—90%:1.7 min—90%. ¹H NMR (400 MHz, CD₃OD) δ ppm 7.55 (s, 1H), 7.01-7.09 (m, 3H), 4.51 (dd, J=9.54, 7.03 Hz, 1H), 3.86-3.96 (m, 4H), 3.86 (s, 3H), 3.15 (dd, J=16.06, 9.04 Hz, 1H), 2.88 (dd, J=16.06, 7.03 Hz, 1H), 2.44-2.57 (m, 2H), 1.59-1.78 (m, 4H), 1.36 (s, 9H), 1.29 (s, 3H).

Tert-butyl 3-(3-fluoro-4-methoxyphenyl)-3-(4-(4-oxopentyl)oxazol-2-yl)propanoate (178G)

To a cooled solution of tert-butyl 3-(3-fluoro-4-methoxyphenyl)-3-(4-(3-(2-methyl-1,3-dioxolan-2-yl)propyl)oxazol-2-yl)propanoate 178F (300 mg, 0.667 mmol) in THF (2 mL) was added HCl (0.890 mL, 1.335 mmol, 1.5 M) at 0° C. and the solution was stirred at the same temperature for 6 h. After completion of the reaction, the reaction mixture was diluted with water (25 mL) and extracted with ethyl acetate (2×50 mL). The combined organic layer was washed with 10% sodium bicarbonate solution (300 mL), water (30 mL), brine solution (30 mL), and dried over anhydrous sodium sulphate, filtered and concentrated to afford the title compound 178G (250 mg, 92%) as an off white gummy liquid. LC-MS retention time=3.00 min; m/z=406.2 [M+H]⁺ KINETIX XB-C18, (3×75) mm, 2.6 micron column; Flow rate: 1 mL/min; Mobile Phase A: 10 mM HCO₂NH₄ in 98% water/2% ACN; Mobile Phase B: 10 mM HCO₂NH₄ in 2% water/98% ACN; 20% B to 100% B over 4.6 min, then hold 0.5 min. at 20% B with flow rate 1-1.5 mL/min; Detection: UV at 220 nm. ¹H NMR (400 MHz, CDCl₃) δ ppm 7.26 (s, 1H), 6.98-7.05 (m, 2H), 6.86-6.93 (m, 1H), 4.49 (t, J=8.0 Hz, 1H), 3.86 (s, 3H), 3.16 (dd, J=16.01, 8.51 Hz, 1H), 2.83 (dd, J=16.01, 7.50 Hz, 1H), 2.41-2.53 (m, 4H), 2.13 (s, 3H), 1.87-1.93 (m, 2H), 1.36 (s, 9H).

Tert-butyl 3-(4-(3-(1,8-naphthyridin-2-yl)propyl)oxazol-2-yl)-3-(3-fluoro-4-methoxyphenyl)propanoate (178H)

To a solution of tert-butyl 3-(3-fluoro-4-methoxyphenyl)-3-(4-(4-oxopentyl)oxazol-2-yl)propanoate 178G (250 mg, 0.617 mmol) in ethanol (15 mL) was added pyrrolidine (0.102 mL, 1.233 mmol) and stirred at the RT under nitrogen atmosphere for 10 min. 2-Aminonicotinaldehyde (90 mg, 0.740 mmol) was added and the resulting reaction mixture was heated to 80° C. and stirred for 16 h. After completion of the reaction, the reaction mixture was concentrate and the crude product was purified by combiflash chromatography (12 g Redisep® SiO₂ column, eluting with 65% ethyl acetate in n-hexanes) to afford the title compound 178H (180 mg, 59%) as a pale brown gummy liquid. LC-MS retention time=2.79 min; m/z=492.2 [M+H]⁺ KINETIX XB-C18, (3×75) mm, 2.6 micron column; Flow rate: 1 mL/min; Mobile Phase A: 10 mM HCO₂NH₄ in 98% water/2% ACN; Mobile Phase B: 10 mM HCO₂NH₄ in 2% water/98% ACN; 20% B to 100% B over 4.6 min, then hold 0.5 min. at 20% B with flow rate 1-1.5 mL/min; Detection: UV at 220 nm. ¹H NMR (400 MHz, DMSO-d₆) δ ppm 9.04 (dd, J=4.52, 2.01

Hz, 1H), 8.42 (dd, J=7.6, 2.0 Hz, 1H), 8.37 (d, J=8.4 Hz, 1H), 7.74 (s, 1H), 7.57 (dd, J=8.0, 4.0 Hz, 1H), 7.55 (d, J=8.0 Hz, 1H), 7.16 (dd, J=12.2, 2.0 Hz, 1H), 7.10 (m, 1H), 7.05 (m, 1H), 4.46 (dd, J=9.54, 6.53 Hz, 1H), 3.80 (s, 3H), 3.10 (dd, J=14.8, 11.6 Hz, 1H), 3.03 (t, J=7.6 Hz, 2H), 2.88 (dd, J=16.06, 7.03 Hz, 1H), 2.02-2.15 (m, 2H), 1.28 (s, 9H).

Tert-butyl 3-(3-fluoro-4-methoxyphenyl)-3-(4-(3-(5,6,7,8-tetrahydro-1,8-naphthyridin-2-yl)propyl)-oxazol-2-yl)propanoate (178I)

To a degassed solution of tert-butyl 3-(4-(3-(1,8-naphthyridin-2-yl)propyl)oxazol-2-yl)-3-(3-fluoro-4-methoxyphenyl)propanoate 178H (80 mg, 0.163 mmol) in THF (10 mL), was purged with nitrogen for 5 min. Platinum(IV) oxide (8 mg, 0.035 mmol) was added and the reaction mixture was stirred under hydrogen balloon atmosphere at RT for 2 h. After completion of the reaction, the reaction mixture was filtered through Celite pad and the filtrate was concentrated to afford the title compound 178I (70 mg, 87%) as a pale brown liquid. LC-MS retention time=1.72 min; m/z=496.2 [M+H]+ Column-Luna 3.0 C18(2) 100A° LC column (20× 4.0 mm) Mercury MS™, Mobile phase A: 0.1% TFA in water, Mobile phase B: 0.1% TFA in ACN, Flow: 1 mL/min, Gradient B: 0 min—20%, 2.7 min—90%.

Example 178: first eluting enantiomer of 3-(3-fluoro-4-methoxyphenyl)-3-(4-(3-(5,6,7,8-tetrahydro-1,8-naphthyridin-2-yl)propyl)oxazol-2-yl) propanoic acid Example 179: second eluting enantiomer of 3-(3-fluoro-4-methoxyphenyl)-3-(4-(3-(5,6,7,8-tetrahydro-1,8-naphthyridin-2-yl)propyl)oxazol-2-yl) propanoic acid To a cooled solution of tert-butyl 3-(3-fluoro-4-methoxyphenyl)-3-(4-(3-(5,6,7,8-tetrahydro-1,8-naphthyridin-2-yl)propyl)oxazol-2-yl)propanoate (130 mg, 0.262 mmol) in DCM (5 mL) was added TFA (0.061 mL, 0.787 mmol) at 0° C. The reaction mixture was slowly warmed to RT and stirred for 18 h. After completion of the reaction, the reaction mixture was concentrated and the crude product was purified by preparative reverse phase HPLC (SUNFIRE C18 (150× 19) mm; 5 micron; Mobile Phase A: 10 mM ammonium acetate in water; Mobile Phase B: Acetonitrile; flow rate: 17 mL/min; Time (min)/% B: 0/20, 12/40) to afford the title compound (60 mg) as racemic mixture. The individual enantiomers were separated by chiral SFC (Luxcellulose-4 (250×21.5) mm, 5 micron; 50% CO2 and 50% of 0.2% NH4OH in Methanol and ACN (1:1) as co-solvent; Total Flow: 70 g/min; Back Pressure: 100 bar; Temperature: 30° C.; Detection: UV at 230 nM). The first eluting enantiomer Example 178 (Retention time 4.7 min., 20 mg, 16%) was isolated as an off white solid. LC-MS retention time=1.42 min; m/z=440.2 [M+H]+ KINETIX XB-C18, (3 20×75) mm, 2.6 micron column; Flow rate: 1 mL/min; Mobile Phase A: 10 mM HCO2NH4 in 98% water/2% ACN; Mobile Phase B: 10 mM HCO2NH4 in 2% water/98% ACN; 20% B to 100% B over 4.6 min, then hold 0.5 min. at 20% B with flow rate 1-1.5 mL/min; Detection: UV at 220 nm. 1H NMR (400 MHz, CD3OD) δ ppm 7.58 (s, 1H), 7.46 (d, J=7.03 Hz, 1H), 7.01-7.12 (m, 3H), 6.54 (d, J=7.53 Hz, 1H), 4.54 (dd, J=1.55, 5.02 Hz, 1H), 3.87 (s, 3H), 3.47 (t, J=5.6 Hz, 2H), 3.10 (dd, J=14.8, 11.6 Hz, 1H), 2.71-2.82 (m, 3H), 2.51-2.63 (m, 4H), 1.89-2.09 (m, 4H). Human αVβ6 IC50 (nM)=1.4. Second eluting enantiomer Example 179 (Retention time.

6.8 min., 18 mg, 15%) was isolated as an off white solid. LC-MS retention time=1.42 min; m/z=440.2 [M+H]+ KINETIX XB-C18, (3×75) mm, 2.6 micron column; Flow rate: 1 mL/min; Mobile Phase A: 10 mM HCO2NH4 in 98% water/2% ACN; Mobile Phase B: 10 mM HCO2NH4 in 2% water/98% ACN; 20% B to 100% B over 4.6 min, then hold 0.5 min. at 20% B with flow rate 1-1.5 mL/min; Detection: UV at 220 nm. 1H NMR (400 MHz, CD3OD) δ ppm 7.58 (s, 1H), 7.46 (d, J=7.03 Hz, 1H), 7.01-7.12 (m, 3H), 6.54 (d, J=7.53 Hz, 1H), 4.54 (dd, J=11.55, 5.02 Hz, 1H), 3.87 (s, 3H), 3.47 (t, J=5.6 Hz, 2H), 3.10 (dd, J=14.8, 11.6 Hz, 1H), 2.71-2.82 (m, 3H), 2.51-2.63 (m, 4H), 1.89-2.09 (m, 4H). Human αVβ6 IC50 (nM)=66.

Example 180 and Example 181

Example 180: first eluting enantiomer of 3-(3-fluoro-4-methoxyphenyl)-3-(5-methyl-4-(4-(5,6,7,8-tetrahydro-1,8-naphthyridin-2-yl)butyl)oxazol-2-yl) propanoic acid Example 181: second eluting enantiomer of 3-(3-fluoro-4-methoxyphenyl)-3-(5-methyl-4-(4-(5,6,7,8-tetrahydro-1,8-naphthyridin-2-yl)butyl)oxazol-2-yl) propanoic acid

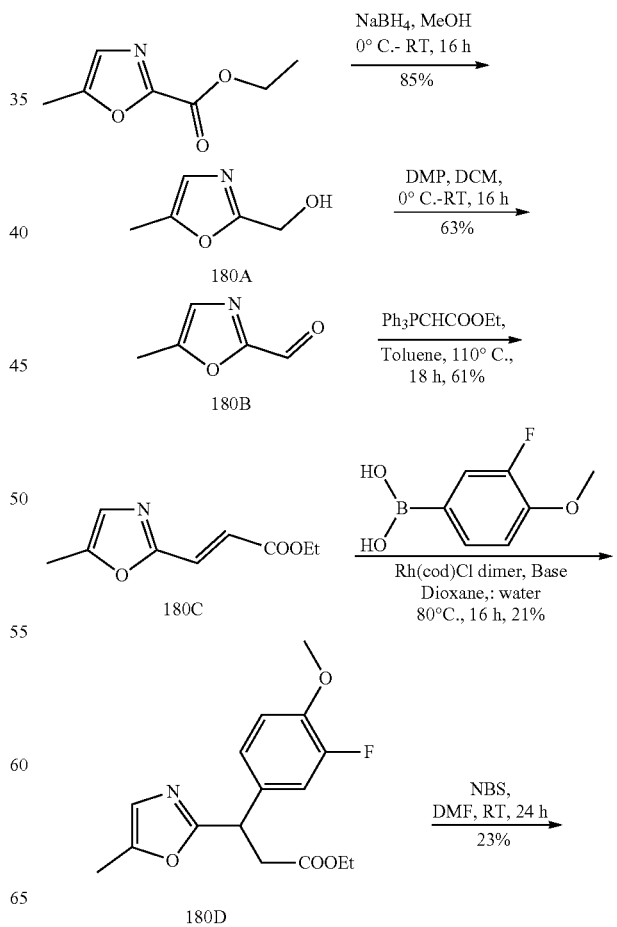

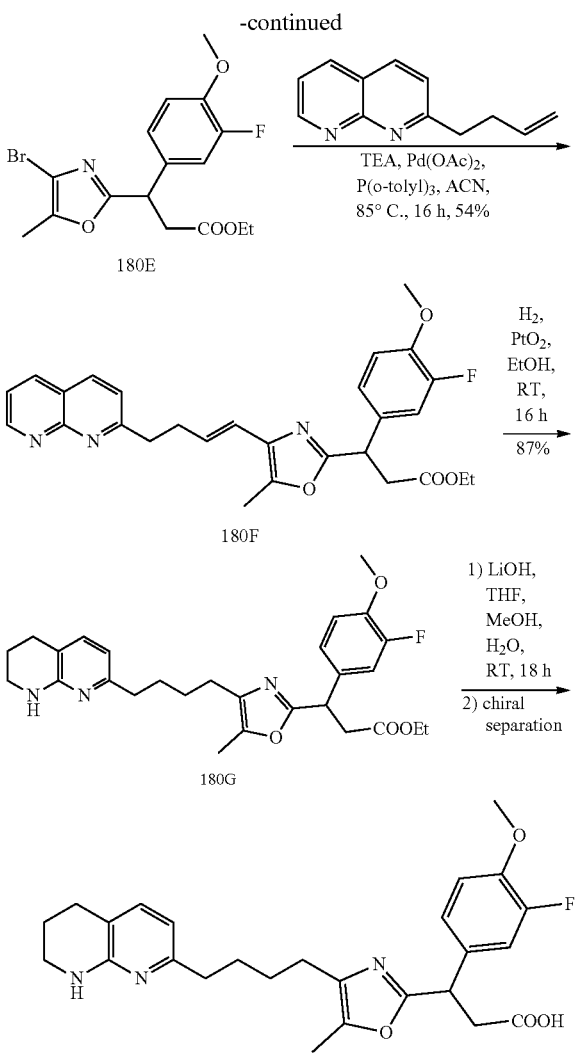

Example 180: first eluting enantiomer
Example 181: second eluting enantiomer (5-methyloxazol-2-yl)methanol (180A)

To a stirred solution of ethyl 5-methyloxazole-2-carboxylate (2.1 g, 13.54 mmol) in MeOH (30 mL) was added NaBH$_4$ (1.280 g, 33.8 mmol) portion wise at 0° C. The resulting mixture slowly warmed to RT and stirred for 16 h. The reaction mixture was them concentrated and residue was diluted with water (20 mL) and extracted with DCM (2×50 mL). The combined organic layer was washed with water, brine, dried (Na$_2$SO$_4$), filtered and the filtrate concentrated to afford the title compound 180A (1.3 g, 85%) as a light yellow oil. LC-MS retention time=0.395 min; m/z=114.2 [M+H]$^+$ KINETEX XB-C18, (3×75) mm, 2.6 micron column; Flow rate: 1 mL/min; Mobile Phase A: 10 mM NH$_4$COOH in 98% water/2% ACN; Mobile Phase B: 10 mM NH$_4$COOH in 2% water/98% ACN; 20% B to 100% B over 4.6 min, then hold 0.4 min. at 20% B with flow rate 1-1.5 mL/min; Detection: UV at 220 nm. $^1$H NMR (400 MHz, DMSO-d$_6$) δ ppm 6.75-6.63 (s, 1H), 5.53 (br. s., 1H), 4.40 (s, 2H), 2.24 (s, 3H).

5-methyloxazole-2-carbaldehyde (180B)

To a stirred solution of (5-methyloxazol-2-yl)methanol 180A (1.3 g, 11.49 mmol) in DCM (30 mL) was added Dess-Martin periodinane (7.31 g, 17.24 mmol) at 0° C. portion wise. The resulting reaction mixture was allowed to warm to RT and stirred for 16 h. The reaction mass was diluted with dichloromethane (50 mL), washed with 20% sodium bicarbonate solution (50 mL), brine solution (50 mL), dried over (Na$_2$SO$_4$), filtered and the filtrate concentrated. The crude product was purified by combiflash chromatography (40 g Redisep® SiO$_2$ column, eluting with 20% EtOAc in n-hexane) to afford the title compound 180B (0.8 g, 62.7%) as a yellow oil. $^1$H NMR (400 MHz, CDCl$_3$) δ ppm 9.68 (s, 1H), 7.08 (s, 1H), 2.46 (s, 3H).

Ethyl 3-(5-methyloxazol-2-yl)acrylate (180C)

To a solution of 5-methyloxazole-2-carbaldehyde 180B (100 mg, 0.900 mmol) in toluene (3 mL) was added ethyl 2-(triphenyl-l5-phosphanylidene)acetate (470 mg, 1.350 mmol) at RT. The resulting mixture was heated to 110° C. and stirred for 18 h. The reaction mixture was cooled to RT and concentrated under reduce pressure. The crude product was purified by combiflash chromatography (4 g Redisep® SiO$_2$ column, eluting with 15% EtOAc in n-hexane) to afford the title compound 180C (0.1 g, 61%) as a yellow oil. LC-MS retention time=1.805 min; m/z=182.2 [M+H]$^+$ KINETEX XB-C18, (3×75) mm, 2.6 micron column; Flow rate: 1 mL/min; Mobile Phase A: 10 mM NH$_4$COOH in 98% water/2% ACN; Mobile Phase B: 10 mM NH$_4$COOH in 2% water/98% ACN; 20% B to 100% B over 4.6 min, then hold 0.4 min. at 20% B with flow rate 1-1.5 mL/min; Detection: UV at 254 nm. $^1$H NMR (400 MHz, CDCl$_3$) δ ppm 7.40 (d, J=15.89 Hz, 1H), 6.89 (s, 1H), 6.66 (d, J=16.14 Hz, 1H), 4.26 (q, J=7.09 Hz, 2H). 2.36 (s, 3H), 1.34 (t, J=7.09 Hz, 3H).

Ethyl 3-(3-fluoro-4-methoxyphenyl)-3-(5-methyloxazol-2-yl)propanoate (180D)

To a stirred solution of ethyl 3-(5-methyloxazol-2-yl)acrylate 180C (0.7 g, 3.86 mmol) in dioxane (16 mL) and water (4 mL) was added (3-fluoro-4-methoxyphenyl)boronic acid (0.985 g, 5.79 mmol) at RT. The reaction mixture was purged with argon for 15 min., and added triethylamine (1.077 mL, 7.73 mmol), chloro(1,5-cyclooctadiene)rhodium (I) dimer (0.095 g, 0.193 mmol). The reaction mixture was warmed to 80° C. and stirred for 16 h. The reaction mixture was cooled RT, filtered through Celite and the filtrate was concentrated. The crude product was purified by combiflash chromatography (12 g Redisep® SiO$_2$ column, eluting with 20% EtOAc in n-hexanes) to afford the title compound 180D (250 mg, 21%) as a yellow oil. LC-MS retention time=2.556 min; m/z=308.2 [M+H]$^+$ KINETEX XB-C18, (3×75) mm, 2.6 micron column; Flow rate: 1 mL/min; Mobile Phase A: 10 mM NH$_4$COOH in 98% Water/2% ACN; Mobile Phase B: 10 mM NH$_4$COOH in 2% Water/98% ACN; 20% B to 100% B over 4.6 min, then hold 0.4 min. at 20% B with flow rate 1-1.5 mL/min; Detection: UV at 220 nm. $^1$H NMR (400 MHz, CDCl$_3$) δ ppm 6.93-7.04 (m, 2H), 6.89-6.91 (m, 1H), 6.65 (m, 1H), 4.52 (t, J=7.78 Hz, 1H), 4.12 (q, J=7.36 Hz, 2H), 3.87 (s, 3H), 3.26 (dd, J=16.31, 8.28 Hz, 1H), 2.92 (dd, J=16.31, 8.28 Hz, 1H), 2.25 (s, 3H), 1.20 (t, J=1.2 Hz, 3H).

Ethyl 3-(4-bromo-5-methyloxazol-2-yl)-3-(3-fluoro-4-methoxyphenyl)propanoate (180E)

To a stirred solution of ethyl 3-(3-fluoro-4-methoxyphenyl)-3-(5-methyloxazol-2-yl)propanoate 180D (900 mg, 2.93 mmol) in DMF (5 mL) was added NBS (1042 mg, 5.86 mmol) portion wise at RT and the resulting reaction mixture was stirred for 24 h. The reaction mixture was diluted with ice cold water (10 mL) and extracted with EtOAc (2×25 mL). The combined organic layer was washed with water, brine, dried ($Na_2SO_4$), filtered and the filtrate was concentrated. The crude product was purified by combiflash chromatography (12 g Redisep® $SiO_2$ column, eluting with 10% EtOAc in n-hexanes) to afford the title compound 180E (275 mg, 23%) as a yellow oil. LC-MS retention time=2.978 min; m/z=386.0 $[M+H]^+$ KINETEX XB-C18, (3×75) mm, 2.6 micron column; Flow rate: 1 mL/min; Mobile Phase A: 10 mM $NH_4COOH$ in 98% water/2% ACN; Mobile Phase B: 10 mM $NH_4COOH$ in 2% water/98% ACN; 20% B to 100% B over 4.6 min, then hold 0.4 min. at 20% B with flow rate 1-1.5 mL/min; Detection: UV at 254 nm. $^1H$ NMR (400 MHz, $CDCl_3$) δ ppm 6.98-7.03 (m, 2H), 6.89 (t, J=8.4 Hz, 1H), 4.48 (t, J=1.15 Hz, 1H), 4.08 (qd, J=7.13, 2.13 Hz, 2H), 3.86 (s, 3H), 3.26 (dd, J=16.51, 8.51 Hz, 1H), 2.87 (dd, J=16.51, 7.25 Hz, 1H), 2.22 (s, 3H), 1.19 (t, J=7.13 Hz, 3H).

(E)-Ethyl 3-(4-(4-(1,8-naphthyridin-2-yl)but-1-en-1-yl)-5-methyloxazol-2-yl)-3-(3-fluoro-4-methoxyphenyl)propanoate (180F)

To a stirred solution of ethyl 3-(4-bromo-5-methyloxazol-2-yl)-3-(3-fluoro-4-methoxyphenyl)propanoate 180E (250 mg, 0.647 mmol) in acetonitrile (5 mL) was added 2-(but-3-en-1-yl)-1,8-naphthyridine (179 mg, 0.971 mmol) and resulting reaction mixture was purged with nitrogen for 15 min. Then added triethylamine (0.271 mL, 1.942 mmol), tri-o-tolylphosphine (19.70 mg, 0.065 mmol) and palladium acetate (2.91 mg, 0.013 mmol) and reaction mixture was heated to 85° C. and stirred for 16 h. The reaction mixture was cooled RT, filtered through Celite bed and the filtrate was concentrated. The crude product was purified by combiflash chromatography (12 g Redisep® $SiO_2$ column, eluting with 80% EtOAc in pet ether) to afford the title compound 180F (170 mg, 54%) as a yellow oil (mixture of isomers). LC-MS retention time=3.22 and 3.313 min; m/z=490.2 $[M+H]^+$ KINETEX XB-C18, (3×75) mm, 2.6 micron column; Flow rate: 1 mL/min; Mobile Phase A: 10 mM $NH_4COOH$ in 98% water/2% ACN; Mobile Phase B: 10 mM $NH_4C00H$ in 2% water/98% ACN; 20% B to 100% B over 4.6 min, then hold 0.4 min. at 20% B with flow rate 1-1.5 mL/min; Detection: UV at 220 nm.

Ethyl 3-(3-fluoro-4-methoxyphenyl)-3-(5-methyl-4-(4-(5,6,7,8-tetrahydro-1,8-naphthyridin-2-yl)butyl)-oxazol-2-yl)propanoate (180G)

To a solution of ethyl (E)-3-(4-(4-(1,8-naphthyridin-2-yl)but-1-en-1-yl)-5-methyloxazol-2-yl)-3-(3-fluoro-4-methoxyphenyl)propanoate 180F (170 mg, 0.347 mmol) in ethanol (10 mL) was purged with nitrogen for 5 min and was added platinum(IV) oxide (20 mg, 0.088 mmol) at RT. The reaction mixture was stirred at RT under hydrogen balloon atmosphere for 16 h. The reaction mixture was filtered through Celite and the filtrate was concentrated to afford the title compound 180G (150 mg, 87%) as yellow oil. LC-MS retention time=3.385 min; m/z=496.2 $[M+H]^+$ KINETEX XB-C18, (3×75) mm, 2.6 micron column; Flow rate: 1 mL/min; Mobile Phase A: 10 mM $NH_4COOH$ in 98% Water/2% ACN; Mobile Phase B: 10 mM $NH_4COOH$ in 2% Water/98% ACN; 20% B to 100% B over 4.6 min, then hold 0.4 min. at 20% B with flow rate 1-1.5 mL/min; Detection: UV at 220 nm. $^1H$ NMR (400 MHz, $CDCl_3$) δ ppm 6.95-7.10 (m, 3H), 6.83 (t, J=7.6 Hz, 1H), 6.31 (d, J=7.6 Hz, 1H), 4.47 (t, J=7.63 Hz, 1H), 4.00-4.14 (m, 2H), 3.85 (s, 3H), 3.38-3.40 (m, 2H), 3.22 (dd, J=16.26, 7.75 Hz, 1H), 2.87 (dd, J=16.39, 7.88 Hz, 1H), 2.68 (t, J=6.25 Hz, 2H), 2.55 (t, J=7.38 Hz, 2H), 2.39 (t, J=6.88 Hz, 2H), 2.14 (s, 3H), 1.83-1.94 (m, 2H), 1.58-1.71 (m, 4H), 1.16 (t, J=7.13 Hz, 3H).

Example 180: first eluting enantiomer of 3-(3-fluoro-4-methoxyphenyl)-3-(5-methyl-4-(4-(5,6,7,8-tetrahydro-1,8-naphthyridin-2-yl)butyl)oxazol-2-yl) propanoic acid Example 181: second eluting enantiomer of 3-(3-fluoro-4-methoxyphenyl)-3-(5-methyl-4-(4-(5,6,7,8-tetrahydro-1,8-naphthyridin-2-yl)butyl)oxazol-2-yl) propanoic acid To a stirred solution of ethyl 3-(3-fluoro-4-methoxyphenyl)-3-(5-methyl-4-(4-(5,6,7,8-tetrahydro-1,8-naphthyridin-2-yl)butyl)oxazol-2-yl)propanoate 180G (150 mg, 0.303 mmol) in THF (2 mL) and MeOH (2 mL) was added a solution of $LiOH·H_2O$ (50.8 mg, 1.211 mmol) in water (1 mL) and the resulting reaction mixture was stirred at RT for 18 h. After completion of the reaction, reaction mixture was added citric acid (174 mg, 0.908 mmol) and stirred at the RT for 10 min. Then reaction mixture was concentrated and the crude product was purified by preparative reverse phase HPLC (Inertsil DS (250×19) mm; 5 micron, Mobile phase A: 10 mM $CH_3COONH_4$ (pH=4.5); Mobile phase B: Acetonitrile, Flow: 17 mL/min, Gradient: Time (Min)/% B 0/20, 20/60 to afford the title compound (85 mg) as racemic. The individual enantiomers were separated by chiral SFC (Chiralpak IC (250×21) mm; 5 micron; 60% $CO_2$ and 40% (0.2% $NH_4OH$) in MeOH+ACN (1:1) as co-solvent; Total Flow: 70 g/min; Back Pressure: 100 bar; Temperature: 30° C.; Detection: UV at 230 nM. Example 180 (Retention time 4.7 min., 25 mg, 17%) was isolated as off white solid. LC-MS retention time=1.98 min; m/z=468.2 $[M+H]^+$ KINETEX XB-C18, (3×75) mm, 2.6 micron column; Flow rate: 1 mL/min; Mobile Phase A: 10 mM $NH_4COOH$ in 98% water/2% ACN; Mobile Phase B: 10 mM $NH_4COOH$ in 2% water/98% ACN; 20% B to 100% B over 4.6 min, then hold 0.4 min. at 20% B with flow rate 1-1.5 mL/min; Detection: UV at 220 nm. $^1H$ NMR (400 MHz, $CD_3OD$) δ ppm 7.41 (d, J=7.03 Hz, 1H), 7.02-7.10 (m, 3H), 6.45 (d, J=7.03 Hz, 1H), 4.48 (dd, J=11.80, 4.77 Hz, 1H), 3.86 (s, 3H), 3.43 (t, J=5.6 Hz, 2H), 3.07-3.14 (dd, J=15.2 11.6 Hz, 1H), 2.73-2.78 (m, 3H), 2.57 (m, 2H), 2.48 (t, J=7.2 Hz, 2H), 2.19 (s, 3H), 1.90-1.93 (m, 2H), 1.69-1.81 (m, 2H), 1.50-1.54 (m, 2H). Human αVβ6 IC50 (nM)=250. Example 181 (Retention time 5.6 min., 29 mg, 19%) was isolated as off white solid. LC-MS retention time=1.983 min; m/z=468.2 $[M+H]^+$ KINETEX XB-C18, (3×75) mm, 2.6 micron column; Flow rate: 1 mL/min; Mobile Phase A: 10 mM $NH_4COOH$ in 98% water/2% ACN; Mobile Phase B: 10 mM $NH_4COOH$ in 2% water/98% ACN; 20% B to 100% B over 4.6 min, then hold 0.4 min. at 20% B with flow rate 1-1.5 mL/min; Detection: UV at 300 nm. $^1H$ NMR (400 MHz, $CD_3OD$) δ ppm 7.41 (d, J=7.03 Hz, 1H), 7.02-7.10 (m, 3H), 6.45 (d, J=7.03 Hz, 1H), 4.48 (dd, J=11.80, 4.77 Hz, 1H), 3.86 (s, 3H), 3.43 (t, J=5.6 Hz, 2H), 3.07-3.14 (dd, J=15.2 11.6 Hz, 1H), 2.73-2.78 (m, 3H), 2.57 (m, 2H), 2.48 (t, J=7.2 Hz, 2H), 2.19 (s, 3H), 1.90-1.93 (m, 2H), 1.69-1.81 (m, 2H), 1.50-1.54 (m, 2H). Human αVβ6 IC50 (nM)=1060.

Biological Evaluation

All binding assays used the HTRF (homogeneous time resolved fluorescence) technology from Cisbio International, therefore all assays are described as HTRF binding assays. The assay results for the Examples are listed above together with the characterization data. The HTRF binding assays are established for the following integrins: human αVβ6, human αVβ1, human αVβ3, human αVβ5, and human αVβ8. All assays used the following assay buffer: 20 mM Tris, pH 7.4, 1 mM $MgCl_2$, 1 mM $MnCl_2$, 0.01% Tween 20, and 0.01% BSA. Alternatively, a SPA-based assay was used for evaluation of receptor binding.

The following describes the components and a representative procedure for the human αVβ6 HTRF binding assay: Recombinant human αVβ6 Integrin (R & D systems, 3817-AV) was biotinylated. Biotinylated human αVβ6 Integrin was added to assay vessel at a final concentration of 1.25 nM. FITC-conjugated fibronectin (Cytoskeleton, FNR02) was then added at the final concentration of 5 nM. The mixture was centrifuged at 600 rpm for three minutes using Thermo Fisher Heraeus Multifuge X3 centrifuge and then incubated at RT for an hour. Streptavidin Terbium (Cisbio international 610STLB) was then added at the final concentration of 0.625 nM. The resulting mixture was centrifuged at 600 rpm for three minutes using Thermo Fisher Heraeus Multifuge X3 centrifuge and then incubated at room temperature overnight in dark before reading HTRF signals.

The SPA-based assay was carried out according to the protocol and procedures similar to the ones described in the following reference with appropriate modifications to agents and ligands which are readily understood by one skilled in the art: Pachter J A, Zhang R, Mayer-Ezell R., "Scintillation proximity assay to measure binding of soluble fibronectin to antibody-captured αVβ1 integrin" Anal Biochem. 1995 Sep. 1; 230(1): 101-7.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:
1. A compound of Formula (I):

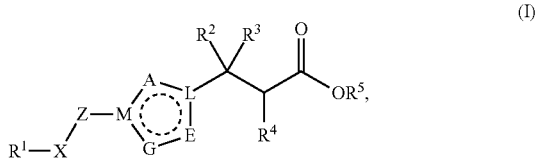

or a pharmaceutically acceptable salt thereof, wherein:
A is $CR^{6b}$;
E is $CR^{6b}$;
G is N;
L is C;
M is N;
X is a $C_{1-6}$ alkylene substituted with 0, 1, or 2 $R^{7b}$;
Z is a covalent bond;

$R^1$ is:

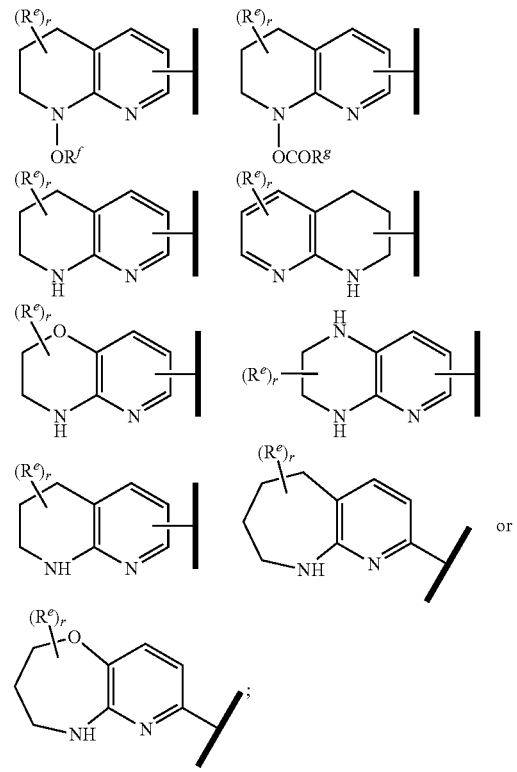

$R^2$ is hydrogen or $C_{1-6}$ alkyl;

$R^3$ is hydrogen;

$R^4$ is $NR^aR^b$, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$ $R^5$ is hydrogen or $R^{5a}$;

$R^{5a}$ is $C_{1-6}$ alkyl, phenyl, or 5- to 7-membered heterocyclyl, wherein the alkyl, phenyl, and heterocyclyl are each independently substituted with 0 to 3 $R^{5d}$;

$R^{5d}$, at each occurrence, is independently halo, OH, alkoxy, oxo, or alkyl;

$R^{6b}$ is each independently hydrogen, halo, cyano, nitro, amino, OH, $C_{1-6}$ alkyl, haloalkyl, alkoxy, haloalkoxy, hydroxyalkyl, aminoalkyl, or $C_{3-5}$ cycloalkyl, wherein the cycloalkyl is substituted with 0, 1, 2, or 3 halo, cyano, nitro, amino, or OH;

$R^{7b}$ is each independently halo, cyano, hydroxyl, amino, $C_{1-6}$ alkyl, haloalkyl, hydroxyalkyl, aminoalkyl, alkoxy, haloalkoxy, amido, carbamate, or sulfonamide;

$R^{10}$ is $C_{1-6}$ alkyl, 3- to 10-membered carbocyclyl, 3- to 10-membered heterocyclyl, 6- to 10-membered aryl, or 5- to 10-membered heteroaryl; wherein the alkyl, carbocyclyl, heterocyclyl are each independently substituted with 0, 1, 2, or 3 $R^{11}$;

$R^{11}$ is halo, cyano, nitro, OH, amino, $C_{1-6}$ alkyl, alkoxy, 3- to 10-membered carbocyclyl, 3- to 10-membered heterocyclyl, 6- to 10-membered aryl, or 5- to 10-membered heteroaryl; wherein the aryl, alkyl, and heteroaryl are each independently substituted with 0, 1, 2, or 3 $R^{13}$;

$R^{13}$ and $R^{14}$, at each occurrence, are independently halo, cyano, nitro, OH, amino, $C_{1-6}$ alkyl, alkoxy, aminoalkyl, haloalkyl, haloalkoxy, haloaminoalkyl, 3 to 6 membered carbocyclyl, 3 to 6 membered heterocyclyl, 6- to 10-membered aryl, or 5- to 10-membered heteroaryl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^a$ and $R^b$, at each occurrence, are independently hydrogen, $C_{1-10}$ alkyl, 3- to 10-membered carbocyclyl, or 3- to 10-membered heterocyclyl; wherein the alkyl, carbocyclyl, heterocyclyl are each independently substituted with 0, 1, 2, or 3 $R^{14}$;

$R^e$ is OH, $C_{1-4}$ alkyl, halo, haloalkyl, $C_{1-4}$ cycloalkyl, amino, amido, carbamate, or sulfonamide;

$R^f$ is hydrogen, $CH_3$, $CH_2CH_3$, or $COOCH_2CH_3$;

$R^g$ is selected from $CH_3$, $CH_2CH_3$, $CH_2CCl_3$, phenyl, 4-fluorophenyl, 4-methoxyphenyl, benzyl,

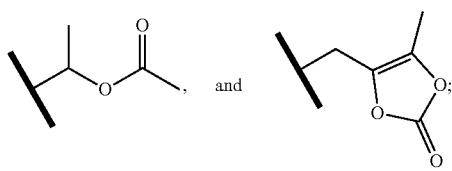

n is 2; and r is an integer of 0, 1, 2, or 3.

2. The compound according to claim 1 or a pharmaceutically acceptable salt thereof, wherein:

X is a $C_{1-6}$ alkylene;

$R^2$ is hydrogen;

$R^{6b}$ is each independently hydrogen, halo, cyano, amino, OH, $C_{1-6}$ alkyl, or $C_{3-5}$ cycloalkyl; and $R^{5a}$ is $C_{1-6}$ alkyl or phenyl.

3. The compound according to claim 1 or a pharmaceutically salt thereof, wherein:

$R^4$ is $NHR^b$, $OR^a$, $S(O)_nR^{10}$, $C(O)NHR^b$, $NHC(O)OR^a$, $NHC(O)NHR^b$, $NHC(O)R^{10}$, $OC(O)NR^b$, $OC(O)R^{10}$, $NHS(O)_nNR^b$, or $NHS(O)_nR^{10}$.

4. The compound of claim 1 or a pharmaceutically acceptable salt thereof, wherein:

$R^4$ is $S(O)_nR^{10}$, $C(O)NR^b$, $NHC(O)OR^a$, $NHC(O)NR^b$, $NHC(O)R^{10}$, $NHS(O)_nNR^b$, or $NHS(O)_nR^{10}$.

5. The compound of claim 1 or a pharmaceutically acceptable salt thereof, wherein:

$R^4$ is $NHC(O)OR^a$ or $NHS(O)_nR^{10}$.

6. The compound of claim 1 or a pharmaceutically acceptable salt thereof, having the structure:

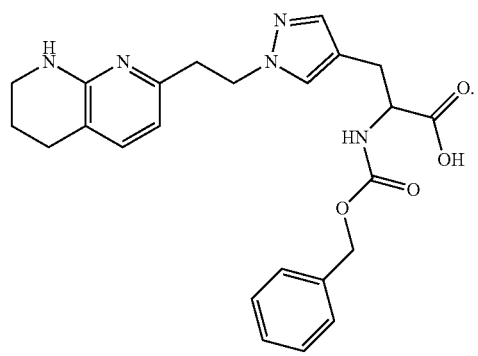 [SMILES: O=C(NC(Cc1cnn(CCc2ccc3c(n2)NCCC3)c1)C(=O)O)OCc1ccccc1]

7. The compound of claim 1 or a pharmaceutically acceptable salt thereof, having the structure:

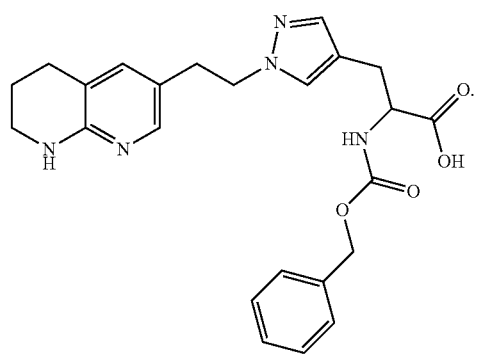 [SMILES: O=C(NC(Cc1cnn(CCc2cnc3c(c2)CCCN3)c1)C(=O)O)OCc1ccccc1]

8. The compound of claim 1 or a pharmaceutically acceptable salt thereof, having the structure:

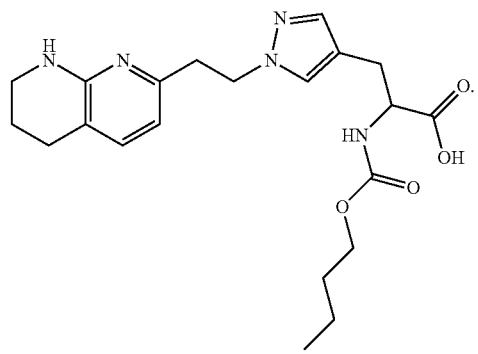 [SMILES: CCCCOC(=O)NC(Cc1cnn(CCc2ccc3c(n2)NCCC3)c1)C(=O)O]

9. The compound of claim 1 or a pharmaceutically acceptable salt thereof, having the structure:

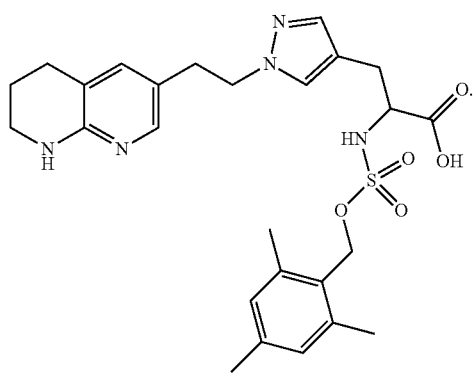 [SMILES: Cc1cc(C)c(COS(=O)(=O)NC(Cc2cnn(CCc3cnc4c(c3)CCCN4)c2)C(=O)O)c(C)c1]

10. The compound of claim 1 or a pharmaceutically acceptable salt thereof, wherein said compound is:
- (±)-2-(((Benzyloxy)carbonyl)amino)-3-(1-(2-(5,6,7,8-tetrahydro-1,8-naphthyridin-2-yl)ethyl)-1H-pyrazol-4-yl)propanoic acid (5);
- (±)-2-(((Benzyloxy)carbonyl)amino)-3-(1-(3-(5,6,7,8-tetrahydro-1,8-naphthyridin-2-yl)propyl)-1H-pyrazol-4-yl)propanoic acid (6);
- (±)-2-((Butoxycarbonyl)amino)-3-(1-(2-(5,6,7,8-tetrahydro-1,8-naphthyridin-2-yl)ethyl)-1H-pyrazol-4-yl)propanoic acid (23); or
- (±)-3-(1-(3-(5,6,7,8-Tetrahydro-1,8-naphthyridin-2-yl)propyl)-1H-pyrazol-4-yl)-2-((2,4,6-trimethylphenyl)sulfonamido)propanoic acid (25).

11. A pharmaceutical composition comprising a compound of claim 1, or a pharmaceutically acceptable salt thereof, and a carrier.

* * * * *